US009604980B2

(12) United States Patent
Menichincheri et al.

(10) Patent No.: US 9,604,980 B2
(45) Date of Patent: Mar. 28, 2017

(54) SUBSTITUTED PYRIMIDINYL AND PYRIDINYL-PYRROLOPYRIDINONES, PROCESS FOR THEIR PREPARATION AND THEIR USE AS KINASE INHIBITORS

(71) Applicant: NERVIANO MEDICAL SCIENCES S.r.l, Nerviano (MI) (IT)

(72) Inventors: Maria Menichincheri, Milan (IT); Mauro Angiolini, Gavirate (IT); Jay Aaron Bertrand, Didcot (GB); Michele Caruso, Milan (IT); Paolo Polucci, Cassina Rizzardi (IT); Francesca Quartieri, Arona (IT); Barbara Salom, Vedano al Lambro (IT); Matteo Salsa, Bellinzago Novarese (IT); Fabio Zuccotto, Milan (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

(21) Appl. No.: 14/647,940

(22) PCT Filed: Oct. 31, 2013

(86) PCT No.: PCT/EP2013/072793
§ 371 (c)(1),
(2) Date: May 28, 2015

(87) PCT Pub. No.: WO2014/072220
PCT Pub. Date: May 15, 2014

(65) Prior Publication Data
US 2015/0299192 A1    Oct. 22, 2015

(30) Foreign Application Priority Data

Nov. 7, 2012    (EP) .................................. 12191679

(51) Int. Cl.
C07D 471/04    (2006.01)
A61K 31/506   (2006.01)
A61K 45/06    (2006.01)
A61K 31/496   (2006.01)
A61N 5/10     (2006.01)

(52) U.S. Cl.
CPC .......... *C07D 471/04* (2013.01); *A61K 31/496* (2013.01); *A61K 31/506* (2013.01); *A61K 45/06* (2013.01); *A61N 5/10* (2013.01)

(58) Field of Classification Search
CPC ... C07D 471/04; A61K 31/496; A61K 31/506
USPC ............ 544/295, 330, 331, 362; 514/252.14, 514/253.04, 275
See application file for complete search history.

(56) References Cited

FOREIGN PATENT DOCUMENTS

| WO | WO 2004/058762 A1 | 7/2004 |
| WO | WO 2005/013986 A1 | 2/2005 |
| WO | WO 2005/014572 A1 | 2/2005 |
| WO | WO 2010/043000 A1 | 4/2010 |
| WO | WO 2010/145998 A1 | 12/2010 |

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, 20th Edition, vol. 1, pp. 1004-1101 O, 1996.*
Douglas, Jr., Introduction to Viral Diseases, Cecil Textbook of Medicine, 20th Edition, vol. 2, pp. 1739-1747, 1996.*
Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Anderson D.R. et al., "Pyrrolopyridine Inhibitors of Mitogen-Activated Protein Kinase-Activated Protein Kinase 2 (MK-2)", Journal of Medicinal Chemistry 50(11):2647-2654 (2007).
Arighi E. et al., "RET Tyrosine Kinase Signaling in Development and Cancer", Cytokine & Growth Factor Reviews 16:441-467 (2005).
Boulay A. et al., "The Ret Receptor Tyrosine Kinase Pathway Functionally Interacts with the ERa Pathway in Breast Cancer", Cancer Research 68(10):3743-3751 (May 15, 2008).
Colombo M. et al., "A Fully Automated Method for Accurate Mass Determination Using High-Performance Liquid Chromatography with a Quadrupole/Orthogonal Acceleration Time-of-Flight Mass Spectrometer", Rapid Communications in Mass Spectrometry 18:511-517 (2004).
Degroot J W B et al., "RET as a Diagnostic and Therapeutic Target in Sporadic and Hereditary Endocrine Tumors", Endocrine Reviews 27(5):535-560 (2006).
Futami H. et al., "A Novel Somatic Point Mutation of the RET Proto-Oncogene in Tumor Tissues of Small Cell Lung Cancer Patients", Jpn. J. Cancer Res. 86:1127-1130 (Dec. 1995).
Gil Z. et al., "Paracrine Regulation of Pancreatic Cancer Cell Invasion by Peripheral Nerves", JNCI 102(2):107-118 (Jan. 20, 2010).

(Continued)

*Primary Examiner* — Deepak Rao
(74) *Attorney, Agent, or Firm* — Scully, Scott, Murphy & Presser, P.C.

(57) ABSTRACT

The present invention relates to substituted pyrimidinyl- and pyridinylpyrrolopyridinone compounds which modulate the activity of protein kinases and are therefore useful in treating diseases caused by dysregulated protein kinase activity, in particular RET family kinases. The present invention also provides methods for preparing these compounds, pharmaceutical compositions comprising these compounds, and methods of treating diseases utilizing pharmaceutical compositions containing these compounds.

10 Claims, No Drawings

(56) References Cited

OTHER PUBLICATIONS

Greco A. et al., "Molecular Pathology of Differentiated Thyroid Cancer", The Quarterly Journal of Nuclear Medicine and Molecular Imaging 53(5):440-454 (Oct. 2009).

Grieco M. et al., "PTC is a Novel Rearranged Form of the Ret Proto-Oncogene and is Frequently Detected In Vivo in Human Thyroid Papillary Carcinomas", Cell 60:557-563 (Feb. 23, 1990).

Huang W-S et al., "Discovery of 3-[2-(Imidazo[1,2-b]Pyridazin-3-yl)Ethynyl]-4-Methyl-N-{4-[(4-Methylpiperazin-1-yl)-Methyl]-3-(Trifluoromethyl)Phenyl}Benzamide (AP24534), a Potent, Orally Active Pan-Inhibitor of Breakpoint Cluster Region-Abelson (BCR-ABL) Kinase Including the T3151 Gatekeeper Mutant", J. Med. Chem. 53(12):4701-4719 (2010).

Ito Y. et al., "Expression of Glial Cell Line-Derived Neurotrophic Factor Family Members and Their Receptors in Pancreatic Cancers", Surgery 138(4):788-794 (Oct. 2005).

Iwahashi N et al., "Expression of Glial Cell Line-Derived Neurotrophic Factor Correlates with Perineural Invasion of Bile Duct Carcinoma", Cancer 94(1):167-174 (Jan. 1, 2002).

Ju Y S et al., "A Transforming KIF5B and RET Gene Fusion in Lung Adenocarcinoma Revealed from Whole-Genome and Transcriptome Sequencing", Genome Research 22:436-445 (2012).

Klapars A. et al., "Copper-Catalyzed Halogen Exchange in Aryl Halides: An Aromatic Finkelstein Reaction", J. Am. Chem. Soc. 124(50):14844-14845 (2002).

Kohno T. et al., "KIF5B-RET Fusions in Lung Adenocarcinoma", Nature Medicine 18(3):375-377 (Mar. 2012).

Lipson D. et al., "Identification of New ALK and RET Gene Fusions from Colorectal and Lung Cancer Biopsies", Nature Medicine 18(3):382-384 (Mar. 2012).

Plaza-Menacho I et al., "Targeting the Receptor Tyrosine Kinase RET Sensitizes Breast Cancer Cells to Tamoxifen Treatment and Reveals a Role for RET in Endocrine Resistance", Oncogene 29:4648-4657 (Jun. 7, 2010).

Santoro M. et al., "Development of Thyroid Papillary Carcinomas Secondary to Tissue-Specific Expression of the RET/PTC1 Oncogene in Transgenic Mice", Oncogene 12:1821-1826 (1996).

Schuchardt A. et al., "Defects in the Kidney and Enteric Nervous System of Mice Lacking the Tyrosine Kinase Receptor Ret", Nature 367:380-383 (Jan. 27, 1994).

Takeuchi K. et al., "RET, ROS1 and ALK Fusions in Lung Cancer", Nature Medicine 18(3):378-381 (Mar. 2012).

Wells S.A. et al., "Targeting the RET Pathway in Thyroid Cancer", Clinical Cancer Research 15(23):7119-7123 (Dec. 1, 2009).

Wood L.D. et al., "The Genomic Landscapes of Human Breast and Colorectal Cancers", Science 318:1108-1113 (Nov. 16, 2007).

International Search Report dated Jan. 20, 2014 issued in PCT/EP2013/072793.

* cited by examiner

SUBSTITUTED PYRIMIDINYL AND PYRIDINYL-PYRROLOPYRIDINONES, PROCESS FOR THEIR PREPARATION AND THEIR USE AS KINASE INHIBITORS

The present invention relates to certain substituted pyrimidinyl- and pyridinylpyrrolopyridinone compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

RET is a single-pass transmembrane receptor belonging to the tyrosine kinase superfamily (reviewed in Arighi et al., Cytokine Growth Factor Rev, 2005, 16, 441-67). The extracellular portion of the RET protein contains four calcium-dependent cadherin-like repeats involved in ligand binding and a juxtamembrane cysteine-rich region necessary for the correct folding of RET extracellular domain, while the cytoplasmic portion of the receptor includes two tyrosine kinase subdomains. RET is the signaling component of a multiprotein complex: binding of RET to the glial-derived neurotrophic factor (GDNF) family ligands (GDNF, artemin, neurturin and persephin) through ligand-specific GDNF-family receptor alpha co-receptors (GFRα1-4) induces the formation of active RET dimers and the autophosphorylation of specific tyrosine residues in the cytoplasmic domain. These phosphorylated tyrosines function as docking sites for effector/adaptor proteins such as PLC-γ, PI3K, Shc, Grb2, Src, Enigma, STAT3, which in turn activate downstream signaling pathways, including Ras/Raf/ERK, PI3K/Akt/mTOR and PLC-γ/PKC. During embryogenesis RET signaling is critical for development of the enteric nervous system and for kidney organogenesis (Schuchardt et al., Nature, 1994, 367, 380-3). In adults RET is expressed in neural crest-derived cell types, such as neuroendocrine cells (thyroid parafollicular cells and adrenal medullary cells), peripheral ganglia, urogenital tract cells and spermatogonia.

Aberrant RET expression and/or activity have been demonstrated in different human cancers.

The oncogenic role of RET was firstly described in papillary thyroid carcinoma (PTC) (Grieco et al., Cell, 1990, 60, 557-63), which arises from follicular thyroid cells and is the most common thyroid malignancy. Approximately 20-30% of PTC harbor somatic chromosomal rearrangements (translocations or inversions) linking the promoter and the 5' portions of constitutively expressed, unrelated genes to the RET tyrosine kinase domain (reviewed in Greco et al., Q. J. Nucl. Med. Mol. Imaging, 2009, 53, 440-54), therefore driving its ectopic expression in thyroid cells. To date, twelve different fusion partners have been identified, all providing a protein/protein interaction domain that induces ligand-independent RET dimerization and constitutive kinase activity. The role of RET-PTC rearrangements in the pathogenesis of PTC has been confirmed in transgenic mice (Santoro et al., Oncogene, 1996, 12, 1821-6). Recently, a 10.6 Mb pericentric inversion in chromosome 10, where ret gene maps, has been identified in about 2% of lung adenocarcinoma patients, generating different variants of the chimeric gene KIF5B-RET (Ju et al., Genome Res., 2012, 22, 436-45; Kohno et al., 2012, Nature Med., 18, 375-7; Takeuchi et al., Nature Med., 2012, 18, 378-81; Lipson et al., 2012, Nature Med., 18, 382-4). The fusion transcripts are highly expressed and all the resulting chimeric proteins contain the N-terminal portion of the coiled-coil region of KIF5B, which mediates homodimerization, and the entire RET kinase domain. None of RET positive patients harbor other known oncogenic alterations (such as EGFR or K-Ras mutation, ALK translocation), supporting the possibility that KIF5B-RET fusion could be a driver mutation of lung adenocarcinoma. The oncogenic potential of KIF5B-RET has been confirmed by transfecting the fusion gene into cultured cell lines: similarly to what observed with RET-PTC fusion proteins, KIF5B-RET is constitutively phosphorylated and induces NIH-3T3 transformation and IL-3 independent growth of BA-F3 cells.

Besides rearrangements of the RET sequence, gain of function point mutations of RET proto-oncogene are also driving oncogenic events, as shown in medullary thyroid carcinoma (MTC), which arises from parafollicular calcitonin-producing cells (reviewed in: de Groot et al., Endocrine Rev., 2006, 27, 535-60; Wells and Santoro, Clin. Cancer Res., 2009, 15, 7119-7122). Around 25% of MTC are associated with multiple endocrine neoplasia type 2 (MEN2), a group of inherited cancer syndromes affecting neuroendocrine organs caused by germline activating point mutations of RET. In MEN2 subtypes (MEN2A, MEN2B and Familial MTC/FMTC) RET gene mutations have a strong phenotype-genotype correlation defining different MTC aggressiveness and clinical manifestations of the disease. In MEN2A syndrome mutations involve one of the six cysteine residues (mainly C634) located in the cysteine-rich extracellular region, leading to ligand-independent homodimerization and constitutive RET activation. Patients develop MTC at a young age (onset at 5-25 years) and may also develop pheochromocytoma (50%) and hyperparathyroidism. MEN2B is mainly caused by M918T mutation, which is located in the kinase domain. This mutation constitutively activates RET in its monomeric state and alters substrate recognition by the kinase. MEN2B syndrome is characterized by an early onset (<1 year) and very aggressive form of MTC, pheochromocytoma (50% of patients) and ganglioneuromas. In FMTC the only disease manifestation is MTC, usually occurring at an adult age. Many different mutations have been detected, spanning the entire RET gene. The remaining 75% of MTC cases are sporadic and about 50% of them harbor RET somatic mutations: the most frequent mutation is M918T that, as in MEN2B, is associated with the most aggressive phenotype. Somatic point mutations of RET have also been described in other tumors such as colorectal cancer (Wood et al., Science, 2007, 318, 1108-13) and small cell lung carcinoma (Jpn. J. Cancer Res., 1995, 86, 1127-30).

RET signaling components have been found to be expressed in primary breast tumors and to functionally interact with estrogen receptor-α pathway in breast tumor cell lines (Boulay et al., Cancer Res. 2008, 68, 3743-51; Plaza-Menacho et al., Oncogene, 2010, 29, 4648-57), while RET expression and activation by GDNF family ligands could play an important role in perineural invasion by different types of cancer cells (Ito et al., Surgery, 2005, 138, 788-94; Gil et al., J Natl Cancer Inst., 2010, 102, 107-18; Iwahashi et al., Cancer, 2002, 94, 167-74).

Given the relevant role of RET in human cancers, RET tyrosine kinase inhibitors could be of high therapeutic value. Pyridylpyrrole and pyrimidylpyrrole derivatives active as kinase inhibitors, particularly as Cdk2 and Cdc7 inhibitors, have been disclosed in WO2005/013986 and in WO2005/014572, in the name of Pharmacia Italia SpA, for the treatment of hyperproliferative diseases such as cancer.

Substituted pyrimidinylpyrrolopyridinone derivatives are disclosed in WO2010/145998 and are useful in the treatment of diseases associated with a disregulated protein kinase activity, particularly RAF family kinases activity, like cancer. Despite these developments, there is still need for effective agents for said diseases.

The present inventors have now discovered the compounds of formula (I) described below, which, other than having a remarkable kinase inhibitory activity, have a significantly improved solubility so that to obtain better formulation and/or pharmacokinetic/pharmacodynamic properties. These compounds are thus useful in therapy as antitumor agents.

Accordingly, a first object of the present invention is to provide a substituted pyrimidinyl- and pyridinylpyrrolopyridinone compound represented by formula (I),

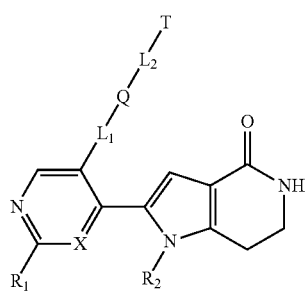

(I)

wherein:

X is CH or N;

$R_1$ is H or $NHR_3$, wherein $R_3$ is H, an optionally substituted group selected from straight or branched $C_1$-$C_6$ alkyl, heterocyclyl and COR', wherein R' is an optionally substituted group selected from straight or branched $C_1$-$C_6$ alkyl, $C_3$-$C_6$ carbocyclyl, aryl and heteroaryl;

$L_1$ is $CH_2$—$CH_2$, CH=CH or C≡C;

Q is an optionally substituted group selected from aryl and heteroaryl;

$L_2$ is C(RaRb)NRa, C(RaRb)C(RaRb)NRa, C(RaRb)NRaC(RaRb), NRaC(RaRb), NRaC(RaRb)C(RaRb), COO, C(RaRb)COO, C(RaRb)C(RaRb)COO, NRaSO$_2$, SO$_2$NRa, C(RaRb)SO$_2$NRa, NRaCONRa, NRaCSNRa, NRaCOO, CONRa, C(RaRb)CONRa, C(RaRb)C(RaRb)CONRa, CONRaC(RaRb), CONRaC(RaRb)C(RaRb), NRaCO, C(RaRb)NRaCO, C(RaRb)C(RaRb)NRaCO, NRaCOC(RaRb), NRaCOC(RaRb)C(RaRb), OC(RaRb)CONRa, C(RaRb)OC(RaRb), OC(RaRb)(C(RaRb))nC(RaRb),

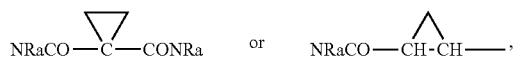

wherein

Ra and Rb are independently H or an optionally substituted straight or branched $C_1$-$C_6$ alkyl and n is 0 or 1;

T is H or an optionally substituted group selected from straight or branched $C_1$-$C_6$ alkyl, $C_3$-$C_6$ carbocyclyl, heterocyclyl, aryl and heteroaryl;

$R_2$ is H or an optionally substituted group selected from straight or branched $C_1$-$C_6$ alkyl, $C_3$-$C_6$ carbocyclyl, heterocyclyl, aryl and heteroaryl;

or pharmaceutically acceptable salts thereof, with the proviso that the compound 1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(4-trifluoromethylphenyl)-urea is excluded.

The present invention also provides methods of preparing the substituted pyrimidinyl- and pyridinylpyrrolopyridinone compounds, represented by formula (I), prepared through a process consisting of standard synthetic transformations.

The present invention also provides a method for treating diseases caused by and/or associated with dysregulated protein kinase activity, particularly RAF family, protein kinase C in different isoforms, RET, Abl, Aurora A, Aurora B, Aurora C, EphA, EphB, FLT3, KIT, LCK, LYN, EGF-R, PDGF-R, FGF-R, PAK-4, P38 alpha, TRKA, TRKB, VEGFR, more particularly RET family kinases, which comprises administering to a mammal in need thereof, more particularly a human, an effective amount of a substituted pyrimidinyl- and pyridinylpyrrolopyridinone compound represented by formula (I) as defined above.

A preferred method of the present invention is to treat a disease caused by and/or associated with dysregulated protein kinase activity selected from the group consisting of cancer, cell proliferative disorders, viral infections, immune-related and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukaemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid cancers, such as papillary thyroid carcinoma and medullary thyroid carcinoma, and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, comprising the prevention of AIDS development in HIV-infected individuals.

Another preferred method of the present invention is to treat immune-related disorders including but not limited to: transplant rejection, skin disorders like psoriasis, allergies, asthma and autoimmune-mediated diseases such as rheumatoid arthritis (RA), systemic lupus erythematosus (SLE), Crohn's disease and amyotrophic lateral sclerosis. Another preferred method of the present invention is to treat neurodegenerative disorders including but not limited to:

Alzheimer's disease, degenerative nerve diseases, encephalitis, Stroke, Parkinson's Disease, Multiple Sclerosis, Amyotrophic Lateral Sclerosis (ALS or Lou Gehrig's Disease), Huntington's Disease and Pick's Disease.

In addition, the method of the present invention also provides tumor angiogenesis and metastasis inhibition as well as the treatment of organ transplant rejection and host versus graft disease.

Moreover, the method of the present invention further comprises subjecting the mammal in need thereof to a radiation therapy or chemotherapy regimen in combination with at least one cytostatic or cytotoxic agent.

The present invention also provides a pharmaceutical composition comprising a therapeutically effective amount of a compound of formula (I) or a pharmaceutically acceptable salt thereof, as defined above, and at least one pharmaceutically acceptable excipient, carrier and/or diluent.

The present invention further provides a pharmaceutical composition of a compound of the formula (I) further comprising one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Moreover the invention provides an in vitro method for inhibiting the RET family protein activity which comprises contacting the said protein with an effective amount of a compound of formula (I) as defined above.

Additionally, the invention provides a product or kit comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

N-oxides are compounds of formula (I) wherein nitrogen and oxygen are tethered through a dative bond.

If a stereogenic center or another form of an asymmetric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form. Pharmaceutically acceptable salts of the compounds of formula (I) include the salts with inorganic or organic acids. Pharmaceutically acceptable salts of the compounds of formula (I) also include the salts with inorganic or organic bases.

With the term "straight or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_1$-$C_3$ alkyl", we intend any of the groups such as, for instance, methyl, ethyl, n-propyl, isopropyl.

With the term "$C_3$-$C_6$ carbocyclyl" we intend, unless otherwise provided, a 3- to 6-membered all-carbon monocyclic ring, which may contain one or more double bonds but does not have a completely conjugated π-electron system. Examples of carbocyclyl groups, without limitation, are cyclopropane, cyclobutane, cyclopentane, cyclopentene, cyclohexane, cyclohexene and cyclohexadiene. The $C_3$-$C_6$ carbocyclyl ring can be optionally further fused or linked to aromatic and non-aromatic carbocyclic and heterocyclic rings.

With the term "heterocyclyl" we intend a 3- to 7-membered saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, 1,4-diazepanyl, morpholine and the like. The heterocyclyl ring can be optionally further fused or linked to aromatic and non-aromatic carbocyclic and heterocyclic rings.

With the term "$C_2$-$C_6$ alkenyl" we intend an aliphatic $C_2$-$C_8$ hydrocarbon chain containing at least one carbon-carbon double bond and which can be straight or branched. Representative examples include, but are not limited to, ethenyl, 1-propenyl, 2-propenyl, 1- or 2-butenyl and the like.

With the term "$C_2$-$C_6$ alkynyl" we intend an aliphatic $C_2$-$C_8$ hydrocarbon chain containing at least one carbon-carbon triple bond and which can be straight or branched. Representative examples include, but are not limited to, ethynyl, 1-propynyl, 2-propynyl, 1- or 2-butynyl and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl, α- or β-tetrahydronaphthalenyl, biphenyl and indanyl groups. The aryl ring can be optionally further fused or linked to aromatic and non-aromatic carbocyclic and heterocyclic rings.

The term "heteroaryl" refers to aromatic heterocyclic rings, typically 5- to 7-membered heterocycles, with from 1 to 3 heteroatoms selected among nitrogen, oxygen and sulfur; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, thiadiazolyl, isoxazolyl, isothiazolyl, oxadiazolyl, indazolyl, cinnolinyl, benzo[1,3]dioxolyl, benzo[1,4]dioxinyl, benzothiazolyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl and the like.

According to the present invention and unless otherwise provided, any of the above $R_2$, $R_3$, R', Ra, Rb, T and Q groups may be optionally substituted, in any of their free positions, by one or more groups, for instance 1 to 6 groups, independently selected from: halogen, nitro, oxo groups (=O), cyano, $C_1$-$C_6$ alkyl, polyfluorinated alkyl, polyfluorinated alkoxy, $C_2$-$C_6$ alkenyl, $C_2$-$C_6$ alkynyl, hydroxyalkyl, aryl, arylalkyl, heteroaryl, heteroarylalkyl, heterocyclyl, heterocyclylalkyl, heterocyclylheterocyclyl, $C_3$-$C_6$ cycloalkyl, hydroxy, polyhydroxyalkyl, alkoxy, aryloxy, heterocyclyloxy, methylenedioxy, alkylcarbonyloxy, alkylheterocyclyl, alkylheteroaryl, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term "halogen" we intend a fluorine, chlorine, bromine or iodine atom.

With the term "polyfluorinated alkyl" or "polyfluorinated alkoxy" we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "hydroxyalkyl" we intend any of the above $C_1$-$C_6$ alkyl, bearing a hydroxyl group such as, for instance, hydroxymethyl, 2-hydroxyethyl, 3-hydroxypropyl and the like.

From all of the above, it is clear to the skilled person that any group which name is a composite name such as, for instance, "arylamino" has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_6$ cycloalkyl and heterocyclyl moieties are as above defined.

A preferred class of compounds of formula (I) are the compounds wherein:
$R_1$ is H or $NHR_3$, wherein $R_3$ is H, an optionally substituted group selected from straight or branched $C_1$-$C_3$ alkyl, heterocyclyl and COR';
$L_1$ is C≡C;
Q is an optionally substituted group selected from aryl and heteroaryl, wherein the heteroaryl is monocyclic or bicyclic, and said bicyclic heteroaryl contains a nitrogen atom which the $L_2$ group is attached to; and X, R', $L_2$, T and $R_2$ are as defined above.

Another further preferred class of compounds of formula (I) are the compounds wherein:
Q is an optionally substituted aryl or heteroaryl selected from:

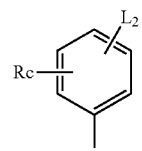

A

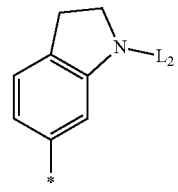

B

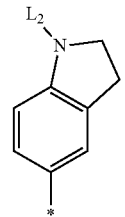

C

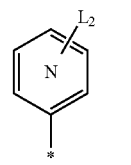

D

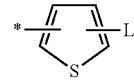

E

-continued

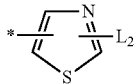

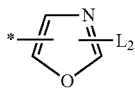

wherein Rc is selected from methyl and halogen, preferably fluorine;
L₂ is CONRa, C(RaRb)CONRa, C(RaRb)C(RaRb)CONRa, CONRaC(RaRb), OC(RaRb)CONRa, SO₂NRa or C(RaRb) SO₂NRa, wherein Ra and Rb are both hydrogen;
T is a substituted aryl of formula J:

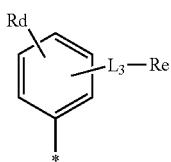

wherein
Rd is halogen, optionally substituted straight or branched $C_1$-$C_4$ alkyl, $C_3$-$C_6$ cycloalkyl or trifluoromethyl;
$L_3$ is direct linkage, O, NH, NCH₃, CH₂, CH₂NH, CH₂NCH₃ or C=O;
Re is
  an optionally substituted heterocyclyl or
  an optionally substituted straight or branched $C_1$-$C_6$ alkyl chain, wherein
    from 1 to 3 carbon atoms of said alkyl may be independently substituted by N or O, or
  NRfRg, wherein
    Rf and Rg are each independently hydrogen or
    an optionally substituted straight or branched $C_1$-$C_6$ alkyl chain, wherein
      from 1 to 3 carbon atoms of said alkyl may be independently substituted by N or O, or
    Rf and Rg joined together with the nitrogen atom might represent a heterocyclic ring;
and X, $R_1$, $R_2$ and $L_1$ are as defined above.

Another further preferred class of compounds of formula (I) are the compounds wherein:
Q is an optionally substituted aryl of structure A:

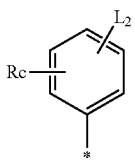

wherein Rc is as defined above;
L₂ is NRaCONRa, NRaCSNRa, NRaCOO, NRaCO, NRaCOC(RaRb), NRaCOC(RaRb)C(RaRb), C(RaRb)NRaCO, NRaSO₂,

wherein Ra and Rb are both hydrogen;
and X, $R_1$, $R_2$, $L_1$ and T are as defined above.

Another further preferred class of compounds of formula (I) are the compounds wherein:
L₂ is C(RaRb)NRaC(RaRb), C(RaRb)OC(RaRb), and OC(RaRb)(C(RaRb))nC(RaRb), wherein
Ra and Rb are both hydrogen and
n is 0 or 1;
and X, $R_1$, $R_2$, $L_1$, Q and T are as defined above.

Specific, not limiting, preferred compounds (cmpds) of the present invention, whenever appropriate in the form of pharmaceutically acceptable salts, are the compounds listed below:

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[4-(4-ethyl-piperazin-1-ylmethyl)-3-trifluoromethyl-phenyl]-urea (Cmpd 8), 1-{3-[4-(1-Methyl-4-oxo-4,5,6,7-tetrahydro-1H-pyrrolo[3,2-c]pyridin-2-yl)-2-(piperidin-4-ylamino)-pyrimidin-5-ylethynyl]-phenyl}-3-(4-trifluoromethyl-phenyl)-urea hydrochloride (Cmpd 18), 1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[3-(4-ethyl-piperazin-1-ylmethyl)-4-trifluoromethyl-phenyl]-urea (Cmpd 22), 1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(4trifluoromethyl-cyclohexyl)-urea (trans isomer) (Cmpd 27), 1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[3-(4-ethyl-piperazin-1-ylmethyl)-5-trifluoromethyl-phenyl]-urea (Cmpd 29), 1-{4-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[4-(4-ethyl-piperazin-1-ylmethyl)-3-trifluoromethyl-phenyl]-urea (Cmpd 30), 1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[3-(4-ethyl-piperazine-1-carbonyl)-5-trifluoromethyl-phenyl]-urea (Cmpd 31), 1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[3-(4-methyl-piperazin-1-yl)-phenyl]-urea (Cmpd 33), 1-{5-[2-Amino-4-(1-methyl-4-oxo-4,5,6,7-tetrahydro-1H-pyrrolo[3,2-c]pyridin-2-yl)-pyrimidin-5-ylethynyl]-2-fluoro-phenyl}-3-[4-(4-ethyl-piperazin-1-ylmethyl)-3-trifluoromethyl-phenyl]-urea (Cmpd 36), 1-[4-(4-Ethyl-piperazin-1-ylmethyl)-3-trifluoromethyl-phenyl]-3-{3-[4-(1-methyl-4-oxo-4,5,6,7-tetrahydro-1H-pyrrolo[3,2-c]pyridin-2-yl)-pyridin-3-ylethynyl]-phenyl}-urea (Cmpd 38), 1-[4-(4-Ethyl-piperazin-1-ylmethyl)-3-trifluoromethyl-phenyl]-3-{3-[2-(2-hydroxy-ethylamino)-4-(1-methyl-4-oxo-4,5,6,7-tetrahydro-1H-pyrrolo[3,2-c]pyridin-2-yl)-pyrimidin-5-ylethynyl]-phenyl}-urea (Cmpd 43), 6-[2-Amino-4-(1-methyl-4-oxo-4,5,6,7-tetrahydro-1H-pyrrolo[3,2-c]pyridin-2-yl)-pyrimidin-5-ylethynyl]-2,3-dihydro-indole-1-carboxylic acid [4-(4-ethyl-piperazin-1-ylmethyl)-3-trifluoromethyl-phenyl]-amide (Cmpd 44), 5-[2-Amino-4-(1-methyl-4-oxo-4,5,6,7-tetrahydro-1H-pyrrolo[3,2-c]pyridin-2-yl)-pyrimidin-5-ylethynyl]-2,3-dihydro-indole-1-carboxylic acid [4-(4-ethyl-piperazin-1-ylmethyl)-3-trifluoromethyl-phenyl]-amide (Cmpd 45), 3-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-benzamide (Cmpd 48), N-[4-(4-Ethyl-piperazin-1-yl methyl)-3-trifluoromethyl-phenyl]-3-[2-methylamino-4-(1-methyl-4-oxo-4,5,6,7-tetrahydro-1H-pyrrolo[3,2-c]pyridin-2-yl)-pyrimidin-5-ylethynyl]-benzamide (Cmpd 49), 3-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-4-methyl-benzamide (Cmpd 50), 5-[2-Amino-4-(1-methyl-4-oxo-4,5,6,7-tetrahydro-1H-pyrrolo[3,2-c]pyridin-2-yl)-pyrimidin-5-ylethynyl]-thiophene-2-carboxylic acid [4-(4-ethyl-piperazin-1-ylmethyl)-3-trifluoromethyl-phenyl]-amide (Cmpd 51), 2-[2-Amino-4-(1-methyl-4-oxo-4,5,6,7-tetrahydro-1H-pyrrolo[3,2-c]pyridin-2-yl)-pyrimidin-5-ylethynyl]-thiazole-5-carboxylic acid [4-(4-ethyl-piperazin-1-ylmethyl)-3-trifluoromethyl-phenyl]-amide (Cmpd 52), N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-4-trifluoromethyl-benzamide (Cmpd 57), N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-2-(4-trifluoromethyl-phenyl)-acetamide (Cmpd 58), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenoxy}-N-phenyl-acetamide hydrochloride (Cmpd 59), N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(3-trifluoromethyl-phenyl)-propionamide hydrochloride (Cmpd 73), 3-[2-Amino-4-(1-methyl-4-oxo-4,5,6,7-tetrahydro-1H-pyrrolo[3,2-c]pyridin-2-yl)-pyrimidin-5-ylethynyl]-N-(3-trifluoromethyl-benzyl)-benzamide hydrochloride (Cmpd 74), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-ethyl-piperazin-1-ylmethyl)-3-trifluoromethyl-phenyl]-acetamide (Cmpd 77), N-[4-(4-Ethyl-piperazin-1-yl methyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (Cmpd 78), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-(4-ethyl-piperazin-1-ylmethyl)-4-trifluoromethyl-phenyl]-acetamide (Cmpd 82), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-indan-5-yl-acetamide (Cmpd 100), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-benzothiazol-6-yl-acetamide (Cmpd 102), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(5-tert-butyl-2-methyl-2H-pyrazol-3-yl)-acetamide (Cmpd 105), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-quinolin-3-yl-acetamide (Cmpd 106), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-trifluoromethyl-benzyl)-acetamide (Cmpd 111), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-ethyl-piperazin-1-ylmethyl)-3-fluoro-phenyl]-acetamide (Cmpd 120), 2-{5-[2-Amino-4-(1-methyl-4-oxo-4,5,6,7-tetrahydro-1H-pyrrolo[3,2-c]pyridin-2-yl)-pyrimidin-5-ylethynyl]-pyridin-3-yl}-N-[4-(4-ethyl-piperazin-1-ylmethyl)-3-trifluoromethyl-phenyl]-acetamide (Cmpd 122), 2-{4-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-ethyl-piperazin-1-ylmethyl)-3-trifluoromethyl-phenyl]-acetamide (Cmpd 123), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-(4-ethyl-piperazine-1-carbonyl)-4-trifluoromethyl-phenyl]-acetamide (Cmpd 127), 2-{5-[2-Amino-4-(1-methyl-4-oxo-4,5,6,7-tetrahydro-1H-pyrrolo[3,2-c]pyridin-2-yl)-pyrimidin-5-ylethynyl]-thiophen-2-yl}-N-[4-(4-ethyl-piperazin-1-ylmethyl)-3-trifluoromethyl-phenyl]-acetamide (Cmpd 129), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-isopropyl-phenyl)-acetamide (Cmpd 133), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-chloro-3-(4-ethyl-piperazin-1-ylmethyl)-phenyl]-acetamide (Cmpd 138), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-chloro-3-trifluoromethyl-phenyl)-acetamide (Cmpd 141), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-[1,4]diazepan-1-ylmethyl)-3-trifluoromethyl-phenyl]-acetamide (Cmpd 149), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-cyclopropyl-4-(4-methyl-piperazin-1-ylmethyl)-phenyl]-acetamide (Cmpd 154), 2-{3-[2-Amino-4-(1-methyl-4-oxo-4,5,6,7-tetrahydro-1H-pyrrolo[3,2-c]pyridin-2-yl)-pyrimidin-5-ylethynyl]-4-fluoro-phenyl}-N-[4-(4-ethyl-piperazin-1-ylmethyl)-3-trifluoromethyl-phenyl]-acetamide (Cmpd 155), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-propyl-piperazin-1-ylmethyl)-3-trifluoromethyl-phenyl]-acetamide (Cmpd 164), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-{[methyl-(1-methyl-piperidin-4-yl)-amino]-methyl}-3-trifluoromethyl-phenyl)-acetamide (Cmpd 166), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(1-methyl-piperidin-4-yloxy)-3-trifluoromethyl-phenyl]-acetamide (Cmpd 172), 2-{3-[2-Methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (Cmpd 174), N-[4-(4-Isopropyl-piperazin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (Cmpd 176), 2-{3-[2-Methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-propyl-piperazin-1-ylmethyl)-3-trifluoromethyl-phenyl]-acetamide (Cmpd 179), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(3-oxo-piperazin-1-ylmethyl)-3-trifluoromethyl-phenyl]-acetamide (Cmpd 184), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-{[(2-hydroxy-ethyl)-methyl-amino]-methyl}-3-trifluoromethyl-phenyl)-acetamide (Cmpd 189), 2-{4-Fluoro-3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (Cmpd 190), 2-(3-{2-Amino-4-[1-(2-hydroxy-ethyl)-4-oxo-4,5,6,7-tetrahydro-1H-pyrrolo[3,2-c]pyridin-2-yl]-pyrimidin-5-ylethynyl}-phenyl)-N-[4-(4-ethyl-piperazin-1-ylmethyl)-3-trifluoromethyl-phenyl]-acetamide (Cmpd 191), 2-{3-[2-Ethylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (cmpd 193), 2-(3-{2-Amino-4-[1-(1-methyl-piperidin-4-yl)-4-oxo-4,5,6,7-tetrahydro-1H-pyrrolo[3,2-c]pyridin-2-yl]-pyrimidin-5-ylethynyl}-phenyl)-N-(4-chloro-3-trifluoromethyl-phenyl)-acetamide (Cmpd 195), N-[4-((S)-3-Dimethylamino-pyrrolidin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (Cmpd 198), 2-{3-[2-Acetylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (Cmpd 200), 2-{3-[6-Amino-4-(1-methyl-4-oxo-4,5,6,7-tetrahydro-1H-pyrrolo[3,2-c]pyridin-2-yl)-pyrimidin-3-ylethynyl]-phenyl}-N-[4-(4-methyl-piperazin-1-ylmethyl)-3-trifluoromethyl-phenyl]-acetamide (Cmpd 201), 2-{3-[2-Isopropylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (Cmpd 202) and {3-[2-Amino-4-(1-methyl-4-oxo-4,5,6,7-tetrahydro-1H-pyrrolo[3,2-c]pyridin-2-yl)-pyrimidin-5-ylethynyl]-phenyl}-carbamic acid phenyl ester (Cmpd 203).

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

A compound of formula (I) can be prepared according to the general synthetic processes described hereafter in Schemes from 1 to 11.

In the following Scheme 1 the general preparation of a compound of formula (I) is shown, Scheme 1

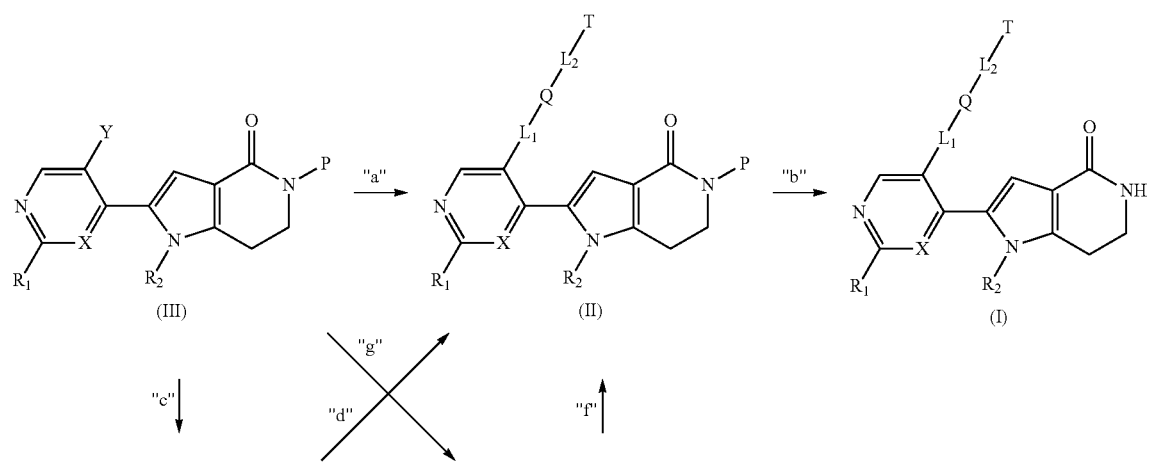

-continued

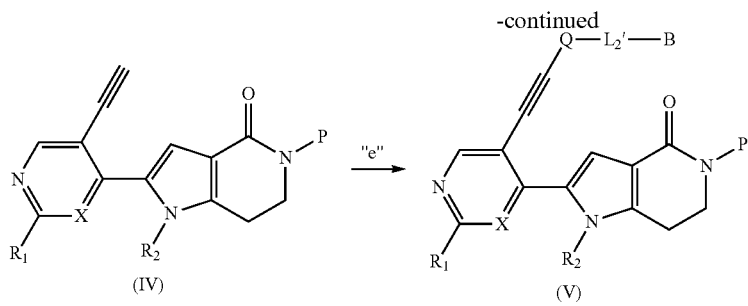

wherein P is hydrogen or a suitable protecting group such as the tert-butoxycarbonyl group, Y is a suitable halogen (e.g. Cl, Br, I), B is COOH or NHRa, $L_2'$ is direct linkage, C(RaRb), C(RaRb)C(RaRb) or OC(RaRb) and $R_1$, $R_2$, X, $L_1$, Q, $L_2$, T, Ra and Rb are as defined above.

Compounds of formula (I) are prepared by deprotection of compounds of formula (II), when P is a suitable protecting group, or directly by compounds of formula (III), (IV) or (V), when P is hydrogen.

A compound of formula (I) is prepared according to any of the four alternative synthetic Methods A, B, C or D, summarized below.

Scheme 2

Method A:
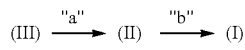
Method B:
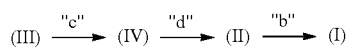
Method C:
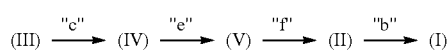
Method D:
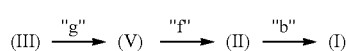

Generally, the process for preparing a compound of formula (I) as defined above comprises the following steps:
Method A:
step a: coupling of a pyrrolopyridinone derivative of formula (III)

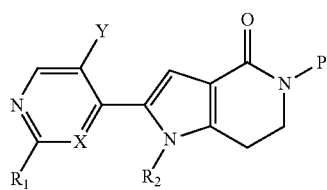

(III)

wherein X, $R_1$ and $R_2$ are as defined above, Y is halogen and P is a suitable protecting group such as the tert-butoxycarbonyl group, with an intermediate of formula (1a)-(1h)

≡-Q-L$_2$-T        (1a)-(1h)

wherein Q, T and $L_2$ are as defined above, under Sonogashira reaction conditions;

step b: deprotection of the resultant intermediate of formula (II)

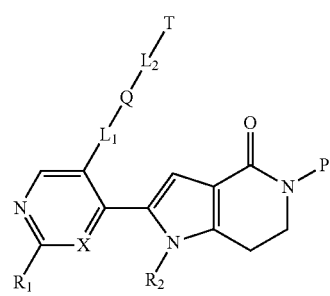

(II)

wherein X, $R_1$, $R_2$, $L_1$, $L_2$, P, Q and T are as defined above, under acid conditions to yield a compound of formula (I) as defined above;

alternatively, Method B:
step c: coupling of a pyrrolopyridinone derivative of formula (III), as defined above, with ethynyl-trimethylsilane under Sonogashira reaction conditions, followed by removal of the trimethylsilyl group under basic conditions;
step d: reaction of the resultant intermediate of formula (IV)

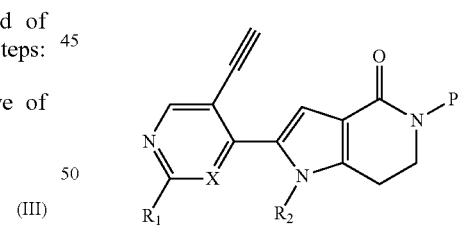

(IV)

wherein X, P, $R_1$ and $R_2$ are as defined above, with an intermediate of formula (3a)-(3h)

Y-Q-L$_2$-T        (3a)-(3h)

wherein Y is halogen and Q, $L_2$ and T are as defined above, under Sonogashira reaction conditions;
step b: deprotection of the resultant intermediate of formula (II) as defined above;
alternatively, Method C:
step c: coupling of a pyrrolopyridinone derivative of formula (III), as defined above, with ethynyl-trimethylsilane under Sonogashira reaction conditions, followed by removal of the trimethylsilyl group under basic conditions;

step e: reaction of the resultant intermediate of formula (IV) as defined above, with an intermediate of formula Y-Q-L$_2$'-CO—Y'' wherein L$_2$' is direct linkage, —C(RaRb)—, —C(RaRb)C(RaRb)— or —OC(RaRb)—, Y is halogen, Y' is OH and Q, Ra and Rb are as defined above, or with an intermediate of formula Y-Q-L$_2$'-NH—Ra wherein Y, Q, L$_2$' and Ra are as defined above under Sonogashira reaction conditions;

step f: coupling the resultant intermediate of formula (V)

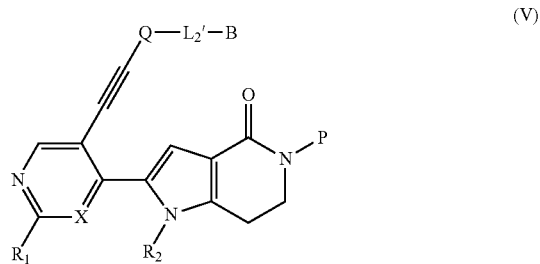

(V)

wherein B is COOH or NHRa and X, Q, Ra, R$_1$, R$_2$, L$_2$' and P are as defined above, with a suitable intermediate in the presence of a coupling agent to give an intermediate of formula (II) as defined above;

step b: deprotection of the intermediate of formula (II) as defined above;

alternatively, Method D:

step g: reaction of an intermediate of formula (III) as defined above with an intermediate of formula ≡-Q-L$_2$'-CO—Y' wherein L$_2$', Y, Y' and Q are as defined above, or with an intermediate of formula ≡-Q-L$_2$'-NH—Ra wherein Y, Q, L$_2$' and Ra are as defined above under Sonogashira reaction conditions to yield an intermediate of formula (V), as defined above;

step f: coupling the resultant intermediate of formula (V) with a suitable intermediate in the presence of a coupling agent to give an intermediate of formula (II) as defined above;

step b: deprotection of the intermediate of formula (II) as defined above;

optionally converting a compound of formula (I) into a different compound of formula (I) by known chemical reactions; and/or, if desired, converting a compound of formula (I) into a pharmaceutically acceptable salt thereof or converting a salt into a free compound of formula (I).

Method a

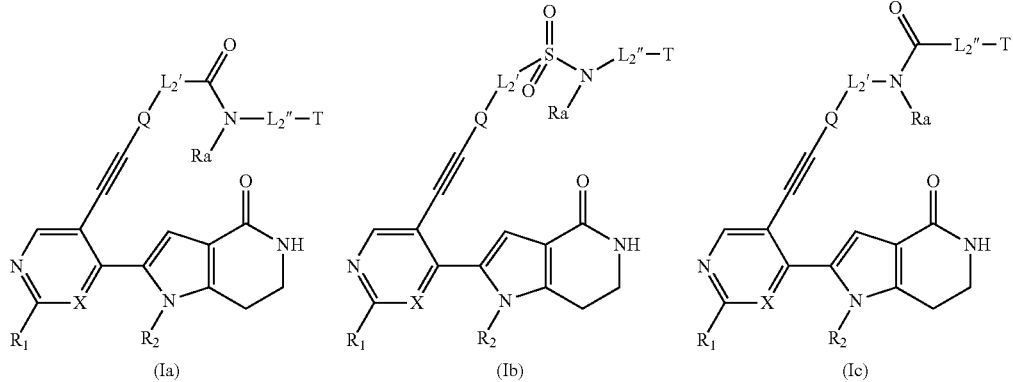

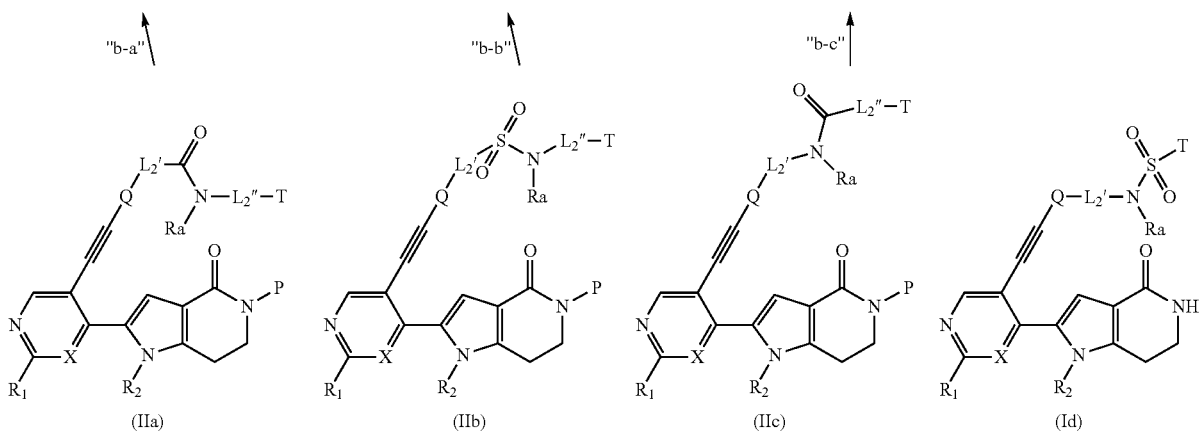

-continued

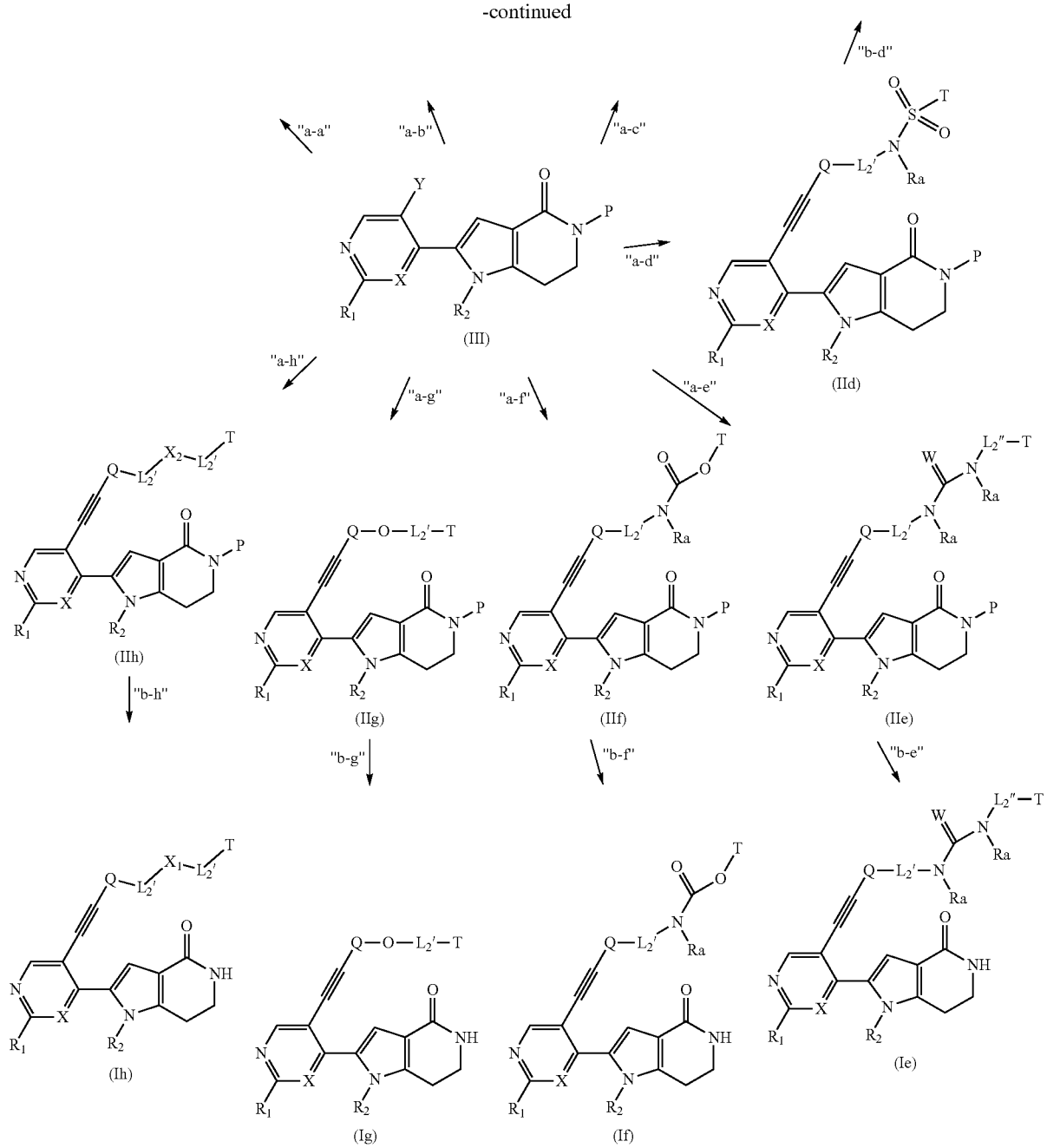

In the above Scheme, $R_1$, $R_2$, X, Q, T, P and Ra are as defined above, Y is halogen, W is O or S, $X_1$ is O or NH, $X_2$ is O or NP where P is H or a suitable protecting group preferably tert-butoxycarbonyl group, and the meanings of $L_2'$ and $L_2''$ are as follows:

for compounds of formula (Ia): $L_2'$ is direct linkage, —C(RaRb)—, —C(RaRb)C(RaRb)— or —OC(RaRb)— and $L_2''$ is direct linkage, —C(RaRb)— or —C(RaRb)C(RaRb)—;

for compounds of formula (Ib): $L_2'$ is direct linkage or —C(RaRb)— and $L_2''$ is direct linkage;

for compounds of formula (Ic): $L_2'$ is direct linkage, —C(RaRb)— or —C(RaRb)C(RaRb)— and $L_2''$ is direct linkage, —C(RaRb)—, —C(RaRb)C(RaRb)—, —C—CONRa  or  —CH-CH—;

for compounds of formula (Id): $L_2'$ is direct linkage;
for compounds of formula (Ie): $L_2'$ is direct linkage and $L_2''$ is direct linkage;
for compounds of formula (If): $L_2'$ is direct linkage;
for compounds of formula (Ig): $L_2'$ is —C(RaRb)(C(RaRb))nC(RaRb);
for compounds of formula (Ih): $L_2'$ is —C(RaRb)—;
wherein Ra, Rb and n are as defined above.

According to steps "a-a", "a-b", "a-c", "a-d", "a-e", "a-f", "a-g" and "a-h" of Method A, the reaction can be carried out reacting an intermediate of formula (III) with an intermediate of formula (1a)-(1h) reported in the following Table 1, under Sonogashira reaction conditions to yield an intermediate of formula (IIa)-(IIh).

TABLE 1

| Intermediate structure | Intermediate # |
|---|---|
| ≡≡≡—Q—$L_2'$—CO—NRa—$L_2''$—T | (1a) |
| ≡≡≡—Q—$L_2'$—$SO_2$—NRa—$L_2''$—T | (1b) |
| ≡≡≡—Q—$L_2'$—NRa—CO—$L_2''$—T | (1c) |
| ≡≡≡—Q—$L_2'$—NRa—$SO_2$—T | (1d) |
| ≡≡≡—Q—$L_2'$—NRa—CW—NRa—$L_2''$—T | (1e) |
| ≡≡≡—Q—$L_2'$—NRa—COO—T | (1f) |
| ≡≡≡—Q—O—$L_2'$—T | (1g) |
| ≡≡≡—Q—$L_2'$—$X_2$—$L_2'$—T | (1h) |

The Sonogashira reaction can be carried out in the presence of a suitable palladium catalyst such as bis(triphenylphosphine)palladium dichloride ($PdCl_2(PPh_3)_2$), tetrakis(triphenylphosphine)palladium(0) ($Pd(PPh_3)_4$), and the like, and of a suitable copper catalyst, such as CuI. Said reaction is carried out in the presence of a suitable base, such as triethylamine, diethylamine, diisopropylamine and the like, optionally in the presence of a phosphine ligand, such as triphenylphosphine in solvents like acetonitrile, DMF, toluene, $Et_2O$, dioxane at temperatures ranging from −20° C. to reflux or using a microwave apparatus and for a time ranging from 30 minutes to about 48 hours.

According to steps "b-a", "b-b", "b-c", "b-d", "b-e", "b-f", "b-g" and "b-h", intermediates of formula (IIa)-(IIh), wherein P is a suitable protecting group such as a tert-butoxycarbonyl group, can be deprotected under acid conditions for example with hydrochloric acid (HCl) in dioxane, THF, $Et_2O$ or trifluoroacetic acid (TFA) in DCM at temperatures ranging from 0° C. to 40° C. for a time varying from 30 minutes to 24 hours to finally yield compounds of formula (Ia)-(Ih).

Intermediates of formula (1a)-(1h) are prepared as described in the following Scheme 3, steps 1 and 2:

Scheme 3

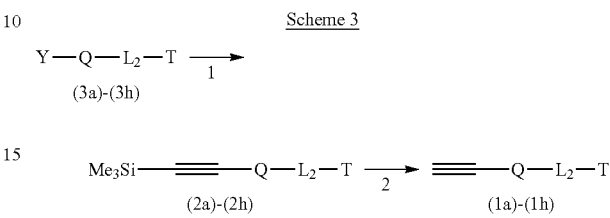

wherein:
$L_2$ is -$L_2'$-CONRa-$L_2''$-for intermediates (1a), (2a) and (3a);
$L_2$ is -$L_2'$-$SO_2$NRa-$L_2''$-for intermediates (1b), (2b) and (3b);
$L_2$ is -$L_2'$-NRaCO-$L_2''$-for intermediates (1c), (2c) and (3c);
$L_2$ is -$L_2'$-NRa$SO_2$— for intermediates (1d), (2d) and (3d);
$L_2$ is -$L_2'$-NRaCWNRa-$L_2''$-for intermediates (1e), (2e) and (3e);
$L_2$ is -$L_2'$-NRaCOO— for intermediates (1f), (2f) and (3f);
$L_2$ is —O-$L_2'$-for intermediates (1g), (2g) and (3g);
$L_2$ is -$L_2'$-$X_2$-$L_2'$-for intermediates (1h), (2h) and (3h);

According to step "1" in Scheme 3, intermediates (2a)-(2h) are obtained by reacting intermediates (3a)-(3h), wherein Y is as defined above, by reaction with ethynyl-trimethyl-silane under Sonogashira conditions as described for steps "a" of Method A.

According to step "2", from intermediates (2a)-(2h) intermediates (1a)-(1h) are obtained after removal of the trimethylsilyl group upon basic conditions with a base such as potassium carbonate, triethylamine (TEA) in solvents like MeOH, EtOH or in the presence of catalytic amount of Silver salts like triflate or nitrate in mixture of solvents like MeOH, $H_2O$ and DCM at temperatures ranging from −20° C. to 50° C. for 1 hour to 24 hours.

A compound of formula (I) is alternatively prepared according to the Method B shown below.
Method B

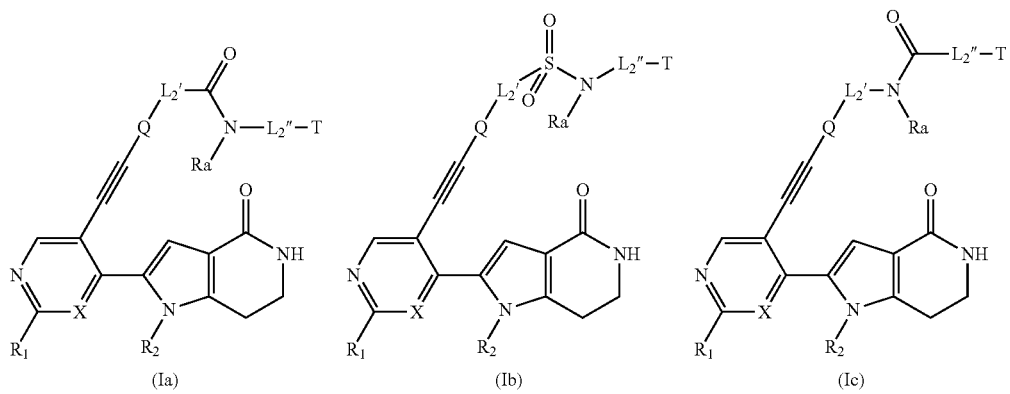

-continued
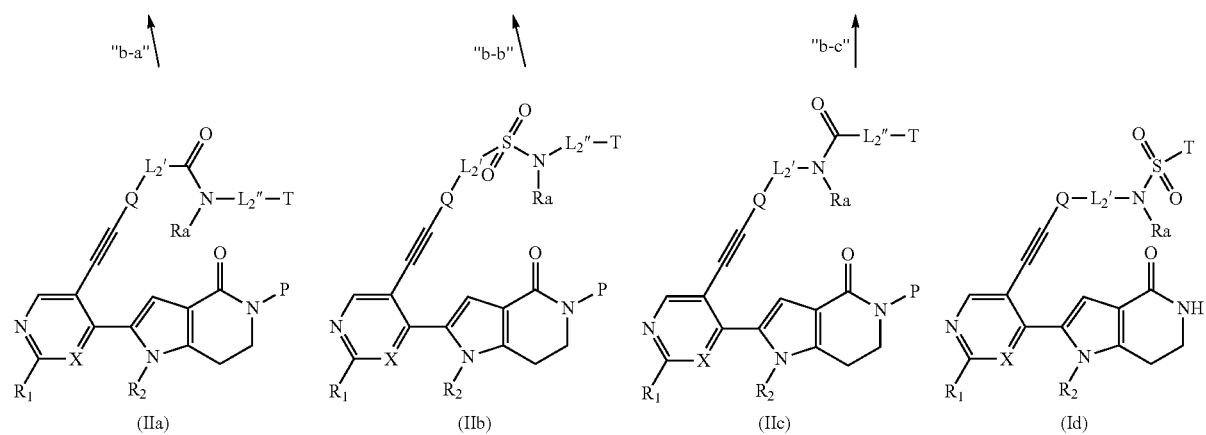
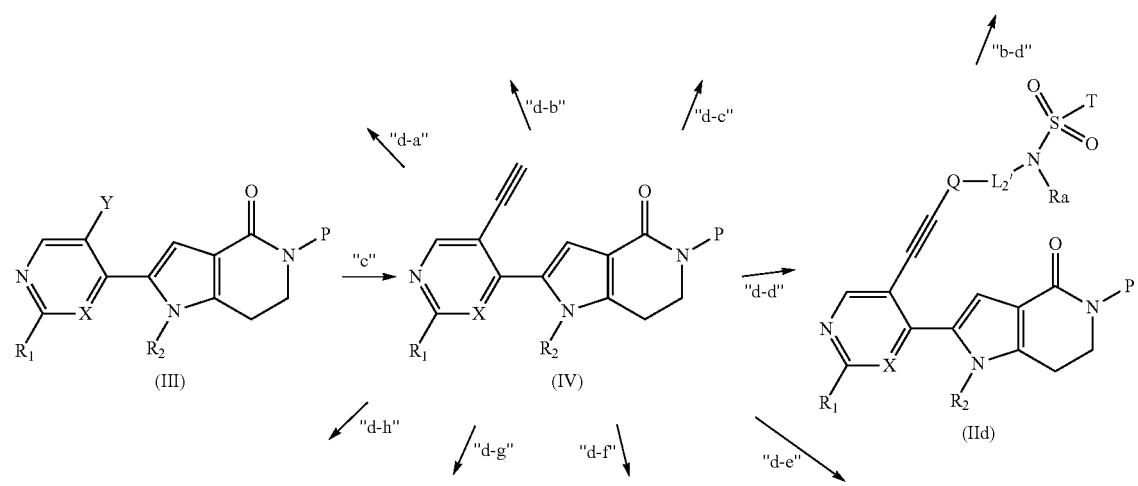
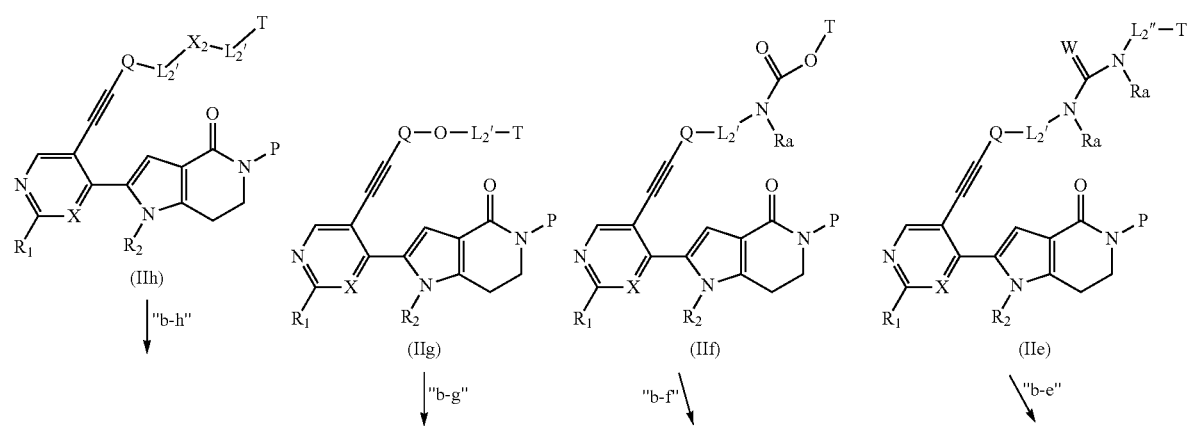

-continued

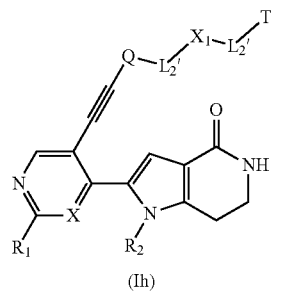

(Ih)

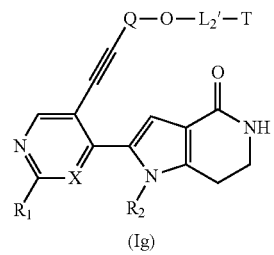

(Ig)

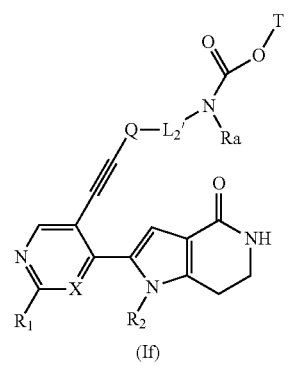

(If)

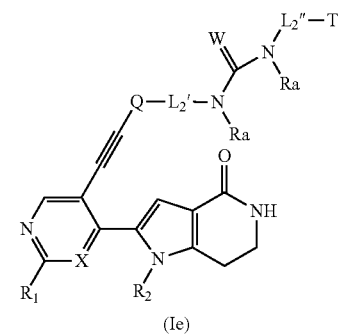

(Ie)

In the above Scheme $R_1$, $R_2$, X, Y, Q, T, P, Ra, W, $X_1$, $X_2$, $L_2'$ and $L_2''$ are as defined above.

According to step "c" of Method B, the reaction can be carried out reacting an intermediate of formula (III) with ethynyl-trimethyl-silane under Sonogashira reaction conditions as reported in step 1 of Scheme 3 followed by desilylation, as described in step 2 of Scheme 3.

According to steps "d-a", "d-b", "d-c", "d-d", "d-e", "d-f", "d-g" and "d-h" of Method B, the reaction can be carried out reacting an intermediate of formula (IV) with an intermediate of formula (3a)-(3h) to yield an intermediate of formula (IIa)-(IIh) under Sonogashira reaction conditions, as described in steps "a" of Method A.

Steps "b-a", "b-b", "b-c", "b-d", "b-e", "b-f", "b-g" and "b-h" are performed as already described for steps "b" of Method A.

Further processes of the present invention, alternative to Methods A and B, are reported below (Methods C and D). The following procedures are valid only for the compounds of formula (Ia), (Ic), (Id), (Ie) and (If).

Methods C and D

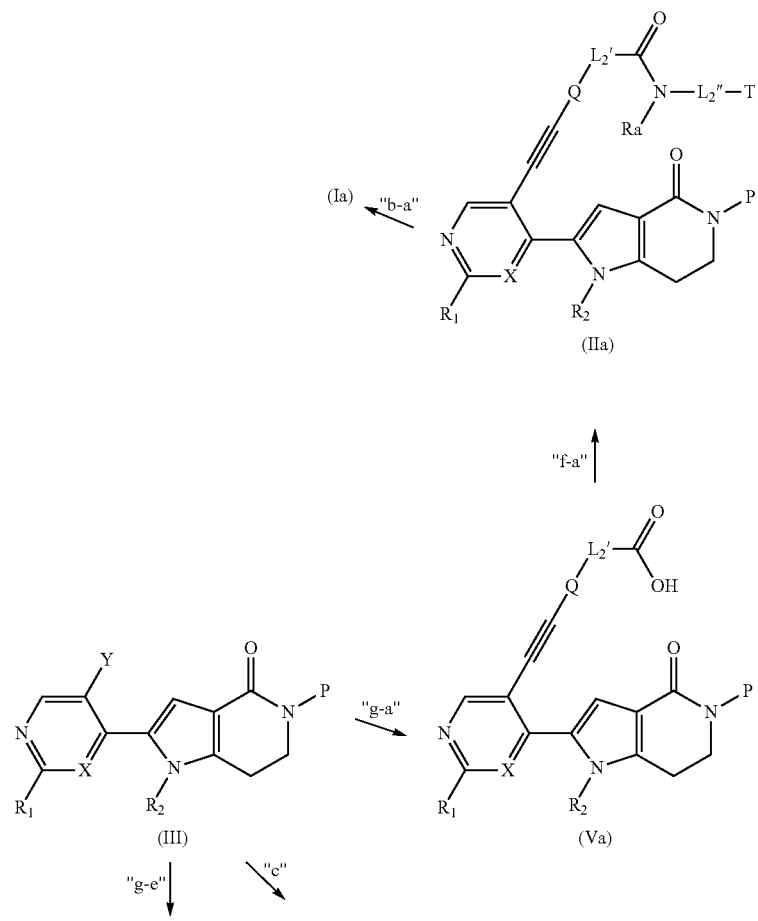

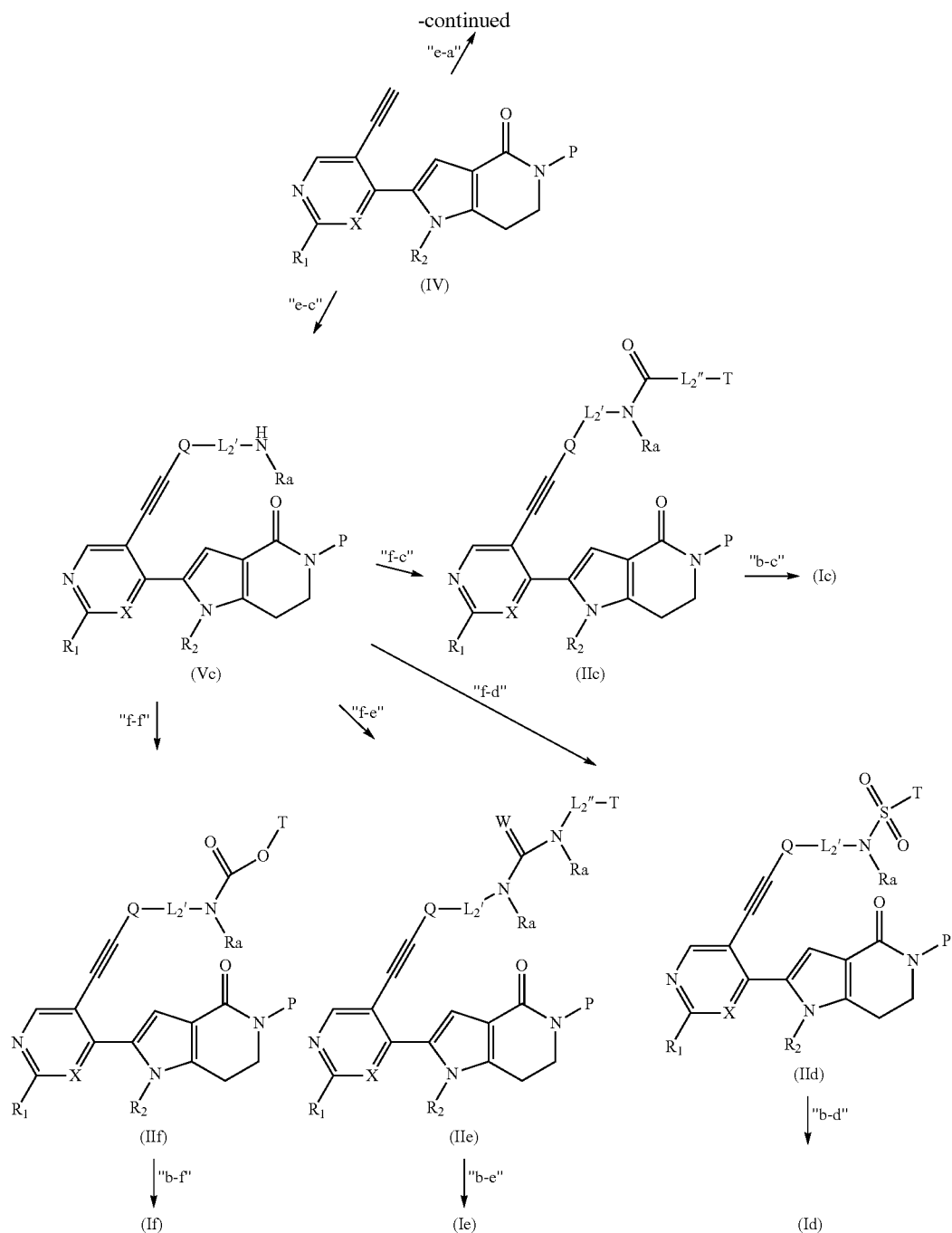

In the above Scheme $R_1$, $R_2$, X, Y, Q, T, P, Ra, W, $L_2'$ and $L_2''$ are as defined above.

According to step "c" of Method C, the reaction can be carried out as previously described for Method B.

According to step "e-a" of Method C, the reaction can be carried out reacting an intermediate of formula (IV) with an intermediate of formula (4) (Y-Q-$L_2'$-COY', depicted in the following Scheme 4) where Y' is OH, i.e. a carboxylic acid, to yield an intermediate of formula (Va) under Sonogashira reaction conditions as described for steps "a" of Method A.

According to step "e-c" of Method C, the reaction can be carried out reacting an intermediate of formula (IV) with an intermediate of formula (7) (Y-Q-$L_2'$-NHRa, depicted in the following Scheme 4), to yield an intermediate of formula (Vc) under Sonogashira reaction conditions as described for steps "a" of Method A.

According to step "f-a" of Method C, an intermediate of formula (Va) is reacted with an intermediate of formula (5) (RaNH-$L_2''$-T, depicted in the following Scheme 4) to obtain an intermediate of formula (IIa) in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N-propyloxymethyl polystyrene or N-cyclohexylcarbodiimide-N-methyl polystyrene, in a suitable solvent such as, for instance, dichloromethane, chloroform, tetrahydrofuran, diethyl ether, 1,4-dioxane, acetonitrile, toluene, or N,N-dimethylformamide, N,N-dimethylacetamide at a temperature ranging from about −10° C. to reflux and for a suitable time, for instance from about 30 minutes to about 96 hours.

According to step "f-c" of Method C, an intermediate of formula (Vc) is reacted with an intermediate of formula (8) (Y'—CO-$L_2$"-T, depicted in the following Scheme 4) to obtain an intermediate of formula (IIc). Compound (8), where Y' is a halogen, preferably Cl, is reacted with intermediate (Vc) under a variety of conditions, for example in a suitable solvent such as dichloromethane, chloroform, tetrahydrofuran, diethyl ether, 1,4-dioxane, acetonitrile, toluene, or N,N-dimethylformamide or the like at a temperature ranging from about −10° C. to reflux and for a suitable time, for instance from about 30 minutes to about 96 hours. The reaction is carried out in the presence of an opportune proton scavenger such as triethylamine, N,N-diisopropylethylamine or pyridine. Compound (8), where Y' is a hydroxyl group, is reacted in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N-propyloxymethyl polystyrene or N-cyclohexylcarbodiimide-N-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. The said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

According to step "f-d" of Method C, an intermediate of formula (Vc) is reacted with an intermediate of formula (9) (Cl—$SO_2$-T, depicted in the following Scheme 4) to obtain an intermediate of formula (IId). Such a reaction is carried out in the presence of a suitable base, such as for instance, pyridine, N-methyl morpholine, diisopropyl ethylamine, in the appropriate solvent such as pyridine, dichloromethane or tetrahydrofuran, at a temperature ranging from 0° C. to reflux and for a time varying from about 1 hour to about 7 days.

According to step "f-e" of Method C, an intermediate of formula (Vc) is reacted with an intermediate of formula (10) (W=C=N-$L_2$"-T, depicted in the following Scheme 4) to obtain an intermediate of formula (IIe). Such intermediate of formula (IIe), which can be an urea compound when W=O or a thiourea compound when W=S, can be prepared by reacting an intermediate of formula (Vc) with the appropriate isocyanate or thioisocyanate of formula (10) respectively. Such a reaction is carried out in a suitable solvent such as dichloromethane or tetrahydrofuran, normally at a temperature ranging from about −10° C. to reflux and for a time varying from about 30 minutes to about 96 hours.

Alternatively an urea of formula (IIe) can be prepared reacting an intermediate of formula (5) (RaNH-$L_2$"-T, depicted in the following Scheme 4) with triphosgene (bis(trichloromethyl) carbonate, O=C(OCCl$_3$)$_2$) followed by the addition of the intermediate of formula (Vc). This reaction can be carried out in the presence of a base like diisopropylethylamine (DIPEA), triethylamine (TEA), Na$_2$CO$_3$, in solvents like dichloromethane, chloroform, at a temperatures ranging from about −10° C. to reflux and for a time varying from about 30 minutes to about 96 hours.

According to step "f-f" of Method C, an intermediate of formula (Vc) is reacted with an intermediate of formula (II) (Cl—CO—O-T, depicted in the following Scheme 4) to obtain an intermediate of formula (IIf). Such a reaction is carried out in the appropriate solvent such as tetrahydrofuran, N,N-dimethylformamide, dichloromethane, chloroform, acetonitrile, toluene or mixtures thereof, at a temperature ranging from about −10° C. to reflux and for a time varying from about 30 minutes to about 96 hours. The reaction is normally carried out in the presence of an opportune proton scavenger such as triethylamine, N,N-diisopropylethylamine or pyridine.

According to step "g-a" of Method D, an intermediate of formula (III) is reacted with an intermediate of formula (27) (≡-Q-$L_2$'-COY', wherein Y' is OH, as depicted in the following Scheme 5) to directly yield an intermediate of formula (Va) under Sonogashira reaction conditions as described for steps "a" of Method A.

According to step "g-e" of Method D, an intermediate of formula (III) is reacted with an intermediate of formula (28) (C≡C-Q-$L_2$'-NHRa, as depicted in the following Scheme 5) to directly yield an intermediate of formula (Vc) under Sonogashira reaction conditions as described for steps "a" of Method A.

Steps "b-a", "b-c", "b-d", "b-e" and "b-f" are carried out as already described for Method A.

A further process to obtain a compound of formula (Ie) can also involve the conversion of an intermediate of formula (IIf) directly into an intermediate of formula (IIe) followed by deprotection of the tert-butoxycarbonyl group, as described before. In particular an intermediate (IIf), wherein T is a p-NO$_2$Ph (para-nitrophenyl) group, can be reacted with an amine of formula (5) (NHRa-$L_2$"-T, as depicted in the following Scheme 4) in solvents like DCM, acetonitrile, DMSO, DMF and eventually a mixture of such solvents, in the presence of a tertiary amine such as TEA, at temperatures ranging from room temperature to reflux for a time varying from 30 minutes to 72 hours.

Compounds of formula (Ie) can be also obtained converting an intermediate of formula (IIe) where $R_1$ is NH$_2$ into other intermediates of formula (IIe) where $R_1$ is NHR$_3$ wherein $R_3$ is CHR$_4$R$_5$ and wherein $R_4$ and $R_5$ are each independently H, optionally substituted straight or branched $C_1$-$C_6$ alkyl, or $R_4$ and $R_5$ joined together represent a heterocyclyl. This process is carried out by reacting an intermediate (IIe), where $R_1$ is NH$_2$, with a carbonylic compound of formula R$_4$R$_5$CO under reductive alkylation conditions. In particular this reaction is carried out in a suitable solvent such as, for instance, methanol, N,N-dimethylformamide, dichloromethane, tetrahydrofuran, or a mixture thereof, in the presence of a suitable reducing agents such as, for instance, sodium borohydride, tetra-alkylammonium borohydride, sodium cyano borohydride, sodium triacetoxyborohydride, tetramethylammonium triacetoxy borohydride, hydrogen and a hydrogenation catalyst, and in the presence of an acid catalyst, such as, for instance, acetic acid, trifluoroacetic acid, at a temperature ranging from about 0° C.

to reflux and for a time varying from about 1 hour to about 96 hours. This reaction is followed by removal of the protecting group P to yield the compound (Ie). This process described for compounds of formula (Ie), is suitable to convert also compounds of formula (IIa)-(IId) and (IIf)-(IIh) into the corresponding compounds (Ia)-(Id) and (If)-(Ih).

Preparation of the Intermediates of Formula (3a)-(3h)

Compounds of formula (3a)-(3h) are prepared as described in the following Scheme 4, steps i1-10, wherein Y' is halogen or hydroxyl and the other variables are as defined above.

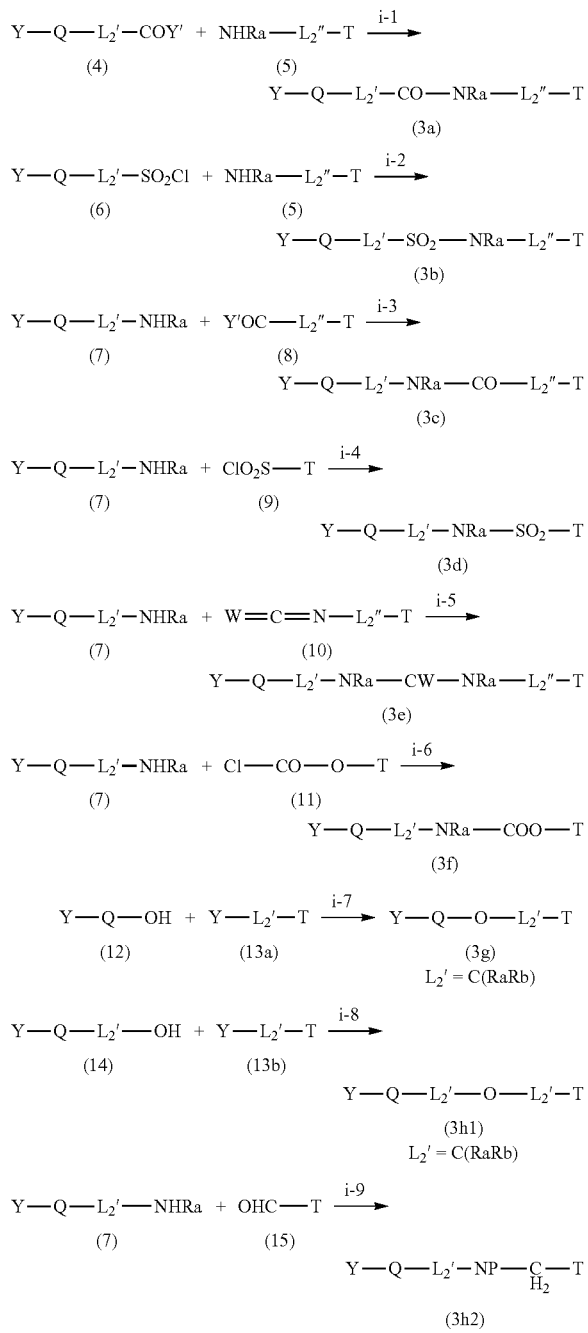

Scheme 4

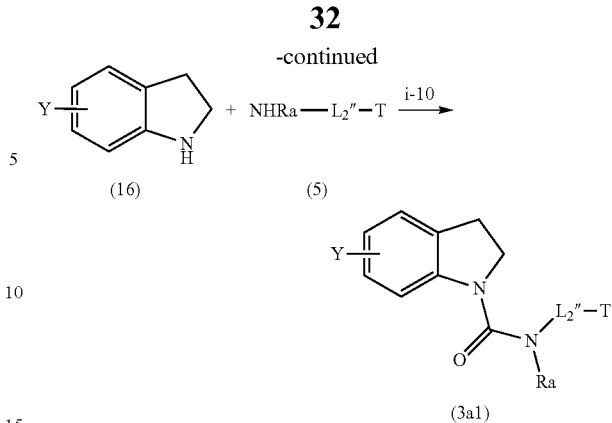

According to step i-1, an intermediate (3a) is obtained reacting an intermediate (4) with an intermediate of formula (5) under the reaction conditions reported for step "f-c" of Method C.

According to step i-2, an intermediate of formula (5) is reacted with a sulfonyl chloride of formula (6) to afford an intermediate of formula (3b). Such a reaction is carried out under the reaction conditions reported for step "f-d" of Method C.

According to step i-3, an intermediate of formula (3c) can be prepared analogously to step i-1, by reacting an intermediate of formula (7) with an intermediate of formula (8).

According to step i-4, an intermediate of formula (3d) can be prepared analogously to step i-2, by reacting an intermediate of formula (7) with a sulfonyl chloride of formula (9).

According to step i-5, an intermediate of formula (3e), which can be an urea compound when W=O or a thiourea compound when W=S, can be prepared by reacting an intermediate of formula (7) with the appropriate isocyanate or thioisocyanate of formula (10) respectively. Such a reaction is carried out under the same reaction conditions reported for step "f-e" of Method C. Alternatively an urea of formula (3e) can be prepared reacting an intermediate of formula (7) with triphosgene (bis(trichloromethyl) carbonate, $O=C(OCCl_3)_2$) followed by the addition of an intermediate of formula (5) or viceversa reacting an intermediate of formula (5) with triphosgene followed by the addition of an intermediate of formula (7), a well known method for the formation of ureas. This reaction can be carried out under the same reaction conditions described for step "f-e" of Method C.

According to step i-6, an intermediate of formula (3f) can be prepared by reacting a chloroformate of formula (II) with an intermediate of formula (7) under the same reaction conditions reported for step "f-f" of Method C.

According to step i-7, an intermediate of formula (3g) can be prepared by reacting an intermediate of formula (12) with an intermediate of formula (13a) under Williamson reaction conditions, a general method for the preparation of ethers, or through similar methods. Such a reaction can be carried out in the presence of a suitable base such as $K_2CO_3$, $Na_2CO_3$, KOH, NaH, pyridine and the like, eventually in the presence of NaI to allow the exchange of less reactive halide with iodide, in suitable solvents like acetone, DMF, DMSO, acetonitrile and the like, or under phase transfer catalysis conditions at temperatures ranging from 0° C. to reflux for 6 to 48 hours.

According to step i-8, an intermediate of formula (3h1) can be prepared analogously to step i-7, by reacting an intermediate of formula (14) with an intermediate of formula (13b).

According to step i-9, an intermediate of formula (3h2) can be prepared by reacting an aminic compound of formula (7) with an aldehyde of formula (15) in reductive alkylation conditions. In particular this reaction is carried out in a suitable solvent such as, for instance, methanol, N,N-dimethylformamide, dichloromethane, tetrahydrofuran, or a mixture thereof, in the presence of a suitable reducing agents such as, for instance, sodium borohydride, tetra-alkylammonium borohydride, sodium cyano borohydride, sodium triacetoxyborohydride, tetramethylammonium triacetoxy borohydride, hydrogen and a hydrogenation catalyst, and in the presence of an acid catalyst, such as, for instance, acetic acid, trifluoroacetic acid, at a temperature ranging from about 0° C. to reflux and for a time varying from about 1 hour to about 96 hours. In case a protecting group is needed for further synthetic steps, compound (3h2) where P is H, can be converted into compound (3h2), where P is a tert-butoxycarbonyl group, using di-tert-butyldicarbonate ((Boc)$_2$O, in the presence of dimethylaminopyridine (DMAP) and in solvents like DCM at temperature ranging from 0° C. to reflux and for time varying from 1 hour to 24 hours.

A particular case of the present invention is represented by an intermediate of formula (3a), wherein Q is one of the bicyclic ring systems B or C, L$_2$' is direct linkage, L$_2$" and Y are as defined above, i.e. the intermediate of formula (3a1).

According to step i-10, an intermediate of formula (3a1) is prepared analogously to the method described in step i-5, reacting an intermediate of formula (5), RaNH-L$_2$"-T, with triphosgene (bis(trichloromethyl) carbonate, O═C(OCCl$_3$)$_2$) followed by the addition of an intermediate of formula (16).

Compounds (4)-(16) can be either commercially available or prepared according to methods well known in the literature and to the skilled in the art. For example, indolines of formula (16) can be prepared according to the procedures described in *J. Am. Chem. Soc.* 2002, 124, 14844-14845 and in WO2010/043000.

Specific compounds of formula (5), RaNH-L$_2$"-T, can be prepared according to different methods. For example compounds of formula (5) where Ra is hydrogen, L$_2$" is direct linkage and T is J, wherein J is as defined above, can be synthesized through several procedures depending on L$_3$, in some cases based on methods described in the literature (see for example *Journal of Medicinal Chemistry* 2010, 53, 4701-4719).

These particular cases of amines (5a)-(5e) are reported in the following Scheme 4a, wherein L$_3$ is direct linkage, O, NH, NCH$_3$, CH$_2$ or C═O, and Rd and Re are as defined above.

Scheme 4a

A)

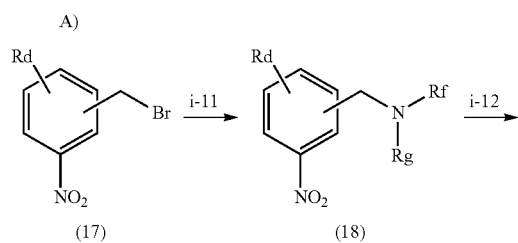

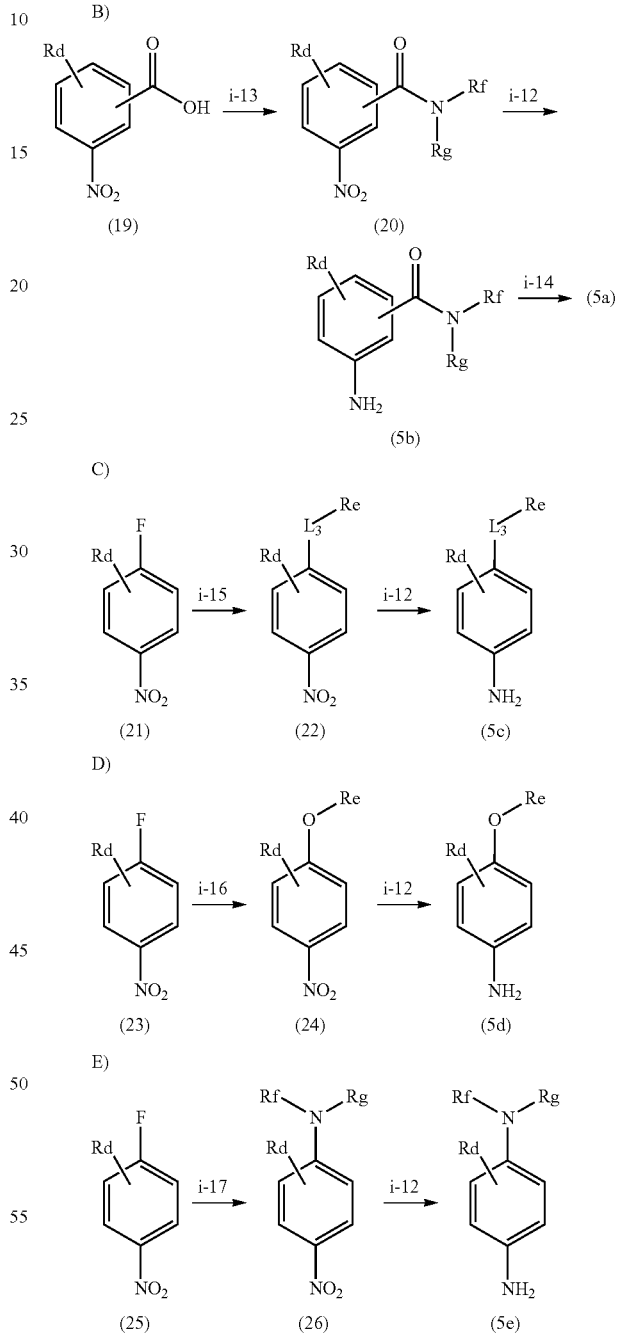

L$_3$ = NH or NCH$_3$

In Scheme 4a, amines (5a), wherein L$_3$ is CH$_2$ and Re is NRfRg, can be prepared according to procedure A).

Amines of formula (5b), wherein L$_3$ is CO and Re is NRfRg are obtained through the procedure B).

From compounds (5b), described in Scheme 4a, compounds (5a) can also be obtained.

Amines of formula (5c), wherein $L_3$ is NH or $NCH_3$ and Re is as defined above, are obtained through procedure C).

Amines of formula (5d), wherein $L_3$ is O and Re is as defined above, are obtained through procedure D).

Amines of formula (5e), wherein $L_3$ is direct linkage and Re is NRfRg, are obtained through procedure E).

Procedure A): According to step i-11, an intermediate of formula (17) is reacted with an intermediate RfRgNH neat or in solvents like anhydrous acetonitrile, DCM and THF at temperatures ranging from 0° C. to reflux to yield compound (18) for time ranging from 1 hour to 48 hours. According to step i-12 the compound of formula (18) is reacted with iron powder in the presence of ammonium chloride, in solvents like EtOH, MeOH and mixture with water at temperatures ranging from room temperature to reflux for a time ranging from 1 hour to 48 hours to obtain compound of formula (5a). A variety of alternative methods available in the literature and well known to the skilled in the art can be used to carry out step i-12. For example the reaction can be carried out in the presence of Pd/C catalyst and ammonium formate ($HCOONH_4$) in a solvent like methanol, ethanol and the like at temperatures ranging from room temperatures to reflux and for 30 minutes to 48 hours. Alternatively the reaction can be carried out reacting (18) with Stannous chloride ($SnCl_2.2H_2O$) in solvents like ethanol, methanol, DCM, ethyl acetate or a mixture of them, at temperatures ranging from room temperature to reflux for 1 hour to 48 hours. In some cases further synthetic modifications of groups Rf or Rg might be necessary to achieve the final product.

Procedure B): According to step i-13 of Scheme 4a, an intermediate of formula (19) is reacted with an intermediate RfRgNH as described for step "f-c" of Method C to yield compound (20). According to step i-12, compound (20) is reacted under the same conditions already reported for step i-12 of procedure A) to yield an amine of formula (5b). According to step i-14 compound (5b) can be transformed into compound (5a) by reduction with borane tetrahydrofuran complex ($BH_3.THF$) in THF as the solvent at temperatures ranging from 0° C. to reflux for one hour to 72 hours.

Procedure C): According to step i-15, an intermediate of formula (21) is reacted with an intermediate $ReNH_2$ or $ReNHCH_3$, neat or in the presence of solvents like anhydrous acetonitrile, DCM and THF, at temperatures ranging from room temperature to reflux for a time ranging from 1 hour to 72 hours to yield compound (22), which is reacted as already described in step i-12 to yield compound (5c).

Procedure D): According to step i-16, an intermediate of formula (23) is reacted with an intermediate of formula Re—OH, in the presence of NaH (sodium hydride) in solvents like anhydrous THF, at temperatures ranging from −10° C. to room temperature for 1 hour to 24 hours to yield compound (24), which is reacted as already described in step i-12 to yield an intermediate of formula (5d).

Procedure E): According to step i-17, an intermediate of formula (25) is reacted with an intermediate RfRgNH neat or in the presence of solvents like anhydrous acetonitrile, DCM and THF, at temperatures ranging from room temperature to reflux for a time ranging from 1 hour to 72 hours to yield compound (26), which is reacted as already described in step i-12 to yield an intermediate of formula (5e).

Alternatively specific compounds of formula (1a), (1c), (1d), (1e) and (1g) can be prepared reacting compounds of formula (27), (28) and (29) already functionalized with the ethynyl group with compounds of formula (5), (8), (9), (10) and (13a), as described in the following Scheme 5, wherein all the variables are as defined above.

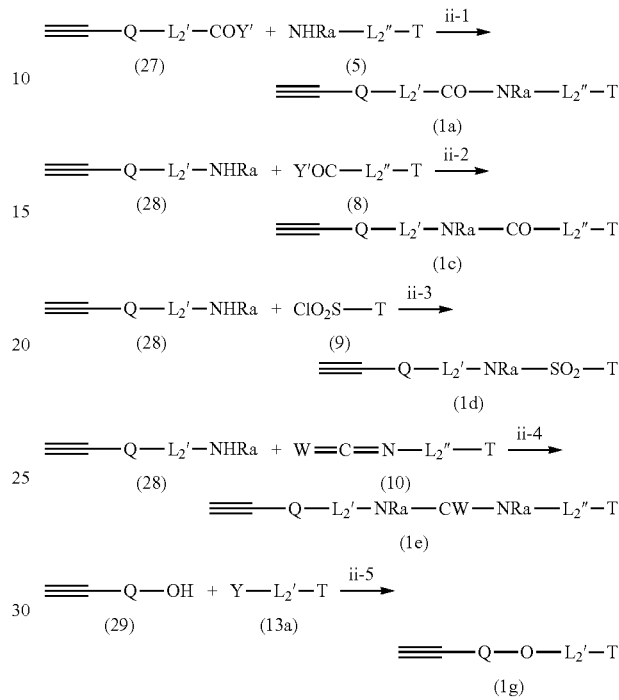

Scheme 5

According to step ii-1, an intermediate of formula (1a) can be prepared reacting an intermediate of formula (27), wherein Y' is OH, with an intermediate of formula (5) under the same reaction conditions described for step "f-c" of Method C.

According to step ii-2, an intermediate of formula (1c) can be prepared reacting an intermediate of formula (28) with an intermediate of formula (8) under the same reaction conditions described for step "f-c" of Method C.

According to step ii-3, an intermediate of formula (1d) can be prepared reacting an intermediate of formula (28) with an intermediate of formula (9) under the same reaction conditions described for step "f-d" of Method C.

According to step ii-4, an intermediate of formula (1e) can be prepared reacting an intermediate of formula (28) with an intermediate of formula (10) under the same reaction conditions described for step "f-e" of Method C.

According to step ii-5, an intermediate of formula (1g) can be prepared reacting an intermediate of formula (29) with an intermediate of formula (13a) under the same reaction conditions described for step i-7 of Scheme 4.

Specific compounds of formula (27), (28) and (29) are either commercially available or easily prepared according to methods well known to the skilled in the art.

Preparation of Intermediates of Formula (III) and (IV)

The present invention further provides the processes for the preparation of the intermediates of formula (III) useful for the synthesis of different intermediates of formula (II), which are prepared according to the following Schemes 6 to 11 reported below.

In particular, compounds of formula (III) where X is N, Y is I or Br, $R_1$ is $NH_2$ and P and $R_2$ are as defined above, can be prepared from an intermediate of formula (VI) upon halogenation according to the methods reported in the literature (WO2010/145998), as described in the following Scheme 6.

Scheme 6

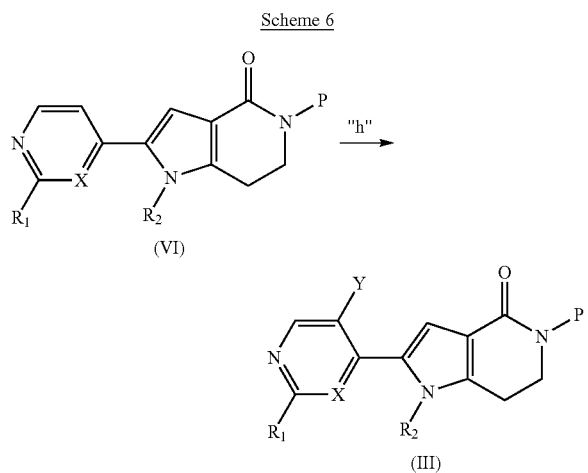

(VI)

(III)

According to step "h" an intermediate of formula (VI) is reacted with Silver trifluoroacetate and iodine thus obtaining an intermediate of formula (III) wherein Y is I, provided that $R_1$ is $NH_2$ or $NHR_3$, wherein $R_3$ is as defined above but not COR'. Alternatively compound (VI) can be reacted with NBS, in solvents like DMF thus obtaining an intermediate of formula (III) wherein Y is Br, provided that $R_1$ is $NH_2$ or $NHR_3$, wherein $R_3$ is as defined above but not COR'.

Compounds of formula (III) can be also obtained according to a number of different methods, depending on the specific structural moieties of the compounds. For example, compounds of formula (IIIa), wherein Y is I or Br, $R_3$ is H or an optionally substituted straight or branched $C_1$-$C_6$ alkyl or a heterocyclyl, and $R_2$ and P are as described above, can be prepared according to the procedure reported in the following Scheme 7.

Scheme 7

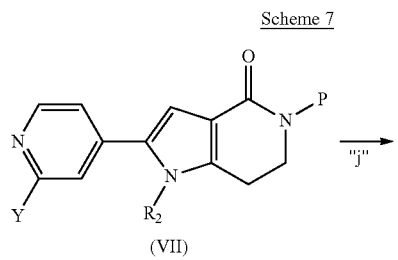

(VII)

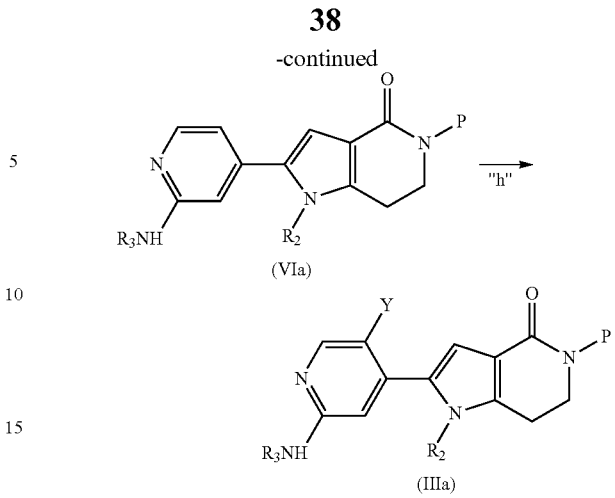

(VIa)

(IIIa)

According to step "j" of Scheme 7, an intermediate of formula (VII), wherein Y is Cl and $R_2$ and P are as defined above, prepared as described in WO2004/058762 and in *Journal of Medicinal Chemistry* 2007, 50, 2647-54, is reacted with tert-butyl carbamate (t-BuCOONH$_2$) (when $R_3$ and P are H in (VIa)) after acidic treatment according to step "b" of Method A) or with an amine $R_3NH_2$ (when $R_3$ is a straight or branched optionally substituted $C_1$-$C_6$ alkyl or a heterocyclyl in (VIa)) in the presence of a Palladium catalyst (Pd(AcO)$_2$, PdCl$_2$, Pd$_2$dba$_3$) and a suitable ligand (PPh$_3$, 9,9-dimethyl-4,5-bis(diphenylphosphino)xanthene (Xantphos), rac-2,2'-bis(diphenylphosphino)-1,1-binaphthyl (rac-Binap)) using a base such as Cs$_2$CO$_3$, LiHMDS, NaHMDS in solvents like DMF, toluene, dioxane, acetonitrile and the like at temperatures ranging from room temperature to reflux, for a time period ranging from 1 hour to 48 hours, to yield an intermediate of formula (VIa). Intermediate (VII) can also be reacted with an amine $R_3NH_2$ (wherein $R_3$ is H or a straight or branched optionally substituted $C_1$-$C_6$ alkyl or a heterocyclyl) in solvents like methanol, ethanol, N,N-dimethylformamide, dimethoxyethane at temperatures ranging from room temperature to reflux or under microwave irradiation for times ranging from 1 hour to 48 hours.

According to step "h", an intermediate of formula (VIa) is reacted under the same reaction conditions previously described in Scheme 6 to finally yield an intermediate of formula (IIIa).

Compounds of formula (III) can be also prepared, such that depicted in the following Scheme 8. This synthetic approach involves a Palladium catalyzed cross-coupling reaction between an intermediate of formula (VIII), wherein $R_1$ and X are as defined above, and M is a suitable reacting group, such as for example a boronic acid B(OH)$_2$, a boronic ester B(OAlk)$_2$, or Sn(Alk)$_3$, wherein Alk is $C_1$-$C_6$ alkyl, and an intermediate of formula (IX), wherein Y is Br or I and $R_2$ and P are as defined above.

Scheme 8

1)

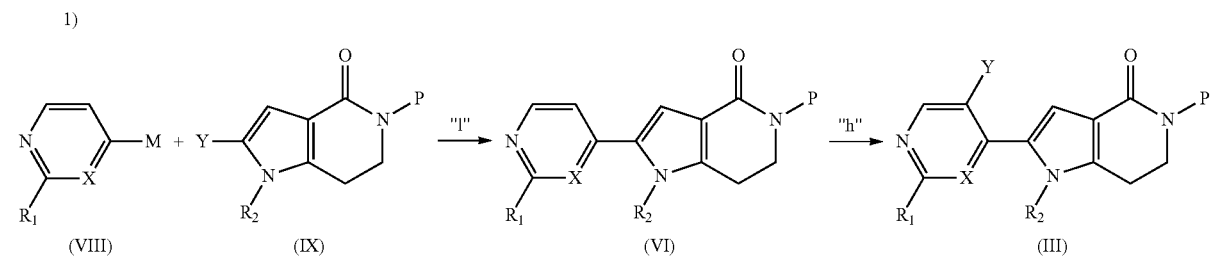

(VIII)   (IX)   (VI)   (III)

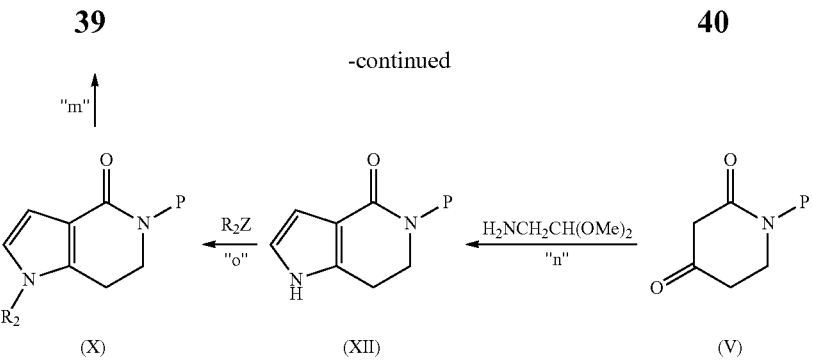

(X)  (XII)  (V)

2)

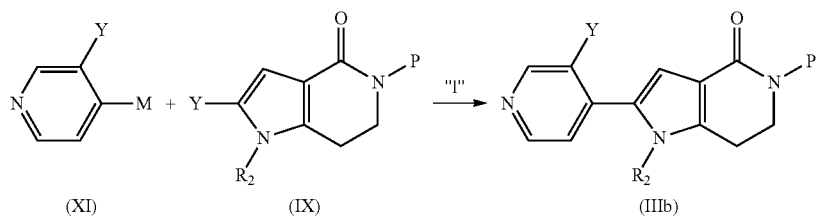

(XI)  (IX)  (IIIb)

Accordingly, a process 1) in Scheme 8 of the present invention comprises the following steps:

Step "l": cross-coupling reaction of compounds of formula (VIII) with compounds of formula (IX). These cross-coupling reactions can be performed under standard conditions as for Suzuki coupling using a Pd-based catalyst (Pd(dppf)$_2$Cl$_2$, PdCl$_2$(PPh$_3$)$_2$, Pd(PPh$_3$)$_4$) with a suitable base such as Sodium Carbonate (Na$_2$CO$_3$), Caesium Carbonate (Cs$_2$CO$_3$), potassium phosphate (K$_3$PO$_4$) in suitable organic solvents such as dioxane, DMF, toluene and the like at temperatures ranging from room temperature to reflux, for a time period ranging from 1 hour to 48 hours.

Step "h": reacting the intermediate of formula (VI) under the same conditions described for step "h" in Scheme 6, to yield an intermediate of formula (III), provided that R$_1$ is NHR$_3$ and R$_3$ is as defined above but not COR'.

Compounds of formula (VIII) might be commercially available or prepared according to methods known to the skilled in the art.

The intermediate of formula (IX) can be prepared according to the following procedure:

Step "m": reacting an intermediate of formula (X) wherein P and R$_2$ are as defined above by standard halogenation with NBS or NIS in suitable organic solvents such as THF-Methanol mixture, DMF from −20° C. to 40° C. for a time ranging from 30 minutes to 48 hours.

The intermediate of formula (X) can be prepared according to the following steps:

Step "n": reacting an intermediate of formula (V) wherein P is H or tert-butoxycarbonyl group, with 2,2-dimethoxyethylamine in solvents like toluene, N,N-dimethylformamide, N,N-dimethylacetamide, N-methylpirrolidone at temperatures ranging from room temperature to reflux and for a time ranging from 1 hour to 72 hours, to yield an intermediate that is further treated under acidic condition (HCl, TFA) in a variaty of solvents such as DCM, diethylether, dioxane at temperatures varying from 0° C. to reflux for a time period ranging from 1 hour to 48 hours to yield intermediate of formula (XII) where P is H. Compound (XII) can be protected again when needed, for example with di-tert-butyl dicarbonate (Boc$_2$O), providing compound (X) where P is tert-butoxycarbonyl group.

Step "o": reacting the intermediate of formula (XII) with an alkylating agent R$_2$Z wherein R$_2$ is as defined above but not hydrogen and Z is halogen, tosyl, methylsulphonyl, trifluoromethylsulphonyl, or another suitable leaving group, in the presence of a base such as TEA, DIPEA, Caesium carbonate (Cs$_2$CO$_3$), Potassium Carbonate (K$_2$CO$_3$), Sodium Hydride (NaH), NaOH, DBU, LiHMDS and the like, in solvents like 1,2-dimethoxyethane, methanol, ethanol, isopropanol, acetonitrile, N,N-dimethylformamide, N,N-dimethylacetamide, dimethylsulfoxide, and THF, at temperatures ranging from 0° C. to reflux for a time ranging from 30 minutes to 72 hours.

The process 2) in Scheme 8 of the present invention reports the synthesis of a particular compound of formula (IIIb) obtained by reacting an intermediate (XI), wherein M is a pinacolboronic ester group and Y is Br, with an intermediate of formula (IX) wherein Y is Br and P and R$_2$ are as defined above.

Accordingly, the process 2) in Scheme 8 comprises the following step:

Step "l'": reacting an iintermediate of formula (XI) with an intermediate of formula (IX) under the same conditions as previously described for step "l" via cross-coupling reaction.

Intermediate (X) is useful also to obtain other compounds of formula (III). In the following Scheme 9 is shown the process for the preparation of compounds of formula (IIIc) wherein P, R$_1$, R$_2$ and Y are as defined above.

Scheme 9

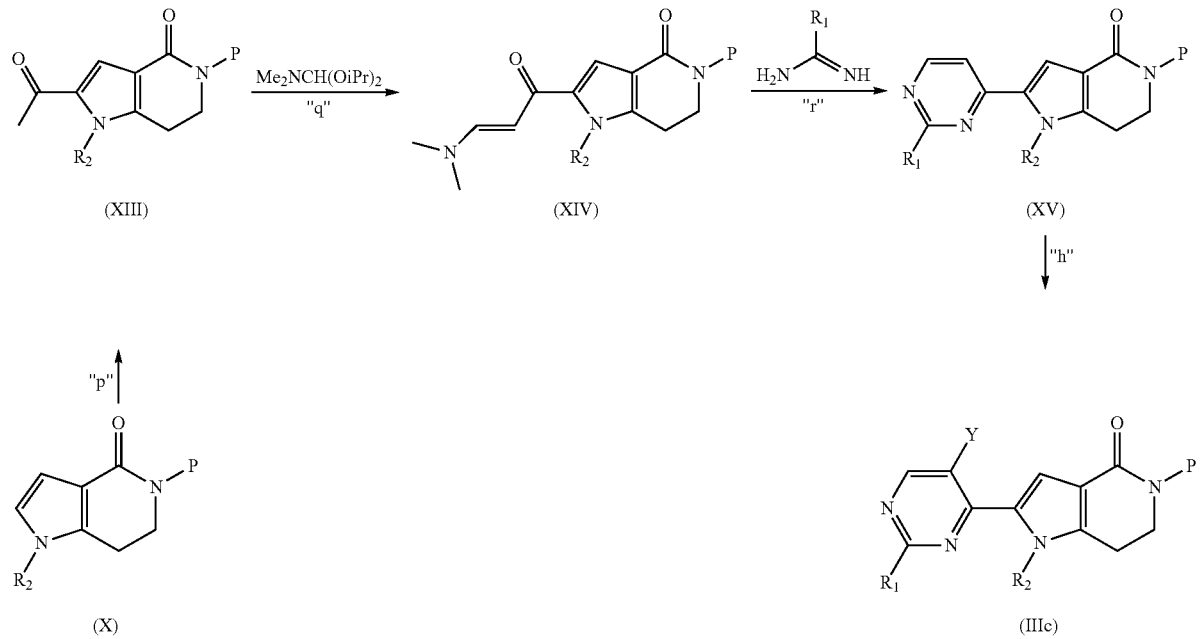

Accordingly, a further process of the present invention comprises the following steps:

Step "p": reacting an intermediate of formula (X) wherein P is H or tert-butoxycarbonyl group, with acetyl chloride or acetic anhydride in solvents like dichloromethane, dichloroethane, chlorobenzene, THF, dioxane in the presence of a catalyst such as aluminium trichloride ($AlCl_3$), titanium tetrachloride ($TiCl_4$), boron trifluoride diethylether complex ($BF_3 \cdot Et_2O$), zinc dichloride ($ZnCl_2$) at temperatures ranging from 0° C. to reflux for a time ranging from 30 minutes to 72 hours.

Step "q": reacting an intermediate of formula (XIII) wherein P is H or tert-butoxycarbonyl group, with dimethylformamide diisopropylacetal, dimethylformamide dimethylacetal, dimethylformamide diethylacetal, dimethylformamide ditert-butylacetal in solvents like N,N-dimethylformamide, N,N-dimethylacetamide, N-methylpirrolidone, dimethylsulfoxide at temperatures ranging from 0° C. to reflux for a time ranging from 30 minutes to 72 hours.

Step "r": reacting an intermediate of formula (XIV) wherein P is H or tert-butoxycarbonyl group, with a suitable guanidine wherein $R_1$ is $NH_2$ or $R_3NH$ and $R_3$ is optionally substituted straight or branched $C_1$-$C_6$ alkyl or heterocyclyl, in solvents like methanol, ethanol, N,N-dimethylformamide, N,N-dimethylacetamide, N-methylpirrolidone, dimethylsulfoxide in the presence of a base such as sodium methylate (MeONa), sodium ethylate (EtONa), sodium tert-butoxide (tBuONa), potassium acetate (AcONa), at temperatures ranging from 0° C. to reflux for a time ranging from 30 minutes to 72 hours.

Step "h": halogenation of the resultant intermediate of formula (XV), under the same conditions described for step "h" in Scheme 6, to yield the compound of formula (IIIc), provided that $R_1$ is $NHR_3$ and $R_3$ is H, a straight or branched optionally substituted $C_1$-$C_6$ alkyl, or a heterocyclyl.

The Scheme 10 below shows an alternative process for the preparation of compounds of formula (IIId) wherein P is hydrogen, $R_3$ is a straight or branched optionally substituted $C_1$-$C_6$ alkyl, $R_2$, X and Y are as defined above.

Scheme 10

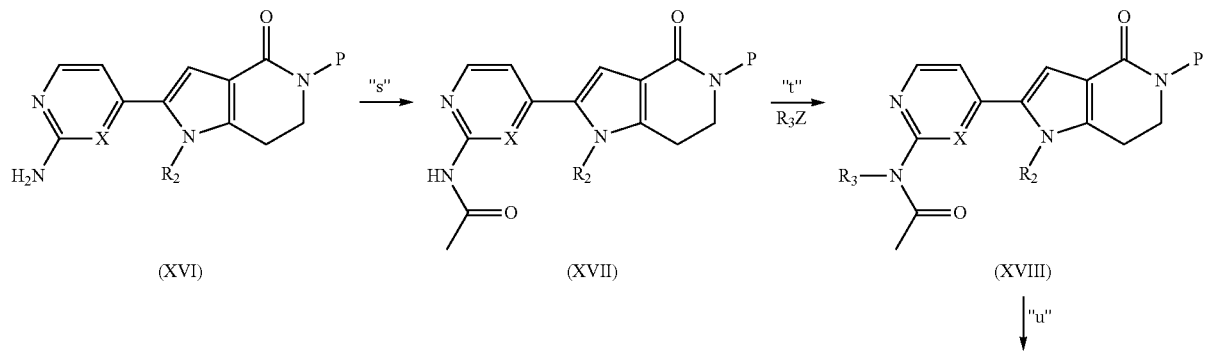

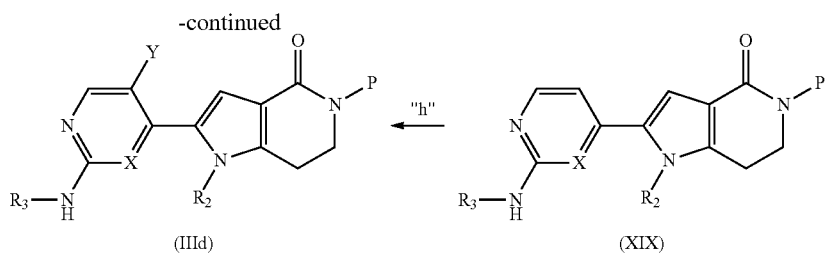

Accordingly, a further process of the present invention comprises the following steps:

Step "s": reacting an intermediate of formula (XVI), wherein P is a suitable protecting group (for example a tert-butoxycarbonyl group) and R₂ and X are as defined above, with acetic anhydride or acetyl chloride in solvents like dichloromethane, THF, in the presence of a base such as triethylamine (TEA), diisopropylethylamine (DIPEA) and a catalytic amount of an acyl transfer like pyridine, dimethylaminopyridine (DMAP) at temperatures ranging from room to reflux, for a time ranging from 1 hour to 72 hours to yield an intermediate of formula (XVII);

Step "t": alkylation of the resultant compound of formula (XVII) with an alkylating agent R₃Z wherein Z is as defined above and R₃ is a straight or branched optionally substituted C₁-C₆ alkyl, according to the method described for step "o" in scheme 8, followed by removal of the protecting group P (for example when it is a tert-butoxycarbonyl group) under acidic conditions according to steps "b" of Method A, to achieve the intermediate of formula (XVIII), wherein P is H;

Step "u": reacting compound of formula (XVIII), wherein P is H, under basic conditions using potassium carbonate (K₂CO₃), triethylamine (TEA) in solvents like methanol, ethanol and the like, at temperatures ranging from 0° C. to reflux for a time period ranging from 30' to 24 hours, thus obtaining the intermediate of formula (XIX);

Step "h": halogenation of the intermediate of formula (XIX), under the same conditions described for step "h" in Scheme 6, providing compounds of formula (IIId) wherein P is H and R₂, R₃, X and Y are as defined above.

The present invention further provides the processes for the preparation of the intermediates of formula (IVa) and (IVb), useful for the synthesis of compounds of formula (I), wherein R₁ is NHR₃, wherein R₃ is a straight or branched optionally substituted C₁-C₆ alkyl, a heterocyclyl, or R'CO and the other variables are as defined above. In the intermediate (IVa) R' is preferentially a methyl group.

The preparation of the intermediates of formula (IVa) and (IVb) is reported in the following Scheme 11.

Scheme 11

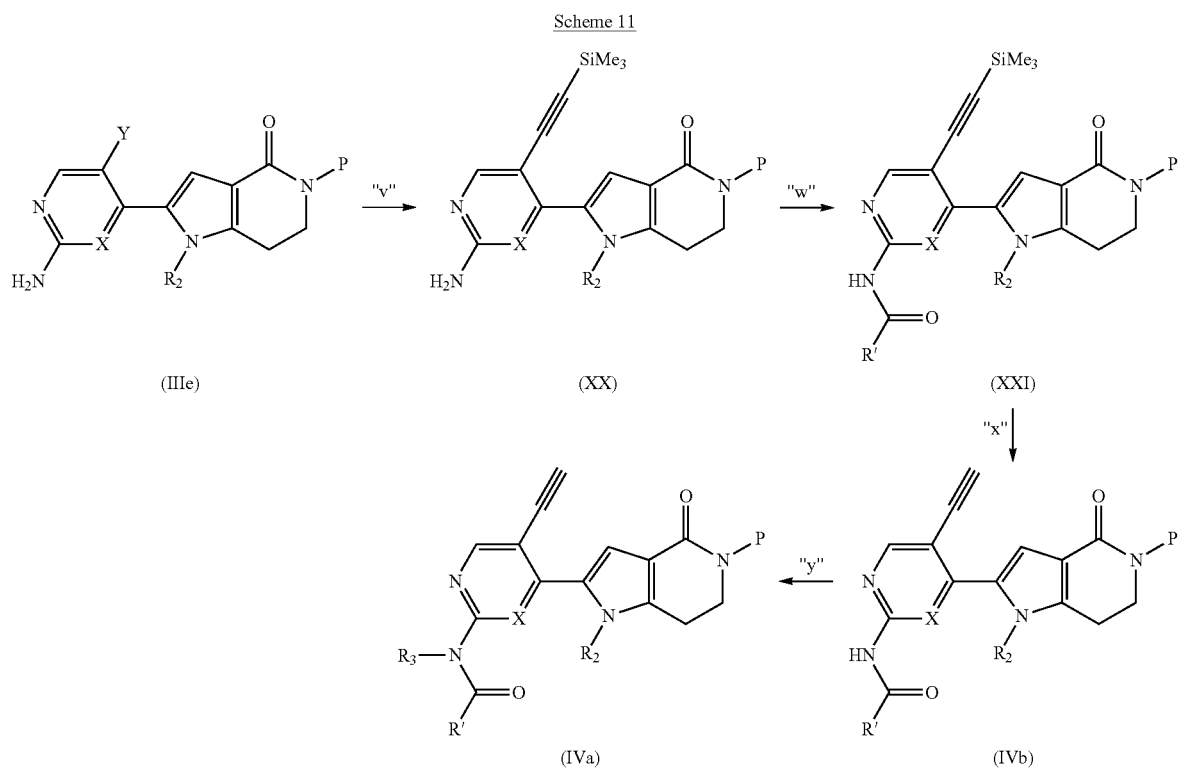

Accordingly, a further process of the present invention comprises the following steps:

Step "v": reaction of an intermediate of formula (IIIe), wherein P is a tert-butoxycarbonyl protecting group and Y and R₂ are as defined above, with trimethylsilylacetilene under Sonogashira reaction conditions as described for steps "a" of Method A;
Step "w": reacting an intermediate of formula (XX) with acid anhydride (R'CO)₂O or acyl chloride R'COCl in solvents like dichloromethane, THF, in the presence of a base such as triethylamine (TEA), diisopropylethylamine (DIPEA) and a catalytic amount of an acyl transfer like pyridine, dimethylaminopyridine (DMAP) at temperatures ranging from room temperature to reflux, for a time ranging from 1 hour to 72 hours to yield an intermediate of formula (XXI);
Step "x": compound of formula (XXI) is reacted with a base such as triethylamine (TEA), potassium carbonate (K₂CO₃), Caesium carbonate (Cs₂CO₃) in solvents like methanol, ethanol and the like at temperatures ranging from room temperature to 40° C., for a time ranging from 1 hour to 48 hours to obtain compound (IVb);
Step "y": reaction with an alkylating agent R₃Z wherein Z is as defined above and R₃ is a straight or branched optionally substituted $C_1$-$C_6$ alkyl under the same reaction conditions described for step "o" in Scheme 8, providing the intermediate of formula (IVa).

An intermediate of formula (IVa) can be further transformed into a compound of formula (I) reacting it with intermediates of formula (3a)-(3h) under the same reaction conditions described for steps "d" of Method B, followed by removal of the tert-butoxycarbonyl protecting group P under the same acidic conditions previously reported and finally removing the acyl group R'CO, where R' is preferentially a methyl group, under the same basic conditions previously described for step "u" in Scheme 10.

An intermediate of formula (IVb) can be further transformed into a compound of formula (I) reacting it with intermediates of formula (3a)-(3h) under the same reaction conditions described for steps "d" of Method B, followed by removal of the tert-butoxycarbonyl protecting group P under the same acidic conditions previously reported.

Pharmacology

In Vitro Cell Proliferation Assay

To evaluate the antiproliferative activity of a compound of formula (I) the following human cell lines were used: A2780 ovarian and MCF-7 breast carcinoma; TT and MZ-CRC-1 medullary thyroid carcinoma, harboring a mutated RET-C634W and RET-M918T receptor respectively, LC-2/ad Non Small Cell Lung Carcinoma, expressing the CCDC6-RET fusion gene product. Exponentially growing cells were seeded and incubated at 37° C. in a humidified 5% C02 atmosphere using appropriate medium supplemented with 10% Fetal Bovine Serum. 24 hours following cell plating, scalar doses of the compounds dissolved in 0.1% DMSO were added to the medium and cells were exposed to drugs for either 72 hours (MCF-7 and A2780) or 144 hours (TT, MZ-CRC-1 and LC-2/ad), according to their different proliferation rate. At the end of treatment, cell proliferation was determined by an intracellular ATP monitoring system (Cell-TiterGlo—Promega), following manufacturer's instructions, and using an Envision instrument (PerkinElmer) as reader. Data obtained from compound versus vehicle treated cells were compared using Assay Explorer (Symyx Technologies Inc) software. IC50 values were calculated using sigmoidal interpolation curve fitting.

High-Throughput Solubility Assay

A nominal 200 μM suspensions/solutions of a compound of formula (I) in aqueous potassium phosphate buffer at pH=7 and aqueous citric acid buffer at pH=3 were prepared on a "Multiscreen-HTS", 0.2 μm filter plate (Millipore, Billerica, Mass.). These solutions were stirred for 10 min and stored for 24 h at room temperature to pre-saturate the membrane filter and to reach a "pseudo-thermodynamic solubility". Then the plate was put on a 500 μL 96 multiwell plate containing 200 μL of acetonitrile in each well and centrifuged at 2000 rpm for 5 minutes. The so obtained solutions were then analyzed simultaneously by HPLC-UV with standard solutions for quantification.

In the following Table A the antiproliferative activity of representative compounds of formula (I) on two medullary thyroid carcinoma cell lines expressing the aforementioned mutated forms of RET (TT and MZ-CRC-1) is reported. As control, two unrelated non RET-dependent cell lines (A2780 and MCF7) were tested. All these compounds show remarkable activity on RET-driven cellular models with respect to the unrelated ones. In addition, most of the compounds displays superior activity compared to the Reference compound, which corresponds to compound of Example 11 of the patent application WO2010/145998 cited above and is the disclaimed compound in the present formula (I).

In Table A solubility data of representative compounds of formula (I) at neutral, physiological pH (pH 7) are also reported. These data are useful to evaluate the improvement of the compounds of the present invention with respect to the reference compound. In fact they are endowed with a largely improved solubility, thus allowing to evaluate them in vivo both after i.v. (intravenous) and after os (oral) administration. The lack of solubility of the reference compound instead makes it hardly suitable for in vivo studies. Furthermore, the improved solubility allows obtaining compounds with better formulation and/or pharmaocokinetic/pharmacodynamic properties.

TABLE A

| Cmpd # | Solubility (μM) @ pH 7 | A2780 IC$_{50}$ (μM) | MCF7 IC$_{50}$ (μM) | TT IC$_{50}$ (μM) (144h) | MZ-CRC-1 IC$_{50}$ (μM) (144h) | LC-2/ad IC$_{50}$ (μM) (144h) |
|---|---|---|---|---|---|---|
| Reference cmpd (Example 11 of WO2010/145998) | <1 | 2.746 | 4.543 | 0.041 | 0.317 | |
| 8 | 6.5 | 1.761 | 4.783 | 0.002 | 0.074 | 0.038 |
| 22 | 5.8 | 1.148 | 2.806 | 0.007 | | |
| 30 | 1.7 | 1.002 | 2.189 | 0.008 | | |
| 29 | 7.4 | 2.229 | 9.162 | 0.085 | | |
| 38 | 10.8 | 1.950 | 5.038 | 0.038 | | |
| 44 | 4.7 | 1.718 | 3.483 | 0.069 | 0.231 | |
| 48 | 26.9 | 0.085 | 1.836 | 0.0005 | 0.004 | 0.004 |
| 77 | 23 | 2.817 | 6.653 | 0.002 | 0.023 | 0.003 |
| 78 | 1.4 | 2.223 | 2.310 | 0.007 | 0.026 | 0.014 |
| 105 | 15.3 | 2.738 | >10 | 0.025 | | |

TABLE A-continued

| Cmpd # | Solubility (μM) @ pH 7 | A2780 IC$_{50}$ (μM) | MCF7 IC$_{50}$ (μM) | TT IC$_{50}$ (μM) (144h) | MZ-CRC-1 IC$_{50}$ (μM) (144h) | LC-2/ad IC$_{50}$ (μM) (144h) |
|---|---|---|---|---|---|---|
| 122 | 9.4 | 0.704 | 2.687 | 0.001 | | |
| 123 | 25.1 | 3.898 | >10 | 0.060 | | |
| 129 | 26.4 | 0.105 | 8.182 | 0.002 | | |
| 149 | 30.4 | 1.906 | 3.725 | 0.013 | | |
| 150 | 40.2 | 1.927 | 5.637 | 0.006 | | |
| 164 | 8.9 | 2.022 | 5.623 | 0.002 | | |
| 174 | 3.5 | 1.147 | | 0.005 | 0.015 | 0.010 |
| 176 | 7.6 | 3.833 | | 0.014 | 0.023 | 0.020 |
| 179 | 1.2 | 3.243 | | 0.017 | 0.038 | |
| 190 | 2.9 | 2.310 | | 0.008 | 0.039 | 0.051 |
| 193 | <1 | 0.910 | | 0.016 | 0.039 | 0.015 |

From all of the above, the novel compounds of formula (I) of the present invention appear to be particularly advantageous in the therapy of diseases caused by dysregulated protein kinase activity, such as cancer.

The compounds of the present invention can be administered either as single agents or, alternatively, in combination with known anticancer treatments, such as radiation therapy or chemotherapy regimen, in combination with, for example, antihormonal agents, such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight and conditions of the patient and administration route.

For example, a suitable dosage adopted for oral administration of a compound of formula (I) may range from about 10 to about 1 g per dose, from 1 to 5 times daily. The compounds of the invention can be administered in a variety of dosage forms, e.g. orally, in the form tablets, capsules, sugar or film coated tablets, liquid solutions or suspensions; rectally in the form suppositories; parenterally, e.g. intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g. lactose, dextrose saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine methylcellulose, carboxymethylcellulose or polyvinyl pyrrolidone; disintegrating agents, e.g. starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g. syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g. cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:
g (grams) mg (milligrams)
mL (milliliters) mM (millimolar)
M (micromolar) mmol (millimoles)
h (hours) MHz (Mega-Hertz)

mm (millimeters) Hz (Hertz)
M (molar) min (minutes)
mol (moles) TLC (thin layer chromatography)
$NaHCO_3$ (sodium bicarbonate) $Na_2SO_4$ (sodium sulfate)
$K_3PO_4$ (potassium phosphate tribasic) $Cs_2CO_3$ (cesium carbonate)
$NH_4Cl$ (ammonium chloride) HOBT (1-hydroxybenzotriazole)
$K_2CO_3$ (potassium carbonate) MeI (methyl iodide)
$SnCl_2.2H_2O$ (tin(II) chloride dihydrate) TBAF (Tetrabutylammonium fluoride)
$PdCl_2(PPh_3)_2$ (Bis(triphenylphosphine)palladium(II) dichloride
EDAC (N-(3-dimethylaminopropyl)-N-ethylcarbodiimide hydrochloride)
$Pd(PPh_3)_4$ (tetrakis(triphenylphosphine)palladium(0)) NBS (N-Bromosuccinimide)
$PdCl_2(dppf)_2$ (1,1'-Bis(diphenylphosphino)ferrocene-palladium(II)dichloride dichloromethane complex)
$Pd(OAc)_2$ (palladium acetate) DMA (dimethylacetamide)
Xantphos (4,5-Bis(diphenylphosphino)-9,9-dimethylxanthene)
$NaBH(OAc)_3$ (sodium triacetoxyborohydride)
$NaCNBH_3$ (sodium cyanoborohydride) $TMSCH_2N_2$ (trimethylsilyldiazomethane)
MTBE (methyl tert-butyl ether) $AlCl_3$ (aluminium chloride)
tBuONa (sodium tert-butoxide) $Na_2S_2O_5$ (sodium metabisulfite)
$NH_3$ (33% in water ammonium hydroxide solution) Fe (iron powder)
NaI (sodium iodide) DMAP (dimethylaminopyridine)
r.t. (room temperature) TEA (triethylamine)
$HCOONH_4$ (ammonium formate) $Na_2CO_3$ (sodium carbonate)
EtOAc (ethyl acetate) MeCN (acetonitrile)
TFA (trifluoroacetic acid) DMF (N,N-dimethyl formamide)
DIPEA (N,N-diisopropyl-N-ethylamine) DCM (dichloromethane)
THF (tetrahydrofuran) Hex (hexane)
EtOH (ethanol) NaOH (sodium hydroxide solution)
HCl (hydrochloric acid solution) CuI (copper(I) iodide)
MeOH (Methanol) DMSO (dimethylsulfoxide)
$Et_2O$ (ethyl ether) PTSA (p-toluenesulfonic acid monohydrate)
TIPS (triisopropylsilyl) bs (broad singlet)
TBDMSCl (dimethyl-tert-butylsilyl chloride) AcOH (glacial acetic acid)
BOC (tert-butyloxycarbonyl) $Ac_2O$ (acetic anhydride)
NaH=sodium hydride, 60% in mineral oil ESI=electrospray ionization
TBTU ((2-(1H-benzotriazol-1-yl)-1,1,3,3-tetramethyluronium tetrafluoroborate)
RP-HPLC (reverse phase high performance liquid chromatography)

With the aim to better illustrate the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, DCM and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A).

Electrospray (ESI) mass spectra were obtained on a Thermo Finnigan LCQ Deca XP ion trap. HPLC-UV-MS analyses, used to assess compound purity, were carried out combining the ion trap MS instrument with HPLC system Surveyor (Thermo Finnigan) equipped with an autosampler and a diode array detector (UV detection 215-400 nm). Instrument control, data acquisition and processing were performed by using Xcalibur 1.4 SR1 software (Thermo Finnigan). HPLC chromatography was run at room temperature, and 1 ml/min flow rate, using a Phenomenex Gemini NX C18 column (4.6×50 mm; 3 µm). Mobile phase A was ammonium acetate 5 mM buffer (pH 5.5 with acetic acid)/acetonitrile 95:5, and mobile phase B was ammonium acetate 5 mM buffer (pH 5.5 with acetic acid)/acetonitrile 5:95; the gradient was from 0 to 100% B in 7 minutes then hold 100% B for 2 minutes before requilibration.

Exact mass data ESI(+) were obtained on a Waters Q-Tof Ultima directly connected with micro HPLC 1100 Agilent as previously described [M. Colombo, F. Riccardi-Sirtori, V. Rizzo, *Rapid Commun. Mass Sectrom.* 2004, 18, 511-517].

Mass are given as m/z ratio.

When necessary, compounds were purified by preparative HPLC on a Waters Symmetry C18 (19×50 mm, 5 µm) column or on a Waters X Terra RP 18 (30×150 mm, 5 µm) column using a Waters preparative HPLC 600 equipped with a 996 Waters PDA detector and a Waters ZQ single quadrupole mass spectrometer, electron spray ionization, positive mode. Mobile phase A was water/0.1% trifluoroacetic acid and mobile phase B was acetonitrile. Gradient from 10 to 90% B in 8 min, hold 90% B 2 min. Flow rate 20 mL/min. In alternative, mobile phase A was water/0.05% $NH_3$, and mobile phase B was acetonitrile. Gradient from 10 to 100% B in 8 min, hold 100% B 2 min. Flow rate 20 mL/min.

1H-NMR spectrometry was performed on a Mercury VX 600 operating at 600 MHz equipped with a 5 mm double resonance probe [1H (15N-31P) ID_PFG Varian].

Preparation 1

1-Cyclopropylmethyl-4-(4-nitro-2-trifluoromethyl-benzyl)-piperazine

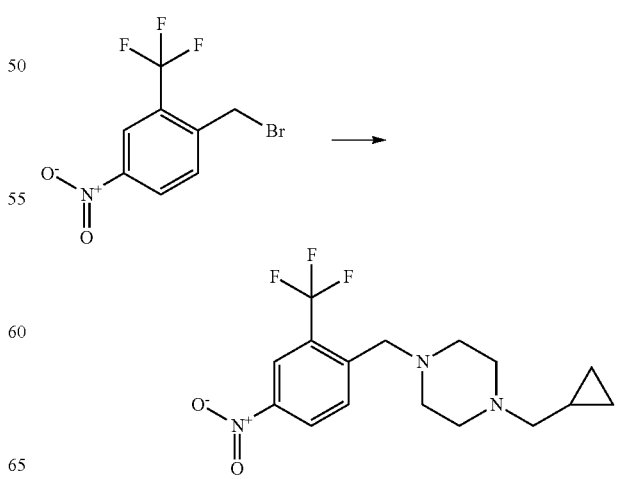

To solution of 1-bromomethyl-4-nitro-2-trifluoromethyl-benzene (0.25 g, 0.88 mmol) in anhydrous MeCN (5 mL), 1-cyclopropylmethyl-piperazine (0.37 g, 2.64 mmol) was added. The reaction was stirred at r.t. for 1 h, then a saturated solution of NaHCO$_3$ was added and the mixture was extracted with EtOAc (2×10 mL). The organic phase was washed with brine, dried with anhydrous Na$_2$SO$_4$ and evaporated under vacuum to obtain the title compound (0.29 g, 96%) as yellow oil.

$^1$H NMR (600 MHz, DMSO-d$_6$) δ ppm 0.00-0.09 (m, 2H) 0.39-0.49 (m, 2H) 0.80 (d, J=8.06 Hz, 1H) 3.65-3.79 (m, 2H) 8.09 (d, J=8.79 Hz, 1H) 8.41 (d, J=2.38 Hz, 1H) 8.51 (dd, J=8.61, 2.38 Hz, 1H).

According to this same methodology, but employing suitable substituted derivatives, the following intermediates were prepared:

1-Methyl-4-(4-nitro-2-trifluoromethyl-benzyl)-piperazine (ESI) m/z 304 [(M+H)$^+$]. HRMS (ESI) calculated for C$_{13}$H$_{17}$F$_3$N$_3$O$_2$$^+$ [(M+H)$^+$] 304.2802. found 304.2803.

1-Ethyl-4-(4-nitro-2-trifluoromethyl-benzyl)-piperazine (ESI) m/z 318 [(M+H)$^+$]. HRMS (ESI) calculated for C$_{14}$H$_{19}$F$_3$N$_3$O$_2$$^+$ [(M+H)$^+$] 318.3068. found 318.3070.

1-(4-Nitro-2-trifluoromethyl-benzyl)-4-propyl-piperazine $^1$H NMR (600 MHz, DMSO-d$_6$) δ ppm 0.82-0.87 (m, 3H) 1.42 (t, J=7.40 Hz, 2H) 2.19-2.25 (m, 2H) 2.30-2.48 (m, 7H) 3.72 (s, 2H) 8.09 (d, J=8.61 Hz, 1H) 8.41 (d, J=2.20 Hz, 1H) 8.51 (dd, J=8.61, 2.20 Hz, 1H).

1-Isopropyl-4-(4-nitro-2-trifluoromethyl-benzyl)-piperazine $^1$H NMR (600 MHz, DMSO-d$_6$) δ ppm 0.96 (d, J=6.41 Hz, 6H) 2.59-2.67 (m, 1H) 3.71 (s, 2H) 8.09 (d, J=8.61 Hz, 1H) 8.41 (d, J=2.38 Hz, 1H) 8.51 (dd, J=8.61, 2.20 Hz, 1H).

1-(4-Nitro-2-trifluoromethyl-benzyl)-piperidine $^1$H NMR (600 MHz, DMSO-d$_6$) δ ppm 1.42 (d, J=5.31 Hz, 2H) 1.53 (quin, J=5.59 Hz, 4H) 2.34-2.40 (m, 4H) 3.68 (s, 2H) 8.10 (d, J=8.42 Hz, 1H) 8.40 (d, J=2.38 Hz, 1H) 8.51 (dd, J=8.61, 2.20 Hz, 1H).

4-(4-Nitro-2-trifluoromethyl-benzyl)-morpholine $^1$H NMR (600 MHz, DMSO-d$_6$) δ ppm 2.40-2.46 (m, 4H) 3.57-3.64 (m, 4H) 3.74 (s, 2H) 8.12 (d, J=8.61 Hz, 1H) 8.42 (d, J=2.20 Hz, 1H) 8.51 (dd, J=8.52, 2.29 Hz, 1H).

Dimethyl-[(S)-1-(4-nitro-2-trifluoromethyl-benzyl)-pyrrolidin-3-yl]-amine $^1$H NMR (600 MHz, DMSO-d$_6$) δ ppm 1.60-1.71 (m, 1H) 1.84-1.94 (m, 1H) 2.09 (s, 6H) 2.40 (dd, J=8.97, 6.78 Hz, 1H) 2.53-2.57 (m, 1H) 2.59-2.65 (m, 1H) 2.66-2.70 (m, 1H) 2.74-2.80 (m, 1H) 3.78-3.90 (m, 2H) 8.05 (d, J=8.61 Hz, 1H) 8.40 (d, J=2.20 Hz, 1H) 8.51 (dd, J=8.61, 2.38 Hz, 1H).

Dimethyl-[(R)-1-(4-nitro-2-trifluoromethyl-benzyl)-pyrrolidin-3-yl]-amine $^1$H NMR (600 MHz, DMSO-d$_6$) δ ppm 1.60-1.71 (m, 1H) 1.84-1.94 (m, 1H) 2.09 (s, 6H) 2.40 (dd, J=8.97, 6.78 Hz, 1H) 2.53-2.57 (m, 1H) 2.59-2.65 (m, 1H) 2.66-2.70 (m, 1H) 2.74-2.80 (m, 1H) 3.78-3.90 (m, 2H) 8.05 (d, J=8.61 Hz, 1H) 8.40 (d, J=2.20 Hz, 1H) 8.51 (dd, J=8.61, 2.38 Hz, 1H).

1-Methyl-4-(4-nitro-2-trifluoromethyl-benzyl)-[1,4]diazepane $^1$H NMR (600 MHz, DMSO-d$_6$) δ ppm 2.26 (s, 3H) 2.53-2.55 (m, 2H) 2.56-2.60 (m, 2H) 2.64-2.71 (m, 4H) 3.88 (s, 2H) 8.14 (d, J=8.61 Hz, 1H) 8.40 (d, J=2.01 Hz, 1H) 8.52 (dd, J=8.52, 2.29 Hz, 1H).

2-[4-(4-Nitro-2-trifluoromethyl-benzyl)-piperazin-1-yl]-ethanol $^1$H NMR (600 MHz, DMSO-d$_6$) δ ppm 2.38 (t, J=6.32 Hz, 3H) 2.43 (br. s., 6H) 3.48 (q, J=6.23 Hz, 2H) 3.72 (s, 2H) 4.36 (t, J=5.31 Hz, 1H) 8.09 (d, J=8.61 Hz, 1H) 8.41 (d, J=2.20 Hz, 1H) 8.51 (dd, J=8.61, 2.20 Hz, 1H).

1-(4-Nitro-2-trifluoromethyl-benzyl)-piperazine $^1$H NMR (600 MHz, DMSO-d$_6$) δ ppm 2.35 (br. s., 4H) 2.73 (t, J=4.67 Hz, 5H) 3.69 (s, 2H) 8.11 (d, J=8.43 Hz, 1H) 8.41 (d, J=2.20 Hz, 1H) 8.51 (dd, J=8.70, 2.11 Hz, 1H).

1-[1-(4-Nitro-2-trifluoromethyl-benzyl)-azetidin-3-yl]-pyrrolidine $^1$H NMR (600 MHz, DMSO-d$_6$) δ ppm 1.68 (br. s., 4H) 2.26-2.48 (m, 4H) 2.98-3.05 (m, 2H) 3.11 (br. s., 1H) 3.44 (t, J=6.96 Hz, 2H) 3.86 (s, 2H) 7.99 (d, J=8.61 Hz, 1H) 8.39 (d, J=2.38 Hz, 1H) 8.49 (dd, J=8.52, 2.29 Hz, 1H).

Methyl-(1-methyl-piperidin-4-yl)-(4-nitro-2-trifluoromethyl-benzyl)-amine $^1$H NMR (600 MHz, DMSO-d$_6$) δ ppm 1.50 (qd, J=12.00, 3.94 Hz, 2H) 1.68 (d, J=11.90 Hz, 2H) 1.78-1.90 (m, 2H) 2.12 (s, 2H) 2.13 (s, 3H) 2.33-2.39 (m, 1H) 2.79 (d, J=10.62 Hz, 2H) 3.79 (s, 2H) 8.10 (d, J=8.43 Hz, 1H) 8.37 (d, J=2.20 Hz, 1H) 8.48 (dd, J=8.61, 2.20 Hz, 1H).

Dimethyl-[1-(4-nitro-2-trifluoromethyl-benzyl)-piperidin-4-yl]-amine $^1$H NMR (600 MHz, DMSO-d$_6$) δ ppm 1.42 (qd, J=11.90, 3.66 Hz, 2H) 1.73 (d, J=12.82 Hz, 2H) 1.95-2.13 (m, 3H) 2.18 (s, 6H) 2.80 (d, J=11.72 Hz, 2H) 3.70 (s, 2H) 8.10 (d, J=8.61 Hz, 1H) 8.40 (d, J=2.20 Hz, 1H) 8.51 (dd, J=8.61, 2.38 Hz, 1H).

(2R,5S)-1,2,5-Trimethyl-4-(4-nitro-2-trifluoromethyl-benzyl)-piperazine $^1$H NMR (600 MHz, DMSO-d$_6$) δ ppm 0.86 (d, J=6.23 Hz, 3H) 0.95-1.00 (m, 3H) 1.86-1.95 (m, 2H) 1.98 (d, J=6.23 Hz, 1H) 2.40-2.47 (m, 1H) 2.70 (d, J=11.26, 2.66 Hz, 1H) 4.15 (d, J=15.93 Hz, 1H) 8.16 (d, J=8.61 Hz, 1H) 8.40 (d, J=2.38 Hz, 1H) 8.51 (dd, J=8.61, 2.20 Hz, 1H).

1,2,6-Trimethyl-4-(4-nitro-2-trifluoromethyl-benzyl)-piperazine

¹H NMR (600 MHz, DMSO-d₆) δ ppm 0.92-0.98 (m, 6H) 1.89 (t, J=10.62 Hz, 2H) 2.18 (d, J=6.23 Hz, 2H) 2.60-2.66 (m, 2H) 3.66 (s, 2H) 8.09 (d, J=8.61 Hz, 1H) 8.41 (d, J=2.20 Hz, 1H) 8.51 (dd, J=8.52, 2.29 Hz, 1H).

1-Cyclopropyl-4-(4-nitro-2-trifluoromethyl-benzyl)-piperazine

¹H NMR (600 MHz, DMSO-d₆) δ ppm 0.27-0.30 (m, 2H) 0.36-0.43 (m, 2H) 1.61 (dt, J=6.73, 3.14 Hz, 1H) 2.39 (d, J=1.65 Hz, 4H) 2.54-2.60 (m, 3H) 3.71 (s, 2H) 8.10 (d, J=8.61 Hz, 1H) 8.41 (d, J=2.38 Hz, 1H) 8.52 (dd, J=8.61, 2.20 Hz, 1H).

4-(4-Nitro-2-trifluoromethyl-benzyl)-piperazine-1-carboxylic acid tert-butyl ester ¹H NMR (600 MHz, DMSO-d₆) δ ppm 1.40 (s, 9H) 2.38 (t, J=4.95 Hz, 4H) 3.35 (br. s., 3H) 3.76 (s, 2H) 8.11 (d, J=8.61 Hz, 1H) 8.42 (d, J=2.20 Hz, 1H) 8.51 (dd, J=8.61, 2.20 Hz, 1H).

4-(4-Nitro-2-trifluoromethyl-benzyl)-piperazin-2-one

¹H NMR (600 MHz, DMSO-d₆) δ ppm 2.58-2.63 (m, 2H) 3.02 (s, 2H) 3.16-3.21 (m, 2H) 3.83 (s, 2H) 7.80 (br. s., 1H) 8.10 (d, J=8.61 Hz, 1H) 8.42 (d, J=2.20 Hz, 1H) 8.51 (dd, J=8.52, 2.29 Hz, 1H).

1-(4-Nitro-2-trifluoromethyl-benzyl)-piperidin-3-ol

¹H NMR (600 MHz, DMSO-d₆) δ ppm 1.06-1.16 (m, 1H) 1.40-1.51 (m, 1H) 1.65 (dt, J=13.23, 3.37 Hz, 1H) 1.75-1.83 (m, 1H) 1.86 (t, J=9.80 Hz, 1H) 1.97-2.03 (m, 1H) 2.58-2.64 (m, 1H) 2.74 (dd, J=10.35, 3.57 Hz, 1H) 3.51 (td, J=9.39, 4.67 Hz, 1H) 3.65-3.78 (m, 2H) 4.63 (d, J=4.95 Hz, 1H) 8.10 (d, J=8.43 Hz, 1H) 8.41 (d, J=2.20 Hz, 1H) 8.51 (dd, J=8.61, 2.38 Hz, 1H).

1-(4-Nitro-2-trifluoromethyl-benzyl)-piperidin-4-ol

¹H NMR (600 MHz, DMSO-d₆) δ ppm 1.39-1.48 (m, 2H) 1.69-1.76 (m, 2H) 2.15 (t, J=9.62 Hz, 2H) 2.62-2.70 (m, 2H) 3.49 (dt, J=8.20, 4.24 Hz, 1H) 3.70 (s, 2H) 4.58 (d, J=4.03 Hz, 1H) 8.10 (d, J=8.43 Hz, 1H) 8.40 (d, J=2.20 Hz, 1H) 8.51 (dd, J=8.52, 2.29 Hz, 1H).

2-[Methyl-(4-nitro-2-trifluoromethyl-benzyl)-amino]-ethanol

¹H NMR (600 MHz, DMSO-d₆) δ ppm 2.22 (s, 3H) 2.51-2.53 (m, 2H) 3.54 (q, J=6.04 Hz, 2H) 3.79 (s, 2H) 4.48 (t, J=5.31 Hz, 1H) 8.19 (d, J=8.61 Hz, 1H) 8.40 (d, J=2.20 Hz, 1H) 8.50 (dd, J=8.52, 2.29 Hz, 1H).

3-[Methyl-(4-nitro-2-trifluoromethyl-benzyl)-amino]-propane-1,2-diol

¹H NMR (600 MHz, DMSO-d₆) δ ppm 2.27-2.42 (m, 1H) 2.45 (dd, J=11.72, 7.14 Hz, 1H) 2.58-2.65 (m, 1H) 3.52-3.60 (m, 1H) 3.99 (br. s., 2H) 4.48 (t, J=5.49 Hz, 1H) 4.61 (d, J=4.95 Hz, 1H) 8.13 (d, J=8.61 Hz, 1H) 8.40 (d, J=2.20 Hz, 1H) 8.51 (dd, J=8.70, 2.29 Hz, 1H).

1-Ethyl-4-(2-fluoro-4-nitro-benzyl)-piperazine (ESI) m/z 268 [(M+H)⁺]. HRMS (ESI) calculated for C₁₃H₁₉FN₃O₂⁺ [(M+H)⁺] 268.2993. found 268.2991.

1-Ethyl-4-(2-nitro-4-trifluoromethyl-benzyl)-piperazine (ESI) m/z 318 [(M+H)⁺]. HRMS (ESI) calculated for C₁₄H₁₉F₃N₃O₂⁺ [(M+H)⁺] 318.3068. found 318.3066.

1-(2-Chloro-5-nitro-benzyl)-4-ethyl-piperazine (ESI) m/z 284 [(M+H)⁺]. HRMS (ESI) calculated for C₁₃H₁₉ClN₃O₂⁺ [(M+H)⁺] 284.7539. found 284.7540.

[2-(4-Nitro-2-trifluoromethyl-benzylamino)-ethyl]-carbamic acid tert-butyl ester ¹H NMR (600 MHz, DMSO-d₆) δ ppm 1.32-1.40 (m, 9H) 2.53-2.59 (m, 2H) 3.04 (q, J=5.92 Hz, 2H) 3.96 (s, 2H) 6.76 (br. s., 1H) 8.12 (d, J=8.61 Hz, 1H) 8.39 (d, J=2.01 Hz, 1H) 8.50 (dd, J=8.42, 2.20 Hz, 1H).

1-(2-Bromo-4-nitro-benzyl)-4-methyl-piperazine

¹H NMR (600 MHz, DMSO-d₆) δ ppm 2.16 (s, 3H) 3.62 (s, 2H) 7.75 (d, J=8.61 Hz, 1H) 8.24 (dd, J=8.43, 2.38 Hz, 1H) 8.40 (d, J=2.38 Hz, 1H).

Preparation 2

1-(2-Cyclopropyl-4-nitro-benzyl)-4-methyl-piperazine

A solution of 1-(2-bromo-4-nitro-benzyl)-4-methyl-piperazine (0.22 g, 0.7 mmol), cyclopropaneboronic acid (0.18 g, 2.1 mmol), K₃PO₄ (0.67 g, 3.15 mmol), palladium acetate (0.016 g, 0.14 mmol) and tricyclohexylphosphine (0.04 g, 0.14 mmol) in toluene (3 mL) and water (0.6 mL) was degassed with argon and then heated at reflux for 5 h. The mixture was cooled at r.t., poured in water (15 mL) and extracted with EtOAc (2×15 mL). The organic phase was washed with brine, dried with anhydrous Na₂SO₄ and evaporated under vacuum to afford a crude that was purified by flash column chromatography (DCM-MeOH 90:10). The title compound (0.15 g, 76%) was obtained as yellow oil.

¹H NMR (600 MHz, DMSO-d₆) δ ppm 0.69-0.75 (m, 2H) 0.98-1.05 (m, 2H) 2.16 (s, 3H) 2.19-2.25 (m, 1H) 2.44-2.52 (m, 8H) 3.71 (s, 2H) 7.58 (d, J=8.43 Hz, 1H) 7.72 (d, J=2.56 Hz, 1H) 8.01 (dd, J=8.43, 2.38 Hz, 1H).

Preparation 3

4-Methyl-1-(4-nitro-2-trifluoromethyl-benzyl)-piperazin-2-one

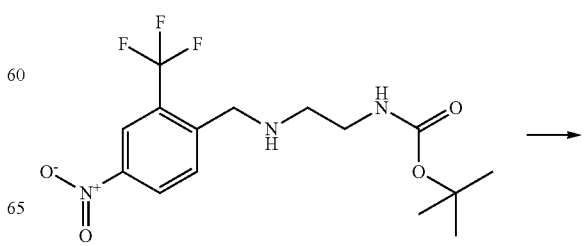

-continued

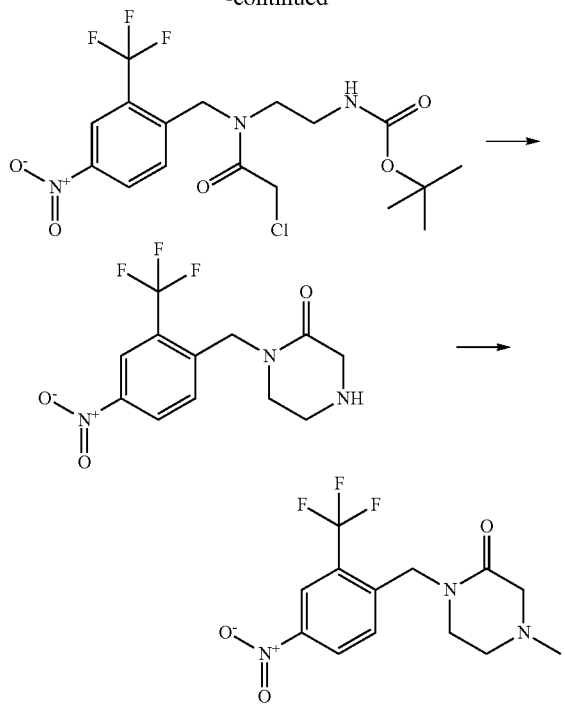

Step 1. {2-[(2-Chloro-acetyl)-(4-nitro-2-trifluoromethyl-benzyl)-amino]-ethyl}-carbamic acid tert-butyl ester To a solution of [2-(4-nitro-2-trifluoromethyl-benzylamino)-ethyl]-carbamic acid tert-butyl ester (0.4 g, 1.1 mmol) and TEA (0.23 mL, 1.67 mmol) in anhydrous THF (5 mL), cooled at 0-5° C., chloro-acetyl chloride (0.1 mL, 1.25 mmol) was added. The reaction was stirred at 0-5° C. for 1 h, then a saturated solution of NaHCO$_3$ was added and the mixture was extracted with EtOAc (2×15 mL). The organic phase was washed with brine, dried with anhydrous Na$_2$SO$_4$ and evaporated under vacuum to give a crude that was purified by flash column chromatography (DCM-MeOH 96:4). The title compound (0.32 g, 67%) was obtained as yellow oil.

$^1$H NMR (600 MHz, DMSO-d$_6$) δ ppm 1.34-1.37 (m, 9H) 1.94-1.94 (m, 0H) 3.16 (q, J=6.04 Hz, 2H) 3.45 (t, J=5.86 Hz, 2H) 4.57 (s, 2H) 4.76 (s, 2H) 7.05 (t, J=5.68 Hz, 1H) 7.59 (d, J=8.06 Hz, 1H) 8.42-8.49 (m, 2H).

Step 2. 1-(4-Nitro-2-trifluoromethyl-benzyl)-piperazin-2-one

To a solution of {2-[(2-chloro-acetyl)-(4-nitro-2-trifluoromethyl-benzyl)-amino]-ethyl}-carbamic acid tert-butyl ester (0.32 g, 0.73 mmol) in DCM (3 mL), TFA (0.5 mL) was added and the reaction was stirred at r.t. overnight. The suspension was evaporated under vacuum, MeCN (3 mL) and Cs$_2$CO$_3$ (0.27 g, 0.82 mmol) were added and the mixture was stirred at 50° C. for 1 h. The reaction was then poured in water (20 mL) and extracted with EtOAc (2×15 mL), the organic phase was washed with brine, dried with anhydrous Na$_2$SO$_4$ and evaporated under vacuum. The crude was purified by flash column chromatography (DCM/MeOH 90/10) to give the title compound (0.08 g, 32%) as white solid.

$^1$H NMR (600 MHz, DMSO-d$_6$) δ ppm 2.86 (d, J=14.10 Hz, 1H) 2.96 (t, J=5.40 Hz, 2H) 3.24-3.28 (m, 2H) 3.37 (s, 2H) 4.76 (s, 2H) 7.66 (d, J=8.61 Hz, 1H) 8.45 (d, J=2.20 Hz, 1H) 8.48 (dd, J=8.61, 2.20 Hz, 1H).

Step 3. 4-Methyl-1-(4-nitro-2-trifluoromethyl-benzyl)-piperazin-2-one

To a solution of 1-(4-nitro-2-trifluoromethyl-benzyl)-piperazin-2-one (0.07 g, 0.23 mmol) in MeOH (2 mL) 37% formaldehyde (0.1 mL, 1.2 mmol) and AcOH (0.05 mL, 0.94 mmol) were added. The mixture was stirred at r.t. for 15 min., then NaCNBH$_3$ (0.03 g, 0.47 mmol) was added. The reaction was stirred at r.t. for 1 h, then poured in a saturated solution of NaHCO$_3$ and extracted with EtOAc (2×15 mL). The organic phase was washed with brine, dried with anhydrous Na$_2$SO$_4$ and evaporated under vacuum to obtain the title compound (0.07 g, 95%) as white solid.

$^1$H NMR (600 MHz, DMSO-d$_6$) δ ppm 2.27 (s, 3H) 2.67 (t, J=5.49 Hz, 2H) 3.10 (s, 2H) 4.78 (s, 2H) 7.57 (d, J=8.61 Hz, 1H) 8.45 (d, J=2.38 Hz, 1H) 8.51 (dd, J=8.61, 2.20 Hz, 1H).

Preparation 4

(1-Methyl-piperidin-4-yl)-(4-nitro-2-trifluoromethyl-phenyl)-amine

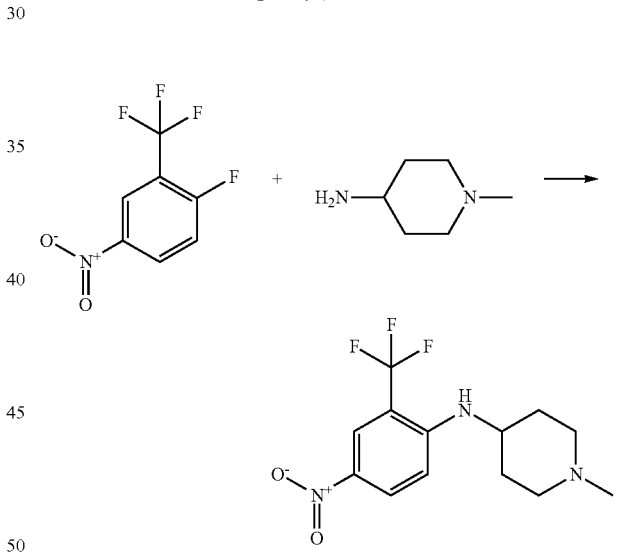

A mixture of 1-fluoro-4-nitro-2-trifluoromethyl-benzene (0.3 g, 1.43 mmol) and 1-methyl-piperidin-4-ylamine (0.73 mL, 5.72 mmol) in THF (7 mL) was stirred at r.t. for 4 h. The reaction was poured in a saturated solution of NaHCO$_3$ and extracted with EtOAc (2×15 mL). The organic phase was washed with brine, dried with anhydrous Na$_2$SO$_4$ and evaporated under vacuum to obtain the title compound (0.41 g, 95%) as yellow solid.

$^1$H NMR (600 MHz, DMSO-d$_6$) δ ppm 1.63-1.75 (m, 2H) 1.82 (d, J=11.17 Hz, 2H) 2.01-2.07 (m, 2H) 2.17 (s, 3H) 2.73 (d, J=11.54 Hz, 2H) 3.52-3.64 (m, 1H) 6.05 (d, J=7.88 Hz, 1H) 7.09 (d, J=9.16 Hz, 1H) 8.20-8.25 (m, 2H).

According to this same methodology, but employing suitable substituted derivatives, the following intermediates were prepared:

Methyl-(1-methyl-piperidin-4-yl)-(4-nitro-2-trifluoromethyl-phenyl)-amine $^1$H NMR (600 MHz, DMSO-d$_6$) δ ppm 1.60-1.66 (m, 2H) 1.72 (qd, J=11.90, 3.66 Hz, 2H) 1.87 (t, J=10.99 Hz, 2H) 2.14 (s, 2H) 2.76-2.83 (m, 5H) 3.23 (tt, J=11.17, 3.66 Hz, 1H) 7.53 (d, J=9.16 Hz, 1H) 8.33 (dd, J=9.25, 2.84 Hz, 1H) 8.38 (d, J=2.75 Hz, 1H).

1-Ethyl-4-(4-nitro-2-trifluoromethyl-phenyl)-piperazine $^1$H NMR (600 MHz, DMSO-d$_6$) δ ppm 1.03 (t, J=7.23 Hz, 3H) 2.39 (q, J=7.14 Hz, 2H) 3.11-3.17 (m, 4H) 7.54 (d, J=8.97 Hz, 1H) 8.36-8.42 (m, 2H).

Preparation 5

1-Methyl-4-(4-nitro-2-trifluoromethyl-phenoxy)-piperidine

To a solution of 1-methyl-piperidin-4-ol (0.4 g, 3.47 mmol) in anhydrous THF (10 mL), cooled at 0-5° C., NaH (0.14 g, 3.47 mmol) was added. The mixture was stirred at 0-5° C. for 30 min, then 1-fluoro-4-nitro-2-trifluoromethyl-benzene (0.33 mL, 2.31 mmol) was added. The reaction was stirred at r.t. for 1 h, then poured in water and extracted with EtOAc (2×20 mL). The organic phase was washed with brine, dried with Na$_2$SO$_4$ and evaporated under vacuum to obtain the title compound (0.65 g, 93%) as yellow oil.

$^1$H NMR (600 MHz, DMSO-d$_6$) δ ppm 1.67-1.79 (m, 2H) 1.95 (td, J=8.43, 4.03 Hz, 2H) 2.18 (s, 3H) 2.27-2.37 (m, 2H) 2.47 (br. s., 2H) 4.87 (br. s., 1H) 7.57 (d, J=9.34 Hz, 1H) 8.38 (d, J=2.75 Hz, 1H) 8.47 (dd, J=9.34, 2.93 Hz, 1H).

Preparation 6

3-(Isopropyl-dimethyl-silanyloxy)-1-(4-nitro-2-trifluoromethyl-benzyl)-piperidine

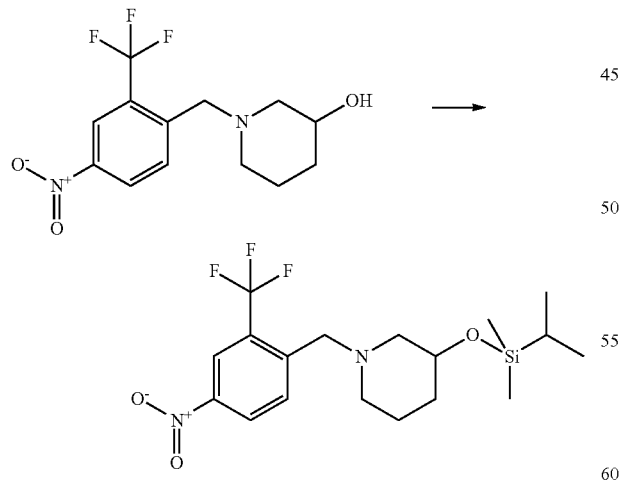

A mixture of 1-(4-nitro-2-trifluoromethyl-benzyl)-piperidin-3-ol (0.17 g, 0.55 mmol), imidazole (0.09 g, 1.37 mmol) and TBDMSCl (0.1 g, 0.66 mmol) in DMF (5 mL) was stirred at r.t. for 6 h. The reaction was poured in a saturated solution of NaHCO$_3$ and extracted with Et$_2$O (2×20 mL). The organic phase was washed with brine, dried with anhydrous Na$_2$SO$_4$ and evaporated under vacuum to give the title compound (0.19 g, 83%) as white solid.

$^1$H NMR (600 MHz, DMSO-d$_6$) δ ppm 0.00 (s, 3H) 0.01-0.03 (m, 3H) 0.83 (s, 9H) 1.13-1.25 (m, 1H) 1.41-1.50 (m, 1H) 1.66 (dt, J=13.55, 3.48 Hz, 1H) 1.78-1.84 (m, 1H) 1.98 (t, J=9.71 Hz, 1H) 2.01-2.06 (m, 1H) 2.56-2.62 (m, 1H) 2.75 (d, J=6.78 Hz, 1H) 3.68-3.80 (m, 2H) 8.09 (d, J=8.61 Hz, 1H) 8.41 (d, J=2.38 Hz, 1H) 8.49 (dd, J=8.61, 2.38 Hz, 1H).

According to this same methodology, but employing suitable substituted derivatives, the following intermediates were prepared:

4-(Isopropyl-dimethyl-silanyloxy)-1-(4-nitro-2-trifluoromethyl-benzyl)-piperidine $^1$H NMR (600 MHz, DMSO-d$_6$) δ ppm 0.02-0.05 (m, 6H) 0.86 (s, 9H) 1.43-1.53 (m, 2H) 1.68-1.79 (m, 2H) 2.24 (t, J=8.97 Hz, 2H) 2.56-2.66 (m, 2H) 3.70 (s, 2H) 3.76 (m, J=3.85 Hz, 1H) 8.10 (d, J=8.42 Hz, 1H) 8.40 (d, J=2.20 Hz, 1H) 8.50 (dd, J=8.52, 2.29 Hz, 1H).

[2-(Isopropyl-dimethyl-silanyloxy)-ethyl]-methyl-(4-nitro-2-trifluoromethyl-benzyl)-amine $^1$H NMR (600 MHz, DMSO-d$_6$) δ ppm 0.01-0.05 (m, 6H) 0.81-0.88 (m, 10H) 2.24 (s, 3H) 2.57-2.61 (m, 2H) 3.73 (t, J=5.77 Hz, 2H) 3.85 (s, 2H) 8.16 (d, J=8.61 Hz, 1H) 8.40 (d, J=2.20 Hz, 1H) 8.49 (dd, J=8.61, 2.20 Hz, 1H).

Preparation 7

(2,2-Dimethyl-[1,3]dioxolan-4-ylmethyl)-methyl-(4-nitro-2-trifluoromethyl-benzyl)-amine To a solution of 3-[methyl-(4-nitro-2-trifluoromethyl-benzyl)-amino]-propane-1,2-diol (0.23 g, 0.74 mmol) in DCM (5 mL), 2-methoxypropene (0.21 mL, 2.22 mmol) and PTSA (0.16 g, 0.81 mmol) were added. The mixture was stirred at r.t. for 2 h, then poured in a saturated solution of NaHCO$_3$ and extracted with DCM (2×10 mL). The organic phase was washed with brine, dried with anhydrous Na$_2$SO$_4$ and evaporated under vacuum to obtain the title compound (0.18 g, 70%) as yellow oil.

$^1$H NMR (600 MHz, DMSO-d$_6$) δ ppm 1.26 (s, 6H) 2.24 (s, 3H) 2.58 (d, J=5.86 Hz, 2H) 3.55 (dd, J=7.88, 6.96 Hz, 1H) 3.77-3.87 (m, 2H) 4.03 (dd, J=8.06, 6.41 Hz, 1H) 4.26 (t, J=6.23 Hz, 1H) 8.13 (d, J=8.79 Hz, 1H) 8.41 (d, J=2.20 Hz, 1H) 8.52 (dd, J=8.61, 2.20 Hz, 1H).

Preparation 8

Acetic acid 2-[4-(4-nitro-2-trifluoromethyl-benzyl)-piperazin-1-yl]-ethyl ester To a solution of 2-[4-(4-nitro-2-trifluoromethyl-benzyl)-piperazin-1-yl]-ethanol (0.30 g, 0.895 mmol) and TEA (0.18 mL, 1.34 mmol) in anhydrous THF (5 mL), cooled at 0-5° C., acetyl chloride (0.1 mL, 1.34 mmol) was added. The reaction was stirred at 0-5° C. for 1h, then was poured in a saturated solution of NaHCO$_3$ and extracted with EtOAc (2×15 mL). The organic phase was washed with brine, dried with anhydrous Na$_2$SO$_4$ and evaporated under vacuum to afford the title compound (0.31 g, 92%) as yellow oil.

¹H NMR (600 MHz, DMSO-d₆) δ ppm 2.00 (s, 3H) 2.53-2.56 (m, 2H) 3.72 (s, 2H) 4.09 (t, J=5.95 Hz, 2H) 8.08 (d, J=8.43 Hz, 1H) 8.41 (d, J=2.01 Hz, 1H) 8.51 (dd, J=8.61, 2.20 Hz, 1H).

Preparation 9

4-(4-Cyclopropylmethyl-piperazin-1-ylmethyl)-3-trifluoromethyl-phenylamine

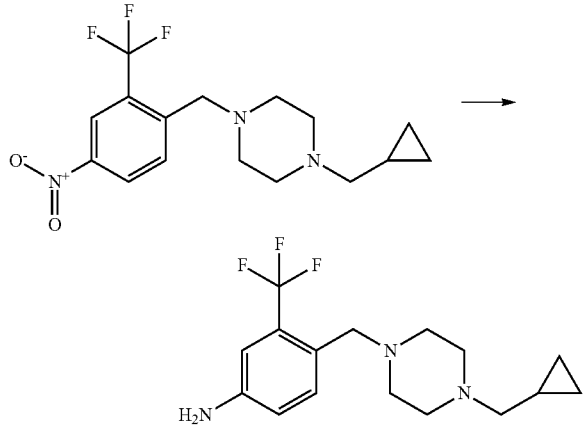

To a solution of 1-cyclopropylmethyl-4-(4-nitro-2-trifluoromethyl-benzyl)-piperazine (0.33 g, 0.954 mmol) in a mixture of EtOH (10 mL) and water (3 mL), Fe (0.27 g, 4.77 mmol) and NH₄Cl (0.51 g, 9.54 mmol) were added. The reaction was heated at 80° C. for 5 h, then was cooled at room temperature and filtered through celite washing with EtOH. The solution was evaporated under vacuum, the residue dissolved with EtOAc (20 mL) and washed with a saturated solution of NaHCO₃. The organic phase was washed with brine, dried with anhydrous Na₂SO₄ and evaporated under vacuum to give the title compound (0.28 g, 94%) as yellow solid.

¹H NMR (600 MHz, DMSO-d₆) δ ppm −0.01-0.07 (m, 2H) 0.39-0.47 (m, 2H) 0.72-0.84 (m, 1H) 2.14 (d, J=6.59 Hz, 2H) 3.38 (s, 1H) 5.41 (s, 1H) 6.75 (dd, J=8.42, 2.01 Hz, 1H) 6.85 (d, J=2.20 Hz, 1H) 7.29 (d, J=8.24 Hz, 1H).

According to this same methodology, but employing suitable substituted derivatives, the following intermediates were prepared:

4-(4-Methyl-piperazin-1-ylmethyl)-3-trifluoromethyl-phenylamine

¹H NMR (600 MHz, DMSO-d₆) δ ppm 2.14 (s, 4H) 2.17-2.41 (m, 9H) 3.38 (s, 2H) 5.41 (s, 2H) 6.74 (dd, J=8.33, 2.11 Hz, 1H) 6.85 (d, J=2.38 Hz, 1H) 7.28 (d, J=8.43 Hz, 1H).

4-(4-Ethyl-piperazin-1-ylmethyl)-3-trifluoromethyl-phenylamine

¹H NMR (401 MHz, DMSO-d₆) δ ppm 0.97 (t, J=7.20 Hz, 3H) 2.20-2.45 (m, 8H) 3.38 (s, 2H) 5.41 (s, 2H) 6.75 (dd, J=8.24, 2.26 Hz, 1H) 6.85 (d, J=2.32 Hz, 1H) 7.28 (d, J=8.42 Hz, 1H).

4-(4-Isopropyl-piperazin-1-ylmethyl)-3-trifluoromethyl-phenylamine

¹H NMR (600 MHz, DMSO-d₆) δ ppm 0.90-0.99 (m, 6H) 2.26-2.47 (m, 7H) 2.56-2.61 (m, 1H) 3.37 (s, 2H) 5.41 (s, 2H) 6.75 (dd, J=8.43, 2.20 Hz, 1H) 6.83-6.86 (m, 1H) 7.29 (d, J=8.24 Hz, 1H).

4-(4-Propyl-piperazin-1-ylmethyl)-3-trifluoromethyl-phenylamine

¹H NMR (600 MHz, DMSO-d₆) δ ppm 0.83 (t, J=7.42 Hz, 3H) 1.40 (sxt, J=7.36 Hz, 2H) 2.16-2.23 (m, 2H) 2.26-2.47 (m, 7H) 3.38 (s, 2H) 5.41 (s, 2H) 6.74 (dd, J=8.33, 2.11 Hz, 1H) 6.85 (d, J=2.38 Hz, 1H) 7.28 (d, J=8.24 Hz, 1H).

4-Piperidin-1-ylmethyl-3-trifluoromethyl-phenylamine

¹H NMR (600 MHz, DMSO-d₆) δ ppm 1.38 (d, J=4.95 Hz, 2H) 1.47 (quin, J=5.54 Hz, 5H) 2.28 (br. s., 4H) 5.39 (s, 2H) 6.75 (dd, J=8.61, 2.20 Hz, 1H) 6.81-6.85 (m, 1H) 7.30 (d, J=8.42 Hz, 1H).

4-Morpholin-4-ylmethyl-3-trifluoromethyl-phenylamine

¹H NMR (600 MHz, DMSO-d₆) δ ppm 2.31 (br. s., 4H) 3.39 (s, 2H) 3.55 (t, J=4.49 Hz, 4H) 5.44 (s, 2H) 6.75 (dd, J=8.24, 2.01 Hz, 1H) 6.86 (d, J=2.20 Hz, 1H) 7.30 (d, J=8.42 Hz, 1H).

[(S)-1-(4-Amino-2-trifluoromethyl-benzyl)-pyrrolidin-3-yl]-dimethyl-amine

¹H NMR (600 MHz, DMSO-d₆) δ ppm 1.58 (ddt, J=12.50, 8.65, 6.18, 6.18 Hz, 1H) 1.78-1.86 (m, 1H) 2.04-2.07 (m, 6H) 2.26 (dd, J=8.79, 6.59 Hz, 1H) 2.39-2.44 (m, 1H) 2.56-2.60 (m, 1H) 2.65-2.73 (m, 1H) 3.43-3.55 (m, 2H) 5.40 (s, 2H) 6.74 (dd, J=8.24, 1.83 Hz, 1H) 6.84 (d, J=2.38 Hz, 1H) 7.28 (d, J=8.42 Hz, 1H).

[(R)-1-(4-Amino-2-trifluoromethyl-benzyl)-pyrrolidin-3-yl]-dimethyl-amine

¹H NMR (600 MHz, DMSO-d₆) δ ppm 1.58 (ddt, J=12.50, 8.65, 6.18, 6.18 Hz, 1H) 1.78-1.86 (m, 1H) 2.04-2.07 (m, 6H) 2.26 (dd, J=8.79, 6.59 Hz, 1H) 2.39-2.44 (m, 1H) 2.56-2.60 (m, 1H) 2.65-2.73 (m, 1H) 3.43-3.55 (m, 2H) 5.40 (s, 2H) 6.74 (dd, J=8.24, 1.83 Hz, 1H) 6.84 (d, J=2.38 Hz, 1H) 7.28 (d, J=8.42 Hz, 1H).

4-(4-Methyl-[1,4]diazepan-1-ylmethyl)-3-trifluoromethyl-phenylamine

¹H NMR (600 MHz, DMSO-d₆) δ ppm 1.68 (quin, J=5.95 Hz, 2H) 2.23 (s, 4H) 3.51 (s, 2H) 5.39 (s, 2H) 6.75 (dd, J=8.24, 2.01 Hz, 1H) 6.84 (d, J=2.38 Hz, 1H) 7.34 (d, J=8.43 Hz, 1H).

4-(3-Pyrrolidin-1-yl-azetidin-1-ylmethyl)-3-trifluoromethyl-phenylamine (ESI) m/z 300 [(M+H)⁺]. HRMS (ESI) calculated for C₁₅H₂₁N₃F₃⁺ [(M+H)⁺] 300.1682. found 300.1678.

(4-Amino-2-trifluoromethyl-benzyl)-methyl-(1-methyl-piperidin-4-yl)-amine $^1$H NMR (600 MHz, DMSO-d$_6$) δ ppm 1.49 (qd, J=12.03, 3.85 Hz, 3H) 1.64 (d, J=11.90 Hz, 2H) 1.76-1.83 (m, 3H) 2.05 (s, 3H) 2.09-2.12 (m, 4H) 2.20-2.25 (m, 2H) 2.26-2.35 (m, 1H) 2.78 (d, J=11.36 Hz, 2H) 3.48 (s, 2H) 5.38 (s, 2H) 6.72-6.78 (m, 1H) 6.82-6.85 (m, 1H) 7.32 (d, J=8.42 Hz, 1H).

[1-(4-Amino-2-trifluoromethyl-benzyl)-piperidin-4-yl]-dimethyl-amine $^1$H NMR (600 MHz, DMSO-d$_6$) δ ppm 1.33 (qd, J=11.87, 3.75 Hz, 2H) 1.68 (d, J=12.64 Hz, 2H) 1.88 (t, J=10.81 Hz, 2H) 1.97-2.05 (m, 1H) 2.14 (s, 6H) 2.77 (d, J=11.72 Hz, 2H) 5.40 (s, 2H) 6.73-6.77 (m, 1H) 6.84 (d, J=2.38 Hz, 1H) 7.30 (d, J=8.24 Hz, 1H).

3-Trifluoromethyl-4-((2S,5R)-2,4,5-trimethyl-piperazin-1-ylmethyl)-phenylamine $^1$H NMR (600 MHz, DMSO-d$_6$) δ ppm 0.83 (d, J=6.23 Hz, 3H) 1.00 (d, J=6.04 Hz, 3H) 1.67 (t, J=10.71 Hz, 1H) 1.82-1.90 (m, 2H) 2.10 (s, 3H) 2.32 (dt, J=6.50, 3.34 Hz, 1H) 2.42 (dd, J=11.17, 2.56 Hz, 1H) 2.64 (dd, J=11.17, 2.56 Hz, 1H) 2.90 (d, J=13.92 Hz, 1H) 3.95 (d, J=14.10 Hz, 1H) 5.39 (s, 2H) 6.75 (dd, J=8.33, 1.92 Hz, 1H) 6.84 (d, J=2.20 Hz, 1H) 7.33 (d, J=8.24 Hz, 1H).

3-Trifluoromethyl-4-(3,4,5-trimethyl-piperazin-1-ylmethyl)-phenylamine $^1$H NMR (600 MHz, DMSO-d$_6$) δ ppm 0.93 (d, J=6.04 Hz, 6H) 1.73 (t, J=10.71 Hz, 2H) 2.05-2.10 (m, 1H) 2.12 (s, 3H) 2.57-2.61 (m, 2H) 5.42 (s, 2H) 6.74 (dd, J=8.33, 2.11 Hz, 1H) 6.85 (d, J=2.38 Hz, 1H) 7.28 (d, J=8.24 Hz, 1H).

4-(4-Amino-2-trifluoromethyl-benzyl)-piperazine-1-carboxylic acid tert-butyl ester $^1$H NMR (600 MHz, DMSO-d$_6$) δ ppm 1.35-1.40 (m, 9H) 2.22-2.30 (m, 4H) 3.20-3.31 (m, 4H) 3.38-3.43 (m, 2H) 5.44 (s, 2H) 6.75 (dd, J=8.24, 2.01 Hz, 1H) 6.86 (d, J=2.38 Hz, 1H) 7.30 (d, J=8.24 Hz, 1H).

4-(4-Amino-2-trifluoromethyl-benzyl)-piperazin-2-one $^1$H NMR (600 MHz, DMSO-d$_6$) δ ppm 2.87 (s, 2H) 3.09-3.15 (m, 2H) 3.46 (s, 2H) 5.48 (s, 2H) 6.76 (dd, J=8.33, 2.11 Hz, 1H) 6.87 (d, J=2.38 Hz, 1H) 7.29 (d, J=8.42 Hz, 1H) 7.71 (br. s., 1H).

4-[3-(Isopropyl-dimethyl-silanyloxy)-piperidin-1-ylmethyl]-3-trifluoromethyl-phenylamine $^1$H NMR (600 MHz, DMSO-d$_6$) δ ppm −0.04-0.00 (m, 6H) 0.79-0.83 (m, 9H) 1.36-1.47 (m, 1H) 1.57-1.66 (m, 1H) 1.72-1.82 (m, 2H) 1.88 (t, J=10.44 Hz, 1H) 2.58 (d, J=11.17 Hz, 1H) 2.70 (d, J=7.51 Hz, 1H) 3.36-3.42 (m, 2H) 3.62 (dq, J=9.25, 4.49 Hz, 1H) 5.40 (s, 2H) 6.74 (dd, J=8.33, 2.11 Hz, 1H) 6.85 (d, J=2.20 Hz, 1H) 7.30 (d, J=8.43 Hz, 1H).

4-[4-(Isopropyl-dimethyl-silanyloxy)-piperidin-1-ylmethyl]-3-trifluoromethyl-phenylamine $^1$H NMR (600 MHz, DMSO-d$_6$) δ ppm 0.84-0.86 (m, 11H) 1.38-1.46 (m, 3H) 1.68 (d, J=11.54 Hz, 3H) 2.04-2.14 (m, 3H) 2.55 (d, J=12.64 Hz, 3H) 3.70 (br. s., 1H) 5.40 (s, 2H) 6.75 (dd, J=8.33, 1.92 Hz, 1H) 6.84 (d, J=2.38 Hz, 1H) 7.30 (d, J=8.24 Hz, 1H).

4-({[2-(Isopropyl-dimethyl-silanyloxy)-ethyl]-methyl-amino}-methyl)-3-trifluoromethyl-phenylamine $^1$H NMR (600 MHz, DMSO-d$_6$) δ ppm 0.01 (s, 8H) 0.84 (s, 10H) 2.13-2.17 (m, 3H) 2.43-2.46 (m, 2H) 3.44-3.47 (m, 2H) 3.65-3.67 (m, 2H) 5.38-5.42 (m, 2H) 6.71-6.77 (m, 1H) 6.82-6.85 (m, 1H) 7.32-7.37 (m, 1H).

4-{[(2,2-Dimethyl-[1,3]dioxolan-4-ylmethyl)-methyl-amino]-methyl}-3-trifluoromethyl-phenylamine $^1$H NMR (600 MHz, DMSO-d$_6$) δ ppm 1.26 (s, 6H) 2.24 (s, 3H) 2.58 (d, J=5.86 Hz, 2H) 3.55 (dd, J=7.88, 6.96 Hz, 1H) 3.77-3.87 (m, 2H) 4.03 (dd, J=8.06, 6.41 Hz, 1H) 4.26 (t, J=6.23 Hz, 1H), 6.68-6.75 (m, 1H) 6.80-6.82 (m, 1H) 7.30-7.35 (m, 1H).

Acetic acid 2-[4-(4-amino-2-trifluoromethyl-benzyl)-piperazin-1-yl]-ethyl ester $^1$H NMR (600 MHz, DMSO-d$_6$) δ ppm 2.00 (s, 3H) 2.53-2.56 (m, 2H) 3.72 (s, 2H) 4.09 (t, J=5.95 Hz, 2H) 6.60-6.70 (m, 1H) 6.83-6.88 (m, 1H) 7.40-7.55 (m, 1H).

1-(4-Amino-2-trifluoromethyl-benzyl)-4-methyl-piperazin-2-one $^1$H NMR (600 MHz, DMSO-d$_6$) δ ppm 2.22 (s, 3H) 2.56 (t, J=5.49 Hz, 2H) 3.02 (s, 2H) 3.10 (t, J=5.59 Hz, 2H) 4.50 (s, 2H) 5.51 (s, 2H) 6.76 (dd, J=8.24, 2.01 Hz, 1H) 6.90 (d, J=2.20 Hz, 1H) 6.95 (d, J=8.24 Hz, 1H).

4-(4-Cyclopropyl-piperazin-1-ylmethyl)-3-trifluoromethyl-phenylamine $^1$H NMR (600 MHz, DMSO-d$_6$) δ ppm 0.25-0.28 (m, 2H) 0.35-0.39 (m, 2H) 1.57 (tt, J=6.62, 3.46 Hz, 1H) 2.09-2.40 (m, 5H) 5.42 (s, 2H) 6.75 (dd, J=8.15, 2.11 Hz, 1H) 6.85 (d, J=2.38 Hz, 1H) 7.29 (d, J=8.42 Hz, 1H).

N$^1$-(1-Methyl-piperidin-4-yl)-2-(trifluoromethyl)benzene-1,4-diamine $^1$H NMR (600 MHz, DMSO-d$_6$) δ ppm 1.31-1.43 (m, 2H) 1.84 (d, J=11.54 Hz, 2H) 2.01 (t, J=10.90 Hz, 2H) 2.15 (s, 3H) 2.60-2.69 (m, 2H) 3.14-3.25 (m, 1H) 3.69 (d, J=8.06 Hz, 1H) 4.70 (s, 2H) 6.70-6.75 (m, 3H).

N$^1$-Methyl-N$^1$-(1-methyl-piperidin-4-yl)-2-trifluoromethyl-benzene-1,4-diamine $^1$H NMR (600 MHz, DMSO-d$_6$) δ ppm 1.31 (qd, J=12.03, 3.66 Hz, 3H) 1.61 (br. s., 3H) 1.76 (t, J=11.26 Hz, 2H) 2.10 (s, 3H) 2.46 (s, 3H) 2.55-2.60 (m, 1H) 2.67-2.74 (m, 3H) 5.30 (s, 2H) 6.76 (dd, J=8.43, 2.56 Hz, 1H) 6.79 (d, J=2.56 Hz, 1H) 7.18 (d, J=8.61 Hz, 1H).

4-(4-Ethyl-piperazin-1-yl)-3-trifluoromethyl-phenylamine $^1$H NMR (600 MHz, DMSO-d$_6$) δ ppm 1.00 (t, J=7.23 Hz, 3H) 2.34 (q, J=7.14 Hz, 3H) 2.37-2.48 (m, 4H) 2.72 (t, J=4.40 Hz, 5H) 5.31 (s, 2H) 6.76 (dd, J=8.52, 2.47 Hz, 1H) 6.80 (d, J=2.56 Hz, 1H) 7.23 (d, J=8.61 Hz, 1H).

4-(1-Methyl-piperidin-4-yloxy)-3-trifluoromethyl-phenylamine $^1$H NMR (600 MHz, DMSO-d$_6$) δ ppm 1.52-1.66 (m, 2H) 1.79-1.88 (m, 2H) 2.10-2.19 (m, 5H) 2.51-2.57 (m, 3H) 4.27 (br. s., 1H) 5.00 (s, 2H) 6.75 (dd, J=8.79, 2.75 Hz, 1H) 6.80 (s, 1H) 6.97 (d, J=8.79 Hz, 1H).

4-(4-Ethyl-piperazin-1-ylmethyl)-3-fluoro-phenylamine $^1$H NMR (600 MHz, DMSO-d$_6$) δ ppm 0.96 (t, J=7.14 Hz, 3H) 5.27 (s, 2H) 6.27 (dd, J=12.73, 1.92 Hz, 1H) 6.32 (dd, J=8.06, 2.01 Hz, 1H) 6.93 (t, J=8.43 Hz, 1H).

2-(4-Ethyl-piperazin-1-ylmethyl)-5-trifluoromethyl-phenylamine $^1$H NMR (600 MHz, DMSO-d$_6$) δ ppm 0.97 (t, J=7.23 Hz, 3H) 2.09-2.48 (m, 11H) 3.42 (s, 2H) 5.70 (s, 2H) 6.77 (d, J=7.69 Hz, 1H) 6.91 (d, J=1.28 Hz, 1H) 7.14 (d, J=7.69 Hz, 1H).

4-Chloro-3-(4-ethyl-piperazin-1-ylmethyl)-phenylamine $^1$H NMR (600 MHz, DMSO-d$_6$) δ ppm 0.98 (t, J=7.23 Hz, 3H) 2.30 (q, J=7.14 Hz, 3H) 2.33-2.48 (m, 6H) 3.38 (s, 2H) 5.16 (s, 2H) 6.43 (dd, J=8.52, 2.84 Hz, 1H) 6.69 (d, J=2.75 Hz, 1H) 6.98 (d, J=8.43 Hz, 1H).

3-Bromo-4-(4-methyl-piperazin-1-ylmethyl)-phenylamine (ESI) m/z 285 [(M+H)$^+$]. HRMS (ESI) calculated for C$_{12}$H$_{19}$BrN$_3^+$[(M+H)$^+$] 285.1954. found 285.1955.

3-Cyclopropyl-4-(4-methyl-piperazin-1-ylmethyl)-phenylamine $^1$H NMR (600 MHz, DMSO-d$_6$) δ ppm 0.46-0.57 (m, 2H) 0.81-0.86 (m, 2H) 2.13 (s, 3H) 2.15-2.23 (m, 1H) 2.44-2.52 (m, 8H) 4.65 (s, 2H) 6.14 (d, J=8.43 Hz, 1H) 6.74 (dd, J=8.43, 2.38 Hz, 1H) 6.80 (d, J=2.56 Hz, 1H).

Preparation 10

4-Amino-N-(2-dimethylamino-ethyl)-benzamide

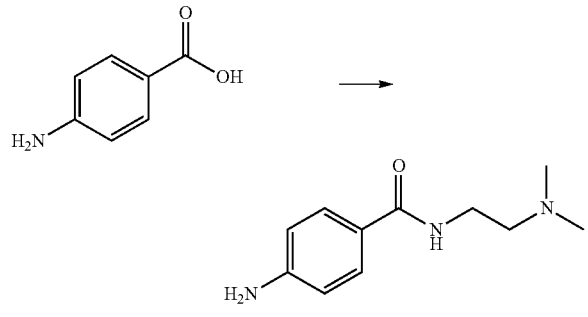

A mixture of 4-amino-benzoic acid (0.30 g, 2.19 mmol), N$^1$,N$^1$-dimethyl-ethane-1,2-diamine (0.29 mL, 2.63 mmol), TEA (0.58 mL, 4.38 mmol), EDAC (0.63 g, 3.29 mmol) and HOBT (0.45 g, 3.29 mmol) in anhydrous DMF (5 mL) was stirred at r.t. overnight. The reaction was poured in 2 N NaOH and extracted with EtOAc (4×15 mL). The organic phase was washed with brine, dried with Na$_2$SO$_4$ and evaporated under vacuum. The crude was purified by flash column chromatography (DCM-MeOH—NH$_3$ 90:10:1) to afford the title intermediate (0.18 g, 40%) as white solid.

$^1$H NMR (600 MHz, DMSO-d$_6$) δ ppm 2.15 (s, 6H) 2.34 (t, J=6.96 Hz, 2H) 5.55 (s, 2H) 6.49-6.54 (m, 2H) 7.53 (d, J=8.61 Hz, 2H) 7.84 (t, J=5.40 Hz, 1H).

According to this same methodology, but employing suitable substituted derivatives, the following intermediates were prepared:

(5-Amino-2-bromo-phenyl)-(4-ethyl-piperazin-1-yl)-methanone $^1$H NMR (600 MHz, DMSO-d$_6$) δ ppm 0.99 (t, J=7.14 Hz, 4H) 2.17-2.46 (m, 8H) 3.13 (t, J=6.04 Hz, 2H) 3.50-3.67 (m, 2H) 5.43 (s, 2H) 6.42 (d, J=2.56 Hz, 1H) 6.51 (dd, J=8.61, 2.75 Hz, 1H) 7.20 (d, J=8.79 Hz, 1H).

(4-Amino-phenyl)-(4-ethyl-piperazin-1-yl)-methanone $^1$H NMR (600 MHz, DMSO-d$_6$) δ ppm 0.92-1.08 (m, 3H) 2.20-2.41 (m, 6H) 3.47 (br. s., 4H) 5.47 (s, 2H) 6.49-6.56 (m, 2H) 7.10 (d, J=8.61 Hz, 2H).

(4-Amino-2-trifluoromethyl-phenyl)-(4-ethyl-piperazin-1-yl)-methanone $^1$H NMR (600 MHz, DMSO-d$_6$) δ ppm 0.98 (t, J=7.14 Hz, 3H) 2.11-2.43 (m, 6H) 3.00-3.20 (m, 2H) 3.56 (d, J=17.77 Hz, 2H) 5.76 (s, 2H) 6.78 (dd, J=8.33, 1.92 Hz, 1H) 6.88 (d, J=2.20 Hz, 1H) 7.00 (d, J=8.24 Hz, 1H).

Preparation 11

3-(4-Ethyl-piperazin-1-ylmethyl)-4-trifluoromethyl-phenylamine

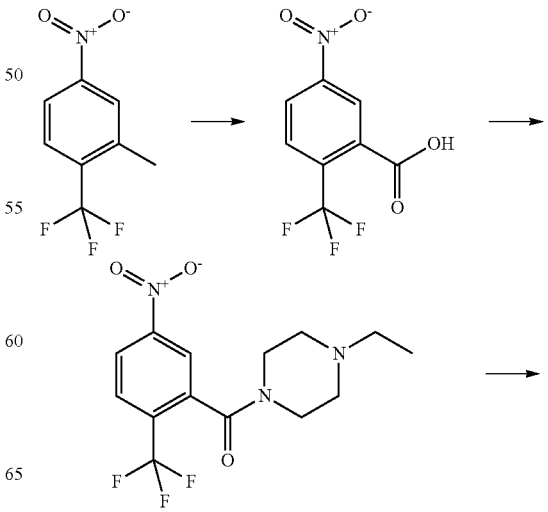

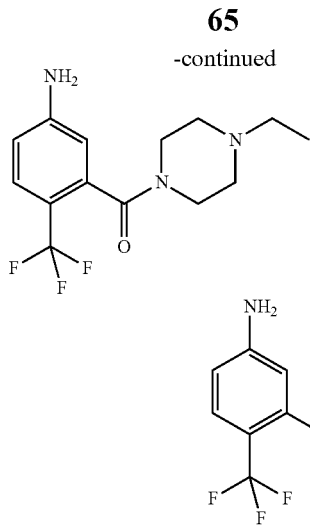

Step 1. 5-Nitro-2-trifluoromethyl-benzoic acid (According to the procedure described in *J. Med. Chem.* 1975, 18, 177). To a solution of 2-methyl-4-nitro-1-trifluoromethyl-benzene (0.50 g, 2.44 mmol) in AcOH (3.3 mL) a mixture of $CrO_3$ (0.61 g, 6.1 mmol) in AcOH (2.4 mL) and $H_2SO_4$ (0.5 mL) in water (1.5 mL) was added drop wise and heated at reflux for 1 h. After cooling to r.t., the mixture was poured in water and ice (40 mL) and treated with 2N NaOH (20 mL). The aqueous layer was extracted with toluene, taken to acidic pH with conc. HCl and extracted with DCM (4×15 mL). The organic layer was dried over anhydrous $Na_2SO_4$, filtered and concentrated under vacuum yielding the title product (0.26 g, 45%) that was used without further purification.

$^1$H NMR (600 MHz, DMSO-$d_6$) δ ppm 8.16 (d, J=8.61 Hz, 1H) 8.47-8.52 (m, 1H) 8.54 (d, J=2.01 Hz, 1H) 14.24 (bs, 1H).

Step 2. (4-Ethyl-piperazin-1-yl)-(5-nitro-2-trifluoromethyl-phenyl)-methanone The mixture of 5-nitro-2-trifluoromethyl-benzoic acid (0.24 g, 1.01 mmol), TBTU (0.39 g, 1.21 mmol), 1-ethyl-piperazine (0.26 mL, 2.02 mmol) and DIPEA (0.86 mL, 5.04 mmol) was let under stirring at r.t. for 2 h. After dilution with EtOAc, the organic layer was washed with a saturated solution of $NaHCO_3$, water and brine, dried over anhydrous $Na_2SO_4$, filtered and concentrated under vacuum. The product was purified by flash column chromatography (EtOAc/MeOH 95/5) and isolated as yellow oil (0.30 g, 90%).

$^1$H NMR (401 MHz, DMSO-$d_6$) δ ppm 0.99 (t, J=7.14 Hz, 3H) 2.10-2.20 (m, 1H) 2.25-2.41 (m, 1H) 2.53-2.58 (m, 1H) 3.01-3.12 (m, 1H) 3.14-3.24 (m, 1H) 3.49-3.62 (m, 1H) 3.72 (ddd, J=13.03, 6.26, 3.42 Hz, 1H) 8.13 (d, J=8.67 Hz, 1H) 8.32 (d, J=2.32 Hz, 1H) 8.42 (ddd, J=8.67, 2.32, 0.85 Hz, 1H).

According to this same methodology, but employing suitable substituted derivatives, the following intermediates were prepared:

(3-Amino-5-trifluoromethyl-phenyl)-(4-ethyl-piperazin-1-yl)-methanone $^1$H NMR (401 MHz, DMSO-$d_6$) δ ppm 1.00 (t, J=7.20 Hz, 3H) 2.24-2.45 (m, 6H) 3.35-3.69 (m, 4H) 5.78 (s, 2H) 6.69 (s, 1H) 6.76 (s, 1H) 6.89 (s, 1H).

(4-Amino-2-chloro-phenyl)-(4-ethyl-piperazin-1-yl)-methanone $^1$H NMR (600 MHz, DMSO-$d_6$) δ ppm 0.99 (t, J=7.14 Hz, 3H) 2.13-2.43 (m, 6H) 3.15 (br. s., 2H) 3.57 (br. s., 2H) 5.59 (s, 2H) 6.51 (dd, J=8.24, 2.20 Hz, 1H) 6.60 (d, J=2.20 Hz, 1H) 6.93 (d, J=8.24 Hz, 1H).

(5-Amino-2-chloro-phenyl)-(4-ethyl-piperazin-1-yl)-methanone $^1$H NMR (600 MHz, DMSO-$d_6$) δ ppm 1.00 (br. s., 3H) 2.12-2.47 (m, 6H) 3.02-3.21 (m, 2H) 3.43-3.75 (m, 2H) 5.41 (br. s., 2H) 6.43 (br. s., 1H) 6.58 (dd, J=8.70, 2.11 Hz, 1H) 7.08 (d, J=8.79 Hz, 1H).

(4-Ethyl-piperazin-1-yl)-(2-nitro-4-trifluoromethyl-phenyl)-methanone $^1$H NMR (600 MHz, DMSO-$d_6$) δ ppm 1.00 (t, J=7.14 Hz, 3H) 2.30 (br. s., 2H) 2.36 (q, J=7.20 Hz, 2H) 2.46 (br. s., 2H) 3.15-3.23 (m, 2H) 3.52-3.77 (m, 2H) 7.80 (d, J=7.88 Hz, 1H) 8.24 (dd, J=7.97, 1.19 Hz, 1H) 8.50 (s, 1H).

Step 3. (5-Amino-2-trifluoromethyl-phenyl)-(4-ethyl-piperazin-1-yl)-methanone A suspension of (4-ethyl-piperazin-1-yl)-(5-nitro-2-trifluoromethyl-phenyl)-methanone (0.30 g, 0.90 mmol), $HCOONH_4$ (0.28 g, 4.49 mmol) and 5% Pd/C (30 mg) in MeOH (20 mL) was refluxed for 3 h. After cooling at r.t., the mixture was filtered over a pad of celite rinsing thoroughly with MeOH. The removal of the solvent afforded a residue that was dissolved in DCM and washed with water. The organic layer was dried over anhydrous $Na_2SO_4$, filtered and concentrated under vacuum affording the product as yellow oil (0.28 g, 84%).

$^1$H NMR (401 MHz, DMSO-$d_6$) δ ppm 0.99 (t, J=7.20 Hz, 3H) 2.12-2.43 (m, 6H) 2.96-3.20 (m, 2H) 3.45-3.70 (m, 2H) 5.97 (s, 2H) 6.41 (d, J=2.20 Hz, 1H) 6.64 (dd, J=8.67, 1.59 Hz, 1H) 7.35 (d, J=8.67 Hz, 1H).

Step 4. 3-(4-Ethyl-piperazin-1-ylmethyl)-4-trifluoromethyl-phenylamine

A solution of (5-amino-2-trifluoromethyl-phenyl)-(4-ethyl-piperazin-1-yl)-methanone (0.22 g, 0.73 mmol) in dry THF (5 mL) was treated drop wise with 1 M $BH_3$·THF in THF (3.60 mL, 3.63 mmol) and let under stirring at r.t. overnight. The reaction was quenched with a solution of conc. HCl/water (1:1), let under stirring overnight and then taken to neutral pH by a portion wise addition of solid $Na_2CO_3$. The mixture was extracted with EtOAc (3×15 mL) and the organic layer was then washed with water and brine, dried over anhydrous $Na_2SO_4$, filtered and concentrated to reduce volume. The product was isolated by flash column chromatography (DCM-MeOH 98:2) as white solid (160 mg, 76%).

$^1$H NMR (401 MHz, DMSO-$d_6$) δ ppm 0.99 (t, J=7.20 Hz, 3H) 2.28-2.35 (m, 2H) 2.36-2.46 (m, 8H) 3.43 (s, 2H) 5.74 (s, 2H) 6.48 (dd, J=8.42, 2.32 Hz, 1H) 6.91 (d, J=2.20 Hz, 1H) 7.27 (d, J=8.54 Hz, 1H).

According to this same methodology, but employing suitable substituted derivatives, the following intermediates were prepared:

3-(4-Ethyl-piperazin-1-ylmethyl)-5-trifluoromethyl-phenylamine $^1$H NMR (600 MHz, DMSO-d$_6$) δ ppm 0.97 (t, J=7.14 Hz, 3H) 2.29 (q, J=7.20 Hz, 3H) 2.30-2.46 (m, 5H) 3.35 (s, 2H) 5.51 (s, 2H) 6.68 (s, 1H) 6.71 (s, 1H) 6.76 (s, 1H).

3-Chloro-4-(4-ethyl-piperazin-1-ylmethyl)-phenylamine $^1$H NMR (600 MHz, DMSO-d$_6$) δ ppm 0.97 (t, J=7.23 Hz, 3H) 1.94-2.48 (m, 10H) 3.35 (s, 2H) 5.26 (s, 2H) 6.47 (dd, J=8.24, 2.38 Hz, 1H) 6.58 (d, J=2.20 Hz, 1H) 7.02 (d, J=8.24 Hz, 1H).

(2-Amino-4-trifluoromethyl-phenyl)-(4-ethyl-piperazin-1-yl)-methanone (4-Ethyl-piperazin-1-yl)-(2-nitro-4-trifluoromethyl-phenyl)-methanone (0.44 g, 1.33 mmol) in a mixture of DCM (5 mL) and EtOAc (12.5 mL) was treated with SnCl$_2$.2H$_2$O (1.50 g, 6.64 mmol) at r.t. overnight. The solvent was removed under vacuum, the residue was suspended in DCM, neutralized with a saturated solution of NaHCO$_3$ and extracted with DCM (2×15 mL). The organic layer was dried over anhydrous Na$_2$SO$_4$, filtered and concentrated under vacuum. The product was purified by flash column chromatography (DCM-MeOH 95:5) and isolated as yellow oil (0.19 g, 47%).

$^1$H NMR (600 MHz, DMSO-d$_6$) δ ppm 0.94-1.03 (m, 4H) 2.38 (dd, J=3.66, 1.65 Hz, 9H) 3.39-3.81 (m, 4H) 5.56 (s, 2H) 6.83 (d, J=7.88 Hz, 1H) 7.02 (s, 1H) 7.16 (d, J=7.69 Hz, 1H).

Preparation 12

5-Ethynyl-2-fluoro-phenylamine

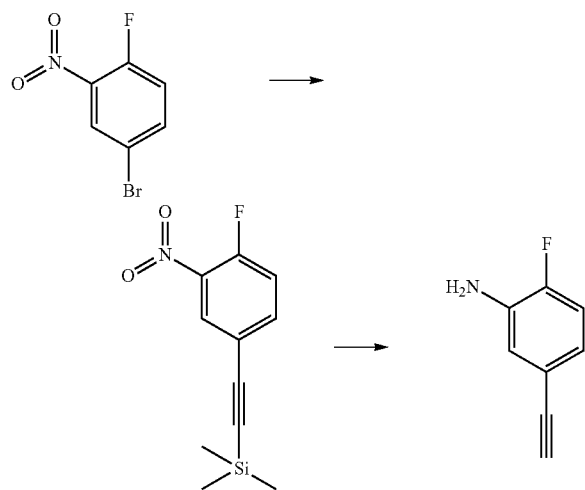

Step 1. (4-Fluoro-3-nitro-phenylethynyl)-trimethyl-silane

To a solution of 4-bromo-1-fluoro-2-nitro-benzene (0.50 g, 2.27 mmol), CuI (10% mol, 43 mg, 0.23 mmol) and PdCl$_2$(PPh$_3$)$_2$ (10% mol, 0.16 g, 0.23 mmol) in degassed THF (12 mL) kept under argon in a microwave vial, trimethylsilylacetilene (0.97 mL, 6.82 mmol) and TEA (3 mL) were added. The resulting mixture was degassed three times back filling with argon each time and then heated at 120° C. for 30 min under microwave irradiation. The solvent was removed under vacuum, the residue was dissolved in DCM and washed with NH$_3$, water and brine. The organic layer was dried over anhydrous Na$_2$SO$_4$, filtered and concentrated under vacuum. The crude product was used without further purification in the subsequent step.

$^1$H NMR (401 MHz, DMSO-d$_6$) δ ppm 0.24-0.27 (m, 9H) 7.61 (dd, J=11.17, 8.73 Hz, 1H) 7.88 (ddd, J=8.70, 4.36, 2.20 Hz, 1H) 8.17 (dd, J=7.14, 2.01 Hz, 1H).

Step 2. 5-Ethynyl-2-fluoro-phenylamine (4-Fluoro-3-nitro-phenylethynyl)-trimethyl-silane (2.27 mmol from the previous step) was dissolved in EtOH (30 mL) and treated with SnCl$_2$.2H$_2$O (3.10 g, 13.60 mmol) at r.t. for 5 h. The mixture was concentrated under vacuum, dissolved with EtOAc and washed with 2 N NaOH and water. The organic layer was dried over anhydrous Na$_2$SO$_4$, filtered and concentrated under vacuum yielding a residue that was treated with TBAF H$_2$O (0.76 g, 2.72 mmol) in THF (30 mL) and was let under stirring at r.t. for 30 min. The mixture was diluted with water and extracted with DCM (3×20 mL). The organic layer was dried over Na$_2$SO$_4$, filtered and concentrated. The product was purified by flash column chromatography (DCM/Hex 60/40) and isolated as solid (0.17 g, 55% over three steps).

$^1$H NMR (401 MHz, DMSO-d$_6$) δ ppm 3.97 (s, 1H) 5.28 (s, 2H) 6.61 (ddd, J=8.27, 4.42, 2.07 Hz, 1H) 6.85 (dd, J=8.67, 2.08 Hz, 1H) 6.97 (dd, J=11.53, 8.24 Hz, 1H).

Preparation 13

(2,4-Dimethoxy-benzyl)-(4-trifluoromethyl-cyclohexyl)-amine (cis and trans isomers)

A mixture of 4-trifluoromethyl-cyclohexanone (60 mg, 0.36 mmol) and 2,4-dimethoxy-benzylamine (78.5 mg, 0.47 mmol) in MeOH (0.5 mL) and AcOH (two drops) was let under stirring at r.t. for 1 h, then NaCNBH$_3$ (11 mg, 0.18 mmol) was added. After 2 h the solvent was removed, the crude dissolved with DCM and washed with water (2×10 mL). The organic layer was dried over anhydrous Na$_2$SO$_4$ and taken to dryness under vacuum. The purification by column chromatography (DCM/MeOH/7N NH$_3$ in MeOH 98/1/1) afforded (2,4-dimethoxy-benzyl)-(4-trifluoromethyl-cyclohexyl)-amine as cis (20 mg) and trans (40 mg) isomers.

(2,4-Dimethoxy-benzyl)-(4-trifluoromethyl-cyclohexyl)-amine (cis) isomer $^1$H NMR (500 MHz, CHLOROFORM-d) δ ppm 1.50-1.59 (m, 2H) 1.65-1.85 (m, 4H) 1.92 (d, J=12.02 Hz, 2H) 2.01-2.11 (m, 1H) 2.92 (br. s., 1H) 3.78 (s, 2H) 3.81 (s, 3H) 3.84 (s, 3H) 6.33-6.56 (m, 2H) 7.17-7.28 (m, 1H).

(2,4-Dimethoxy-benzyl)-(4-trifluoromethyl-cyclohexyl)-amine (trans) isomer $^1$H NMR (500 MHz, CHLOROFORM-d) δ ppm 1.15-1.38 (m, 4H) 1.92-2.03 (m, 3H) 2.07 (d, J=12.02 Hz, 2H)

2.47 (t, J=3.51 Hz, 3H) 3.78 (s, 2H) 3.80 (s, 3H) 3.83 (s, 3H) 6.42-6.47 (m, 2H) 7.15 (d, J=8.01 Hz, 1H).

(S)-1-Phenyl-2-pyrrolidin-1-yl-ethylamine dihydrochloride

Synthesized according to the procedure described in EP 2 070 928.

(S)-2-Morpholin-4-yl-1-phenyl-ethylamine dihydrochloride

Synthesized according to the procedure described in WO 2004/104007.

Preparation 14

3-Bromo-N-[4-(4-ethyl-piperazin-1-ylmethyl)-3-trifluoromethyl-phenyl]-5-fluoro-benzamide

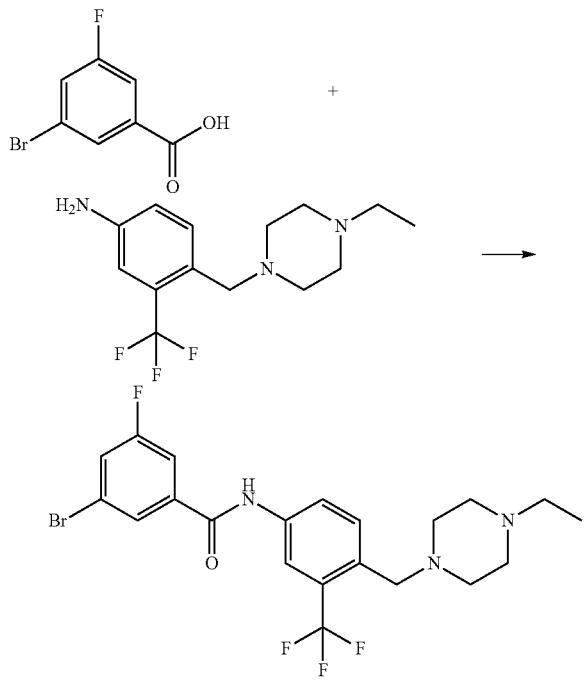

A mixture of (4-Trifluoromethyl-phenyl)-acetic acid (0.14 g, 0.63 mmol), 4-(4-ethyl-piperazin-1-ylmethyl)-3-trifluoromethyl-phenylamine (0.15 g, 0.52 mmol), TBTU (0.20 g, 0.63 mmol) and DIPEA (0.11 mL, 0.63 mmol) in anhydrous DMF (3 mL) was stirred at r.t. overnight. The reaction was poured in a saturated solution of NaHCO$_3$ and extracted with EtOAc (2×15 mL), the organic phase was washed with brine, dried with anhydrous Na$_2$SO$_4$ and evaporated under vacuum. The crude was purified by flash column chromatography (DCM/MeOH 97/3) to obtain the title compound (0.25 g, 80%) as white solid.

$^1$H NMR (600 MHz, DMSO-d$_6$) δ ppm 0.99 (br. s., 3H) 2.17-2.48 (m, 8H) 3.58 (s, 2H) 7.73 (d, J=8.42 Hz, 1H) 7.81 (dd, J=9.25, 1.37 Hz, 1H) 7.85 (dt, J=7.97, 2.06 Hz, 1H) 8.00-8.05 (m, 2H) 8.17 (d, J=2.02 Hz, 1H) 10.61 (s, 1H).

According to this same methodology, but employing suitable substituted derivatives, the following intermediates were prepared:

N-[4-(4-Ethyl-piperazin-1-ylmethyl)-3-trifluoromethyl-phenyl]-3-iodo-benzamide (ESI) m/z 518 [(M+H)$^+$]. HRMS (ESI) calculated for C$_{21}$H$_{24}$F$_{31}$N$_3$O$^+$ [(M+H)$^+$] 518.3265. found 518.3278.

N-[4-(4-Ethyl-piperazin-1-ylmethyl)-3-trifluoromethyl-phenyl]-3-iodo-4-methyl-benzamide $^1$H NMR (600 MHz, DMSO-d$_6$) δ ppm 0.98 (t, J=7.14 Hz, 3H) 2.29-2.35 (m, 3H) 2.36-2.43 (m, 5H) 2.45 (s, 3H) 3.56 (s, 2H) 7.47-7.52 (m, 1H) 7.71 (d, J=8.54 Hz, 1H) 7.91 (dd, J=7.93, 1.83 Hz, 1H) 8.03 (dd, J=8.48, 2.01 Hz, 1H) 8.17 (d, J=2.20 Hz, 1H) 8.42 (d, J=1.83 Hz, 1H) 10.47 (s, 1H).

5-Bromo-thiophene-2-carboxylic acid [4-(4-ethyl-piperazin-1-ylmethyl)-3-trifluoromethyl-phenyl]-amide $^1$H NMR (600 MHz, DMSO-d$_6$) δ ppm 0.98 (t, J=7.14 Hz, 3H) 2.29-2.31 (m, 2H) 2.39 (d, J=1.47 Hz, 7H) 3.56 (s, 2H) 7.39 (d, J=4.03 Hz, 1H) 7.71 (d, J=8.43 Hz, 1H) 7.86 (d, J=4.03 Hz, 1H) 7.95 (dd, J=8.61, 1.65 Hz, 1H) 8.10 (d, J=2.01 Hz, 1H) 10.52 (s, 1H).

2-Bromo-thiazole-5-carboxylic acid [4-(4-ethyl-piperazin-1-ylmethyl)-3-trifluoromethyl-phenyl]-amide $^1$H NMR (600 MHz, DMSO-d$_6$) δ ppm 0.98 (t, J=7.23 Hz, 3H) 2.30 (q, J=7.27 Hz, 3H) 2.33-2.47 (m, 6H) 3.56 (s, 2H) 7.73 (d, J=8.61 Hz, 1H) 7.91-7.97 (m, 1H) 8.08 (d, J=2.01 Hz, 1H) 8.45 (s, 1H) 10.73 (s, 1H).

5-Bromo-N-[4-(4-ethyl-piperazin-1-ylmethyl)-3-trifluoromethyl-phenyl]-nicotinamide $^1$H NMR (600 MHz, DMSO-d$_6$) δ ppm 0.98 (t, J=7.14 Hz, 3H) 2.31 (q, J=7.14 Hz, 3H) 2.39 (dd, J=3.57, 1.74 Hz, 6H) 3.57 (s, 2H) 7.74 (d, J=8.61 Hz, 1H) 8.00 (dd, J=8.42, 1.83 Hz, 1H) 8.17 (d, J=2.01 Hz, 1H) 8.55-8.56 (m, 1H) 8.93 (d, J=2.01 Hz, 1H) 9.07 (d, J=1.65 Hz, 1H) 10.73 (s, 1H).

3-Bromo-N-[4-(4-ethyl-piperazin-1-ylmethyl)-3-trifluoromethyl-phenyl]-2-fluoro-benzamide (ESI) m/z 489 [(M+H)$^+$]. HRMS (ESI) calculated for C$_{21}$H$_{23}$BrF$_4$N$_3$O$^+$ [(M+H)$^+$] 489.3165. found 489.3166.

2-(3-Ethynyl-phenoxy)-N-phenyl-acetamide $^1$H NMR (600 MHz, DMSO-d$_6$) δ ppm 4.18 (s, 1H) 4.72 (s, 2H) 7.02-7.12 (m, 4H) 7.28-7.36 (m, 3H) 7.60-7.66 (m, 2H) 10.05 (s, 1H).

N-(3-Ethynyl-phenyl)-3-phenyl-propionamide $^1$H NMR (600 MHz, DMSO-d$_6$) δ ppm 2.63 (t, J=7.75 Hz, 2H) 2.87-2.95 (m, 2H) 4.15 (s, 1H) 7.13 (dt, J=7.66, 1.24 Hz, 1H) 7.16-7.21 (m, 1H) 7.22-7.33 (m, 5H) 7.53 (dd, J=8.24, 1.04 Hz, 1H) 7.75-7.79 (m, 1H) 9.99 (s, 1H).

(1S,2S)-2-Phenyl-cyclopropanecarboxylic acid (3-ethynyl-phenyl)-amide $^1$H NMR (600 MHz, DMSO-d$_6$) δ ppm 1.36-1.53 (m, 2H) 2.01-2.09 (m, 1H) 2.34-2.42 (m, 1H) 4.15 (s, 1H) 7.14 (dt, J=7.69, 1.22 Hz, 1H) 7.17-7.23 (m, 3H) 7.27-7.35 (m, 3H) 7.53-7.57 (m, 1H) 7.79 (t, J=1.71 Hz, 1H) 10.32 (s, 1H).

N-(3-Iodo-benzyl)-benzamide $^1$H NMR (600 MHz, DMSO-d$_6$) δ ppm 4.44 (d, J=5.86 Hz, 2H) 7.14 (t, J=7.69 Hz, 1H) 7.34 (d, J=7.33 Hz, 1H) 7.45-7.50 (m, 2H) 7.53-7.57 (m, 1H) 7.61 (d, J=7.88 Hz, 1H) 7.69 (s, 1H) 7.86-7.90 (m, 2H) 9.05 (t, J=5.59 Hz, 1H).

3-(3-Iodo-phenyl)-N-phenyl-propionamide $^1$H NMR (600 MHz, DMSO-d$_6$) δ ppm 2.61 (t, J=7.69 Hz, 2H) 2.84-2.89 (m, 2H) 7.02 (s, 1H) 7.09 (s, 1H) 7.25-7.31 (m, 3H) 7.55 (d, J=8.06 Hz, 3H) 7.65 (s, 1H) 9.87 (s, 1H).

N-(3-Ethynyl-phenyl)-2-(3-trifluoromethyl-phenyl)-acetamide $^1$H NMR (600 MHz, DMSO-d$_6$) δ ppm 3.79 (s, 2H) 4.15 (s, 1H) 7.15 (d, J=7.51 Hz, 1H) 7.32 (t, J=7.88 Hz, 1H) 7.52-7.66 (m, 4H) 7.69 (s, 1H) 7.78 (s, 1H) 10.32 (s, 1H).

N-(3-Ethynyl-phenyl)-3-(4-trifluoromethyl-phenyl)-propionamide $^1$H NMR (600 MHz, DMSO-d$_6$) δ ppm 2.65-2.70 (m, 2H) 3.00 (t, J=7.51 Hz, 2H) 4.14 (s, 1H) 7.13 (d, J=7.69 Hz, 1H) 7.30 (t, J=7.97 Hz, 1H) 7.47-7.49 (m, 2H) 7.52 (d, J=9.16 Hz, 1H) 7.64 (d, J=8.06 Hz, 2H) 7.76 (s, 1H) 10.03 (s, 1H).

N-(3-Ethynyl-phenyl)-3-(3-trifluoromethyl-phenyl)-propionamide $^1$H NMR (600 MHz, DMSO-d$_6$) δ ppm 2.67 (t, J=7.69 Hz, 2H) 3.01 (t, J=7.60 Hz, 2H) 4.14 (s, 1H) 7.13 (d, J=7.51 Hz, 1H) 7.30 (t, J=7.88 Hz, 1H) 7.49-7.59 (m, 4H) 7.61 (s, 1H) 7.75 (s, 1H) 10.01 (s, 1H).

3-Ethynyl-N-(3-trifluoromethyl-benzyl)-benzamide $^1$H NMR (600 MHz, DMSO-d$_6$) δ ppm 4.27 (s, 1H) 4.56 (d, J=5.86 Hz, 2H) 7.51 (t, J=7.88 Hz, 1H) 7.56-7.59 (m, 1H) 7.60-7.69 (m, 4H) 7.91 (dt, J=7.97, 1.42 Hz, 1H) 7.99 (t, J=1.37 Hz, 1H) 9.22 (t, J=5.77 Hz, 1H).

N-[4-(4-Ethyl-piperazin-1-ylmethyl)-3-trifluoromethyl-phenyl]-2-(3-iodo-phenyl)-acetamide $^1$H NMR (600 MHz, DMSO-d$_6$) δ ppm 0.97 (t, J=7.14 Hz, 3H) 2.27-2.32 (m, 2H) 2.32-2.46 (m, 4H) 3.52 (s, 2H) 3.64 (s, 2H) 7.14 (t, J=7.78 Hz, 1H) 7.34 (d, J=7.69 Hz, 1H) 7.64 (dd, J=16.48, 8.24 Hz, 2H) 7.72 (s, 1H) 7.76 (d, J=8.43 Hz, 1H) 8.03 (d, J=1.83 Hz, 1H) 10.44 (s, 1H).

N-[4-(4-Ethyl-piperazin-1-ylmethyl)-3-trifluoromethyl-phenyl]-2-(4-iodo-phenyl)-acetamide $^1$H NMR (600 MHz, DMSO-d$_6$) δ ppm 0.97 (t, J=7.14 Hz, 3H) 2.18-2.46 (m, 10H) 3.52 (s, 2H) 3.62 (s, 2H) 7.14 (d, J=8.43 Hz, 2H) 7.65 (d, J=8.61 Hz, 1H) 7.66-7.70 (m, 2H) 7.75 (dd, J=8.52, 1.92 Hz, 1H) 8.02 (d, J=2.02 Hz, 1H) 10.44 (s, 1H).

N-[3-(4-Ethyl-piperazin-1-ylmethyl)-4-trifluoromethyl-phenyl]-2-(3-iodo-phenyl)-acetamide $^1$H NMR (600 MHz, DMSO-d$_6$) δ ppm 0.99 (t, J=7.14 Hz, 3H) 2.23-2.48 (m, 9H) 3.55 (s, 2H) 3.66 (s, 2H) 7.15 (t, J=7.78 Hz, 1H) 7.48 (d, J=7.69 Hz, 1H) 7.61 (dd, J=16.48, 8.24 Hz, 2H) 7.70 (s, 1H) 7.78 (d, J=8.43 Hz, 1H) 8.10 (d, J=1.83 Hz, 1H) 10.49 (s, 1H).

N-[4-(4-Ethyl-piperazin-1-ylmethyl)-3-fluoro-phenyl]-2-(3-iodo-phenyl)-acetamide $^1$H NMR (600 MHz, DMSO-d$_6$) δ ppm 0.96 (t, J=7.14 Hz, 3H) 2.11-2.47 (m, 9H) 3.43 (s, 2H) 3.62 (s, 2H) 7.14 (t, J=7.69 Hz, 1H) 7.22-7.26 (m, 1H) 7.27-7.31 (m, 1H) 7.34 (d, J=7.88 Hz, 1H) 7.54 (dd, J=12.45, 1.47 Hz, 1H) 7.62 (d, J=7.88 Hz, 1H) 7.71 (s, 1H) 10.33 (s, 1H).

N-(2-Dimethylamino-ethyl)-4-[2-(3-iodo-phenyl)-acetylamino]-benzamide $^1$H NMR (600 MHz, DMSO-d$_6$) δ ppm 2.17 (s, 6H) 2.35-2.43 (m, 2H) 3.65 (s, 2H) 7.14 (t, J=7.69 Hz, 1H) 7.35 (d, J=7.69 Hz, 1H) 7.62 (s, 1H) 7.64 (d, J=8.79 Hz, 2H) 7.78 (d, J=8.79 Hz, 2H) 8.23 (t, J=5.59 Hz, 1H) 10.36 (s, 1H).

2-(5-Bromo-pyridin-3-yl)-N-[4-(4-ethyl-piperazin-1-ylmethyl)-3-trifluoromethyl-phenyl]-acetamide $^1$H NMR (600 MHz, DMSO-d$_6$) δ ppm 0.97 (t, J=7.14 Hz, 3H) 2.30 (q, J=7.14 Hz, 3H) 2.33-2.46 (m, 6H) 3.53 (s, 2H) 3.76 (s, 2H) 7.66 (d, J=8.43 Hz, 1H) 7.75 (dd, J=8.52, 1.74 Hz, 1H) 7.99-8.05 (m, 2H) 8.50 (d, J=1.65 Hz, 1H) 8.61 (d, J=2.20 Hz, 1H) 10.51 (s, 1H).

N-[2-(4-Ethyl-piperazin-1-ylmethyl)-5-trifluoromethyl-phenyl]-2-(3-iodo-phenyl)-acetamide $^1$H NMR (600 MHz, DMSO-d$_6$) δ ppm 0.98 (t, J=7.14 Hz, 3H) 1.95-2.46 (m, 9H) 3.61 (s, 2H) 3.72 (s, 2H) 7.17 (t, J=7.78 Hz, 1H) 7.38 (t, J=8.70 Hz, 2H) 7.45 (d, J=7.69 Hz, 1H) 7.66 (d, J=7.88 Hz, 1H) 7.74 (s, 1H) 8.40 (s, 1H) 10.84 (br. s., 1H).

N-[4-Chloro-3-(4-ethyl-piperazine-1-carbonyl)-phenyl]-2-(3-iodo-phenyl)-acetamide $^1$H NMR (600 MHz, DMSO-d$_6$) δ ppm 0.99 (t, J=7.14 Hz, 3H) 2.33-2.36 (m, 3H) 3.12 (t, J=5.04 Hz, 2H) 3.54-3.70 (m, 4H) 7.14 (t, J=7.69 Hz, 1H) 7.34 (d, J=7.88 Hz, 1H) 7.44 (d, J=8.79 Hz, 1H) 7.56 (dd, J=8.79, 2.56 Hz, 1H) 7.61-7.64 (m, 2H) 7.71 (s, 1H) 10.40 (s, 1H).

2-(4-Bromo-thiophen-2-yl)-N-[4-(4-ethyl-piperazin-1-ylmethyl)-3-trifluoromethyl-phenyl]-acetamide $^1$H NMR (600 MHz, DMSO-d$_6$) δ ppm 0.97 (t, J=7.14 Hz, 3H) 2.16-2.43 (m, 9H) 3.53 (s, 2H) 3.91 (s, 2H) 7.00 (d, J=1.28 Hz, 1H) 7.53 (d, J=1.47 Hz, 1H) 7.67 (d, J=8.43 Hz, 1H) 7.75 (dd, J=8.61, 1.83 Hz, 1H) 8.02 (d, J=1.83 Hz, 1H) 10.50 (s, 1H).

2-(2-Bromo-pyridin-4-yl)-N-[4-(4-ethyl-piperazin-1-ylmethyl)-3-trifluoromethyl-phenyl]-acetamide $^1$H NMR (600 MHz, DMSO-d$_6$) δ ppm 0.97 (t, J=7.14 Hz, 3H) 2.17-2.45 (m, 10H) 3.53 (s, 2H) 3.76 (s, 2H) 7.40 (dd, J=5.04, 1.19 Hz, 1H) 7.62 (s, 1H) 7.67 (d, J=8.43 Hz, 1H) 7.75 (dd, J=8.52, 1.74 Hz, 1H) 8.02 (d, J=2.01 Hz, 1H) 8.33 (d, J=5.13 Hz, 1H) 10.52 (s, 1H).

2-(5-Bromo-thiophen-2-yl)-N-[4-(4-ethyl-piperazin-1-ylmethyl)-3-trifluoromethyl-phenyl]-acetamide $^1$H NMR (600 MHz, DMSO-d$_6$) δ ppm 0.97 (t, J=7.14 Hz, 3H) 2.30 (q, J=7.14 Hz, 2H) 2.33-2.45 (m, 8H) 3.53 (s, 1H) 3.89 (s, 1H) 6.83 (d, J=3.85 Hz, 1H) 7.07 (d, J=3.66 Hz, 1H) 7.67 (d, J=8.61 Hz, 1H) 7.75 (dd, J=8.52, 1.74 Hz, 1H) 8.02 (d, J=2.01 Hz, 1H) 10.50 (s, 1H).

N-[4-Chloro-3-(4-ethyl-piperazin-1-ylmethyl)-phenyl]-2-(3-iodo-phenyl)-acetamide $^1$H NMR (600 MHz, DMSO-d$_6$) δ ppm 0.98 (t, J=7.14 Hz, 3H) 2.18-2.49 (m, 10H) 3.46-3.51 (m, 2H) 3.62 (s, 2H) 7.14 (t, J=7.78 Hz, 1H) 7.28-7.36 (m, 2H) 7.58 (dd, J=8.52, 2.11 Hz, 1H) 7.62 (d, J=7.69 Hz, 1H) 7.67 (br. s., 1H) 7.71 (s, 1H) 10.27 (s, 1H).

N-[4-Bromo-3-(4-ethyl-piperazine-1-carbonyl)-phenyl]-2-(3-iodo-phenyl)-acetamide $^1$H NMR (600 MHz, DMSO-d$_6$) δ ppm 0.96-1.02 (m, 3H) 2.19-2.47 (m, 6H) 3.11 (t, J=5.04 Hz, 2H) 3.53-3.70 (m, 4H) 7.14 (t, J=7.78 Hz, 1H) 7.34 (d, J=7.69 Hz, 1H) 7.47-7.50 (m, 1H) 7.57-7.61 (m, 2H) 7.62 (d, J=7.88 Hz, 1H) 7.71 (s, 1H) 10.39 (s, 1H).

2-(3-Iodo-phenyl)-N-[4-(4-methyl-[1,4]diazepan-1-ylmethyl)-3-trifluoromethyl-phenyl]-acetamide $^1$H NMR (600 MHz, DMSO-d$_6$) δ ppm 1.71 (quin, J=5.95 Hz, 2H) 2.25 (s, 3H) 2.55-2.65 (m, 7H) 3.64 (s, 2H) 3.66-3.68 (m, 2H) 7.14 (t, J=7.78 Hz, 1H) 7.35 (d, J=7.88 Hz, 1H) 7.63 (d, J=7.88 Hz, 1H) 7.68-7.74 (m, 2H) 7.75-7.78 (m, 1H) 8.02 (d, J=1.83 Hz, 1H) 10.44 (s, 1H).

N-[4-((S)-3-Dimethylamino-pyrrolidin-1-ylmethyl)-3-trifluoromethyl-phenyl]-2-(3-iodo-phenyl)-acetamide $^1$H NMR (600 MHz, DMSO-d$_6$) δ ppm 1.56-1.67 (m, 1H) 1.84 (dt, J=8.38, 5.24 Hz, 1H) 2.05-2.09 (m, 6H) 2.31 (dd, J=8.70, 6.69 Hz, 1H) 2.46 (td, J=8.75, 5.77 Hz, 1H) 2.53-2.58 (m, 1H) 2.60-2.63 (m, 1H) 2.69-2.75 (m, 1H) 3.58-3.63 (m, 1H) 3.64 (s, 2H) 3.65-3.68 (m, 1H) 7.14 (t, J=7.78 Hz, 1H) 7.35 (d, J=7.88 Hz, 1H) 7.59-7.66 (m, 2H) 7.72 (s, 1H) 7.76 (dd, J=8.61, 1.83 Hz, 1H) 8.02 (d, J=2.01 Hz, 1H) 10.44 (s, 1H).

N-[4-(4-Ethyl-piperazine-1-carbonyl)-phenyl]-2-(3-iodo-phenyl)-acetamide $^1$H NMR (600 MHz, DMSO-d$_6$) δ ppm 0.99 (t, J=7.14 Hz, 3H) 2.18-2.46 (m, 6H) 3.34-3.62 (m, 4H) 3.64 (s, 2H) 7.14 (t, J=7.78 Hz, 1H) 7.30-7.37 (m, 3H) 7.59-7.66 (m, 3H) 7.73 (s, 1H) 10.33 (s, 1H).

N-[3-Cyclopropyl-4-(4-ethyl-piperazin-1-ylmethyl)-phenyl]-2-(3-iodo-phenyl)-acetamide $^1$H NMR (600 MHz, DMSO-d$_6$) δ ppm 0.49-0.56 (m, 2H) 0.86-0.94 (m, 2H) 2.12-2.19 (m, 4H) 2.19-2.47 (m, 8H) 3.51 (s, 2H) 3.56-3.59 (m, 2H) 7.07-7.20 (m, 3H) 7.30-7.37 (m, 2H) 7.61 (d, J=8.06 Hz, 1H) 7.70 (s, 1H) 10.03 (s, 1H).

2-(3-Bromo-4-fluoro-phenyl)-N-[4-(4-ethyl-piperazin-1-ylmethyl)-3-trifluoromethyl-phenyl]-acetamide $^1$H NMR (600 MHz, DMSO-d$_6$) δ ppm 0.97 (t, J=7.14 Hz, 3H) 2.22-2.48 (m, 10H) 3.52 (s, 2H) 3.69 (s, 2H) 7.28-7.39 (m, 2H) 7.63-7.68 (m, 2H) 7.74-7.77 (m, 1H) 8.03 (d, J=1.83 Hz, 1H) 10.44 (s, 1H).

2-(3-Bromo-2-fluoro-phenyl)-N-[4-(4-ethyl-piperazin-1-ylmethyl)-3-trifluoromethyl-phenyl]-acetamide $^1$H NMR (600 MHz, DMSO-d$_6$) δ ppm 0.97 (t, J=7.14 Hz, 3H) 2.20-2.47 (m, 9H) 3.53 (s, 2H) 3.81 (s, 2H) 7.14 (t, J=7.78 Hz, 1H) 7.38-7.42 (m, 1H) 7.60-7.63 (m, 1H) 7.66 (d, J=8.42 Hz, 1H) 7.75 (dd, J=8.52, 1.74 Hz, 1H) 8.04 (d, J=1.83 Hz, 1H) 10.52 (s, 1H).

N-[4-((R)-3-Dimethylamino-pyrrolidin-1-ylmethyl)-3-trifluoromethyl-phenyl]-2-(3-iodo-phenyl)-acetamide $^1$H NMR (600 MHz, DMSO-d$_6$) δ ppm 1.56-1.70 (m, 1H) 1.81-1.91 (m, 1H) 2.08 (s, 6H) 2.28-2.35 (m, 1H) 2.44-2.47 (m, 1H) 2.53-2.58 (m, 1H) 2.60-2.64 (m, 1H) 2.73 (br. s., 1H) 3.57-3.69 (m, 2H) 3.64 (s, 2H) 7.14 (t, J=7.69 Hz, 1H) 7.35 (d, J=7.88 Hz, 1H) 7.61-7.66 (m, 2H) 7.72 (s, 1H) 7.76 (dd, J=8.43, 1.83 Hz, 1H) 8.02 (d, J=2.01 Hz, 1H) 10.44 (s, 1H).

2-(3-Iodo-phenyl)-N-[4-(4-isopropyl-piperazin-1-ylmethyl)-3-trifluoromethyl-phenyl]-acetamide $^1$H NMR (600 MHz, DMSO-d$_6$) δ ppm 0.95 (d, J=6.23 Hz, 6H) 2.25-2.48 (m, 8H) 2.56-2.62 (m, 1H) 3.51 (s, 2H) 3.64 (s, 2H) 7.14 (t, J=7.78 Hz, 1H) 7.35 (d, J=7.88 Hz, 1H) 7.63 (d, J=7.88 Hz, 1H) 7.66 (d, J=8.61 Hz, 1H) 7.72 (s, 1H) 7.74-7.78 (m, 1H) 8.03 (d, J=2.01 Hz, 1H) 10.44 (s, 1H).

2-(3-Iodo-phenyl)-N-(4-piperidin-1-ylmethyl-3-trifluoromethyl-phenyl)-acetamide $^1$H NMR (600 MHz, DMSO-d$_6$) δ ppm 1.39 (br. s., 2H) 1.49 (quin, J=5.49 Hz, 4H) 2.31 (br. s., 4H) 3.48 (s, 2H) 3.64 (s, 2H) 7.14 (t, J=7.69 Hz, 1H) 7.35 (d, J=7.69 Hz, 1H) 7.63 (d, J=7.88 Hz, 1H) 7.67 (d, J=8.61 Hz, 1H) 7.72 (s, 1H) 7.75-7.77 (m, 1H) 8.02 (d, J=2.01 Hz, 1H) 10.43 (s, 1H).

2-(3-Iodo-phenyl)-N-(4-morpholin-4-ylmethyl-3-trifluoromethyl-phenyl)-acetamide $^1$H NMR (600 MHz, DMSO-d$_6$) δ ppm 2.35 (br. s., 4H) 3.54 (s, 2H) 3.57 (t, J=4.40 Hz, 4H) 3.64 (s, 2H) 7.14 (t, J=7.78 Hz, 1H) 7.34 (d, J=7.88 Hz, 1H) 7.63 (d, J=8.43 Hz, 1H) 7.68 (d, J=8.61 Hz, 1H) 7.72 (s, 1H) 7.77 (dd, J=8.52, 1.74 Hz, 1H) 8.04 (d, J=2.01 Hz, 1H) 10.45 (s, 1H).

2-(3-Iodo-phenyl)-N-[4-(4-methyl-piperazin-1-ylmethyl)-3-trifluoromethyl-phenyl]-acetamide $^1$H NMR (600 MHz, DMSO-d$_6$) δ ppm 2.15 (s, 3H) 2.19-2.47 (m, 8H) 3.52 (s, 2H) 3.64 (s, 2H) 7.14 (t, J=7.78 Hz, 1H) 7.34 (d, J=7.69 Hz, 1H) 7.64 (dd, J=13.55, 8.24 Hz, 1H) 7.72 (s, 1H) 7.76 (dd, J=8.42, 1.47 Hz, 1H) 8.03 (d, J=1.83 Hz, 1H) 10.44 (s, 1H).

2-(3-Iodo-phenyl)-N-[4-(3-pyrrolidin-1-yl-azetidin-1-ylmethyl)-3-trifluoromethyl-phenyl]-acetamide $^1$H NMR (600 MHz, DMSO-d$_6$) δ ppm 1.67 (br. s., 4H) 2.31-2.38 (m, 4H) 2.92 (t, J=6.23 Hz, 2H) 3.04 (br. s., 1H) 3.36 (t, J=6.87 Hz, 2H) 3.64 (s, 2H) 3.65 (s, 2H) 7.14 (t, J=7.78 Hz, 1H) 7.34 (d, J=7.51 Hz, 1H) 7.58 (d, J=8.61 Hz, 1H) 7.63 (d, J=7.69 Hz, 1H) 7.72 (s, 1H) 7.74-7.77 (m, 1H) 8.01 (d, J=2.01 Hz, 1H) 10.43 (s, 1H).

2-(3-Iodo-phenyl)-N-[4-(4-propyl-piperazin-1-ylmethyl)-3-trifluoromethyl-phenyl]-acetamide $^1$H NMR (600 MHz, DMSO-d$_6$) δ ppm 0.83 (t, J=7.42 Hz, 3H) 1.37-1.46 (m, 2H) 2.21 (t, J=7.14 Hz, 2H) 2.26-2.47 (m, 7H) 3.52 (s, 2H) 3.64 (s, 2H) 7.14 (t, J=7.78 Hz, 1H) 7.34 (d, J=7.51 Hz, 1H) 7.63 (d, J=7.88 Hz, 1H) 7.66 (s, 1H) 7.72 (s, 1H) 7.76 (dd, J=8.43, 1.83 Hz, 1H) 8.03 (d, J=2.01 Hz, 1H) 10.44 (s, 1H).

N-[4-(4-Ethyl-piperazine-1-carbonyl)-3-trifluoromethyl-phenyl]-2-(3-iodo-phenyl)-acetamide $^1$H NMR (600 MHz, DMSO-d$_6$) δ ppm 7.15 (t, J=7.78 Hz, 1H) 7.36 (d, J=7.51 Hz, 1H) 7.42-7.57 (m, 1H) 7.64 (d, J=7.88 Hz, 1H) 7.74 (s, 1H) 7.88 (d, J=2.38 Hz, 1H) 8.13 (br. s., 1H) 10.37 (br. s., 1H) 10.73 (br. s., 1H).

2-(3-Iodo-phenyl)-N-(4-{[methyl-(1-methyl-piperidin-4-yl)-amino]-methyl}-3-trifluoromethyl-phenyl)-acetamide $^1$H NMR (600 MHz, DMSO-d$_6$) δ ppm 1.48 (qd, J=11.91, 3.48 Hz, 2H) 1.64 (d, J=11.90 Hz, 2H) 1.81 (br. s., 2H) 2.06 (s, 3H) 2.11 (s, 3H) 2.77 (d, J=10.44 Hz, 2H) 3.59-3.60 (m, 2H) 3.60-3.62 (m, 2H) 7.11 (t, J=7.69 Hz, 1H) 7.32 (d, J=7.69 Hz, 1H) 7.60 (d, J=7.88 Hz, 1H) 7.63-7.68 (m, 1H) 7.69 (s, 1H) 7.71-7.73 (m, 1H) 7.99 (d, J=2.01 Hz, 1H) 10.40 (s, 1H).

N-[4-(4-Dimethylamino-piperidin-1-ylmethyl)-3-trifluoromethyl-phenyl]-2-(3-iodo-phenyl)-acetamide $^1$H NMR (600 MHz, DMSO-d$_6$) δ ppm 1.32-1.42 (m, 2H) 1.69 (d, J=11.72 Hz, 2H) 1.95 (t, J=10.81 Hz, 2H) 2.00-2.10 (m, 1H) 2.16 (s, 7H) 2.78 (d, J=11.72 Hz, 2H) 3.50 (s, 2H) 3.64 (s, 2H) 7.14 (t, J=7.78 Hz, 1H) 7.35 (d, J=7.69 Hz, 1H) 7.63 (d, J=7.88 Hz, 1H) 7.67 (d, J=8.43 Hz, 1H) 7.72 (s, 1H) 7.76 (dd, J=8.43, 1.83 Hz, 1H) 8.03 (d, J=2.01 Hz, 1H) 10.44 (s, 1H).

N-[3-Bromo-4-(4-ethyl-piperazin-1-ylmethyl)-phenyl]-2-(3-iodo-phenyl)-acetamide (ESI) m/z 543 [(M+H)$^+$]. HRMS (ESI) calculated for C$_{21}$H$_{26}$BrIN$_3$O$^+$ [(M+H)$^+$] 543.2512. found 543.2519.

Acetic acid 2-(4-{4-[2-(3-iodo-phenyl)-acetylamino]-2-trifluoromethyl-benzyl}-piperazin-1-yl)-ethyl ester $^1$H NMR (600 MHz, DMSO-d$_6$) δ ppm 1.99 (s, 3H) 2.27-2.47 (m, 8H) 2.51-2.53 (m, 2H) 3.52 (s, 2H) 3.64 (s, 2H) 4.08 (t, J=5.95 Hz, 2H) 7.14 (t, J=7.69 Hz, 1H) 7.34 (d, J=7.69 Hz, 1H) 7.63 (d, J=7.88 Hz, 1H) 7.65 (d, J=8.61 Hz, 1H) 7.72 (s, 1H) 7.76 (dd, J=8.61, 1.83 Hz, 1H) 8.03 (d, J=2.01 Hz, 1H) 10.44 (s, 1H).

N-[4-(4-Cyclopropylmethyl-piperazin-1-ylmethyl)-3-trifluoromethyl-phenyl]-2-(3-iodo-phenyl)-acetamide $^1$H NMR (600 MHz, DMSO-d$_6$) δ ppm 0.06 (d, J=3.30 Hz, 2H) 0.45 (br. s., 2H) 0.81 (br. s., 1H) 2.17 (d, J=5.86 Hz, 2H) 2.26-2.48 (m, 7H) 3.53 (br. s., 2H) 3.64 (s, 2H) 7.12-7.16 (m, 1H) 7.34 (d, J=7.33 Hz, 1H) 7.64 (dd, J=16.94, 8.15 Hz, 2H) 7.72 (s, 1H) 7.76 (d, J=8.61 Hz, 1H) 8.03 (d, J=1.83 Hz, 1H) 10.45 (s, 1H).

2-(3-Iodo-phenyl)-N-[4-(1-methyl-piperidin-4-yloxy)-3-trifluoromethyl-phenyl]-acetamide $^1$H NMR (600 MHz, DMSO-d$_6$) δ ppm 1.58-1.71 (m, 2H) 1.88 (td, J=8.01, 3.57 Hz, 2H) 2.15 (s, 3H) 2.22 (br. s., 2H) 3.60 (s, 2H) 4.53 (br. s., 1H) 7.14 (t, J=7.78 Hz, 1H) 7.26 (d, J=9.16 Hz, 1H) 7.34 (d, J=7.69 Hz, 1H) 7.62 (d, J=7.88 Hz, 1H) 7.69-7.72 (m, 2H) 7.91 (d, J=2.56 Hz, 1H) 10.26 (s, 1H).

N-[4-(4-Ethyl-piperazin-1-yl)-3-trifluoromethyl-phenyl]-2-(3-iodo-phenyl)-acetamide $^1$H NMR (600 MHz, DMSO-d$_6$) δ ppm 1.02 (t, J=6.87 Hz, 3H) 2.29-2.48 (m, 4H) 2.82 (br. s., 4H) 3.63 (s, 2H) 7.14 (t, J=7.78 Hz, 1H) 7.34 (d, J=7.69 Hz, 1H) 7.52 (d, J=8.79 Hz, 1H) 7.62 (d, J=7.88 Hz, 1H) 7.71 (s, 1H) 7.77 (d, J=8.42 Hz, 1H) 7.98 (d, J=2.38 Hz, 1H) 10.39 (s, 1H).

N-[4-(4-Cyclopropyl-piperazin-1-ylmethyl)-3-trifluoromethyl-phenyl]-2-(3-iodo-phenyl)-acetamide $^1$H NMR (600 MHz, DMSO-d$_6$) δ ppm 0.25-0.28 (m, 2H) 0.34-0.41 (m, 2H) 1.55-1.63 (m, 1H) 2.32 (br. s., 4H) 2.69 (s, 2H) 3.51 (s, 2H) 3.64 (s, 2H) 7.14 (t, J=7.78 Hz, 1H) 7.35 (d, J=8.24 Hz, 1H) 7.63 (d, J=7.88 Hz, 1H) 7.66 (d, J=8.42 Hz, 1H) 7.72 (s, 1H) 7.76 (dd, J=8.33, 1.74 Hz, 1H) 8.03 (d, J=2.01 Hz, 1H) 10.44 (s, 1H).

2-(3-Iodo-phenyl)-N-[4-(1-methyl-piperidin-4-ylamino)-3-trifluoromethyl-phenyl]-acetamide $^1$H NMR (600 MHz, DMSO-d$_6$) δ ppm 1.43-1.53 (m, 2H) 1.86 (d, J=10.99 Hz, 2H) 2.00-2.07 (m, 2H) 2.16 (s, 3H) 2.65 (d, J=10.44 Hz, 2H) 3.34-3.38 (m, 1H) 3.56 (s, 2H) 4.37 (d, J=7.69 Hz, 1H) 6.89 (d, J=9.16 Hz, 1H) 7.13 (t, J=7.78 Hz, 1H) 7.33 (d, J=7.69 Hz, 1H) 7.54 (dd, J=9.07, 2.29 Hz, 1H) 7.62 (d, J=7.88 Hz, 1H) 7.70 (s, 1H) 7.78 (d, J=2.38 Hz, 1H) 10.06 (s, 1H).

2-(3-Iodo-phenyl)-N-{4-[methyl-(1-methyl-piperidin-4-yl)-amino]-3-trifluoromethyl-phenyl}-acetamide $^1$H NMR (600 MHz, DMSO-d$_6$) δ ppm 1.36 (qd, J=11.97, 3.48 Hz, 2H) 1.62 (d, J=12.27 Hz, 2H) 1.77 (t, J=11.54 Hz, 2H) 2.08-2.12 (m, 2H) 2.16 (s, 3H) 2.68-2.74 (m, 3H) 3.62 (s, 2H) 7.14 (t, J=7.78 Hz, 1H) 7.34 (d, J=7.51 Hz, 1H) 7.51 (d, J=8.79 Hz, 1H) 7.62 (d, J=8.06 Hz, 1H) 7.72 (s, 1H) 7.77 (dd, J=8.70, 2.29 Hz, 1H) 7.96 (d, J=2.38 Hz, 1H) 10.39 (s, 1H).

N-(4-Chloro-3-trifluoromethyl-phenyl)-2-(3-iodo-phenyl)-acetamide $^1$H NMR (600 MHz, DMSO-d$_6$) δ ppm 3.66 (s, 2H) 7.14 (t, J=7.69 Hz, 1H) 7.34 (d, J=8.06 Hz, 1H) 7.63 (d, J=8.06 Hz, 1H) 7.66 (d, J=8.79 Hz, 1H) 7.72 (s, 1H) 7.83 (dd, J=8.79, 2.38 Hz, 1H) 8.18 (d, J=2.38 Hz, 1H) 10.60 (s, 1H).

N-(5-Bromo-pyridin-3-yl)-2-(3-iodo-phenyl)-acetamide $^1$H NMR (600 MHz, DMSO-d$_6$) δ ppm 3.69 (s, 2H) 7.15 (t, J=7.78 Hz, 1H) 7.34 (d, J=8.06 Hz, 1H) 7.63 (d, J=8.06 Hz, 1H) 7.72 (s, 1H) 8.36-8.37 (m, 1H) 8.39 (d, J=2.01 Hz, 1H) 8.65 (d, J=2.01 Hz, 1H) 10.57 (s, 1H)

2-(3-Iodo-phenyl)-N-[3-trifluoromethyl-4-((2S,5R)-2,4,5-trimethyl-piperazin-1-ylmethyl)-phenyl]-acetamide $^1$H NMR (600 MHz, DMSO-d$_6$) δ ppm 0.84 (d, J=6.04 Hz, 3H) 0.99 (d, J=6.23 Hz, 3H) 1.76 (t, J=10.71 Hz, 1H) 1.85-1.97 (m, 2H) 2.11 (s, 3H) 2.32-2.45 (m, 2H) 2.66 (d, J=10.62 Hz, 1H) 3.09 (d, J=14.84 Hz, 1H) 3.64 (s, 2H) 4.04 (d, J=14.47 Hz, 1H) 7.14 (t, J=7.78 Hz, 1H) 7.35 (d, J=7.69 Hz, 1H) 7.63 (d, J=7.88 Hz, 1H) 7.68-7.81 (m, 3H) 8.03 (d, J=1.47 Hz, 1H) 10.43 (s, 1H).

2-(3-Iodo-phenyl)-N-[3-trifluoromethyl-4-(3,4,5-trimethyl-piperazin-1-ylmethyl)-phenyl]-acetamide $^1$H NMR (600 MHz, DMSO-d$_6$) δ ppm 0.94 (br. s., 6H) 1.80 (br. s., 2H) 2.02-2.25 (m, 5H) 2.56-2.65 (m, 2H) 3.43-3.50 (m, 2H) 3.64 (s, 2H) 7.14 (t, J=7.69 Hz, 1H) 7.35 (d, J=8.06 Hz, 1H) 7.63 (d, J=7.88 Hz, 1H) 7.66 (s, 1H) 7.72 (s, 1H) 7.77 (d, J=7.88 Hz, 1H) 8.03 (d, J=1.83 Hz, 1H) 10.45 (s, 1H).

4-{4-[2-(3-Iodo-phenyl)-acetylamino]-2-trifluoromethyl-benzyl}-piperazine-1-carboxylic acid tert-butyl ester $^1$H NMR (600 MHz, DMSO-d$_6$) δ ppm 1.39 (s, 10H) 2.31 (t, J=4.85 Hz, 4H) 3.55 (s, 2H) 3.64 (s, 2H) 7.14 (t, J=7.78 Hz, 1H) 7.35 (d, J=7.69 Hz, 1H) 7.63 (d, J=7.88 Hz, 1H) 7.67 (d, J=8.61 Hz, 1H) 7.72 (s, 1H) 7.77 (dd, J=8.61, 1.83 Hz, 1H) 8.03 (d, J=2.02 Hz, 1H) 10.45 (s, 1H).

2-(3-Iodo-phenyl)-N-[4-(3-oxo-piperazin-1-ylmethyl)-3-trifluoromethyl-phenyl]-acetamide $^1$H NMR (600 MHz, DMSO-d$_6$) δ ppm 2.52-2.55 (m, 2H) 2.94 (s, 2H) 3.14 (t, J=4.30 Hz, 2H) 3.61 (s, 2H) 3.64 (s, 2H) 7.14 (t, J=7.78 Hz, 1H) 7.35 (d, J=7.69 Hz, 1H) 7.63 (d, J=8.06 Hz, 1H) 7.67 (d, J=8.42 Hz, 1H) 7.72 (s, 1H) 7.74 (s, 1H) 7.78 (dd, J=8.43, 1.65 Hz, 1H) 8.05 (d, J=1.83 Hz, 1H) 10.47 (s, 1H).

N-{4-[3-(tert-Butyl-dimethyl-silanyloxy)-piperidin-1-ylmethyl]-3-trifluoromethyl-phenyl}-2-(3-iodo-phenyl)-acetamide $^1$H NMR (600 MHz, DMSO-d$_6$) δ ppm −0.03 (s, 3H) −0.01-0.00 (m, 3H) 0.82 (s, 9H) 1.13-1.22 (m, 1H) 1.43 (d, J=11.72 Hz, 1H) 1.61-1.67 (m, 1H) 1.79 (dd, J=11.91, 3.66 Hz, 1H) 1.86 (t, J=9.71 Hz, 1H) 1.96 (br. s., 1H) 2.58 (d, J=11.17 Hz, 1H) 2.69 (d, J=6.96 Hz, 1H) 3.54 (s, 2H) 3.64 (s, 2H) 3.66 (d, J=4.58 Hz, 1H) 7.12-7.16 (m, 1H) 7.32-7.37 (m, 1H) 7.61-7.65 (m, 1H) 7.65-7.68 (m, 1H) 7.71-7.73 (m, 1H) 7.74-7.76 (m, 1H) 8.03 (d, J=2.02 Hz, 1H) 10.44 (s, 1H).

N-Cyclopropyl-2-(3-iodo-phenyl)-acetamide $^1$H NMR (600 MHz, DMSO-d$_6$) δ ppm 0.36-0.40 (m, 2H) 0.58-0.63 (m, 2H) 2.58-2.62 (m, 1H) 7.10 (t, J=7.78 Hz, 1H) 7.24 (d, J=8.24 Hz, 1H) 7.58 (d, J=7.88 Hz, 1H) 7.62 (s, 1H) 8.13 (br. s., 1H).

2-(3-Iodo-phenyl)-N-[4-(4-methyl-2-oxo-piperazin-1-ylmethyl)-3-trifluoromethyl-phenyl]-acetamide $^1$H NMR (600 MHz, DMSO-d$_6$) δ ppm 2.24 (s, 3H) 2.58-2.63 (m, 2H) 3.06 (s, 2H) 3.18 (t, J=5.40 Hz, 2H) 3.65 (s, 2H) 4.62 (s, 2H) 7.14 (t, J=7.78 Hz, 1H) 7.24 (d, J=8.61 Hz, 1H) 7.34 (d, J=7.69 Hz, 1H) 7.63 (d, J=7.88 Hz, 1H) 7.72 (s, 1H) 7.74-7.77 (m, 1H) 8.10 (d, J=1.83 Hz, 1H) 10.49 (s, 1H).

N-{4-[4-(tert-Butyl-dimethyl-silanyloxy)-piperidin-1-ylmethyl]-3-trifluoromethyl-phenyl}-2-(3-iodo-phenyl)-acetamide $^1$H NMR (600 MHz, DMSO-d$_6$) δ ppm 0.01-0.04 (m, 6H) 0.83-0.89 (m, 9H) 1.40-1.48 (m, 2H) 1.70 (d, J=10.99 Hz, 2H) 2.15 (t, J=9.07 Hz, 2H) 2.55-2.61 (m, 2H) 3.50 (s, 2H) 3.64 (s, 2H) 3.72 (br. s., 1H) 7.14 (t, J=7.78 Hz, 1H) 7.35 (d, J=7.69 Hz, 1H) 7.63 (d, J=8.06 Hz, 1H) 7.67 (d, J=8.43 Hz, 1H) 7.72 (s, 1H) 7.76 (d, J=8.61 Hz, 1H) 8.02 (d, J=1.65 Hz, 1H) 10.44 (s, 1H).

N-[4-({[2-(tert-Butyl-dimethyl-silanyloxy)-ethyl]-methyl-amino}-methyl)-3-trifluoromethyl-phenyl]-2-(3-iodo-phenyl)-acetamide (ESI) m/z 607 [(M+H)$^+$]. HRMS (ESI) calculated for C$_{25}$H$_{35}$F$_3$IN$_2$O$_2$Si$^+$ [(M+H)$^+$] 607.5348. found 607.5344.

2-(3-Bromo-4-fluoro-phenyl)-N-[4-(4-methyl-piperazin-1-ylmethyl)-3-trifluoromethyl-phenyl]-acetamide $^1$H NMR (600 MHz, DMSO-d$_6$) δ ppm 2.15 (s, 3H) 2.19-2.47 (m, 7H) 3.52 (s, 2H) 3.69 (s, 2H) 7.25-7.40 (m, 2H) 7.62-7.67 (m, 2H) 7.76 (dd, J=8.42, 1.65 Hz, 1H) 8.03 (d, J=1.83 Hz, 1H) 10.44 (s, 1H).

N-(4-{[(2,2-Dimethyl-[1,3]dioxolan-4-ylmethyl)-methyl-amino]-methyl}-3-trifluoromethyl-phenyl)-2-(3-iodo-phenyl)-acetamide (ESI) m/z 563 [(M+H)$^+$]. HRMS (ESI) calculated for C$_{23}$H$_{27}$F$_3$IN$_2$O$_3^+$ [(M+H)$^+$] 563.3638. found 563.3640.

2-(3-Bromo-4-fluoro-phenyl)-N-[4-(4-isopropyl-piperazin-1-ylmethyl)-3-trifluoromethyl-phenyl]-acetamide $^1$H NMR (600 MHz, DMSO-d$_6$) δ ppm 0.96 (br. s., 6H) 2.26-2.48 (m, 7H) 3.52 (br. s., 2H) 3.69 (s, 2H) 7.31-7.35 (m, 1H) 7.35-7.39 (m, 1H) 7.64-7.69 (m, 2H) 7.76 (d, J=8.61 Hz, 1H) 8.03 (d, J=2.01 Hz, 1H) 10.45 (s, 1H).

2-(5-Bromo-thiophen-2-yl)-N-[4-(4-methyl-piperazin-1-ylmethyl)-3-trifluoromethyl-phenyl]-acetamide ¹H NMR (600 MHz, DMSO-d₆) δ ppm 2.17 (br. s., 3H) 2.38 (d, J=1.83 Hz, 8H) 3.53 (s, 2H) 3.89 (s, 2H) 6.83 (d, J=3.66 Hz, 1H) 7.07 (d, J=3.66 Hz, 1H) 7.66 (d, J=8.61 Hz, 1H) 7.76 (d, J=8.42 Hz, 1H) 8.02 (d, J=1.65 Hz, 1H) 10.50 (s, 1H).

2-(3-Bromo-4-fluoro-phenyl)-N-[4-(4-propyl-piperazin-1-ylmethyl)-3-trifluoromethyl-phenyl]-acetamide (ESI) m/z 517 [(M+H)⁺]. HRMS (ESI) calculated for $C_{23}H_{27}BrF_4N_3O^+$ [(M+H)⁺] 517.3697. found 517.3695.

3-Iodo-4-methyl-N-[4-(4-methyl-piperazin-1-ylmethyl)-3-trifluoromethyl-phenyl]-benzamide ¹H NMR (600 MHz, DMSO-d₆) δ ppm 2.16 (s, 3H) 2.23-2.43 (m, 8H) 2.45 (s, 3H) 3.56 (s, 2H) 7.45-7.55 (m, 1H) 7.70 (d, J=8.79 Hz, 1H) 7.91 (dd, J=7.87, 1.77 Hz, 1H) 8.03 (dd, J=8.61, 2.01 Hz, 1H) 8.17 (d, J=1.95 Hz, 1H) 8.42 (d, J=1.83 Hz, 1H) 10.47 (s, 1H).

Preparation 44

3-Bromo-N-[4-(4-ethyl-piperazin-1-ylmethyl)-3-trifluoromethyl-phenyl]-benzenesulfonamide To a solution of 4-(4-ethyl-piperazin-1-ylmethyl)-3-trifluoromethyl-phenylamine (0.10 g, 0.35 mmol), and TEA (0.10 mL, 0.70 mmol) in anhydrous THF (5 mL), 3-bromo-benzenesulfonyl chloride (0.10 g, 0.38 mmol) was added. The mixture was heated at 60° C. for 16 h, then was cooled at r.t., poured in a saturated solution of NaHCO₃ (15 mL) and extracted with DCM (2×10 mL). The organic phase was washed with brine, dried with anhydrous Na₂SO₄ and evaporated under vacuum. The crude was purified by flash column chromatography (DCM-MeOH 90:10) to obtain the title compound (0.04 g, 23%) as brown oil.

(ESI) m/z 507 [(M+H)⁺]. HRMS (ESI) calculated for $C_{20}H_{24}BrF_3N_3O_2S^+$ [(M+H)⁺] 507.3797. found 507.3790.

Preparation 15

3-Bromo-N-cyclopropyl-benzenesulfonamide

A mixture of cyclopropylamine (0.12 mL, 1.76 mmol) and 3-bromo-benzenesulfonyl chloride (0.15 g, 0.59 mmol) in anhydrous THF (5 mL) was stirred at r.t. for 2 h. The reaction was poured in a saturated solution of NaHCO₃ (15 mL) and extracted with DCM (2×10 mL), the organic phase was washed with brine, dried with anhydrous Na₂SO₄ and evaporated under vacuum. The title product (0.10 g, 62%) was obtained as brown oil.

¹H NMR (600 MHz, DMSO-d₆) δ ppm 0.33-0.41 (m, 2H) 0.48-0.53 (m, 2H) 2.13 (tt, J=6.91, 3.53 Hz, 1H) 7.59 (t, J=7.78 Hz, 1H) 7.78-7.83 (m, 1H) 7.87-7.90 (m, 1H) 7.93 (t, J=1.74 Hz, 1H) 8.03 (br. s., 1H).

Preparation 16

1-Ethynyl-3-phenethyloxy-benzene

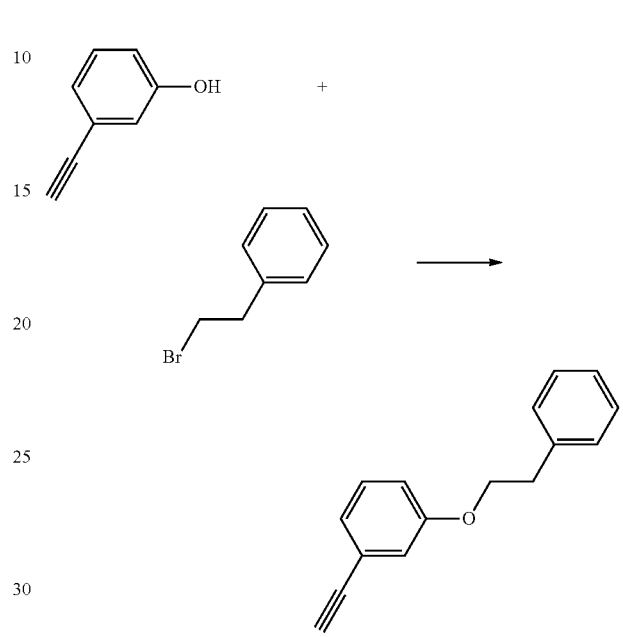

A mixture of 3-ethynyl-phenol (0.20 g, 1.73 mmol), (2-bromo-ethyl)-benzene (0.24 mL, 1.73 mmol), Cs₂CO₃ (1.13 g, 3.46 mmol) and NaI (0.26 g, 1.73 mmol) in acetone (5 mL) was heated at reflux for 12 h. The reaction was cooled at r.t., poured in water (15 mL) and extracted with EtOAc (2×15 mL). The organic phase was washed with brine, dried with anhydrous Na₂SO₄ and evaporated under vacuum. The crude was purified by flash column chromatography (Hex-EtOAc 95:5) to obtain the title product (0.08 g, 21%) as colorless oil.

¹H NMR (401 MHz, DMSO-d₆) δ ppm 3.02 (t, J=6.84 Hz, 2H) 4.14 (s, 1H) 4.21 (t, J=6.84 Hz, 2H) 6.86-7.06 (m, 3H) 7.15-7.38 (m, 6H).

According to this same methodology, but employing suitable substituted derivatives, the following intermediate was prepared:

1-Ethynyl-3-(3-phenyl-propoxy)-benzene

¹H NMR (600 MHz, DMSO-d₆) δ ppm 1.97-2.04 (m, 2H) 2.71-2.75 (m, 2H) 3.97 (t, J=6.32 Hz, 2H) 4.15 (s, 1H) 6.96-7.00 (m, 2H) 7.04 (d, J=7.51 Hz, 1H) 7.16-7.20 (m, 1H) 7.21-7.24 (m, 2H) 7.26-7.32 (m, 3H).

Preparation 17

1-Benzyloxymethyl-3-iodo-benzene

To a solution of (3-iodo-phenyl)-methanol (0.23 mL, 2.14 mmol) in anhydrous DMF (3 mL), cooled at 0-5° C., NaH (0.17 g, 4.28 mmol) was added. The mixture was stirred at 0-5° C. for 30 min and then benzyl chloride (0.31 mL, 2.57 mmol) was added. The reaction was stirred at r.t. for 5 h, then was poured in water (15 mL) and extracted with EtOAc (2×15 mL). The organic phase was washed with brine, dried with anhydrous Na$_2$SO$_4$ and evaporated under vacuum. The crude was purified by flash column chromatography (Hex/EtOAc 95/5) to obtain the title product (0.35 g, 51%) as colorless oil.

$^1$H NMR (600 MHz, DMSO-d$_6$) δ ppm 4.50 (s, 2H) 4.53 (s, 2H) 7.17 (t, J=7.78 Hz, 1H) 7.28-7.32 (m, 1H) 7.33-7.39 (m, 5H) 7.66 (d, J=7.88 Hz, 1H) 7.72 (s, 1H).

Preparation 18

Benzyl-(3-iodo-benzyl)-amine

To a mixture of 3-iodo-benzylamine (0.30 g, 1.29 mmol) and AcOH (0.008 mL, 0.13 mmol) in DCM (5 mL), a solution of benzaldehyde (0.13 mL, 1.29 mmol) in DCM (3 mL) was added drop wise. The reaction was stirred at r.t. for 2 h, then tetramethylammonium triacetoxyborohydride (0.68 g, 2.58 mmol) was added. After 2 h at r.t., the solution was washed with a saturated solution of NaHCO$_3$ (10 mL), water (10 mL) and brine. The organic phase was dried with anhydrous Na$_2$SO$_4$ and evaporated under vacuum to give a crude that was purified by flash column chromatography (DCM-MeOH 97:3). The title product (0.22 g, 53%) was obtained as colorless oil.

$^1$H NMR (600 MHz, DMSO-d$_6$) δ ppm 2.62-2.74 (m, 1H) 3.64 (d, J=10.26 Hz, 5H) 7.12 (t, J=7.69 Hz, 1H) 7.20-7.25 (m, 1H) 7.29-7.37 (m, 6H) 7.58 (d, J=8.06 Hz, 1H) 7.73 (s, 1H).

Preparation 19

Benzyl-(3-iodo-benzyl)-carbamic acid tert-butyl ester

To a solution of benzyl-(3-iodo-benzyl)-amine (0.21 g, 0.67 mmol) in anhydrous DCM (5 mL), di-tert-butyl dicarbonate (0.16 g, 0.73 mmol) and DMAP (0.004 g, 0.03 mmol) were added. The mixture was stirred at r.t. for 1 h, then the solution was evaporated under vacuum and the crude purified by flash column chromatography (DCM) to give the title product (0.23 g, 81%) as colorless oil.

$^1$H NMR (600 MHz, DMSO-d$_6$) δ ppm 1.38 (s, 9H) 4.21-4.48 (m, 4H) 7.11-7.15 (m, 1H) 7.22 (br. s., 2H) 7.25-7.28 (m, 1H) 7.31-7.37 (m, 2H) 7.55 (br. s., 1H) 7.62 (d, J=7.88 Hz, 1H).

Preparation 20

1-Phenylcarbamoyl-cyclopropanecarboxylic acid

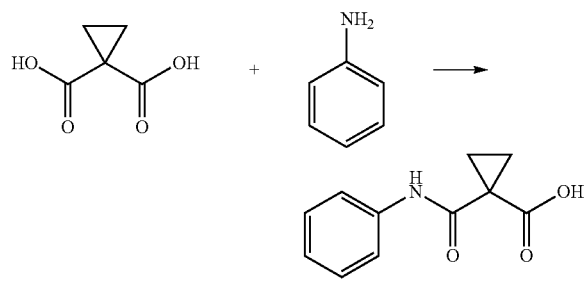

To a mixture of cyclopropane-1,1-dicarboxylic acid (0.36 g, 2.77 mmol) and TEA (0.39 mL, 2.77 mmol) in anhydrous THF (5 mL), cooled at 0-5° C., a solution of thionyl chloride (0.20 mL, 2.77 mmol) in anhydrous THF (2 mL) was added drop wise in 15 min. A solution of aniline (0.28 mL, 3.05 mmol) in anhydrous THF (4 mL) was added drop wise in 1 h. The reaction was stirred, at 0-5° C. a further 1 h, then was diluted with EtOAc (15 mL) and extracted with 2 N NaOH (2×15 mL). The aqueous phase was acidified to pH 1-2 with 2 N HCl and extracted with EtOAc (2×15 mL).

The organic phase was washed with brine, dried with anhydrous Na$_2$SO$_4$ and evaporated under vacuum to give the title product (0.21 g, 37% yield) as white solid.

$^1$H NMR (600 MHz, DMSO-d$_6$) δ ppm 1.42 (s, 4H) 6.97-7.11 (m, 1H) 7.22-7.35 (m, 2H) 7.59 (dd, J=8.54, 0.98 Hz, 2H) 10.57 (s, 1H) 12.35-13.48 (m, 1H).

According to this same methodology, but employing suitable substituted derivatives, the following intermediate was prepared:

1-(4-Trifluoromethyl-phenylcarbamoyl)-cyclopropanecarboxylic acid $^1$H NMR (600 MHz, DMSO-d$_6$) δ ppm 1.43 (s, 4H) 7.67 (d, J=8.61 Hz, 2H) 7.82 (d, J=8.42 Hz, 2H) 10.84 (s, 1H) 13.07 (s, 1H).

Preparation 21

Cyclopropane-1,1-dicarboxylic acid (3-ethynyl-phenyl)-amide phenylamide

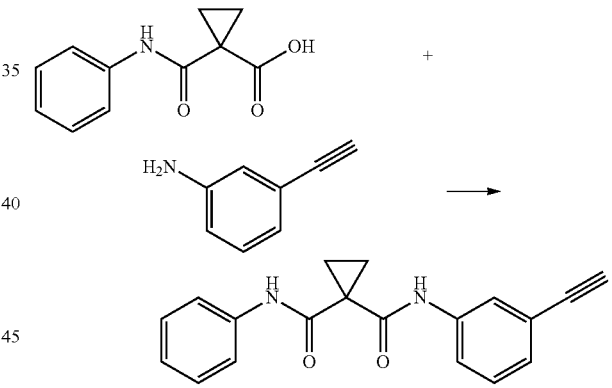

To a solution of 1-phenylcarbamoyl-cyclopropanecarboxylic acid (0.20 g, 0.95 mmol) in anhydrous THF, cooled at 0-5° C., oxalyl chloride (0.09 mL, 1.00 mmol) and DMF (1 drop) were added. The mixture was stirred at r.t. for 1 h, then evaporated under vacuum. The crude acyl chloride was dissolved in anhydrous THF (3 mL) and added drop wise to a solution of 3-ethynyl-phenylamine (0.13 g, 1.14 mmol) and 2,6-lutidine (0.44 mL, 3.80 mmol) in anhydrous THF (5 mL), cooled at 0-5° C. The reaction was then stirred at r.t. for 1 h, poured in 2 N HCl (15 mL) and extracted with EtOAc (2×15 mL). The organic phase was washed with 2 N HCl (10 mL), a saturated solution of NaHCO$_3$ (10 mL), brine (10 mL), dried with anhydrous Na$_2$SO$_4$ and evaporated under vacuum. The title product (0.11 g, 37%) was obtained as white solid.

$^1$H NMR (600 MHz, DMSO-d$_6$) δ ppm 1.46 (s, 4H) 4.15 (s, 1H) 7.02-7.09 (m, 1H) 7.17 (dt, J=7.63, 1.19 Hz, 1H) 7.26-7.34 (m, 3H) 7.59-7.63 (m, 3H) 7.81 (t, J=1.77 Hz, 1H) 9.98 (s, 1H) 10.07 (s, 1H).

According to this same methodology, but employing suitable substituted derivatives, the following intermediate was prepared:

Cyclopropane-1,1-dicarboxylic acid (3-ethynyl-phenyl)-amide (4-trifluoromethyl-phenyl)-amide $^1$H NMR (600 MHz, DMSO-d$_6$) δ ppm 1.45 (s, 4H) 4.14 (s, 1H) 7.02-7.09 (m, 1H) 7.17 (dt, J=7.63, 1.19 Hz, 1H) 7.27-7.33 (m, 2H) 7.67 (d, J=8.61 Hz, 2H) 7.82 (d, J=8.42 Hz, 2H) 10.02 (s, 1H) 10.37 (s, 1H).

Preparation 22

N-(4-Chloro-3-trifluoromethyl-phenyl)-2-(3-trimethylsilanylethynyl-phenyl)-acetamide

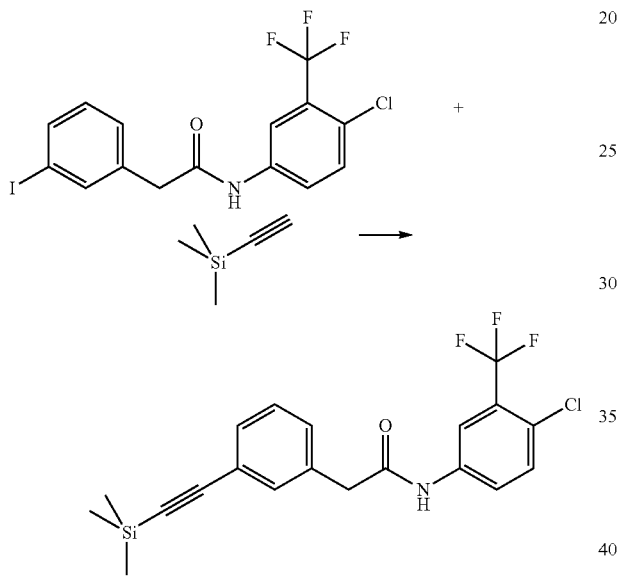

A solution of N-(4-chloro-3-trifluoromethyl-phenyl)-2-(3-iodo-phenyl)-acetamide (0.26 g, 0.59 mmol), ethynyltrimethylsilane (0.12 g, 1.24 mmol), CuI (10% mol, 11 mg, 0.059 mmol), PdCl$_2$(PPh$_3$)$_2$ (10% mol, 41 mg, 0.059 mmol) and TEA (0.81 mL, 5.90 mmol) in MeCN (5 mL) was degassed with argon and stirred at r.t. for 2 h. The reaction was poured in water (15 mL) and extracted with EtOAc (2×15 mL). The organic phase was washed with brine, dried with anhydrous Na$_2$SO$_4$ and evaporated under vacuum to give a crude that was purified by flash column chromatography (Hex-EtOAc 85:15). The title product (0.23 g, 93%) was obtained as colorless oil.

$^1$H NMR (600 MHz, DMSO-d$_6$) δ ppm 0.18-0.27 (m, 9H) 3.68 (s, 2H) 7.28-7.37 (m, 3H) 7.43 (s, 1H) 7.66 (d, J=8.79 Hz, 1H) 7.83 (dd, J=8.79, 2.38 Hz, 1H) 8.18 (d, J=2.56 Hz, 1H) 10.59 (s, 1H).

According to this same methodology, but employing suitable substituted derivatives, the following intermediates were prepared:

N-[4-(4-Ethyl-piperazin-1-ylmethyl)-3-trifluoromethyl-phenyl]-3-trimethylsilanylethynyl-benzamide (ESI) m/z 488 [(M+H)$^+$]. HRMS (ESI) calculated for C$_{26}$H$_{33}$F$_3$N$_3$OSi$^+$ [(M+H)$^+$] 488.6325. found 488.6329.

N-(3-Trimethylsilanylethynyl-benzyl)-benzamide $^1$H NMR (600 MHz, DMSO-d$_6$) δ ppm 0.20-0.23 (m, 9H) 4.46 (d, J=6.04 Hz, 2H) 7.30-7.37 (m, 3H) 7.40 (s, 1H) 7.45-7.50 (m, 2H) 7.52-7.57 (m, 1H) 7.87-7.91 (m, 2H) 9.04 (t, J=5.86 Hz, 1H).

N-Phenyl-3-(3-trimethylsilanylethynyl-phenyl)-propionamide $^1$H NMR (600 MHz, DMSO-d$_6$) δ ppm 0.21-0.23 (m, 9H) 2.62 (t, J=7.60 Hz, 2H) 2.89 (t, J=7.69 Hz, 2H) 7.02 (t, J=7.42 Hz, 1H) 7.21-7.29 (m, 5H) 7.35 (s, 1H) 7.55 (d, J=7.69 Hz, 2H) 9.86 (s, 1H).

(3-Benzyloxymethyl-phenylethynyl)-trimethyl-silane $^1$H NMR (600 MHz, DMSO-d$_6$) δ ppm 4.50-4.55 (m, 4H) 7.27-7.32 (m, 1H) 7.33-7.41 (m, 7H) 7.43 (s, 1H).

Benzyl-(3-trimethylsilanylethynyl-benzyl)-carbamic acid tert-butyl ester $^1$H NMR (600 MHz, DMSO-d$_6$) δ ppm 1.38 (s, 9H) 4.35 (d, J=16.67 Hz, 4H) 7.16-7.38 (m, 9H).

Preparation 23

N-(4-Chloro-3-trifluoromethyl-phenyl)-2-(3-ethynyl-phenyl)-acetamide

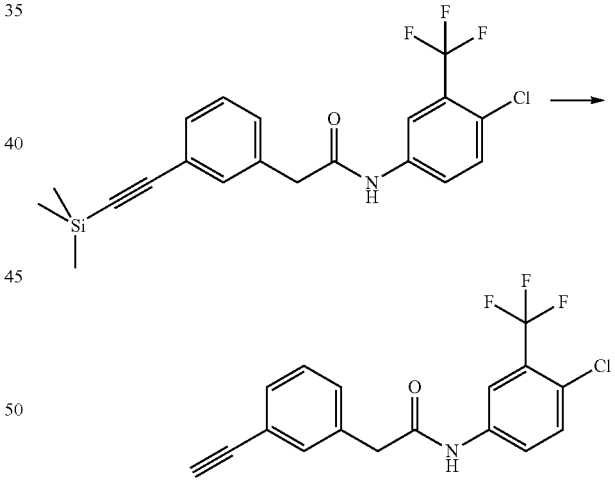

To a solution of N-(4-chloro-3-trifluoromethyl-phenyl)-2-(3-trimethylsilanylethynyl-phenyl)-acetamide (0.20 g, 0.49 mmol) in MeOH (10 mL), K$_2$CO$_3$ (0.07 g, 0.54 mmol) was added. The reaction was degassed with argon and stirred at r.t. for 2 h. The mixture was poured in water (30 mL) and extracted with EtOAc (2×15 mL). The organic phase was washed with brine, dried with anhydrous Na$_2$SO$_4$ and evaporated under vacuum to give the title product (0.15 g, 91%) as colorless oil.

$^1$H NMR (600 MHz, DMSO-d$_6$) δ ppm 3.69 (s, 2H) 4.17 (s, 1H) 7.31-7.40 (m, 3H) 7.44 (s, 1H) 7.66 (d, J=8.79 Hz, 1H) 7.83 (dd, J=8.79, 2.38 Hz, 1H) 8.18 (d, J=2.38 Hz, 1H) 10.61 (s, 1H).

According to this same methodology, but employing suitable substituted derivatives, the following intermediates were prepared:

N-[4-(4-Ethyl-piperazin-1-ylmethyl)-3-trifluoromethyl-phenyl]-3-ethynyl-benzamide (ESI) m/z 416 [(M+H)$^+$]. HRMS (ESI) calculated for $C_{23}H_{25}F_3N_3O^+$ [(M+H)$^+$] 416.4514. found 416.4515.

N-(3-Ethynyl-benzyl)-benzamide $^1$H NMR (600 MHz, DMSO-d$_6$) δ ppm 4.15 (s, 1H) 4.48 (d, J=6.04 Hz, 2H) 7.31-7.36 (m, 3H) 7.39 (s, 1H) 7.45-7.51 (m, 2H) 7.51-7.58 (m, 1H) 7.88-7.91 (m, 2H) 9.06 (t, J=5.86 Hz, 1H).

3-(3-Ethynyl-phenyl)-N-phenyl-propionamide $^1$H NMR (600 MHz, DMSO-d$_6$) δ ppm 2.59-2.65 (m, 2H) 2.90 (t, J=7.60 Hz, 2H) 4.13 (s, 1H) 7.02 (t, J=7.42 Hz, 1H) 7.24-7.32 (m, 5H) 7.37 (s, 1H) 7.55 (d, J=7.69 Hz, 2H) 9.87 (s, 1H).

1-Benzyloxymethyl-3-ethynyl-benzene $^1$H NMR (600 MHz, DMSO-d$_6$) δ ppm 4.17 (s, 1H) 4.54 (d, J=2.93 Hz, 4H) 7.27-7.33 (m, 1H) 7.34-7.42 (m, 7H) 7.45 (s, 1H).

Benzyl-(3-ethynyl-benzyl)-carbamic acid tert-butyl ester $^1$H NMR (600 MHz, DMSO-d$_6$) δ ppm 1.38 (br. s., 9H) 4.16 (s, 1H) 4.37 (br. s., 3H) 7.15-7.31 (m, 4H) 7.31-7.39 (m, 3H) 7.41 (t, J=7.69 Hz, 1H) 7.51 (d, J=7.88 Hz, 1H).

Preparation 24

6-Iodo-2,3-dihydro-indole-1-carboxylic acid [4-(4-ethyl-piperazin-1-ylmethyl)-3-trifluoromethyl-phenyl]-amide

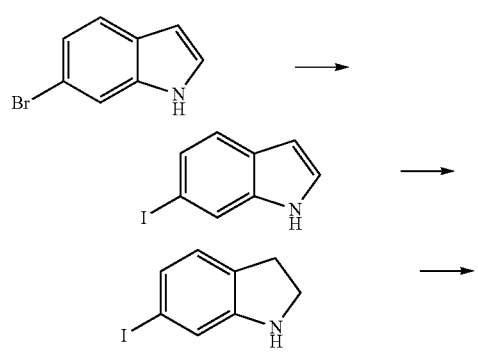

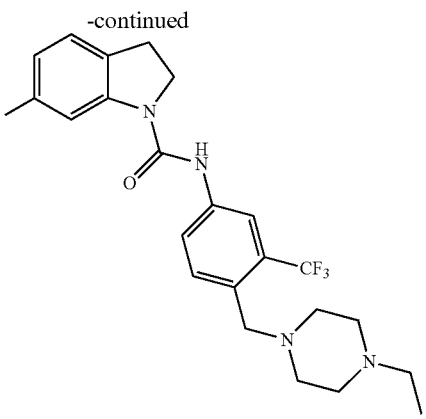

Step 1. 6-Iodo-1H-indole (According to the procedure described in *J. Am. Chem. Soc.* 2002, 124, 14844-14845). 6-Bromo-1H-indole (0.65 g, 3.34 mmol), NaI (2.0 g, 13.34 mmol) and CuI (63.5 mg, 0.33 mmol) were charged in a Shlenk tube and degassed three times back filling with argon each time. Dioxane (6.5 mL) and (1S,2S)—N,N'-dimethyl-cyclohexane-1,2-diamine (0.11 mL, 0.67 mmol) were then added and the mixture was heated at 110° C. for 24 h. The reaction was quenched with NH$_3$, poured in water and extracted with DCM (3×20 mL). The organic layer was dried over anhydrous Na$_2$SO$_4$, filtered and concentrated to reduce volume. The product was purified by flash column chromatography (Hex/EtOAc 98/2) and isolated as white solid (0.53 g, 65%).

$^1$H NMR (600 MHz, DMSO-d$_6$) δ ppm 6.43 (t, J=2.01 Hz, 1H) 7.25 (dd, J=8.24, 1.47 Hz, 1H) 7.31 (t, J=2.75 Hz, 1H) 7.38 (d, J=8.24 Hz, 1H) 7.75 (s, 1H) 11.15 (br. s., 1H).

Step 2. 6-Iodo-2,3-dihydro-1H-indole (According to the procedure described in WO2010/043000) A solution of 6-iodo-1H-indole (0.52 g, 2.14 mmol) in AcOH (6.5 mL) was treated with NaBH$_3$CN (0.62 g, 9.84 mmol) at r.t. for 1 h. The solvent was removed under reduced pressure and the residue was dissolved in Et$_2$O and washed with 1 N NaOH, water and brine. The organic layer was dried over Na$_2$SO$_4$, filtered and concentrated to reduce volume. A flash column chromatography (Hex/EtOAc 95/5) afforded the title product as white solid (0.40 g, 76%).

$^1$H NMR (600 MHz, DMSO-d$_6$) δ ppm 2.85 (t, J=8.61 Hz, 2H) 3.40 (t, J=8.43 Hz, 2H) 5.68 (br. s., 1H) 6.74-6.84 (m, 3H).

According to this same methodology, but employing suitable substituted derivative, the following intermediate was prepared:

5-Iodo-2,3-dihydro-1H-indole (ESI) m/z 245 [(M+H)$^+$]. HRMS (ESI): calculated for $C_8H_9IN$ [(M+H)$^+$] 245.9774. found 245.9798.

Step 3. 6-Iodo-2,3-dihydro-indole-1-carboxylic acid [4-(4-ethyl-piperazin-1-ylmethyl)-3-trifluoromethyl-phenyl]-amide To a suspension of triphosgene (0.16 g, 0.53 mmol) and Na$_2$CO$_3$ (0.67 g, 6.28 mmol) in DCM (10 mL) kept at 0° C. under argon, 4-(4-ethyl-piperazin-1-ylmethyl)-3-trifluoromethyl-phenylamine (0.45 g, 1.57 mmol) was added. The reaction was monitored by HPLC (following the formation of 4-ethyl-piperazine-1-carboxylic acid [4-(4-ethyl-piperazin-1-ylmethyl)-3-trifluoromethyl-phenyl]-amide by treating a sample of the reaction mixture with N-ethylpiperazine). After 1 h, 6-Iodo-2,3-dihydro-1H-indole (0.39 g, 1.61 mmol) was added and the reaction was let under stirring 1 h at r.t. The mixture was diluted with DCM (10 mL), washed with water (3×10 mL), dried over anhydrous $Na_2SO_4$ and concentrated under vacuum. Purification by flash column chromatography (DCM/MeOH 95/5) afforded the product as yellow foam (0.68 g, 77%).

$^1$H NMR (600 MHz, DMSO-$d_6$) δ ppm 1.00 (br. s., 3H) 2.12-2.48 (m, 10H) 3.15 (t, J=8.61 Hz, 2H) 3.55 (br. s., 2H) 4.13 (t, J=8.70 Hz, 2H) 7.03 (d, J=7.88 Hz, 1H) 7.26 (dd, J=7.69, 1.65 Hz, 1H) 7.64 (d, J=8.61 Hz, 1H) 7.83 (d, J=8.43 Hz, 1H) 7.97 (d, J=2.01 Hz, 1H) 8.24 (d, J=1.28 Hz, 1H) 8.84 (s, 1H).

According to this same methodology, but employing suitable substituted derivatives, the following intermediates were prepared:

5-Iodo-2,3-dihydro-indole-1-carboxylic acid [4-(4-ethyl-piperazin-1-ylmethyl)-3-trifluoromethyl-phenyl]-amide $^1$H NMR (600 MHz, DMSO-$d_6$) δ ppm 0.98 (t, J=7.14 Hz, 3H) 2.30 (q, J=7.14 Hz, 3H) 2.32-2.48 (m, 8H) 3.18 (t, J=8.70 Hz, 2H) 3.53 (s, 2H) 4.13 (t, J=8.61 Hz, 2H) 7.45 (dd, J=8.42, 1.83 Hz, 1H) 7.53 (s, 1H) 7.63 (d, J=8.43 Hz, 1H) 7.69 (d, J=8.61 Hz, 1H) 7.79-7.84 (m, 1H) 7.95-7.99 (m, 1H) 8.82 (s, 1H).

Preparation 25

2-(2-Amino-pyrimidin-4-yl)-4-oxo-1,4,6,7-tetrahydro-pyrrolo[3,2-c]pyridine-5-carboxylic acid tert-butyl ester

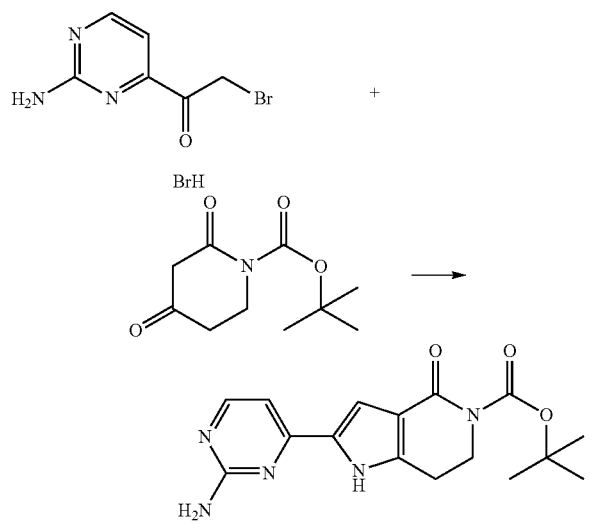

According to the procedure described in WO2004/058762 and in *Journal of Medicinal Chemistry* 2007, 50, 2647-54. According to this same methodology, but employing suitable substituted derivatives, the following intermediates were prepared:

2-(2-Amino-pyrimidin-4-yl)-4-oxo-1-(2-pyrrolidin-1-yl-ethyl)-1,4,6,7-tetrahydro-pyrrolo[3,2-c]pyridine-5-carboxylic acid tert-butyl ester hydrobromide $^1$H NMR (600 MHz, DMSO-$d_6$) δ ppm 1.47 (s, 9H) 1.87 (br. s., 2H) 2.04 (br. s., 2H) 3.06 (t, J=6.04 Hz, 4H) 3.54 (d, J=6.96 Hz, 2H) 3.62 (br. s., 2H) 4.02 (t, J=6.23 Hz, 2H) 4.79 (t, J=7.23 Hz, 2H) 6.68 (br. s., 2H) 7.00 (d, J=5.13 Hz, 1H) 7.25 (s, 1H) 8.20 (d, J=5.31 Hz, 1H) 9.71 (br. s., 1H).

2-(2-Amino-pyrimidin-4-yl)-1-(2-dimethylamino-ethyl)-4-oxo-1,4,6,7-tetrahydro-pyrrolo[3,2-c]pyridine-5-carboxylic acid tert-butyl ester hydrobromide $^1$H NMR (600 MHz, DMSO-$d_6$) δ ppm 1.47 (s, 9H) 2.86 (br. s., 6H) 3.06 (t, J=6.32 Hz, 2H) 3.39-3.47 (m, 2H) 4.01 (t, J=6.32 Hz, 2H) 4.78-4.90 (m, 2H) 6.73 (br. s., 2H) 6.99 (d, J=5.13 Hz, 1H) 7.24 (s, 1H) 8.19 (d, J=5.31 Hz, 1H) 10.20 (br. s., 1H).

2-(2-Amino-pyrimidin-4-yl)-1-(1-methyl-piperidin-4-yl)-1,5,6,7-tetrahydro-pyrrolo[3,2-c]pyridin-4-one dihydrochloride $^1$H NMR (400 MHz, DMSO-$d_6$) δ ppm 2.08-2.16 (m, 2H) 2.53-2.62 (m, 2H) 2.79 (d, J=4.63 Hz, 3H) 3.16 (t, J=6.46 Hz, 2H) 3.24-3.45 (m, 6H overlapped by water signal) 5.77 (br. s., 1H) 7.27 (br. s., 1H) 7.41 (br. s., 1H) 7.46 (br. s., 1H) 8.16 (d, J=6.46 Hz, 1H) 10.59 (br. s., 1H).

2-(3-Bromo-pyridin-4-yl)-4-oxo-1,4,6,7-tetrahydro-pyrrolo[3,2-c]pyridine-5-carboxylic acid tert-butyl ester (ESI) m/z 392 [(M+H)$^+$]. HRMS (ESI) calculated for $C_{17}H_{19}BrN_3O_3$ [(M+H)$^+$] 392.0604. found 392.0621.

Preparation 26

2-Bromo-1-(3-bromo-pyridin-4-yl)-ethanone

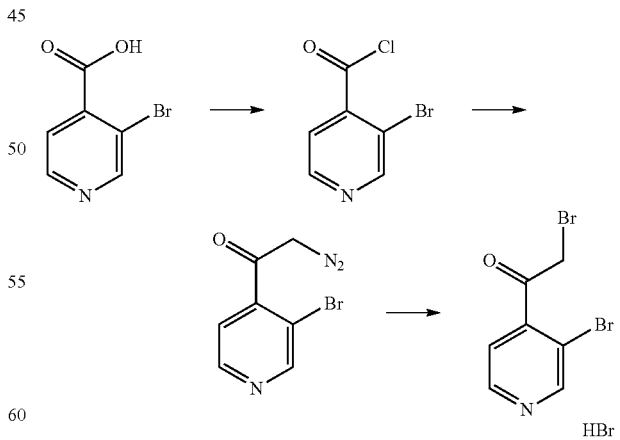

3-Bromo-isonicotinic acid (1.0 g, 4.95 mmol) was suspended in thionyl chloride (10 mL) and refluxed for 1 h when the solubilization was complete (detection of methyl ester by HPLC-MS for treatment of a small sample with methanol). The solvent was removed by stripping with toluene for three times. The acyl chloride was then suspended in dry THF (18 mL) and added drop wise to a 2 M solution of TMSCH$_2$N$_2$ in hexane (6.18 mL, 12.37 mmol) at 0° C. in 15 min. The mixture was let under stirring at 0° C. for 3.5 h, then 48% HBr (4 mL) was carefully added (gas evolution) and the reaction was let at r.t. for 1.5 h. The solvent was reduced to small volume and the precipitate was filtered and rinsed with cold water affording the title product as hydrobromide (1.34 g, 75% over three steps).

(ESI) m/z 277 [(M+H)$^+$]. HRMS (ESI) calculated for C$_7$H$_6$Br$_2$NO [(M+H)$^+$] 277.8811. found 277.8830.

Preparation 45

2-(2-Amino-pyrimidin-4-yl)-1-methyl-4-oxo-1,4,6,7-tetrahydro-pyrrolo[3,2-c]pyridine-5-carboxylic acid tert-butyl ester

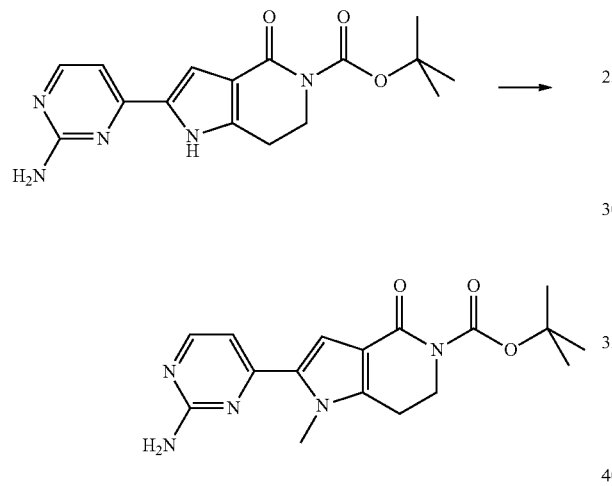

The synthetic procedure has already been described in WO2010/145998.

According to this same methodology, but employing suitable substituted derivatives, the following intermediates were prepared:

2-(2-Amino-pyrimidin-4-yl)-1-(2-tert-butoxycarbonylamino-ethyl)-4-oxo-1,4,6,7-tetrahydro-pyrrolo[3,2-c]pyridine-5-carboxylic acid tert-butyl ester (ESI) m/z 473 [(M+H)$^+$]. HRMS (ESI) calculated for C$_{23}$H$_{33}$N$_6$O$_5$ [(M+H)$^+$] 473.2507. found 473.2521.

2-(2-Amino-pyrimidin-4-yl)-4-oxo-1-[2-(tetrahydro-pyran-2-yloxy)-ethyl]-1,4,6,7-tetrahydro-pyrrolo[3,2-c]pyridine-5-carboxylic acid tert-butyl ester $^1$H NMR (600 MHz, DMSO-d$_6$) δ ppm 1.27-1.64 (m, 6H) 1.47 (s, 9H) 3.01 (t, J=6.32 Hz, 2H) 3.37-3.43 (m, 1H) 3.61-3.68 (m, 1H) 3.82-3.88 (m, 1H) 3.93-3.99 (m, 2H) 4.46 (t, J=3.11 Hz, 1H) 4.75 (t, J=4.85 Hz, 2H) 6.55 (s, 2H) 6.94 (d, J=5.31 Hz, 1H) 7.18 (s, 1H) 8.14 (d, J=5.31 Hz, 1H).

Preparation 27

2-(2-Amino-5-iodo-pyrimidin-4-yl)-4-oxo-1-[2-(tetra hydro-pyran-2-yloxy)-ethyl]-1,4,6,7-tetrahydro-pyrrolo[3,2-c]pyridine-5-carboxylic acid tert-butyl

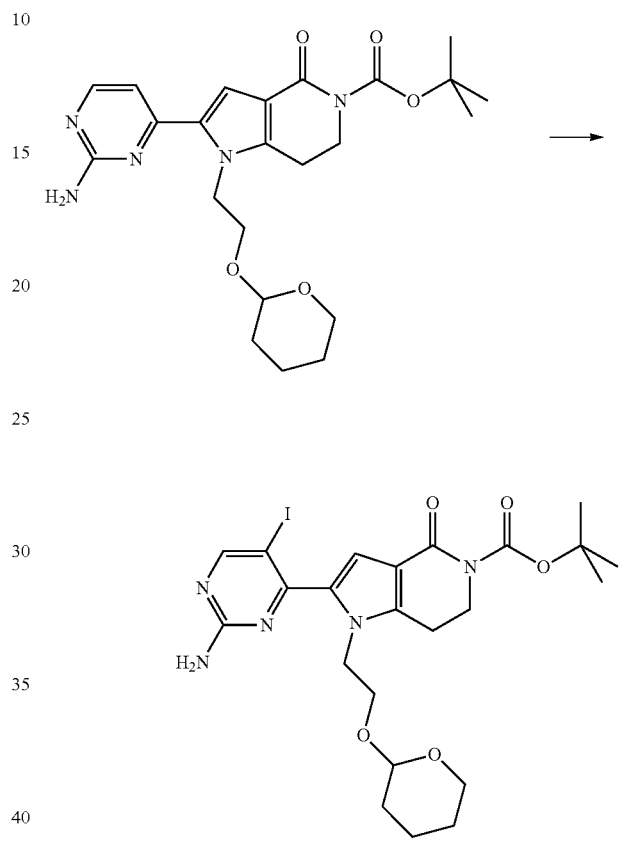

According to the procedure described in WO2010/145998.

To a solution of 2-(2-amino-pyrimidin-4-yl)-4-oxo-1-[2-(tetrahydro-pyran-2-yloxy)-ethyl]-1,4,6,7-tetrahydro-pyrrolo[3,2-c]pyridine-5-carboxylic acid tert-butyl ester (0.48 g, 1.05 mmol) in THF (35 mL), cooled at 0-5° C., iodine (0.53 g, 2.10 mmol) and silver trifluoroacetate (0.46 g, 2.10 mmol) were added. The reaction was stirred at r.t. overnight, then filtered through celite washing with EtOAc. The organic phase was evaporated under vacuum, the crude was dissolved with DMF (10 mL) and precipitated with water (100 mL). The resulting solid was dried at 45° C., under vacuum, to obtain the title product (0.36 g, 60%) as yellow powder.

$^1$H NMR (600 MHz, DMSO-d$_6$) δ ppm 1.24-1.45 (m, 6H) 1.45-1.49 (m, 10H) 3.01 (t, J=6.41 Hz, 2H) 3.40-3.51 (m, 2H) 3.64 (ddd, J=10.62, 6.50, 3.94 Hz, 1H) 3.98 (dq, J=13.60, 6.70 Hz, 2H) 4.26-4.43 (m, 2H) 4.52 (ddd, J=14.65, 6.69, 3.94 Hz, 1H) 6.85 (br. s., 2H) 7.03 (s, 1H) 8.57 (s, 1H).

According to this same methodology, but employing suitable substituted derivatives, the following intermediates were prepared:

2-(2-Amino-5-iodo-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 1.47 (s, 9H) 2.97 (t, J=6.32 Hz, 2H) 3.61 (s, 3H) 3.98 (t, J=6.32 Hz, 2H) 6.86 (s, 2H) 7.01 (s, 1H) 8.56 (s, 1H).

2-(2-Amino-5-iodo-pyrimidin-4-yl)-1-(2-tert-butoxycarbonylamino-ethyl)-4-oxo-1,4,6,7-tetrahydro-pyrrolo[3,2-c]pyridine-5-carboxylic acid tert-butyl ester (ESI) m/z 599 [(M+H)$^+$]. HRMS (ESI) calculated for $C_{23}H_{32}IN_6O_5$ [(M+H)$^+$] 599.1473. found 599.1460.

2-(2-Amino-5-iodo-pyrimidin-4-yl)-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.47 (s, 9H) 2.94 (t, J=6.35 Hz, 2H) 3.95 (t, J=6.23 Hz, 2H) 6.57 (br. s., 2H) 7.69 (d, J=2.44 Hz, 1H) 8.51 (s, 1H) 11.88 (br. s., 1H).

2-(2-Amino-5-iodo-pyrimidin-4-yl)-1-(1-methyl-piperidin-4-yl)-1,5,6,7-tetrahydro-pyrrolo[3,2-c]pyridin-4-one (ESI) m/z 453 [(M+H)$^+$]. HRMS (ESI) calculated for $C_{17}H_{22}IN_6O$ [(M+H)$^+$] 453.0894. found 453.0905.

Preparation 28

2-[2-(Acetyl-methyl-amino)-5-ethynyl-pyrimidin-4-yl]-1-methyl-4-oxo-1,4,6,7-tetrahydro-pyrrolo[3,2-c]pyridine-5-carboxylic acid tert-butyl ester

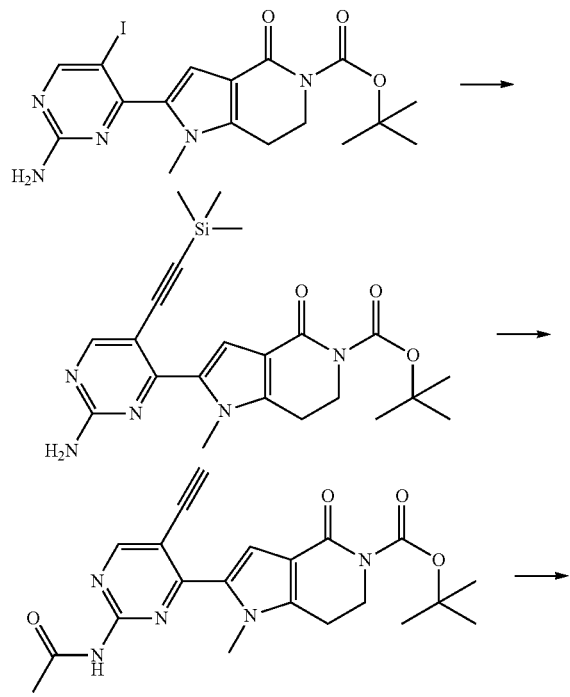

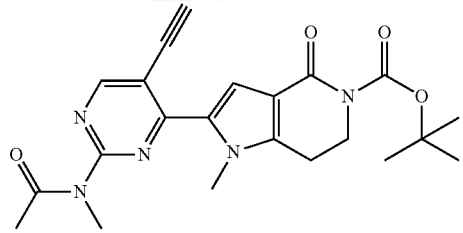

Step 1. 2-(2-Amino-5-trimethylsilanylethynyl-pyrimidin-4-yl)-1-methyl-4-oxo-1,4,6,7-tetrahydro-pyrrolo[3,2-c]pyridine-5-carboxylic acid tert-butyl ester A solution of 2-(2-Amino-5-iodo-pyrimidin-4-yl)-1-methyl-4-oxo-1,4,6,7-tetrahydro-pyrrolo[3,2-c]pyridine-5-carboxylic acid tert-butyl ester (2.00 g, 4.26 mmol), ethynyltrimethylsilane (1.35 mL, 8.52 mmol), CuI (5% mol, 0.04 g, 0.21 mmol), PdCl$_2$(PPh$_3$)$_2$ (5% mol, 0.15 g, 0.21 mmol) and TEA (5.80 mL, 42.60 mmol) in DMF (50 mL) was degassed with argon and stirred at r.t. for 4 h. The solvent was evaporated under vacuum, the crude was dissolved in EtOAc (250 mL), washed with NH$_3$, and brine. The organic phase was dried with anhydrous Na$_2$SO$_4$ and evaporated under vacuum to give a crude that was purified by flash column chromatography (DCM-MeOH 97:3) to give the title product (1.78 g, 95%) as brownish solid.

$^1$H NMR (600 MHz, DMSO-$d_6$) δ ppm 0.19-0.22 (m, 9H) 1.47 (s, 9H) 2.97 (t, J=6.32 Hz, 2H) 3.82 (s, 3H) 3.98 (t, J=6.23 Hz, 2H) 7.10 (s, 2H) 7.55 (s, 1H) 8.34 (s, 1H).

According to this same methodology, but employing suitable substituted derivatives, the following intermediate was prepared:

2-(2-Amino-5-trimethylsilanylethynyl-pyrimidin-4-yl)-4-oxo-1-[2-(tetrahydro-pyran-2-yloxy)-ethyl]-1,4,6,7-tetrahydro-pyrrolo[3,2-c]pyridine-5-carboxylic acid tert-butyl ester $^1$H NMR (600 MHz, DMSO-$d_6$) δ ppm 0.21 (s, 8H) 1.27-1.42 (m, 4H) 1.46 (s, 11H) 3.05 (br. s., 2H) 3.19-3.29 (m, 2H) 3.55-3.62 (m, 1H) 3.73 (ddd, J=10.85, 7.10, 3.66 Hz, 1H) 3.89-4.05 (m, 2H) 4.40-4.46 (m, 1H) 4.63 (ddd, J=14.38, 7.23, 3.66 Hz, 1H) 4.70-4.79 (m, 1H) 7.07 (s, 2H) 7.65 (s, 1H) 8.34 (s, 1H).

Step 2. 2-(2-Acetylamino-5-ethynyl-pyrimidin-4-yl)-1-methyl-4-oxo-1,4,6,7-tetrahydro-pyrrolo[3,2-c]pyridine-5-carboxylic acid tert-butyl ester A mixture of 2-(2-amino-5-trimethylsilanylethynyl-pyrimidin-4-yl)-1-methyl-4-oxo-1,4,6,7-tetrahydro-pyrrolo[3,2-c]pyridine-5-carboxylic acid tert-butyl ester (0.50 g, 1.14 mmol) and Ac$_2$O (10 mL) was stirred at 80° C. for 6 h (the suspension turned to a yellow solution). The solvent was then removed under reduced pressure. EtOH was added and the solvents were evaporated. This process was repeated 3 times. The crude was dissolved in MeOH (10 mL), TEA (1.55 mL, 11.40 mmol) was added and the reaction was stirred at r.t. for 24 h. The suspension was then poured in water (100 mL), the solid precipitated was filtered, washed with water and dried at 45° C. under vacuum to give the title product (0.30 g, 64%) as white solid. $^1$H NMR (600 MHz, DMSO-$d_6$) δ ppm 1.47 (s, 9H) 2.17 (s, 3H) 3.00 (t, J=6.32

Hz, 2H) 3.94 (s, 3H) 3.99 (t, J=6.32 Hz, 2H) 4.73 (s, 1H) 7.65 (s, 1H) 8.74 (s, 1H) 10.77 (s, 1H).

Step 3. 2-[2-(Acetyl-methyl-amino)-5-ethynyl-pyrimidin-4-yl]-1-methyl-4-oxo-1,4,6,7-tetrahydro-pyrrolo[3,2-c]pyridine-5-carboxylic acid tert-butyl ester To a suspension of 2-(2-acetylamino-5-ethynyl-pyrimidin-4-yl)-1-methyl-4-oxo-1,4,6,7-tetrahydro-pyrrolo[3,2-c]pyridine-5-carboxylic acid tert-butyl ester (0.16 g, 0.39 mmol) in anhydrous DMF (5 mL), $Cs_2CO_3$ (0.26 g, 0.78 mmol) and MeI (0.05 mL, 0.78 mmol) were added. The mixture was stirred at r.t. for 3 h, then poured in water (50 mL); the solid precipitated was filtered, washed with water and dried at 45° C. under vacuum. The title product (0.13 g, 78%) was obtained as white solid.

$^1$H NMR (600 MHz, DMSO-$d_6$) δ ppm 1.42-1.51 (m, 9H) 2.35-2.43 (m, 3H) 3.01 (t, J=6.23 Hz, 2H) 3.36-3.41 (m, 3H) 3.79-3.86 (m, 3H) 4.00 (t, J=6.32 Hz, 2H) 4.80 (s, 1H) 7.61 (s, 1H) 8.84 (s, 1H).

By analogous procedure, using EtI instead of MeI the following intermediate was obtained:

2-[2-(Acetyl-ethyl-amino)-5-ethynyl-pyrimidin-4-yl]-1-methyl-4-oxo-1,4,6,7-tetrahydro-pyrrolo[3,2-c]pyridine-5-carboxylic acid tert-butyl ester (ESI) m/z 438 [(M+H)$^+$]. HRMS (ESI) calculated for $C_{23}H_{28}N_5O_4^+$ [(M+H)$^+$] 438.4916. found 438.4920.

Preparation 29

2-(2-Amino-5-ethynyl-pyrimidin-4-yl)-1-methyl-4-oxo-1,4,6,7-tetrahydro-pyrrolo[3,2-c]pyridine-5-carboxylic acid tert-butyl ester

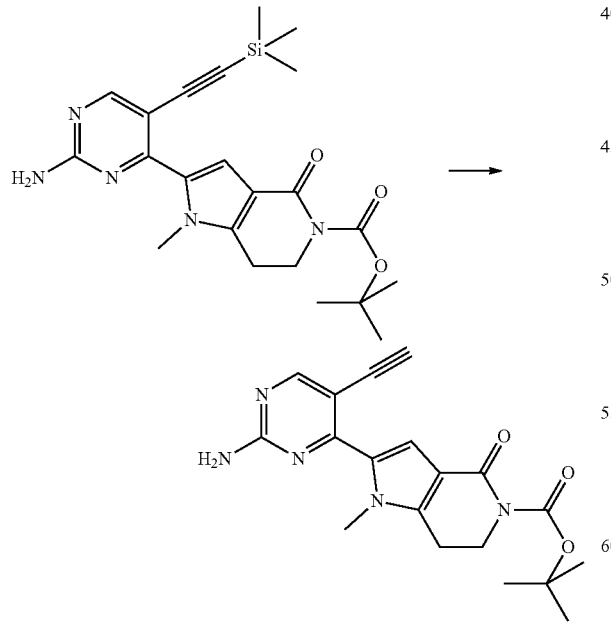

2-(2-Amino-5-trimethylsilanylethynyl-pyrimidin-4-yl)-1-methyl-4-oxo-1,4,6,7-tetrahydro-pyrrolo[3,2-c]pyridine-5-carboxylic acid tert-butyl ester (2.04 g, 4.64 mmol) was dissolved in degassed MeOH (75 mL) and treated with $K_2CO_3$ (0.64 g, 4.64 mmol), under argon, at r.t. for 6 h. The reaction was quenched with 2N HCl (4.64 mL) and the solvent was removed under reduced pressure. The residue was suspended in water and the solid was filtered affording the title product (1.56 g, 91%).

$^1$H NMR (500 MHz, DMSO-$d_6$) δ ppm 1.47 (s, 6H) 2.97 (t, J=6.33 Hz, 2H) 3.78-3.82 (m, 3H) 3.98 (t, J=6.25 Hz, 2H) 4.42 (s, 1H) 7.11 (s, 2H) 7.42 (s, 1H) 8.38 (s, 1H).

According to this same methodology, but employing suitable substituted derivatives, the following intermediate was prepared:

2-(2-Amino-5-ethynyl-pyrimidin-4-yl)-4-oxo-1-[2-(tetrahydro-pyran-2-yloxy)-ethyl]-1,4,6,7-tetrahydro-pyrrolo[3,2-c]pyridine-5-carboxylic acid tert-butyl ester (ESI) m/z 482 [(M+H)$^+$]. HRMS (ESI) calculated for $C_{25}H_{32}N_5O_5^+$ [(M+H)$^+$] 482.5441. found 482.5440.

Preparation 30

2-(5-Iodo-2-methylamino-pyrimidin-4-yl)-1-methyl-1,5,6,7-tetrahydro-pyrrolo[3,2-c]pyridin-4-one

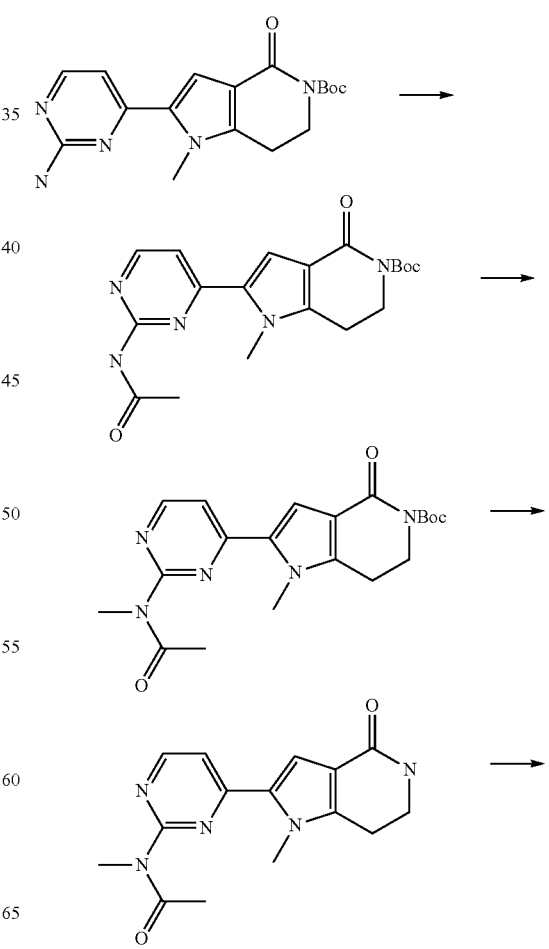

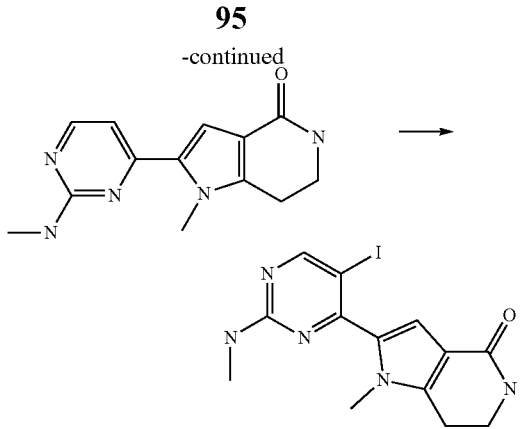

Step 1. 2-(2-Acetylamino-pyrimidin-4-yl)-1-methyl-4-oxo-1,4,6,7-tetrahydro-pyrrolo[3,2-c]pyridine-5-carboxylic acid tert-butyl ester 2-(2-Amino-pyrimidin-4-yl)-1-methyl-4-oxo-1,4,6,7-tetrahydro-pyrrolo[3,2-c]pyridine-5-carboxylic acid tert-butyl ester (0.46 g, 1.34 mmol) was suspended in Ac$_2$O (8 mL) and heated at 80° C. The suspension turned to a yellow solution during 1 h when the reaction reached completion. The solvent was removed under reduced pressure stripping with EtOH for three times affording the product as white solid, which was used in the following step without further purification.

$^1$H NMR (500 MHz, DMSO-d$_6$) δ ppm 1.47 (s, 9H) 2.16 (s, 3H) 2.97 (t, J=6.31 Hz, 2H) 3.93-4.00 (m, 2H) 4.04 (s, 3H) 7.34 (s, 1H) 7.51 (d, J=5.49 Hz, 1H) 8.51 (d, J=5.49 Hz, 1H) 10.56 (s, 1H).

Step 2. 2-[2-(Acetyl-methyl-amino)-pyrimidin-4-yl]-1-methyl-4-oxo-1,4,6,7-tetrahydro-pyrrolo[3,2-c]pyridine-5-carboxylic acid tert-butyl ester 2-(2-Acetylamino-pyrimidin-4-yl)-1-methyl-4-oxo-1,4,6,7-tetrahydro-pyrrolo[3,2-c]pyridine-5-carboxylic acid tert-butyl ester deriving from the previous step was dissolved in dry DMF (9 mL) and treated with Cs$_2$CO$_3$ (0.52 mg, 1.60 mmol) and MeI (0.14 mL, 2.22 mmol) at r.t. overnight. The mixture was then poured in water and let under stirring for 30 min. The resulting white solid was filtered and dried under vacuum (0.41 g, 78% over two steps).

$^1$H NMR (500 MHz, DMSO-d$_6$) δ ppm 1.47 (s, 9H) 2.33-2.37 (m, 3H) 2.99 (t, J=6.31 Hz, 2H) 3.38 (s, 3H) 3.93 (s, 3H) 3.96-4.02 (m, 2H) 7.40 (s, 1H) 7.65 (d, J=5.22 Hz, 1H) 8.63 (d, J=5.22 Hz, 1H).

According to this same methodology, but employing suitable substituted derivatives, the following intermediates were prepared:

2-(2-{Acetyl-[2-(tetrahydro-pyran-2-yloxy)-ethyl]-amino}-pyrimidin-4-yl)-1-methyl-4-oxo-1,4,6,7-tetrahydro-pyrrolo[3,2-c]pyridine-5-carboxylic acid tert-butyl ester (ESI) m/z 514 [(M+H)$^+$]. HRMS (ESI) calculated for C$_{26}$H$_{36}$N$_5$O$_6$ [(M+H)$^+$] 514.2660. found 514.2679.

Step 3. N-Methyl-N-[4-(1-methyl-4-oxo-4,5,6,7-tetrahydro-1H-pyrrolo[3,2-c]pyridin-2-yl)-pyrimidin-2-yl]-acetamide A solution of 2-[2-(acetyl-methyl-amino)-pyrimidin-4-yl]-1-methyl-4-oxo-1,4,6,7-tetrahydro-pyrrolo[3,2-c]pyridine-5-carboxylic acid tert-butyl ester (0.41 g, 1.03 mmol) and TFA (2 mL) in DCM (10 mL) was let under stirring at r.t. for 1 h. The solvent was evaporated under reduced pressure yielding the title product as yellow solid.

(ESI) m/z 300 [(M+H)$^+$]. HRMS (ESI) calculated for C$_{15}$H$_{18}$N$_5$ [(M+H)$^+$] 300.1455. found 300.1432.

According to this same methodology, but employing suitable substituted derivative, the following intermediate was prepared:

N-(2-Hydroxy-ethyl)-N-[4-(1-methyl-4-oxo-4,5,6,7-tetrahydro-1H-pyrrolo[3,2-c]pyridin-2-yl)-pyrimidin-2-yl]-acetamide (ESI) m/z 330 [(M+H)$^+$]. HRMS (ESI) calculated for C$_{16}$H$_{20}$N$_5$O$_3$ [(M+H)$^+$] 330.1561. found 330.1580.

Step 4. 1-Methyl-2-(2-methylamino-pyrimidin-4-yl)-1,5,6,7-tetrahydro-pyrrolo[3,2-c]pyridin-4-one N-Methyl-N-[4-(1-methyl-4-oxo-4,5,6,7-tetrahydro-1H-pyrrolo[3,2-c]pyridin-2-yl)-pyrimidin-2-yl]-acetamide deriving from the previous step was refluxed in MeOH (10 mL) with K$_2$CO$_3$ (0.40 g, 2.89 mmol) for 1 h. The solvent was evaporated and the residue was suspended in water. The resulting solid was filtered giving the title product (0.25 g, 94% over two steps).

$^1$H NMR (600 MHz, DMSO-d$_6$) δ ppm 2.83 (d, J=4.95 Hz, 3H) 2.85 (t, J=6.87 Hz, 2H) 3.42 (td, J=6.87, 2.38 Hz, 2H) 3.96 (br. s, 3H) 6.87 (d, J=5.31 Hz, 1H) 6.97 (d, J=4.21 Hz, 1H) 7.01 (s, 1H) 7.08 (br. s., 1H) 8.16 (d, J=4.40 Hz, 1H).

According to this same methodology, but employing suitable substituted derivative, the following intermediate was prepared:

2-[2-(2-Hydroxy-ethylamino)-pyrimidin-4-yl]-1-methyl-1,5,6,7-tetrahydro-pyrrolo[3,2-c]pyridin-4-one (ESI) m/z 288 [(M+H)$^+$]. HRMS (ESI) calculated for C$_{14}$H$_{18}$N$_5$O$_2$ [(M+H)$^+$] 288.1455. found 288.1455.

Step 5. 2-(5-Iodo-2-methylamino-pyrimidin-4-yl)-1-methyl-1,5,6,7-tetrahydro-pyrrolo[3,2-c]pyridin-4-one According to the experimental procedure described in WO2010/145998.

$^1$H NMR (600 MHz, DMSO-d$_6$) δ ppm 2.79 (d, J=4.76 Hz, 3H) 2.87 (t, J=6.78 Hz, 2H) 3.43 (td, J=6.82, 2.29 Hz, 3H) 3.66 (br. s., 3H) 7.00 (br. s., 1H) 7.09 (br. s., 1H) 7.26 (br. s., 1H) 8.49-8.65 (m, 1H).

According to this same methodology, but employing suitable substituted derivative, the following intermediate was prepared:

2-[2-(2-Hydroxy-ethylamino)-5-iodo-pyrimidin-4-yl]-1-methyl-1,5,6,7-tetrahydro-pyrrolo[3,2-c]pyridin-4-one $^1$H NMR (600 MHz, DMSO-d$_6$) δ ppm 2.87 (t, J=6.78 Hz, 2H) 3.33 (2H overlapped by water signal) 3.43 (td, J=6.87, 2.20 Hz, 2H) 3.50 (t, J=6.32 Hz, 2H) 3.64 (br. s, 3H) 4.67 (br. s., 1H) 6.99 (br. s., 1H) 7.09 (br. s., 1H) 7.23 (t, J=5.68 Hz, 1H) 8.56 (br. s., 1H).

Preparation 31

1-Methyl-2-(2-methylamino-pyrimidin-4-yl)-1,5,6,7-tetrahydro-pyrrolo[3,2-c]pyridin-4-one

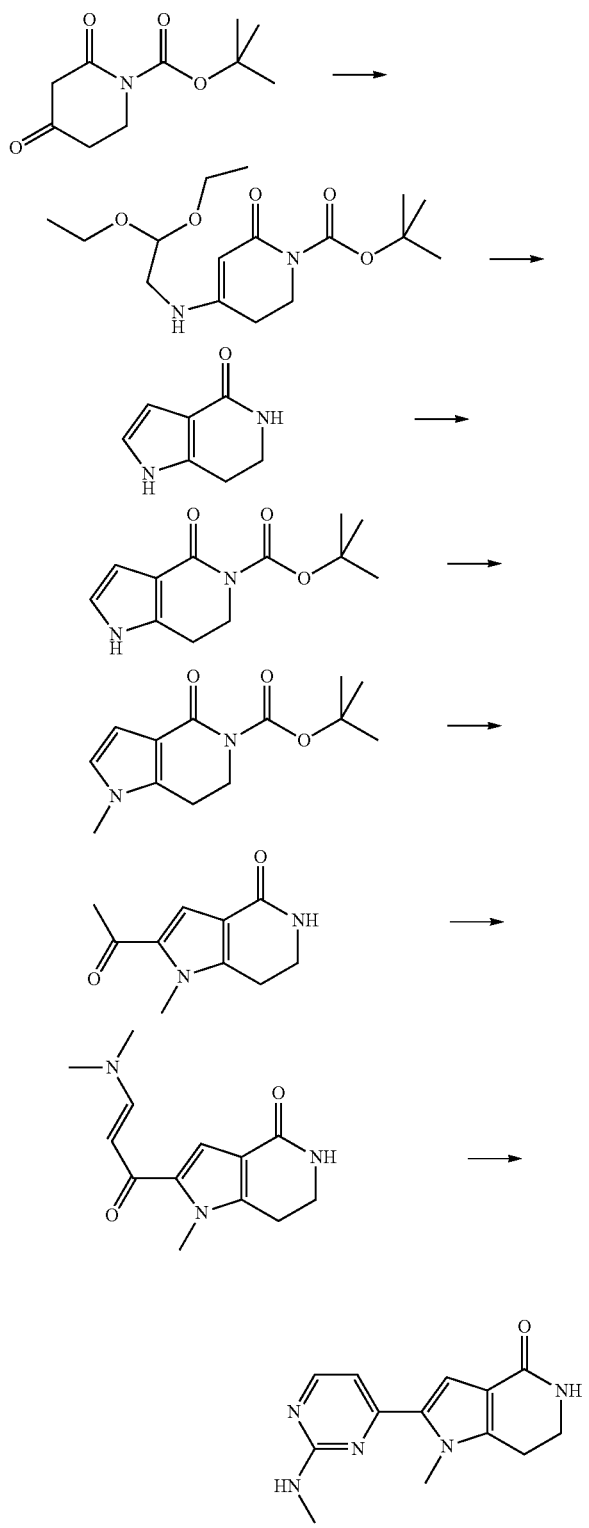

Step 1. 4-(2,2-Diethoxy-ethylamino)-6-oxo-3,6-dihydro-2H-pyridine-1-carboxylic acid tert-butyl ester In a four-necked round bottom flask 4-oxo-1,4,6,7-tetrahydro-pyrrolo[3,2-c]pyridine-5-carboxylic acid tert-butyl ester (50.6 g, 0.24 mol) was suspended in toluene (750 mL). Amino acetaldehyde diethyl acetal (34.5 mL, 0.24 mol) was added dropwise under stirring at r.t. during 15 min when the suspension turned to solution. The mixture was heated at 70° C. for 1 h. After cooling to r.t. the solvent was removed under reduced pressure affording the title product as yellow oil (82.8 g, quantitative yield, 4.8 g of residual of toluene).

$^1$H NMR (401 MHz, DMSO-$d_6$) δ ppm 1.13 (t, J=7.02 Hz, 6H) 1.42 (s, 9H) 2.37-2.44 (m, 2H) 3.06 (t, J=5.43 Hz, 1H) 3.50 (dq, J=9.58, 7.02 Hz, 2H) 3.57-3.68 (m, 4H) 4.50 (s, 1H) 4.53-4.62 (m, 1H) 6.95 (br. s., 1H).

Step 2. 1,5,6,7-Tetrahydro-pyrrolo[3,2-c]pyridin-4-one trifluoroacetate

A solution of 4-(2,2-diethoxy-ethylamino)-6-oxo-3,6-dihydro-2H-pyridine-1-carboxylic acid tert-butyl ester from the previous step (82.8 g, 0.24 theoretical mol) in DCM (150 mL) was added drop wise in 40 min to TFA (500 mL) kept in an ice-cold bath in a four-necked round bottom flask under stirring. When the addition was complete, the mixture was let under stirring at r.t. for 1 h. The solvents were removed under reduced pressure affording a yellow oil that was treated with MTBE (1 L) under stirring for 2 h. The precipitate was filtered and eliminated. After concentration of the filtrate, the resulting solid was treated with MTBE (5 vol) and cyclohexane (3 vol) and filtered yielding a first aliquot of the title product as yellow solid (18.7 g). The mother liquor was concentrated to small volume affording, after filtration, a further aliquot of product that was rinsed with cyclohexane and dried (7.22 g, 43% total yield).

$^1$H NMR (600 MHz, DMSO-$d_6$) δ ppm 2.72 (t, J=6.87 Hz, 2H) 3.33 (m, 2H overlapped by water signal) 6.19 (t, J=2.56 Hz, 1H) 6.64 (t, J=2.56 Hz, 1H) 6.81 (br. s., 1H) 11.07 (br. s., 1H).

Step 3. 4-Oxo-1,4,6,7-tetrahydro-pyrrolo[3,2-c]pyridine-5-carboxylic acid tert-butyl ester 1,5,6,7-Tetrahydro-pyrrolo[3,2-c]pyridin-4-one trifluoroacetate (28.25 g, 0.11 mol) was suspended in MeCN and treated with Boc$_2$O (86.3 g, 0.40 mol), TEA (63 mL, 0.45 mol) and DMAP (10% mol, 1.38 g, 0.011 mol). The mixture was let under stirring at r.t. for 22 h (formation of the bis-Boc derivative detected by HPLC-MS). After removal of the solvent, the residue was dissolved in DCM and washed with 5% solution of citric acid. The aqueous layer was extracted with DCM (2×50 mL). The organic phase was dried over anhydrous Na$_2$SO$_4$, filtered and concentrated to yield the bis-Boc intermediate as brown solid that was suspended in MeOH (445 mL), treated with NH$_3$ (53 mL) and heated at 75° C. for 7 h. The solvent was removed under vacuum, the residue was dissolved in DCM (50 mL) and treated with MTBE (160 mL) affording the title product as brownish solid after filtration (13.36 g, 50%).

$^1$H NMR (600 MHz, DMSO-$d_6$) δ ppm 1.45 (s, 9H) 2.83 (t, J=6.32 Hz, 2H) 3.91 (t, J=6.23 Hz, 2H) 6.31 (t, J=2.11 Hz, 1H) 6.64-6.81 (m, 1H) 11.33 (br. s., 1H).

Step 4. 1-Methyl-4-oxo-1,4,6,7-tetrahydro-pyrrolo[3,2-c]pyridine-5-carboxylic acid tert-butyl ester To a solution of 4-oxo-1,4,6,7-tetrahydro-pyrrolo[3,2-c]pyridine-5-carboxylic acid tert-butyl ester (1 g, 4.23 mmol) in dry DMF (10 mL) Cs$_2$CO$_3$ (1.79 g, 5.50 mmol) and MeI (0.40 mL, 6.35 mmol) were added. The mixture was let under stirring at r.t. for 1 h, then it was diluted with EtOAc and washed with water (2×20 mL) and brine. The organic phase was dried over anhydrous Na$_2$SO$_4$, filtered and taken to dryness under vacuum affording the title product as light yellow solid (0.96 g, 91%).

$^1$H NMR (600 MHz, DMSO-d$_6$) δ ppm 1.45 (s, 9H) 2.83 (t, J=6.32 Hz, 2H) 3.54 (s, 3H) 3.92 (t, J=6.32 Hz, 2H) 6.32 (d, J=3.11 Hz, 1H) 6.75 (d, J=2.93 Hz, 1H).

Step 5. 2-Acetyl-1-methyl-1,5,6,7-tetrahydro-pyrrolo[3,2-c]pyridin-4-one

The solution of 1-methyl-4-oxo-1,4,6,7-tetrahydro-pyrrolo[3,2-c]pyridine-5-carboxylic acid tert-butyl ester (0.94 g, 3.77 mmol) in dry DCM (18 mL) was kept at 0° C. and AlCl$_3$ (1.50 g, 11.30 mmol) was added portionwise under a vigorous stirring. After 20 min, a solution of acetyl chloride (0.40 mL, 5.65 mmol) in dry DCM (1.5 mL) was dropped into the suspension, the mixture was warmed to r.t. and let under stirring for 2 h. The reaction was quenched by pouring into 2 N HCl (20 mL) at 0° C., keeping temperature below 15° C. The aqueous layer was extracted with DCM (4×10 mL), the organic phase was washed with brine, dried over anhydrous Na$_2$SO$_4$, filtered and concentrated under reduced pressure. The residue was treated with Et$_2$O and filtered affording the title product as light orange solid (0.36 g, 50%).

$^1$H NMR (600 MHz, DMSO-d$_6$) δ ppm 2.38 (s, 3H) 2.83 (t, J=6.87 Hz, 2H) 3.41 (td, J=6.87, 2.56 Hz, 2H) 3.77 (s, 3H) 7.23 (br. s., 1H) 7.29 (s, 1H).

Step 6. 2-((E)-3-Dimethylamino-acryloyl)-1-methyl-1,5,6,7-tetrahydro-pyrrolo[3,2-c]pyridin-4-one The mixture of 2-acetyl-1-methyl-1,5,6,7-tetrahydro-pyrrolo[3,2-c]pyridin-4-one (0.35 g, 1.84 mmol) and dimethylformamide diisopropylacetal (1.15 mL, 5.50 mmol) in DMF (5 mL) was heated at 100° C. for 7 h. The solvent was removed under reduced pressure giving the product as red solid that was used in the subsequent step without further purification.

$^1$H NMR (600 MHz, DMSO-d$_6$) δ ppm 2.80 (t, J=6.87 Hz, 2H) 2.86 (br. s., 3H) 3.06 (br. s., 3H) 3.39 (td, J=6.87, 2.38 Hz, 3H) 3.81 (s, 3H) 5.66 (d, J=12.45 Hz, 1H) 7.06 (br. s., 1H) 7.07 (s, 1H) 7.49-7.52 (m, 1H).

Step 7. 1-Methyl-2-(2-methylamino-pyrimidin-4-yl)-1,5,6,7-tetrahydro-pyrrolo[3,2-c]pyridin-4-one The mixture of 2-((E)-3-dimethylamino-acryloyl)-1-methyl-1,5,6,7-tetrahydro-pyrrolo[3,2-c]pyridin-4-one (1.84 theoretical mmol) from the previous step, N-methylguanidine hydrochloride (0.40 g, 3.67 mmol) and tBuONa (0.35 g, 3.67 mmol) in DMF (5 mL) was heated at 100° C. for 4 h. After cooling the mixture was poured into cold water and let under stirring. The white solid was filtered affording a first aliquot of product (0.10 g). The mother liquor was concentrated to reduced volume and a second aliquot of product was recovered by filtration (0.07 g, 36% total yield).

$^1$H NMR (600 MHz, DMSO-d$_6$) δ ppm 2.83 (d, J=4.95 Hz, 3H) 2.85 (t, J=6.87 Hz, 2H) 3.42 (td, J=6.87, 2.38 Hz, 2H) 3.92-4.01 (m, 3H) 6.87 (d, J=5.31 Hz, 1H) 6.97 (d, J=4.21 Hz, 1H) 7.01 (s, 1H) 7.08 (br. s., 1H) 8.16 (d, J=4.40 Hz, 1H).

Example 1

1-[4-(4-Ethyl-piperazin-1-ylmethyl)-3-trifluoromethyl-phenyl]-3-{3-[4-(1-methyl-4-oxo-4,5,6,7-tetrahydro-1H-pyrrolo[3,2-c]pyridin-2-yl)-pyridin-3-ylethynyl]-phenyl}-urea (cmpd 38)

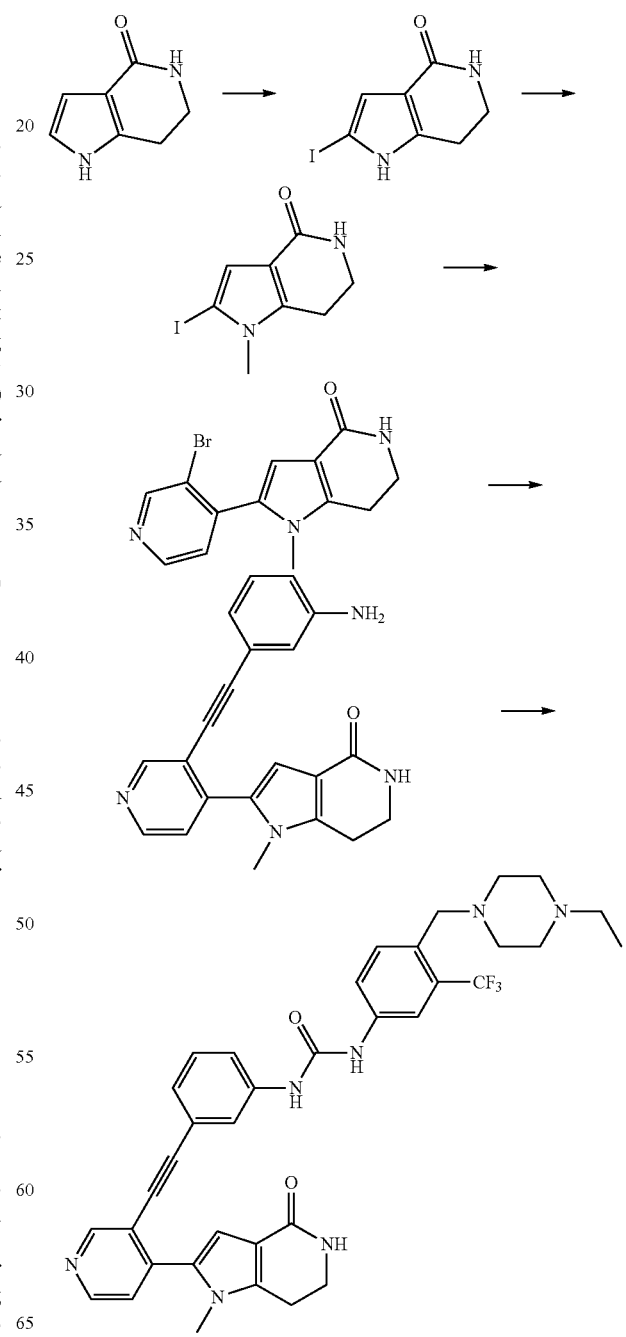

Step 1. 2-Iodo-1,5,6,7-tetrahydro-pyrrolo[3,2-c]pyridin-4-one

To a solution of 1,5,6,7-tetrahydro-pyrrolo[3,2-c]pyridin-4-one (0.12 g, 0.85 mmol) in dry THF (5 mL) and MeOH (1.5 mL), kept at −70° C., N-iodosuccinimide (0.19 g, 0.84 mmol) was added. After 1.5 h the reaction was quenched with a saturated solution of $Na_2S_2O_5$, let to reach r.t. and the solvent was removed under reduced pressure. The residue was suspended in water and the white solid was filtered and rinsed with water (0.16 g), while the filtrate was extracted with DCM (3×10 mL). The organic layer was dried over anhydrous $Na_2SO_4$, filtered and concentrated affording a second aliquot of product (32 mg, 89% total yield).

$^1$H NMR (600 MHz, DMSO-$d_6$) δ ppm 2.72 (t, J=6.87 Hz, 2H) 3.30-3.32 (m, 2H) 6.34 (s, 1H) 6.90 (br. s., 1H) 11.61 (br. s., 1H).

Step 2. 2-Iodo-1-methyl-1,5,6,7-tetrahydro-pyrrolo[3,2-c]pyridin-4-one

2-Iodo-1,5,6,7-tetrahydro-pyrrolo[3,2-c]pyridin-4-one (0.2 g, 0.75 mmol) was dissolved in dry DMF (3.5 mL) and treated with $Cs_2CO_3$ (0.44 g, 1.35 mmol) and MeI (0.12 mL, 1.87 mmol). The mixture was let under stirring at r.t. for 6 h. After dilution with EtOAc, the organic layer was washed with water (2×10 mL) and brine, then it was dried over anhydrous $Na_2SO_4$, filtered and concentrated under reduced pressure. A purification by flash column chromatography afforded the product as yellow solid (0.18 g, 87%).

$^1$H NMR (600 MHz, DMSO-$d_6$) δ ppm 2.80 (t, J=6.87 Hz, 2H) 3.35 (m, 2H under water signal) 3.46 (s, 3H) 6.48 (s, 1H) 6.94 (br. s., 1H).

Step 3. 2-(3-Bromo-pyridin-4-yl)-1-methyl-1,5,6,7-tetrahydro-pyrrolo[3,2-c]pyridin-4-one (Ref. *Tetrahedron* 2003, 59, 10043-10049). To a solution of 2-iodo-1-methyl-1,5,6,7-tetrahydro-pyrrolo[3,2-c]pyridin-4-one (0.30 g, 1.09 mmol) and 3-bromo-4-(4,4,5,5-tetramethyl-[1,3,2]dioxaborolan-2-yl)-pyridine (0.34 g, 1.20 mmol) in dry DMF (30 mL), a 2 N solution of $K_3PO_4$ (1.09 mL, 2.19 mmol) and Pd(PPh$_3$)$_4$ (51 mg, 0.044 mmol) were added. The resulting mixture was degassed three times back filling with argon each time then it was heated at 85° C. for 4 h. After cooling to r.t., the mixture was diluted with EtOAc and treated with water. The resulting emulsion was filtered over a pad of celite rinsing with EtOAc and DCM. The solution was concentrated under reduced pressure. The residue was suspended in water, stirred for 15 min and the precipitate was filtered affording a first aliquot of the product as white solid (0.15 g). The filtrate was evaporated giving a residue that was purified by flash column chromatography (DCM/MeOH 97/3) yielding a second aliquot of product (71 mg, 66% total yield).

$^1$H NMR (600 MHz, DMSO-$d_6$) δ ppm 2.85 (t, J=6.96 Hz, 2H) 3.40 (s, 3H) 3.44 (td, J=6.96, 2.56 Hz, 2H) 6.47 (s, 1H) 7.05 (br. s., 1H) 7.46 (d, J=4.95 Hz, 1H) 8.59 (d, J=4.94 Hz, 1H) 8.86 (s, 1H).

Step 4. 2-[3-(3-Amino-phenylethynyl)-pyridin-4-yl]-1-methyl-1,5,6,7-tetrahydro-pyrrolo[3,2-c]pyridin-4-one To a solution of 2-(3-bromo-pyridin-4-yl)-1-methyl-1,5,6,7-tetrahydro-pyrrolo[3,2-c]pyridin-4-one (0.21 g, 0.69 mmol), CuI (19.2 mg, 0.1 mmol), 3-ethynyl-phenylamine (0.24 g, 2.07 mmol) and TEA (1.16 mL, 8.37 mmol) in degassed dry DMF (13 mL), PdCl$_2$(PPh$_3$)$_2$ (72.6 mg, 0.1 mmol) was added. The resulting mixture was degassed three times back filling with argon each time then it was heated at 50° C. for 8 h. After cooling, the mixture was diluted with EtOAc and washed with water (2×10 mL). The organic layer was dried over anhydrous $Na_2SO_4$, filtered and concentrated under reduced pressure. The residue was purified by flash column chromatography (DCM/MeOH 90/10) affording the title compound as yellowish solid (0.11 g, 46%).

$^1$H NMR (600 MHz, DMSO-$d_6$) δ ppm 2.89 (t, J=6.78 Hz, 2H) 3.46 (td, J=6.69, 2.20 Hz, 2H) 3.54 (s, 3H) 5.22 (s, 2H) 6.53-6.63 (m, 2H) 6.67 (s, 1H) 6.74 (s, 1H) 7.03 (t, J=7.78 Hz, 1H) 7.09 (br. s., 1H) 7.46 (d, J=5.13 Hz, 1H) 8.56 (d, J=4.95 Hz, 1H) 8.77 (s, 1H).

Step 5. 1-[4-(4-Ethyl-piperazin-1-ylmethyl)-3-trifluoromethyl-phenyl]-3-{3-[4-(1-methyl-4-oxo-4,5,6,7-tetrahydro-1H-pyrrolo[3,2-c]pyridin-2-yl)-pyridin-3-ylethynyl]-phenyl}-urea Procedure with triphosgene as already described.

$^1$H NMR (600 MHz, DMSO-$d_6$) δ ppm 0.98 (t, J=7.23 Hz, 3H) 2.30 (q, J=7.20 Hz, 2H) 2.38 (br. s., 8H) 2.92 (t, J=6.87 Hz, 2H) 3.45 (td, J=6.91, 2.66 Hz, 2H) 3.50 (s, 2H) 3.56 (s, 3H) 6.72 (s, 1H) 7.07 (d, J=7.14 Hz, 2H) 7.33 (t, J=7.78 Hz, 1H) 7.39 (d, J=9.16 Hz, 1H) 7.47-7.50 (m, 1H) 7.56-7.59 (m, 1H) 7.61-7.65 (m, 1H) 7.71 (s, 1H) 7.97 (d, J=1.83 Hz, 1H) 8.59 (d, J=5.13 Hz, 1H) 8.83 (s, 1H) 8.97 (br. s., 1H) 9.13 (br. s., 1H).

Example 2

2-{3-[6-Amino-4-(1-methyl-4-oxo-4,5,6,7-tetrahydro-1H-pyrrolo[3,2-c]pyridin-2-yl)-pyridin-3-ylethynyl]-phenyl}-N-[4-(4-methyl-piperazin-1-ylmethyl)-3-trifluoromethyl-phenyl]-acetamide (cmpd 201)

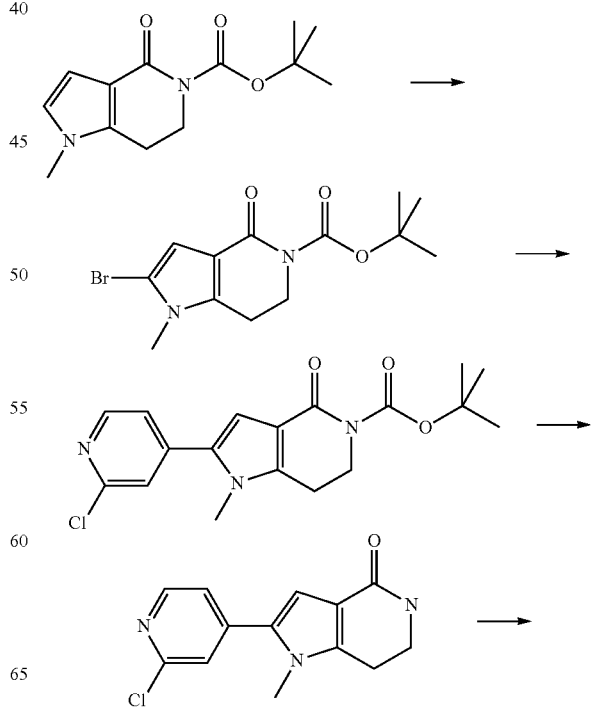

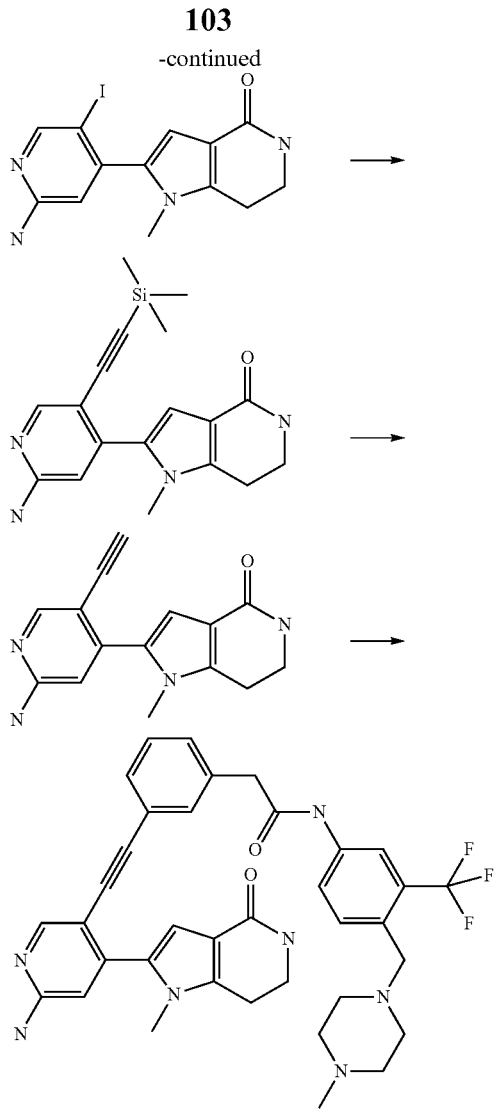

Step 1. 2-Bromo-1-methyl-4-oxo-1,4,6,7-tetrahydro-pyrrolo[3,2-c]pyridine-5-carboxylic acid tert-butyl ester To a solution of 1-methyl-4-oxo-1,4,6,7-tetrahydro-pyrrolo[3,2-c]pyridine-5-carboxylic acid tert-butyl ester (4.32 g, 17.29 mmol) in dry THF (108 mL) and MeOH (32 mL), kept at −70° C., a first portion of NBS (1.54 g, 8.65 mmol) was added. After 45 min, a second portion of NBS (1.54 g, 8.65 mmol) was added and the mixture let under stirring at −70° C. for further 30 min. The temperature was allowed to rise up to r.t. and kept at this temperature for additional 2.5 h. The reaction was quenched with a 10% solution of $Na_2S_2O_5$ (50 mL). After removal of the solvent under reduced pressure, the residue was dissolved with EtOAc and washed with water and brine. The organic layer was dried over anhydrous $Na_2SO_4$, filtered and evaporated. The product was purified by flash column chromatography (DCM/MeOH 98/2) and isolated as white solid (4.40 g, 77%).

$^1$H NMR (600 MHz, DMSO-$d_6$) δ ppm 1.45 (s, 9H) 2.88 (t, J=6.41 Hz, 2H) 3.48 (s, 3H) 3.93 (t, J=6.32 Hz, 2H) 6.49 (s, 1H).

Step 2. 2-(2-Chloro-pyridin-4-yl)-1-methyl-4-oxo-1,4,6,7-tetrahydro-pyrrolo[3,2-c]pyridine-5-carboxylic acid tert-butyl ester 2-Bromo-1-methyl-4-oxo-1,4,6,7-tetrahydro-pyrrolo[3,2-c]pyridine-5-carboxylic acid tert-butyl ester (1.03 g, 3.13 mmol), 2-chloro-4-pyridineboronic acid (0.98 g, 6.26 mmol) and $PdCl_2(dppf)_2$ (0.26 g, 0.31 mmol) were charged in a Schlenk tube under argon. Degassed dioxane (52 mL) and a 2 M solution of $Na_2CO_3$ (4.69 mL) were added and the resulting mixture was degassed three times back filling with argon each time. The reaction was heated at 85° C. for 4.5 h. After cooling, it was filtered over a pad of celite rinsing thoroughly with EtOAc. The filtrate was washed with a saturated solution of $NaHCO_3$, water and brine. The organic layer was dried over anhydrous $Na_2SO_4$, filtered and evaporated. Purification by flash column chromatography (Hex/EtOAc 50/50) afforded the title product as white solid (0.64 g, 56%).

$^1$H NMR (600 MHz, DMSO-$d_6$) δ ppm 1.47 (s, 9H) 2.97 (t, J=6.32 Hz, 2H) 3.65 (s, 3H) 3.98 (t, J=6.32 Hz, 2H) 6.88 (s, 1H) 7.55 (dd, J=5.31, 1.47 Hz, 1H) 7.62-7.64 (m, 1H) 8.41 (d, J=5.31 Hz, 1H).

Step 3. 2-(2-Amino-pyridin-4-yl)-1-methyl-1,5,6,7-tetrahydro-pyrrolo[3,2-c]pyridin-4-one In a Schlenk tube 2-(2-chloro-pyridin-4-yl)-1-methyl-4-oxo-1,4,6,7-tetrahydro-pyrrolo[3,2-c]pyridine-5-carboxylic acid tert-butyl ester (0.50 g, 1.38 mmol) and carbamic acid tert-butyl ester (0.81 g, 6.91 mmol) were charged with degassed dioxane (15 mL) under argon. $Pd(OAc)_2$ (30 mg, 0.14 mmol), Xantphos (0.12 g, 0.14 mmol) and $Cs_2CO_3$ (0.90 g, 2.76 mmol) were added. The resulting mixture was degassed three times back filling with argon each time and heated at 120° C. for 2 h. After cooling, the solvent was removed under reduced pressure and the residue was treated with TFA (10 mL) in DCM (15 mL) overnight. After removal of the solvents to dryness, the product was purified by flash column chromatography (EtOAc/MeOH 80/20) and isolated as white solid (86 mg, 25%).

$^1$H NMR (600 MHz, DMSO-$d_6$) δ ppm 2.83 (t, J=6.87 Hz, 2H) 3.42 (td, J=6.91, 2.47 Hz, 2H) 3.57 (s, 3H) 5.92 (s, 2H) 6.42 (s, 1H) 6.49 (s, 1H) 6.57 (dd, J=5.31, 1.47 Hz, 1H) 7.00 (br. s., 1H) 7.91 (d, J=5.31 Hz, 1H).

Step 4. 2-(2-Amino-5-iodo-pyridin-4-yl)-1-methyl-1,5,6,7-tetrahydro-pyrrolo[3,2-c]pyridin-4-one As described in WO2010/145998

$^1$H NMR (600 MHz, DMSO-$d_6$) δ ppm 2.83 (t, J=6.98 Hz, 1H) 3.33 (s, 3H overlapped by water signal) 3.42 (dd, J=6.96, 2.56 Hz, 2H) 6.23 (s, 1H) 6.25 (br, s, 2H) 6.46 (s, 1H) 6.99 (br. s., 1H) 8.25 (s, 1H).

Step 5. 2-(2-Amino-5-trimethylsilanylethynyl-pyridin-4-yl)-1-methyl-1,5,6,7-tetrahydro-pyrrolo[3,2-c]pyridin-4-one As described for the synthesis of 2-(2-amino-5-trimethylsilanylethynyl-pyrimidin-4-yl)-1-methyl-4-oxo-1,4,6,7-tetrahydro-pyrrolo[3,2-c]pyridine-5-carboxylic acid tert-butyl ester.

(ESI) m/z 339 [(M+H)$^+$]. HRMS (ESI) calculated for $C_{18}H_{23}N_4OSi$ [(M+H)$^+$] 339.1636. found 339.1620.

Step 6. 2-(2-Amino-5-ethynyl-pyridin-4-yl)-1-methyl-1,5,6,7-tetrahydro-pyrrolo[3,2-c]pyridin-4-one As described for the synthesis of 2-(2-amino-5-ethynyl-pyrimidin-4-yl)-1-methyl-4-oxo-1,4,6,7-tetrahydro-pyrrolo[3,2-c]pyridine-5-carboxylic acid tert-butyl ester.

(ESI) m/z 267 [(M+H)+]. HRMS (ESI) calculated for $C_{15}H_{15}N_4O$ [(M+H)+] 267.1240. found 267.1257.

Step 7. 2-{3-[6-Amino-4-(1-methyl-4-oxo-4,5,6,7-tetrahydro-1H-pyrrolo[3,2-c]pyridin-2-yl)-pyridin-3-ylethynyl]-phenyl}-N-[4-(4-methyl-piperazin-1-ylmethyl)-3-trifluoromethyl-phenyl]-acetamide A solution of 2-(2-Amino-5-ethynyl-pyridin-4-yl)-1-methyl-1,5,6,7-tetrahydro-pyrrolo[3,2-c]pyridin-4-one (0.10 g, 0.38 mmol), 2-(3-iodo-phenyl)-N-[4-(4-propyl-piperazin-1-ylmethyl)-3-trifluoromethyl-phenyl]-acetamide (0.19 g, 0.36 mmol), CuI (10% mol, 7 mg, 0.038 mmol), PdCl$_2$(PPh$_3$)$_2$ (10% mol, 30 mg, 0.038 mmol) and TEA (0.52 mL, 3.80 mmol) in DMF (3 mL) was degassed with argon and stirred at r.t. for 4 h. The reaction was poured in water (15 mL) and extracted with EtOAc (2×15 mL). The organic phase was washed with brine, dried with anhydrous Na$_2$SO$_4$ and evaporated under vacuum to give a crude that was purified by flash column chromatography (DCM/MeOH/NH$_3$ 90/10/0.3). The title compound (0.12 g, 51%) was obtained as yellowish solid.

(ESI) m/z 656 [(M+H)+]. HRMS (ESI) calculated for $C_{36}H_{37}F_3N_7O_2$ [(M+H)+] 656.2956. found 656.2959.

Preparation 32

1-[4-(4-Ethyl-piperazin-1-ylmethyl)-3-trifluoromethyl-phenyl]-3-(3-ethynyl-phenyl)-urea

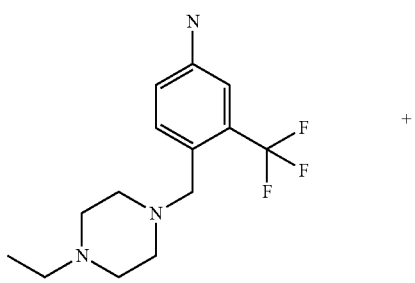

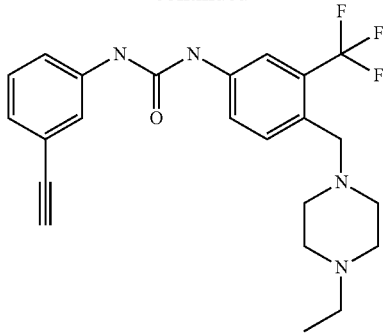

To a suspension of triphosgene (0.21 g, 0.71 mmol) and Na$_2$CO$_3$ (0.45 g, 4.27 mmol) in DCM (18 mL), kept at 0° C. under argon, 4-(4-ethyl-piperazin-1-ylmethyl)-3-trifluoromethyl-phenylamine (0.61 g, 2.13 mmol) was added. The reaction was monitored by HPLC (following the formation of 4-ethyl-piperazine-1-carboxylic acid [4-(4-ethyl-piperazin-1-ylmethyl)-3-trifluoromethyl-phenyl]-amide by treating a sample of the reaction mixture with N-ethylpiperazine). After 1 h, 3-ethynyl-phenylamine (0.26 g, 2.18 mmol) was added and the reaction was let under stirring overnight at r.t. The mixture was diluted with DCM, washed with water (3×10 mL), dried over anhydrous Na$_2$SO$_4$ and concentrated under vacuum. Purification by flash column chromatography (DCM/MeOH 95/5) afforded the product as yellow solid (0.64 g, 70%).

$^1$H NMR (600 MHz, DMSO-d$_6$) δ ppm 0.95-1.00 (m, 3H) 2.22-2.47 (m, 10H) 3.52 (s, 2H) 4.14 (s, 1H) 7.09 (d, J=7.69 Hz, 1H) 7.30 (t, J=7.88 Hz, 1H) 7.41 (dd, J=8.24, 1.28 Hz, 1H) 7.56 (dd, J=8.61, 1.83 Hz, 1H) 7.61-7.64 (m, 1H) 7.66 (t, J=1.65 Hz, 1H) 7.95 (d, J=2.01 Hz, 1H) 8.85 (s, 1H) 9.02 (s, 1H).

According to this same methodology, but employing suitable substituted derivatives, the following intermediates were prepared:

1-[3-(4-Ethyl-piperazin-1-ylmethyl)-5-trifluoromethyl-phenyl]-3-(3-ethynyl-phenyl)-urea $^1$H NMR (401 MHz, DMSO-d$_6$) δ ppm 0.98 (t, J=7.14 Hz, 3H) 3.51 (s, 2H) 4.15 (s, 1H) 7.10 (d, J=7.57 Hz, 1H) 7.22 (s, 1H) 7.30 (t, J=7.81 Hz, 1H) 7.41 (d, J=8.06 Hz, 1H) 7.53 (s, 1H) 7.67 (s, 1H) 7.88 (s, 1H) 8.84 (s, 1H) 9.11 (s, 1H).

1-[4-(4-Ethyl-piperazin-1-ylmethyl)-3-trifluoromethyl-phenyl]-3-(4-ethynyl-phenyl)-urea (ESI) m/z 431 [(M+H)+]. HRMS (ESI) calculated for $C_{23}H_{26}F_3N_4O$ [(M+H)+] 431.2053. found 431.2071.

Preparation 33

2-[2-Amino-5-(3-amino-phenylethynyl)-pyrimidin-4-yl]-1-methyl-4-oxo-1,4,6,7-tetrahydro-pyrrolo[3,2-c]pyridine-5-carboxylic acid tert-butyl ester

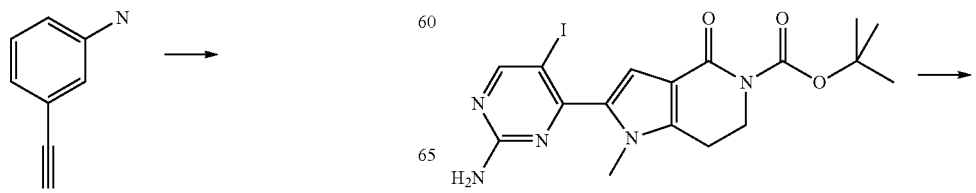

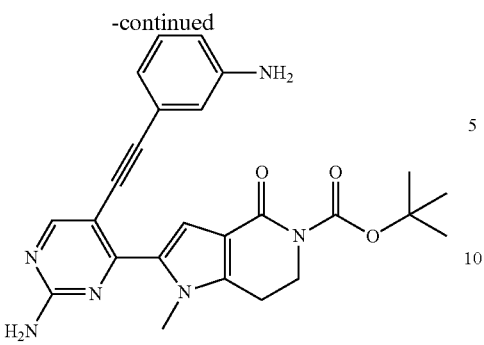

The chemical procedure for the synthesis of this intermediate is the same already described in patent WO2010/145998.

$^1$H NMR (401 MHz, DMSO-$d_6$) δ ppm 1.48 (s, 9H) 3.00 (t, J=6.28 Hz, 2H) 3.85 (s, 3H) 4.01 (t, J=6.28 Hz, 2H) 5.17 (s, 2H) 6.58 (ddd, J=8.11, 2.26, 0.98 Hz, 1H) 6.62 (dt, J=7.53, 1.17 Hz, 1H) 6.69 (t, J=1.83 Hz, 1H) 7.03 (t, J=7.74 Hz, 1H) 7.08 (s, 2H) 7.53 (s, 1H) 8.43 (s, 1H).

According to this same methodology, but employing suitable substituted derivatives, the following intermediates were prepared:

2-[2-Amino-5-(3-amino-phenylethynyl)-pyrimidin-4-yl]-1-(2-tert-butoxycarbonylamino-ethyl)-4-oxo-1,4,6,7-tetrahydro-pyrrolo[3,2-c]pyridine-5-carboxylic acid tert-butyl ester (ESI) m/z 588 [(M+H)$^+$]. HRMS (ESI) calculated for $C_{31}H_{38}N_7O_5$ [(M+H)$^+$] 588.2929. found 588.2943.

2-[2-Amino-5-(4-amino-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 459 [(M+H)$^+$]. HRMS (ESI) calculated for $C_{25}H_{27}N_6O_3$ [(M+H)$^+$] 459.2139. found 459.2153.

2-[2-Amino-5-(3-amino-4-fluoro-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 477 [(M+H)$^+$]. HRMS (ESI) calculated for $C_{25}H_{26}N_6O_3$ [(M+H)$^+$] 477.2045. found 477.2026.

Preparation 34

2-{2-Amino-5-[3-(3-phenyl-ureido)-phenylethynyl]-pyrimidin-4-yl}-1-methyl-4-oxo-1,4,6,7-tetrahydro-pyrrolo[3,2-c]pyridine-5-carboxylic acid tert-butyl ester

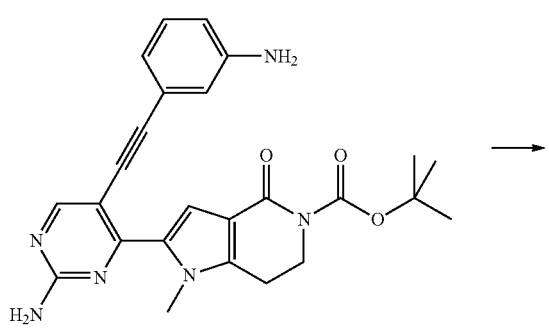

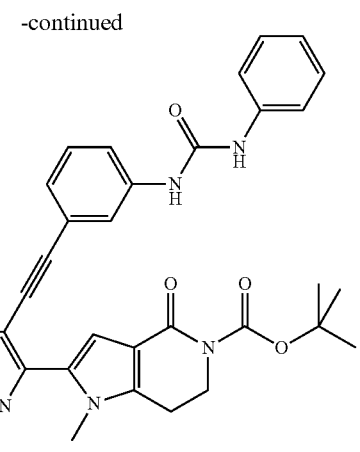

2-[2-Amino-5-(3-amino-phenylethynyl)-pyrimidin-4-yl]-1-methyl-4-oxo-1,4,6,7-tetrahydro-pyrrolo[3,2-c]pyridine-5-carboxylic acid tert-butyl ester (0.10 g, 0.22 mmol) was suspended in DCM (2 mL), dioxane (2 mL) and DMA (0.5 mL) and treated with phenyl-isocyanate (0.026 mL, 0.24 mmol). The mixture was let under stirring overnight, then the solvent was removed under vacuum. The crude was treated with Et$_2$O affording the title product as white solid (94.2 mg, 75%).

$^1$H NMR (401 MHz, DMSO-$d_6$) δ ppm 1.46 (s, 9H) 3.00 (t, J=6.35 Hz, 2H) 3.84 (s, 3H) 4.01 (t, J=6.35 Hz, 2H) 6.95-7.03 (m, 1H) 7.07 (dt, J=7.63, 1.31 Hz, 1H) 7.13 (s, 2H) 7.24-7.34 (m, 3H) 7.35-7.41 (m, 1H) 7.42-7.47 (m, 2H) 7.64 (t, J=1.77 Hz, 1H) 8.49 (s, 1H) 8.68 (s, 1H) 8.75 (s, 1H).

According to this same methodology, but employing suitable substituted derivatives, the following intermediates were prepared:

2-{2-Amino-5-[3-(3-p-tolyl-ureido)-phenylethynyl]-pyrimidin-4-yl}-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.38-1.50 (m, 9H) 2.24 (s, 3H) 3.00 (t, J=6.29 Hz, 2H) 3.84 (s, 3H) 4.01 (t, J=6.35 Hz, 2H) 7.02-7.11 (m, 3H) 7.11-7.16 (m, 2H) 7.25-7.36 (m, 3H) 7.36-7.41 (m, 1H) 7.49-7.50 (m, 1H) 7.63 (t, J=1.71 Hz, 1H) 8.49 (s, 1H) 8.57 (s, 1H) 8.70 (s, 1H).

2-(2-Amino-5-{3-[3-(4-dimethylamino-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.46 (s, 9H) 2.84 (s, 6H) 3.00 (t, J=6.29 Hz, 2H) 3.84 (s, 3H) 3.98-4.03 (m, 2H) 6.70 (d, J=8.67 Hz, 2H) 7.04 (dt, J=7.63, 1.25 Hz, 1H) 7.12 (s, 2H) 7.22-7.31 (m, 3H) 7.35-7.40 (m, 1H) 7.49 (s, 1H) 7.62 (t, J=1.71 Hz, 1H) 8.31 (s, 1H) 8.48 (s, 1H) 8.61 (s, 1H).

2-{2-Amino-5-[3-(3-pyridin-3-yl-ureido)-phenylethynyl]-pyrimidin-4-yl}-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.46 (s, 9H) 3.00 (t, J=6.23 Hz, 2H) 3.85 (s, 3H) 4.01 (t, J=6.23 Hz, 2H)

7.04-7.17 (m, 3H) 7.27-7.38 (m, 2H) 7.39-7.44 (m, 1H) 7.50 (s, 1H) 7.64 (s, 1H) 7.95 (d, 1H) 8.21 (br. s., 1H) 8.49 (s, 1H) 8.62 (br. s., 1H) 8.90 (d, J=6.47 Hz, 2H).

2-(2-Amino-5-{3-[3-(2,6-dichloro-pyridin-4-yl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.44 (s, 9H) 3.00 (t, J=6.35 Hz, 2H) 3.85 (s, 3H) 4.01 (t, J=6.23 Hz, 2H) 7.10-7.18 (m, 3H) 7.31-7.38 (m, 1H) 7.38-7.42 (m, 1H) 7.49 (s, 1H) 7.55-7.57 (m, 2H) 7.65 (t, J=1.65 Hz, 1H) 8.49 (s, 1H) 9.23 (s, 1H) 9.59 (s, 1H).

2-(2-Amino-5-{3-[3-(3-trifluoromethyl-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.45 (s, 9H) 3.00 (t, J=6.29 Hz, 2H) 3.85 (s, 3H) 4.00 (t, J=6.29 Hz, 2H) 7.10 (dt, J=7.66, 1.24 Hz, 2H) 7.13 (s, 2H) 7.26-7.37 (m, 2H) 7.36-7.44 (m, 1H) 7.47-7.55 (m, 2H) 7.57 (s, 1H) 7.66 (t, J=1.71 Hz, 1H) 8.00 (s, 1H) 8.49 (s, 1H) 8.88 (s, 1H) 9.06 (s, 1H).

2-(2-Amino-5-{3-[3-(4-chloro-3-trifluoromethyl-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.44 (s, 9H) 3.00 (t, J=6.23 Hz, 2H) 3.84 (s, 3H) 4.00 (t, J=6.35 Hz, 2H) 7.10 (dt, J=7.63, 1.31 Hz, 1H) 7.13 (s, 2H) 7.27-7.37 (m, 1H) 7.37-7.42 (m, 1H) 7.48-7.51 (m, 1H) 7.57-7.68 (m, 2H) 8.10 (d, J=2.32 Hz, 1H) 8.49 (s, 1H) 8.97 (s, 1H) 9.23 (s, 1H).

2-(2-Amino-5-{3-[3-(4-fluoro-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.42 (s, 9H) 2.97 (t, J=6.35 Hz, 2H) 3.81 (s, 3H) 3.98 (t, J=6.35 Hz, 2H) 6.96-7.13 (m, 5H) 7.22-7.30 (m, 1H) 7.32-7.38 (m, 1H) 7.41-7.45 (m, 2H) 7.46 (s, 1H) 7.56-7.65 (m, 1H) 8.46 (s, 1H) 8.69 (s, 1H) 8.72 (s, 1H).

2-(2-Amino-5-{3-[3-(3-fluoro-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.45 (s, 9H) 3.00 (t, J=6.16 Hz, 2H) 3.85 (s, 3H) 4.01 (t, J=6.10 Hz, 2H) 6.79 (td, J=8.51, 2.50 Hz, 1H) 7.02-7.16 (m, 4H) 7.23-7.34 (m, 1H) 7.36-7.42 (m, 1H) 7.43-7.54 (m, 2H) 7.64 (s, 1H) 8.49 (s, 1H) 8.82 (s, 1H) 8.92 (s, 1H).

2-(2-Amino-5-{3-[3-(4-trifluoromethyl-phenyl)-thioureido]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.46 (s, 9H) 2.99 (t, J=6.29 Hz, 2H) 3.84 (s, 3H) 3.97-4.02 (m, 2H) 7.14 (s, 2H) 7.25 (dt, J=7.72, 1.27 Hz, 1H) 7.38 (t, J=7.87 Hz, 1H) 7.46-7.50 (m, 1H) 7.58 (t, J=1.83 Hz, 1H) 7.65-7.77 (m, 4H) 8.48 (s, 1H) 10.09 (s, 1H) 10.18 (s, 1H).

2-(2-Amino-5-{3-[3-(4-trifluoromethyl-phenyl)-ureido]-phenylethynyl}-pyrimidin-4-yl)-1-(2-tert-butoxycarbonylamino-ethyl)-4-oxo-1,4,6,7-tetrahydro-pyrrolo[3,2-c]pyridine-5-carboxylic acid tert-butyl ester (ESI) m/z 755 [(M+H)$^+$]. HRMS (ESI) calculated for $C_{39}H_{42}F_3N_8O_6$ [(M+H)$^+$] 775.3174. found 775.3189.

2-(2-Amino-5-{4-[3-(4-trifluoromethyl-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 646 [(M+H)$^+$]. HRMS (ESI) calculated for $C_{33}H_{31}F_3N_7O_4$ [(M+H)$^+$] 646.2384. found 646.2369.

Preparation 35

2-(2-Amino-5-{3-[3-(2-diethylamino-ethyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester

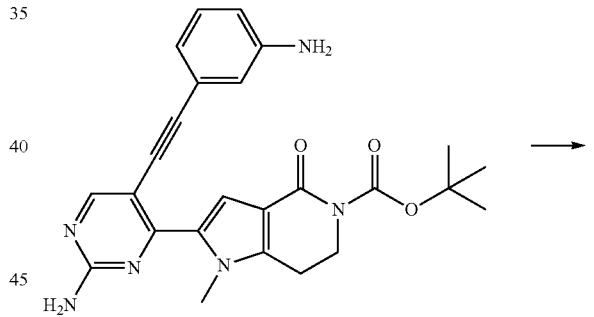

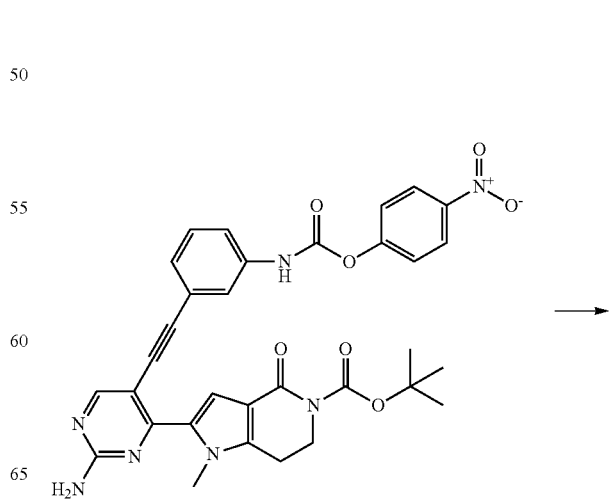

-continued

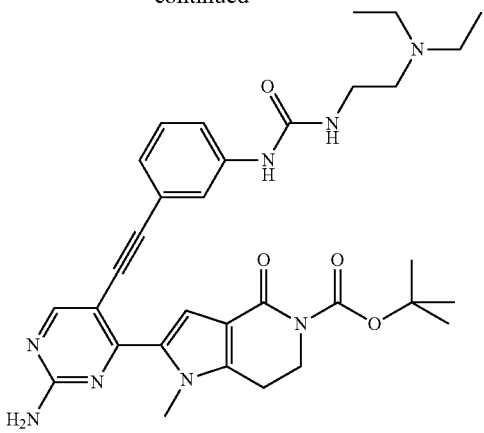

Step 1. 2-{2-Amino-5-[3-(4-nitro-phenoxycarbonylamino)-phenylethynyl]-pyrimidin-4-yl}-1-methyl-4-oxo-1,4,6,7-tetrahydro-pyrrolo[3,2-c]pyridine-5-carboxylic acid tert-butyl ester 2-[2-Amino-5-(3-amino-phenylethynyl)-pyrimidin-4-yl]-1-methyl-4-oxo-1,4,6,7-tetrahydro-pyrrolo[3,2-c]pyridine-5-carboxylic acid tert-butyl ester (0.52 g, 1.13 mmol) was suspended in DCM (10 mL) then pyridine (0.91 mL, 11.34 mmol) and 4-nitrophenyl chloroformate (0.46 g, 2.27 mmol) were added and let under stirring. After 2.5 h the mixture was diluted with DCM, washed with water and brine, dried over anhydrous $Na_2SO_4$ and evaporated under vacuum. The crude was treated with a reduced volume of DCM and Hex and the resulting solid was filtered (0.61 g) and used in the next step without further purification.

Step 2. 2-(2-Amino-5-{3-[3-(2-diethylamino-ethyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester A suspension of 2-{2-amino-5-[3-(4-nitro-phenoxycarbonylamino)-phenylethynyl]-pyrimidin-4-yl}-1-methyl-4-oxo-1,4,6,7-tetrahydro-pyrrolo[3,2-c]pyridine-5-carboxylic acid tert-butyl ester (0.11 g, 0.18 mmol) and N,N-diethyl-ethylenediamine (0.04 mL, 0.27 mmol) in MeCN (5 mL) and DMSO (0.5 mL) was stirred at r.t. for 2 h following the reaction by HPLC-MS and TLC (DCM/MeOH 95/5). The mixture was poured in water and extracted with DCM (3×10 mL). The organic layer was dried over anhydrous $Na_2SO_4$ and taken to dryness under vacuo. After purification by flash column chromatography (DCM/MeOH 90/10 to 80/20), the product was isolated as white solid (21.7 mg, 23%).

$^1$H NMR (401 MHz, DMSO-$d_6$) δ ppm 0.97 (t, J=7.08 Hz, 6H) 1.45 (s, 9H) 2.42-2.49 (m, 6H) 2.99 (t, J=6.35 Hz, 2H) 3.13 (q, J=6.23 Hz, 2H) 3.84 (s, 3H) 4.00 (t, J=6.16 Hz, 2H) 6.09 (t, J=5.49 Hz, 1H) 6.98 (d, J=7.57 Hz, 1H) 7.11 (s, 2H) 7.20-7.27 (m, 1H) 7.29-7.34 (m, 1H) 7.46-7.50 (m, 1H) 7.58 (s, 1H) 8.47 (s, 1H) 8.77 (s, 1H).

According to this same methodology, but employing suitable substituted derivatives, the following intermediates were prepared:

2-[2-Amino-5-(3-{3-[3-(4-ethyl-piperazin-1-ylmethyl)-4-trifluoromethyl-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 0.99 (t, J=7.14 Hz, 3H) 1.44 (s, 9H) 2.27-2.47 (m, 10H) 3.00 (t, J=6.23 Hz, 2H) 3.56 (s, 2H) 3.84 (s, 3H) 4.01 (t, J=6.23 Hz, 2H) 7.08-7.11 (m, 1H) 7.13 (s, 2H) 7.30-7.36 (m, 1H) 7.37-7.42 (m, 1H) 7.48-7.51 (m, 2H) 7.57-7.61 (m, 1H) 7.63 (t, J=1.71 Hz, 1H) 7.64-7.72 (m, 3H) 8.49-8.50 (m, 1H) 8.79-8.85 (m, 1H) 9.16 (s, 1H).

2-(2-Amino-5-{3-[3-(4-tert-butoxycarbonylamino-cyclohexyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (401 MHz, DMSO-$d_6$) δ ppm 1.38 (s, 9H) 1.48 (br. s., 9H) 1.72-1.90 (m, 8H) 2.99 (t, J=6.35 Hz, 2H) 3.84 (s, 3H) 4.01 (t, J=6.29 Hz, 2H) 6.06 (d, J=7.69 Hz, 1H) 6.69 (d, J=7.69 Hz, 1H) 6.98 (dt, J=7.63, 1.19 Hz, 1H) 7.11 (s, 2H) 7.23 (t, J=7.87 Hz, 1H) 7.29-7.34 (m, 1H) 7.48 (s, 1H) 7.54 (t, J=1.83 Hz, 1H) 8.37 (s, 1H) 8.46 (s, 1H).

2-[2-Amino-5-(3-{3-[4-(4-methyl-piperazin-1-ylmethyl)-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 690 [(M+H)$^+$]. HRMS (ESI) calculated for $C_{38}H_{44}N_9O_4$ [(M+H)$^+$] 690.3511. found 690.3532.

2-(2-Amino-5-{3-[3-(4-morpholin-4-ylmethyl-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 677 [(M+H)$^+$]. HRMS (ESI) calculated for $C_{37}H_{41}N_8O_5$ [(M+H)$^+$] 677.3194. found 677.3198.

2-[2-Amino-5-(3-{3-[3-(4-methyl-piperazin-1-ylmethyl)-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 690 [(M+H)$^+$]. HRMS (ESI) calculated for $C_{38}H_{44}N_9O_4$ [(M+H)$^+$] 690.3511. found 690.3502.

2-(2-Amino-5-{3-[3-(3-morpholin-4-ylmethyl-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 677 [(M+H)$^+$]. HRMS (ESI) calculated for $C_{37}H_{41}N_8O_5$ [(M+H)$^+$] 677.3194. found 677.3189.

2-(2-Amino-5-{3-[3-(3-trifluoromethyl-benzyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 660 [(M+H)$^+$]. HRMS (ESI) calculated for $C_{34}H_{33}F_3N_7O_4$ [(M+H)$^+$] 660.2541. found 660.2535.

2-(2-Amino-5-{3-[3-(5-trifluoromethyl-[1,3,4]thiadiazol-2-yl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 654 [(M+H)$^+$]. HRMS (ESI) calculated for $C_{29}H_{27}F_3N_9O_4S$ [(M+H)$^+$] 654.1853. found 654.1860.

2-(2-Amino-5-{3-[3-(2,4-dimethoxy-benzyl)-3-(4-trifluoromethyl-cyclohexyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester (cis isomer)

(ESI) m/z 802 [(M+H)$^+$]. HRMS (ESI) calculated for $C_{42}H_{47}F_3N_7O_6$ [(M+H)$^+$] 802.3534. found 802.3526.

2-(2-Amino-5-{3-[3-(2,4-dimethoxy-benzyl)-3-(4-trifluoromethyl-cyclohexyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester (trans isomer)

(ESI) m/z 802 [(M+H)$^+$]. HRMS (ESI) calculated for $C_{42}H_{47}F_3N_7O_6$ [(M+H)$^+$] 802.3534. found 802.3540.

2-[2-Amino-5-(3-{3-[4-(4-ethyl-piperazin-1-ylmethyl)-3-trifluoromethyl-phenyl]-ureido}-phenylethynyl)-pyrimidin-4-yl]-1-(2-tert-butoxycarbonylamino-ethyl)-4-oxo-1,4,6,7-tetrahydro-pyrrolo[3,2-c]pyridine-5-carboxylic acid tert-butyl ester (ESI) m/z 901 [(M+H)$^+$]. HRMS (ESI) calculated for $C_{46}H_{56}F_3N_{10}O_6$ [(M+H)$^+$] 901.4331. found 901.4312.

Preparation 36

2-[2-Amino-5-(3-{3-[4-(4-ethyl-piperazin-1-ylmethyl)-3-trifluoromethyl-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester

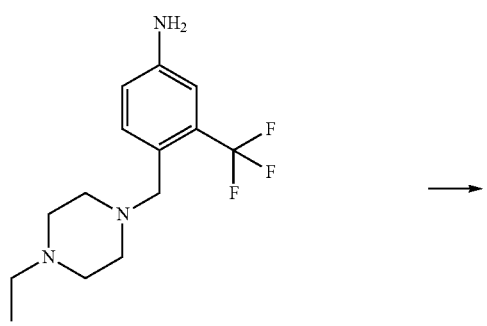

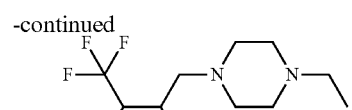

-continued

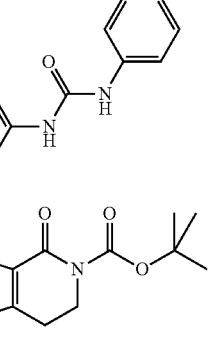

To a suspension of triphosgene (17.2 mg, 0.058 mmol) and $Na_2CO_3$ (37 mg, 0.348 mmol) in DCM (2 mL), kept at 0° C. under argon, 4-(4-ethyl-piperazin-1-ylmethyl)-3-trifluoromethyl-phenylamine (50 mg, 0.174 mmol) was added. The reaction was monitored by HPLC (following the formation of 4-ethyl-piperazine-1-carboxylic acid [4-(4-ethyl-piperazin-1-ylmethyl)-3-trifluoromethyl-phenyl]-amide by treating a sample of the reaction mixture with N-ethylpiperazine). After 1 h a solution of 2-[2-amino-5-(3-aminophenylethynyl)-pyrimidin-4-yl]-1-methyl-1,5,6,7-tetrahydro-pyrrolo[3,2-c]pyridin-4-one (104 mg, 0.226 mmol) in DMA (1.5 mL) was added and the reaction was let under stirring overnight. The mixture was diluted with DCM, washed with water (3×10 mL), dried over anhydrous $Na_2SO_4$ and taken to dryness under vacuum. Purification by flash column chromatography (DCM/MeOH 95/5) afforded the product as yellow solid (70 mg, 52%).

$^1$H NMR (401 MHz, DMSO-d$_6$) δ ppm 0.97 (t, J=7.20 Hz, 3H) 1.45 (s, 9H) 2.23-2.45 (m, 10H) 3.00 (t, J=6.3 Hz, 2H) 3.51 (s, 2H) 3.84 (s, 3H) 4.00 (t, J=6.16 Hz, 2H) 7.06 (d, J=7.69 Hz, 1H) 7.11 (s, 2H) 7.25-7.31 (m, 1H) 7.43 (d, J=8.06 Hz, 1H) 7.49 (s, 1H) 7.56-7.65 (m, 2H) 7.72 (t, J=1.71 Hz, 1H) 8.01 (d, J=1.71 Hz, 1H) 8.50 (s, 1H), 10.00 (bs, 1H), 10.19 (bs, 1H).

According to this same methodology, but employing suitable substituted derivatives, the following intermediates were prepared:

2-[2-Amino-5-(3-{3-[4-(4-dimethylamino-piperidin-1-ylmethyl)-3-trifluoromethyl-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 786 [(M+H)$^+$]. HRMS (ESI) calculated for $C_{41}H_{47}F_3N_9O_4$ [(M+H)$^+$] 786.3698. found 786.3711.

2-[2-Amino-5-(3-{3-[4-(4-methyl-piperazin-1-ylmethyl)-3-trifluoromethyl-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 758 [(M+H)$^+$]. HRMS (ESI) calculated for $C_{39}H_{43}F_3N_9O_4$ [(M+H)$^+$] 758.3385. found 758.3398.

2-[2-Amino-5-(3-{3-[4-(4-methyl-piperazin-1-yl)-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (401 MHz, DMSO-d$_6$) δ ppm 1.46 (s, 9H) 2.21 (s, 3H) 2.41-2.47 (m, 4H) 3.00 (t, J=6.23 Hz, 2H) 3.02-3.09 (m, 4H) 3.84 (s, 3H) 4.01 (t, J=6.29 Hz, 2H) 6.82-6.92 (m, 2H) 7.05 (d, J=7.57 Hz, 1H) 7.12 (s, 2H) 7.24-7.32 (m, 2H) 7.34-7.42 (m, 1H) 7.49 (s, 1H) 7.62 (t, J=1.65 Hz, 1H) 8.41 (s, 1H) 8.48 (s, 1H) 8.64 (s, 1H).

2-[2-Amino-5-(3-{3-[3-(4-methyl-piperazin-1-yl)-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 676 [(M+H)$^+$]. HRMS (ESI) calculated for C$_{37}$H$_{42}$N$_9$O$_4$ [(M+H)$^+$] 676.3354. found 676.3341.

2-[2-Amino-5-(3-{3-[4-(4-methyl-piperazin-1-yl)-3-trifluoromethyl-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (401 MHz, DMSO-d$_6$) δ ppm 1.44 (s, 9H) 2.22 (s, 3H) 2.33-2.47 (m, 4H) 2.77-2.85 (m, 4H) 3.00 (t, J=6.23 Hz, 2H) 3.84 (s, 3H) 4.00 (t, J=6.35 Hz, 2H) 7.09 (d, J=7.57 Hz, 1H) 7.12 (s, 2H) 7.31 (t, J=7.81 Hz, 1H) 7.36-7.41 (m, 1H) 7.44-7.53 (m, 3H) 7.58 (dd, J=8.61, 2.50 Hz, 1H) 7.65 (s, 1H) 7.89 (d, J=2.44 Hz, 1H) 8.49 (s, 1H) 8.82 (s, 1H) 8.95 (s, 1H).

2-[2-Amino-5-(3-{3-[3-(4-ethyl-piperazine-1-carbonyl)-5-trifluoromethyl-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 786 [(M+H)$^+$]. HRMS (ESI) calculated for C$_{40}$H$_{43}$F$_3$N$_9$O$_5$ [(M+H)$^+$] 786.3334. found 786.3356.

Preparation 37

2-[2-Amino-5-(3-{3-[3-(4-ethyl-piperazin-1-ylmethyl)-5-trifluoromethyl-phenyl]-ureido}-phenylethynyl)-pyrimidin-4-yl]-1-methyl-4-oxo-1,4,6,7-tetrahydro-pyrrolo[3,2-c]pyridine-5-carboxylic acid tert-butyl ester

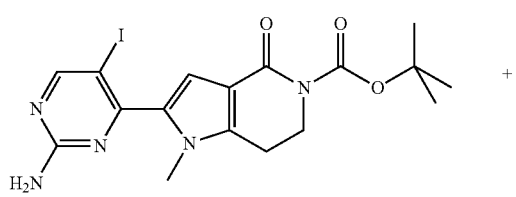

+

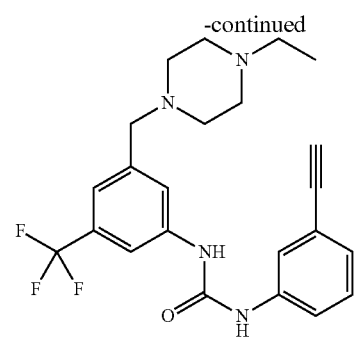

-continued

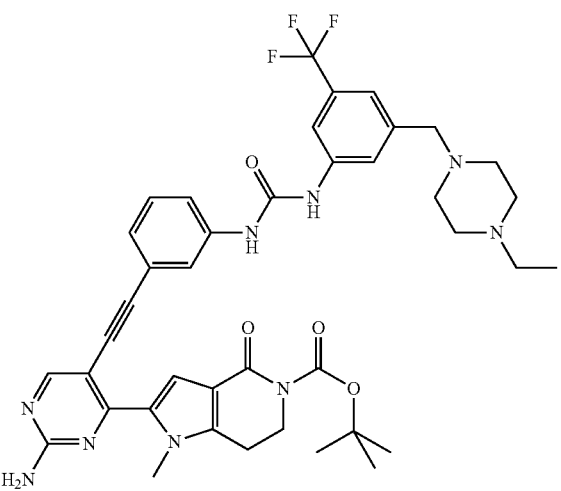

To a solution of 2-(2-amino-5-iodo-pyrimidin-4-yl)-1-methyl-1,5,6,7-tetrahydro-pyrrolo[3,2-c]pyridin-4-one (25 mg, 0.054 mmol), 1-[3-(4-ethyl-piperazin-1-ylmethyl)-5-trifluoromethyl-phenyl]-3-(3-ethynyl-phenyl)-urea (30 mg, 0.070 mmol) and CuI (0.5 mg, 0.003 mmol) in degassed MeCN (2.5 mL), TEA (0.075 mL, 0.54 mmol) and PdCl$_2$(PPh$_3$)$_2$ (2 mg, 0.003 mmol) were added. The resulting mixture was degassed three times back filling with argon each time and then heated at 80° C. for 4.5 h. The mixture was diluted with DCM and washed with NH$_3$, water and brine. The organic layer was dried over anhydrous Na$_2$SO$_4$, filtered and concentrated under reduced pressure. The residue was purified by flash column chromatography (DCM/MeOH 95/5) affording the title product (15 mg, 36%).

$^1$H NMR (401 MHz, DMSO-d$_6$) δ ppm 0.98 (t, J=7.20 Hz, 3H) 1.44 (s, 9H) 2.28-2.34 (m, 2H) 2.39 (br. s., 8H) 3.00 (t, J=6.29 Hz, 2H) 3.51 (s, 2H) 3.85 (s, 3H) 4.00 (t, J=6.35 Hz, 2H) 7.10 (dt, J=7.60, 1.27 Hz, 1H) 7.13 (s, 2H) 7.22 (s, 1H) 7.32 (t, J=7.87 Hz, 1H) 7.38-7.43 (m, 1H) 7.50 (s, 1H) 7.53 (s, 1H) 7.65 (t, J=1.71 Hz, 1H) 7.89 (s, 1H) 8.49 (s, 1H) 8.83 (s, 1H) 9.09 (s, 1H).

According to this same methodology, but employing suitable substituted derivatives, the following intermediates were prepared:

2-[2-Amino-5-(4-{3-[4-(4-ethyl-piperazin-1-ylm-ethyl)-3-trifluoromethyl-phenyl]-ureido}-phenyl-ethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 772 [(M+H)$^+$]. HRMS (ESI) calculated for C$_{40}$H$_{45}$F$_3$N$_9$O$_4$ [(M+H)$^+$] 772.3541. found 772.3523.

2-(2-Amino-5-{3-[3-(4-trifluoromethyl-phenyl)-ureido]-phenylethynyl}-pyrimidin-4-yl)-4-oxo-1,4,6,7-tetrahydro-pyrrolo[3,2-c]pyridine-5-carboxylic acid tert-butyl ester (ESI) m/z 632 [(M+H)$^+$]. HRMS (ESI) calculated for C$_{32}$H$_{29}$F$_3$N$_7$O$_4$ [(M+H)$^+$] 632.2228. found 632.2236. 1-[4-(4-Ethyl-piperazin-1-ylmethyl)-3-trifluoromethyl-phenyl]-3-{3-[2-methylamino-4-(1-methyl-4-oxo-4,5,6,7-tetra-hydro-1H-pyrrolo[3,2-c]pyridin-2-yl)-pyrimidin-5-ylethynyl]-phenyl}-urea (cmpd 41)

$^1$H NMR (600 MHz, DMSO-d$_6$) δ ppm 0.98 (t, J=7.23 Hz, 3H) 2.31 (q, J=7.02 Hz, 3H) 2.33-2.46 (m, 6H) 2.88 (d, J=4.76 Hz, 3H) 2.89-2.96 (m, 2H) 3.42-3.47 (m, 3H) 3.52 (s, 2H) 3.80-3.93 (m, 3H) 7.11 (d, J=7.14 Hz, 2H) 7.31 (t, J=7.88 Hz, 1H) 7.41 (d, J=8.06 Hz, 1H) 7.48-7.55 (m, 2H) 7.56 (dd, J=8.52, 1.74 Hz, 1H) 7.60-7.64 (m, 2H) 7.96 (d, J=2.01 Hz, 1H) 8.46 (br. S, 1H), 8.85 (s, 1H) 9.04 (s, 1H).

(ESI) m/z 686 [(M+H)$^+$]. HRMS (ESI) calculated for C$_{36}$H$_{39}$F$_3$N$_9$O$_2$ [(M+H)$^+$] 686.3174. found 686.3187.

1-{3-[2-Methylamino-4-(1-methyl-4-oxo-4,5,6,7-tetrahydro-1H-pyrrolo[3,2-c]pyridin-2-yl)-pyrimi-din-5-ylethynyl]-phenyl}-3-[4-(4-methyl-piperazin-1-ylmethyl)-3-trifluoromethyl-phenyl]-urea (cmpd 42)

$^1$H NMR (600 MHz, DMSO-d$_6$) δ ppm 2.74 (br. s., 3H) 2.83-2.97 (m, 13H) 3.42-3.48 (m, 2H) 3.62 (s, 2H) 3.90 (br. s., 3H) 7.08-7.14 (m, 2H) 7.32 (t, J=7.97 Hz, 1H) 7.41 (d, J=8.24 Hz, 1H) 7.45-7.57 (m, 2H) 7.58-7.67 (m, 3H) 7.95 (s, 1H) 8.50 (br. s, 1H) 8.87 (s, 1H) 9.07 (s, 1H).

(ESI) m/z 672 [(M+H)$^+$]. HRMS (ESI) calculated for C$_{35}$H$_{37}$F$_3$N$_9$O$_2$ [(M+H)$^+$] 6723017. found 672.3009.

1-[4-(4-Ethyl-piperazin-1-ylmethyl)-3-trifluorom-ethyl-phenyl]-3-{3-[2-(2-hydroxy-ethylamino)-4-(1-methyl-4-oxo-4,5,6,7-tetrahydro-1H-pyrrolo[3,2-c]pyridin-2-yl)-pyrimidin-5-ylethynyl]-phenyl}-urea (cmpd 43)

$^1$H NMR (600 MHz, DMSO-d$_6$) δ ppm 0.98 (t, J=7.14 Hz, 3H) 2.26-2.34 (m, 2H) 2.34-2.46 (m, 4H) 2.90 (t, J=6.87 Hz, 2H) 3.39-3.47 (m, 4H) 3.50-3.57 (m, 4H) 3.86 (s, 3H) 4.72 (t, J=5.31 Hz, 1H) 7.05-7.16 (m, 2H) 7.31 (t, J=7.97 Hz, 1H) 7.41 (d, J=8.42 Hz, 1H) 7.44-7.54 (m, 2H) 7.56 (dd, J=8.43, 1.83 Hz, 1H) 7.60-7.67 (m, 2H) 7.96 (d, J=2.01 Hz, 1H) 8.47 (br. s., 1H) 8.84 (s, 1H) 9.03 (s, 1H).

(ESI) m/z 716 [(M+H)$^+$]. HRMS (ESI) calculated for C$_{35}$H$_{37}$F$_3$N$_9$O$_2$ [(M+H)$^+$] 716.3279. found 716.3265.

Preparation 38

1-Methyl-4-oxo-2-(2-[(pyridin-4-ylmethyl)-amino]-5-{3-[3-(4-trifluoromethyl-phenyl)-ureido]-phenyl-ethynyl}-pyrimidin-4-yl)-1,4,6,7-tetrahydro-pyrrolo[3,2-c]pyridine-5-carboxylic acid tert-butyl ester

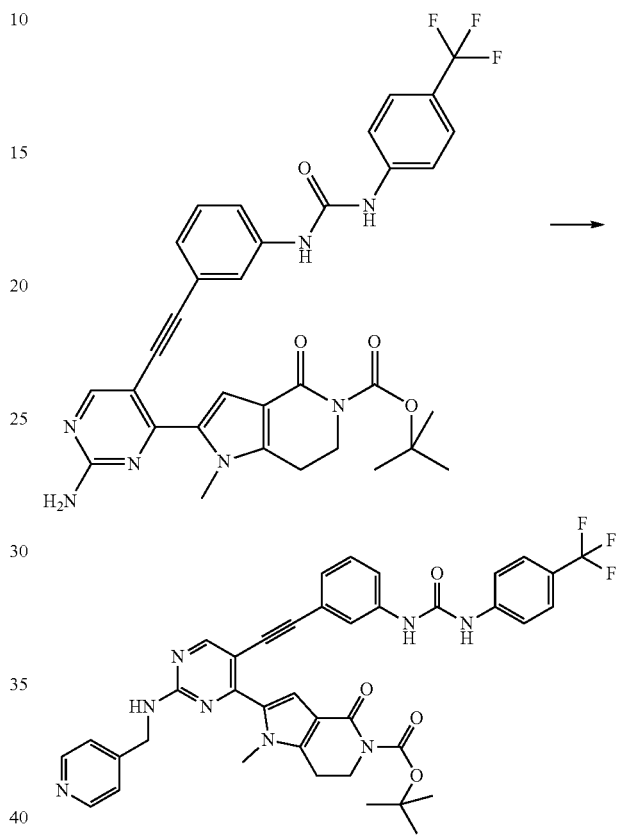

A suspension of 2-(2-amino-5-{3-[3-(4-trifluoromethyl-phenyl)-ureido]-phenylethynyl}-pyrimidin-4-yl)-1-methyl-4-oxo-1,4,6,7-tetrahydro-pyrrolo[3,2-c]pyridine-5-carbox-ylic acid tert-butyl ester (80 mg, 0.124 mmol) in dry DMF (0.65 mL), pyridine-4-carbaldehyde (0.036 mL, 0.382 mmol) and TFA (0.062 mL, 0.805 mmol) was let under stirring at r.t. for 30 min. NaBH(OAc)$_3$ (94 mg, 0.443 mmol) was then added and the reaction let overnight. The mixture was diluted with EtOAc, poured into a solution of water/NaOH 1N (1:1) and extracted with EtOAc (2×10 mL). The organic layer was furthermore washed with water and brine, dried over anhydrous Na$_2$SO$_4$, filtered and concentrated under reduced pressure. The product was purified by flash column chromatography (EtOAc/MeOH 98/2) and isolated as white solid (12.5 mg, 14%).

$^1$H NMR (401 MHz, DMSO-d$_6$) δ ppm 1.44 (s, 9H) 2.87-3.09 (m, 2H) 3.46 (br. s., 3H) 3.84-4.06 (m, 2H) 4.60 (d, J=6.35 Hz, 2H) 7.10 (d, J=7.57 Hz, 1H) 7.28-7.34 (m, 3H) 7.37-7.44 (m, 1H) 7.54 (s, 1H) 7.58-7.71 (m, 5H) 8.31 (br. s., 1H) 8.49 (d, J=5.86 Hz, 2H) 8.58 (br. s., 1H) 8.94 (s, 1H) 9.17 (s, 1H).

According to this same methodology, but employing suitable substituted derivatives, the following intermediates were prepared:

2-(2-(1-tert-Butoxycarbonyl-piperidin-4-ylamino)-5-
{3-[3-(4-trifluoromethyl-phenyl)-ureido]-phenyl-
ethynyl}-pyrimidin-4-yl)-1-methyl-4-oxo-1,4,6,7-
tetrahydro-pyrrolo[3,2-c]pyridine-5-carboxylic acid
tert-butyl ester 1H NMR (401 MHz, DMSO-$d_6$) δ ppm 1.41 (s, 9H) 1.45 (s, 9H) 1.35-1.48 (m, 2H) 1.81-1.92 (m, 2H) 2.87 (br. s., 2H) 3.01 (t, J=6.35 Hz, 2H) 3.85 (s, 3H) 3.87-3.98 (m, 3H) 4.02 (t, J=6.71 Hz, 2H) 7.10 (d, J=7.45 Hz, 1H) 7.33 (t, J=8.06 Hz, 1H) 7.39 (d, J=8.30 Hz, 1H) 7.58-7.74 (m, 7H) 8.52 (br. s., 1H) 8.91 (s, 1H) 9.14 (s, 1H).

2-(2-(1-tert-Butoxycarbonyl-piperidin-4-ylamino)-5-
{3-[3-(4-chloro-3-trifluoromethyl-phenyl)-ureido]-
phenylethynyl}-pyrimidin-4-yl)-1-methyl-4-oxo-1,4,
6,7-tetrahydro-pyrrolo[3,2-c]pyridine-5-carboxylic
acid tert-butyl ester $^1$H NMR (401 MHz, DMSO-$d_6$) δ ppm 1.41 (s, 9H) 1.44 (s, 9H) 1.36-1.47 (m, 2H) 1.86 (d, J=11.47 Hz, 2H) 2.87 (br. s., 2H) 3.00 (t, J=6.29 Hz, 2H) 3.85 (s, 3H) 3.87-3.98 (m, 3H) 4.01 (t, J=6.16 Hz, 2H) 7.11 (d, J=7.45 Hz, 1H) 7.33 (t, J=7.9 Hz, 1H) 7.37-7.42 (m, 1H) 7.50-7.76 (m, 5H) 8.10 (d, J=2.08 Hz, 1H) 8.52 (br. s., 1H) 8.93 (s, 1H) 9.18 (s, 1H).

Example 3

1-{3-[2-Amino-4-(1-methyl-4-oxo-4,5,6,7-tetra-
hydro-1H-pyrrolo[3,2-c]pyridin-2-yl)-pyrimidin-5-
ylethynyl]-phenyl}-3-phenyl-urea hydrochloride
(cmpd 1)

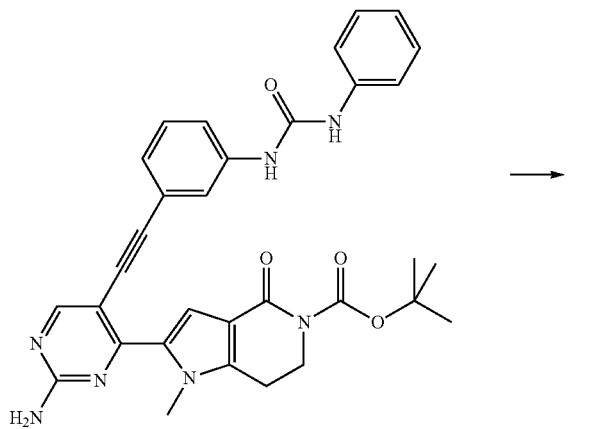

2-{2-Amino-5-[3-(3-phenyl-ureido)-phenylethynyl]-py-
rimidin-4-yl}-1-methyl-4-oxo-1,4,6,7-tetrahydro-pyrrolo[3,
2-c]pyridine-5-carboxylic acid tert-butyl ester (90 mg, 0.156 mmol) was suspended in dioxane (3 mL) and treated with 4 M HCl in dioxane (3 mL). After 3 h the solvent was removed, the compound was triturated with Et$_2$O and isolated by filtration as yellow solid (78 mg, quantitative yield).

$^1$H NMR (401 MHz, DMSO-$d_6$) δ ppm 2.91 (t, J=6.77 Hz, 2H) 3.52 (m, 2H overlapped by water signal) 3.86 (s, 3H) 6.94-7.00 (m, 1H) 7.10 (dt, J=7.57, 1.28 Hz, 1H) 7.12 (br. s., 1H) 7.24-7.34 (m, 3H) 7.39-7.43 (m, 1H) 7.45 (dd, J=8.67, 1.10 Hz, 2H) 7.57 (s, 1H) 7.64 (t, J=1.71 Hz, 1H) 8.51 (s, 1H) 8.87 (s, 1H) 8.96 (s, 1H).

(ESI) m/z 478 [(M+H)$^+$]. HRMS (ESI) calculated for $C_{27}H_{25}ClN_7O_2$ [(M+H)$^+$] 478.1986. found 478.1988.

According to this same methodology, but employing suitable substituted derivatives, the following compounds were prepared:

1-{3-[2-Amino-4-(1-methyl-4-oxo-4,5,6,7-tetra-
hydro-1H-pyrrolo[3,2-c]pyridin-2-yl)-pyrimidin-5-
ylethynyl]-phenyl}-3-p-tolyl-urea hydrochloride
(cmpd 2)

$^1$H NMR (401 MHz, DMSO-$d_6$) δ ppm 2.24 (s, 3H) 2.91 (t, J=6.84 Hz, 2H) 3.42-3.47 (m, 2H overlapped by water signal) 3.86 (s, 3H) 7.05-7.12 (m, 3H) 7.18 (br. s., 1H) 7.28-7.31 (m, 1H) 7.32-7.35 (m, 2H) 7.40 (ddd, J=8.21, 2.17, 0.98 Hz, 1H) 7.58 (s, 1H) 7.64 (t, J=1.71 Hz, 1H) 8.51 (s, 1H) 8.77 (s, 1H) 8.93 (s, 1H).

(ESI) m/z 492 [(M+H)$^+$]. HRMS (ESI) calculated for $C_{28}H_{27}ClN_7O_2$ [(M+H)$^+$] 492.2143. found 492.2143.

1-{3-[2-Amino-4-(1-methyl-4-oxo-4,5,6,7-tetra-
hydro-1H-pyrrolo[3,2-c]pyridin-2-yl)-pyrimidin-5-
ylethynyl]-phenyl}-3-(4-dimethylamino-phenyl)-
urea dihydrochloride (cmpd 3)

$^1$H NMR (401 MHz, DMSO-$d_6$) δ ppm 2.92 (t, J=6.60 Hz, 2H) 3.11 (s, 6H) 3.39 (m, 2H overlapped by water signal) 3.86 (s, 3H) 7.11 (d, J=7.57 Hz, 1H) 7.16 (br. s., 1H) 7.32 (t, J=7.87 Hz, 1H) 7.40-7.45 (m, 1H) 7.55 (s, 1H) 7.58 (br. s., 4H) 7.64 (s, 1H) 8.50 (s, 1H) 9.21 (s, 1H) 9.32 (br. s., 1H).

(ESI) m/z 521 [(M+H)$^+$]. HRMS (ESI) calculated for $C_{29}H_{31}Cl_2N_8O_2$ [(M+H)$^+$] 521.2408. found 521.2405.

1-{3-[2-Amino-4-(1-methyl-4-oxo-4,5,6,7-tetra-
hydro-1H-pyrrolo[3,2-c]pyridin-2-yl)-pyrimidin-5-
ylethynyl]-phenyl}-3-pyridin-3-yl-urea (cmpd 4)

$^1$H NMR (401 MHz, DMSO-$d_6$) δ ppm 2.89 (t, J=6.90 Hz, 2H) 3.45 (td, J=6.90, 2.56 Hz, 2H) 3.85 (s, 3H) 7.07 (s, 2H) 7.08-7.13 (m, 2H) 7.26-7.36 (m, 2H) 7.41 (dd, J=2.20, 0.98 Hz, 1H) 7.44 (s, 1H) 7.61 (t, J=1.71 Hz, 1H) 7.90-7.97 (m, 1H) 8.20 (dd, J=4.70, 1.40 Hz, 1H) 8.46 (s, 1H) 8.61 (d, J=2.44 Hz, 1H) 8.86-8.94 (m, 2H).

(ESI) m/z 479 [(M+H)$^+$]. HRMS (ESI) calculated for $C_{26}H_{23}N_8O_2$ [(M+H)$^+$] 479.1939. found 479.1931.

1-{3-[2-Amino-4-(1-methyl-4-oxo-4,5,6,7-tetra-
hydro-1H-pyrrolo[3,2-c]pyridin-2-yl)-pyrimidin-5-
ylethynyl]-phenyl}-3-(2,6-dichloro-pyridin-4-yl)-
urea (cmpd 5)

$^1$H NMR (401 MHz, DMSO-$d_6$) δ ppm 2.90 (t, J=6.84 Hz, 2H) 3.46 (td, J=6.90, 2.44 Hz, 2H) 3.86 (s, 3H) 7.08 (s, 2H) 7.11 (br. s., 1H) 7.16 (dt, J=7.60, 1.27 Hz, 1H) 7.35 (t, J=7.93 Hz, 1H) 7.41-7.45 (m, 2H) 7.56 (s, 2H) 7.63 (t, J=1.71 Hz, 1H) 8.47 (s, 1H) 9.40 (s, 1H) 9.88 (s, 1H).
(ESI) m/z 547 [(M+H)$^+$]. HRMS (ESI) calculated for C$_{26}$H$_{21}$C$_{12}$N$_8$O$_2$ [(M+H)$^+$] 547.1159. found 547.1159.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(3-trifluoromethyl-phenyl)-urea (cmpd 6)

$^1$H NMR (401 MHz, DMSO-d$_6$) δ ppm 2.89 (t, J=6.90 Hz, 2H) 3.45 (td, J=6.84, 2.56 Hz, 2H) 3.85 (s, 3H) 7.06 (s, 2H) 7.08-7.14 (m, 2H) 7.27-7.35 (m, 2H) 7.38-7.44 (m, 1H) 7.44 (s, 1H) 7.53 (d, J=7.81 Hz, 1H) 7.55-7.61 (m, 1H) 7.63 (t, J=1.71 Hz, 1H) 8.01 (s, 1H) 8.46 (s, 1H) 8.89 (s, 1H) 9.10 (s, 1H).
(ESI) m/z 546 [(M+H)$^+$]. HRMS (ESI) calculated for C$_{28}$H$_{23}$F$_3$N$_7$O$_2$ [(M+H)$^+$] 546.1860. found 546.1856.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[3-(4-methyl-piperazin-1-ylmethyl)-phenyl]-urea (cmpd 7)

$^1$H NMR (401 MHz, DMSO-d$_6$) δ ppm 2.22 (br. s., 3H) 2.32-2.48 (m, 8H) 2.89 (t, J=6.8 Hz, 2H) 3.37-3.48 (m, 4H) 3.85 (s, 3H) 6.90 (d, J=7.6 Hz, 1H) 7.02-7.13 (m, 4H) 7.22 (t, J=7.8 Hz, 1H) 7.30 (t, J=7.9 Hz, 2H) 7.36-7.42 (m, 1H) 7.41-7.43 (m, 1H) 7.44 (s, 1H) 7.61 (t, J=1.8 Hz, 1H) 8.46 (s, 1H) 8.69-8.76 (m, 2H).
(ESI) m/z 590 [(M+H)$^+$]. HRMS (ESI) calculated for C$_{33}$H$_{36}$N$_9$O$_2$ [(M+H)$^+$] 590.2986. found 590.2986.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[4-(4-ethyl-piperazin-1-ylmethyl)-3-trifluoromethyl-phenyl]-urea (cmpd 8)

$^1$H NMR (600 MHz, DMSO-d$_6$) δ ppm 0.98 (t, J=7.14 Hz, 3H) 2.30 (q, J=7.27 Hz, 2H) 2.34-2.44 (m, 8H) 2.89 (t, J=6.78 Hz, 2H) 3.44 (td, J=6.82, 2.47 Hz, 2H) 3.53 (s, 2H) 3.85 (s, 3H) 7.07 (s, 2H) 7.09-7.13 (m, 2H) 7.31 (t, J=7.88 Hz, 1H) 7.41 (dd, J=8.33, 1.19 Hz, 1H) 7.44 (s, 1H) 7.56 (dd, J=8.43, 1.83 Hz, 1H) 7.60-7.66 (m, 2H) 7.96 (d, J=2.01 Hz, 1H) 8.46 (s, 1H) 8.84 (s, 1H) 9.03 (s, 1H).
(ESI) m/z 672 [(M+H)$^+$]. HRMS (ESI) calculated for C$_{35}$H$_{37}$F$_3$N$_9$O$_2$ [(M+H)$^+$] 672.3017. found 672.3018.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(4-chloro-3-trifluoromethyl-phenyl)-urea (cmpd 9)

$^1$H NMR (401 MHz, DMSO-d$_6$) δ ppm 2.89 (t, J=6.84 Hz, 2H) 3.44 (td, J=6.77, 2.56 Hz, 2H) 3.85 (s, 3H) 7.07 (br. s., 2H) 7.09-7.15 (m, 2H) 7.32 (t, J=7.93 Hz, 1H) 7.41 (m, 1H) 7.43 (s, 1H) 7.56-7.72 (m, 3H) 8.10 (d, J=2.32 Hz, 1H) 8.46 (s, 1H) 8.93 (s, 1H) 9.20 (s, 1H).
(ESI) m/z 580 [(M+H)$^+$]. HRMS (ESI) calculated for C$_{28}$H$_{22}$ClF$_3$N$_7$O$_2$ [(M+H)$^+$] 580.1470. found 580.1448.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[4-(4-methyl-piperazin-1-ylethyl)-phenyl]-urea (cmpd 10)

$^1$H NMR (401 MHz, DMSO-d$_6$) δ ppm 2.18 (s, 3H) 2.26-2.45 (m, 8H) 2.89 (t, J=6.8 Hz, 2H) 3.39 (br. s., 2H) 3.45 (td, J=6.9, 2.4 Hz, 2H) 3.85 (s, 3H) 7.04-7.13 (m, 4H) 7.19 (d, J=8.4 Hz, 2H) 7.30 (t, J=7.9 Hz, 1H) 7.35-7.42 (m, 3H) 7.44 (s, 1H) 7.61 (t, J=1.7 Hz, 1H) 8.45 (s, 1H) 8.68 (s, 1H) 8.74 (s, 1H).
(ESI) m/z 590 [(M+H)$^+$]. HRMS (ESI) calculated for C$_{33}$H$_{36}$N$_9$O$_2$ [(M+H)$^+$] 590.2987. found 590.2985.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(4-morpholin-4-ylmethyl-phenyl)-urea (cmpd 11)

$^1$H NMR (401 MHz, DMSO-d$_6$) δ ppm 2.33 (m, 4H) 2.89 (t, J=6.9 Hz, 2H) 3.39 (br. s., 2H) 3.45 (td, J=6.8, 2.4 Hz, 2H) 3.52-3.59 (m, 4H) 3.85 (s, 3H) 7.03-7.12 (m, 4H) 7.20 (d, J=8.5 Hz, 2H) 7.30 (t, J=7.9 Hz, 1H) 7.40 (d, J=8.5 Hz, 3H) 7.44 (s, 1H) 7.60 (t, J=1.8 Hz, 1H) 8.45 (s, 1H) 8.67 (s, 1H) 8.73 (s, 1H).
(ESI) m/z 577 [(M+H)$^+$]. HRMS (ESI) calculated for C$_{32}$H$_{33}$N$_8$O$_3$ [(M+H)$^+$] 577.2670. found 577.2661.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(3-morpholin-4-ylmethyl-phenyl)-urea (cmpd 12)

$^1$H NMR (401 MHz, DMSO-d$_6$) δ ppm 2.29-2.45 (m, 4H) 2.89 (t, J=6.8 Hz, 2H) 3.31 (s, 2H overlapped by water signal) 3.45 (td, J=6.8, 2.6 Hz, 2H) 3.59 (br. s., 4H) 3.85 (s, 3H) 6.93 (br. s., 1H) 7.01-7.14 (m, 4H) 7.24 (br. s., 1H) 7.27-7.36 (m, 2H) 7.37-7.42 (m, 1H) 7.44 (s, 2H) 7.62 (s, 1H) 8.46 (s, 1H) 8.74 (br. s., 2H).
(ESI) m/z 577 [(M+H)$^+$]. HRMS (ESI) calculated for C$_{32}$H$_{33}$N$_8$O$_3$ [(M+H)$^+$] 577.2670. found 577.2670.

1-(4-Chloro-3-trifluoromethyl-phenyl)-3-{3-[4-(1-methyl-4-oxo-4,5,6,7-tetrahydro-1H-pyrrolo[3,2-c]pyridin-2-yl)-2-(piperidin-4-ylamino)-pyrimidin-5-ylethynyl]-phenyl}-urea (cmpd 13)

$^1$H NMR (401 MHz, DMSO-d$_6$) δ ppm 1.43-1.60 (m, 2H) 1.84-1.98 (m, 2H) 2.67-2.75 (m, 2H) 2.90 (t, J=6.84 Hz, 2H) 3.06-3.13 (m, 2H) 3.45 (td, J=6.77, 2.32 Hz, 2H) 3.86 (s, 3H) 3.89-4.02 (m, 1H) 7.12 (d, J=7.32 Hz, 2H) 7.32 (t, J=7.87 Hz, 1H) 7.41 (d, J=8.30 Hz, 1H) 8.11 (d, J=2.20 Hz, 1H) 8.50 (s, 1H) 9.09 (s, 1H) 9.37 (s, 1H).
(ESI) m/z 663 [(M+H)$^+$]. HRMS (ESI) calculated for C$_{33}$H$_{31}$ClF$_3$N$_8$O$_2$ [(M+H)$^+$] 663.2205. found 663.2217.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(2-diethylamino-ethyl)-urea (cmpd 14)

$^1$H NMR (401 MHz, DMSO-d$_6$) δ ppm 0.97 (t, J=7.14 Hz, 6H) 2.41-2.49 (m, 6H) 2.62-2.71 (m, 1H) 2.89 (t, J=6.84 Hz, 2H) 3.14 (q, J=6.27 Hz, 2H) 3.44 (td, J=6.84, 2.44 Hz, 2H) 3.84 (s, 3H) 6.07 (t, J=5.43 Hz, 1H) 7.00 (dt, J=7.63, 1.25 Hz, 1H) 7.04 (s, 2H) 7.10 (t, J=1.95 Hz, 1H) 7.23 (t, J=7.93 Hz, 1H) 7.29-7.36 (m, 1H) 7.42 (s, 1H) 7.56 (t, J=1.77 Hz, 1H) 8.44 (s, 1H) 8.77 (s, 1H).
(ESI) m/z 501 [(M+H)$^+$]. HRMS (ESI) calculated for C$_{27}$H$_{33}$N$_8$O$_2$ [(M+H)$^+$] 501.2721. found 501.2727.

1-(4-Amino-cyclohexyl)-3-{3-[2-amino-4-(1-methyl-4-oxo-4,5,6,7-tetrahydro-1H-pyrrolo[3,2-c]pyridin-2-yl)-pyrimidin-5-ylethynyl]-phenyl}-urea (trans isomer) (cmpd 15)

$^1$H NMR (401 MHz, DMSO-d$_6$) δ ppm 1.16-1.48 (m, 4H) 1.94 (br. s., 4H) 2.89 (t, J=6.84 Hz, 2H) 2.98 (br. s., 1H) 3.44 (td, J=6.77, 2.44 Hz, 2H) 3.85 (s, 3H) 6.22 (d, J=7.57 Hz, 1H) 6.96-7.08 (m, 1H) 7.10 (br. s., 1H) 7.23 (t, J=7.87 Hz, 1H) 7.27 (s, 2H) 7.33 (dd, J=7.75, 1.65 Hz, 1H) 7.42 (s, 1H) 7.52 (t, J=1.77 Hz, 1H) 7.75-7.92 (m, 2H) 8.43 (s, 1H) 8.57 (s, 1H).

(ESI) m/z 499 [(M+H)$^+$]. HRMS (ESI) calculated for C$_{27}$H$_{31}$N$_8$O$_2$ [(M+H)$^+$] 499.2565. found 499.2542.

1-{3-[2-Amino-4-(4-oxo-4,5,6,7-tetrahydro-1H-pyrrolo[3,2-c]pyridin-2-yl)-pyrimidin-5-ylethynyl]-phenyl}-3-(4-trifluoromethyl-phenyl)-urea (cmpd 16)

$^1$H NMR (401 MHz, DMSO-d$_6$) δ ppm 2.87 (t, J=6.9 Hz, 2H) 3.37-3.43 (m, 2H) 6.78 (br. s., 2H) 7.10 (s, 1H) 7.18 (d, J=7.8 Hz, 1H) 7.37 (t, J=7.9 Hz, 1H) 7.47-7.52 (m, 1H) 7.59-7.66 (m, 3H) 7.66-7.72 (m, 3H) 8.43 (s, 1H) 9.30 (br. s., 1H) 9.51 (br. s., 1H) 11.73 (br. s., 1H).

(ESI) m/z 532 [(M+H)$^+$]. HRMS (ESI) calculated for C$_{27}$H$_{21}$F$_3$N$_7$O$_2$ [(M+H)$^+$] 532.1704. found 532.1686.

1-(3-{4-(1-Methyl-4-oxo-4,5,6,7-tetrahydro-1H-pyrrolo[3,2-c]pyridin-2-yl)-2-[(pyridin-4-ylmethyl)-amino]-pyrimidin-5-ylethynyl}-phenyl)-3-(4-trifluoromethyl-phenyl)-urea (cmpd 17)

$^1$H NMR (401 MHz, DMSO-d$_6$) δ ppm 2.77-2.93 (m, 2H) 3.38-3.53 (m, 2H) 3.89 (br. s., 3H) 4.61 (d, J=6.23 Hz, 2H) 7.12 (d, J=7.81 Hz, 2H) 7.28-7.36 (m, 3H) 7.39-7.45 (m, 1H) 7.48 (s, 1H) 7.59-7.69 (m, 6H) 8.24 (br. s., 1H) 8.49 (d, J=5.86 Hz, 1H) 8.54 (br. s., 1H) 8.96 (s, 1H) 9.21 (s, 1H).

(ESI) m/z 637 [(M+H)$^+$]. HRMS (ESI) calculated for C$_{34}$H$_{28}$F$_3$N$_8$O$_2$ [(M+H)$^+$] 637.2282. found 637.2276.

1-{3-[4-(1-Methyl-4-oxo-4,5,6,7-tetrahydro-1H-pyrrolo[3,2-c]pyridin-2-yl)-2-(piperidin-4-ylamino)-pyrimidin-5-ylethynyl]-phenyl}-3-(4-trifluoromethyl-phenyl)-urea hydrochloride (cmpd 18)

$^1$H NMR (401 MHz, DMSO-d$_6$) δ ppm 1.61-1.75 (m, 2H) 1.96-2.09 (m, 2H) 2.87-2.92 (m, 2H) 2.93-3.01 (m, 2H) 3.22-3.36 (m, 2H overlapped by water signal) 3.46 (td, J=6.84, 2.44 Hz, 2H) 3.86 (s, 3H) 3.98-4.07 (m, 1H) 7.08-7.17 (m, 2H) 7.32 (t, J=7.87 Hz, 1H) 7.40 (d, J=8.67 Hz, 1H) 7.48 (s, 1H) 7.59-7.71 (m, 5H) 7.82 (br. s., 2H) 8.52 (s, 1H) 9.09 (s, 1H) 9.33 (s, 1H).

(ESI) m/z 629 [(M+H)$^+$]. HRMS (ESI) calculated for C$_{33}$H$_{33}$ClF$_3$N$_8$O$_2$ [(M+H)$^+$] 629.2595. found 629.2582.

1-(3-{2-Amino-4-[1-(2-amino-ethyl)-4-oxo-4,5,6,7-tetrahydro-1H-pyrrolo[3,2-c]pyridin-2-yl]-pyrimidin-5-ylethynyl}-phenyl)-3-(4-trifluoromethyl-phenyl)-urea hydrochloride (cmpd 19)

$^1$H NMR (401 MHz, DMSO-d$_6$) δ ppm 2.95 (t, J=6.8 Hz, 2H) 3.21-3.25 (m, 2H) 3.48 (t, J=6.96 Hz, 2H) 4.57-4.68 (m, 2H) 7.13-7.17 (m, 1H) 7.21-7.25 (m, 1H) 7.33 (t, J=7.9 Hz, 1H) 7.40-7.46 (m, 1H) 7.49 (m, 3H) 7.56-7.71 (m, 4H) 7.77 (s, 1H) 7.97-8.19 (m, 2H) 8.49 (s, 1H) 9.26 (s, 1H) 9.50 (s, 1H).

(ESI) m/z 575 [(M+H)$^+$]. HRMS (ESI) calculated for C$_{29}$H$_{27}$ClF$_3$N$_8$O$_2$ [(M+H)$^+$] 575.2126. found 575.2125.

1-(3-{2-Amino-4-[1-(2-amino-ethyl)-4-oxo-4,5,6,7-tetrahydro-1H-pyrrolo[3,2-c]pyridin-2-yl]-pyrimidin-5-ylethynyl}-phenyl)-3-[4-(4-ethyl-piperazin-1-ylmethyl)-3-trifluoromethyl-phenyl]-urea (cmpd 20)

$^1$H NMR (401 MHz, DMSO-d$_6$) δ ppm 0.98 (t, J=7.7 Hz, 3H) 2.30 (q, J=7.4 Hz, 2H) 2.35-2.44 (m, 8H) 2.93 (t, J=6.8 Hz, 2H) 3.43-3.48 (m, 2H) 3.52 (s, 2H) 4.42-4.47 (m, 2H) 7.09 (s, 2H) 7.11-7.14 (m, 1H) 7.15 (br. s., 1H) 7.31 (t, J=7.9 Hz, 1H) 7.40-7.44 (m, 1H) 7.55-7.59 (m, 1H) 7.60-7.64 (m, 3H) 7.97 (d, J=2.1 Hz, 1H) 8.47 (s, 1H) 9.09 (br. s., 1H) 9.27 (br. s., 1H).

(ESI) m/z 701 [(M+H)$^+$]. HRMS (ESI) calculated for C$_{36}$H$_{40}$F$_3$N$_{10}$O$_2$ [(M+H)$^+$] 701.3283. found 701.3276.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(3-trifluoromethyl-benzyl)-urea (cmpd 21)

$^1$H NMR (401 MHz, DMSO-d$_6$) δ ppm 2.88 (t, J=6.9 Hz, 2H) 3.44 (td, J=6.8, 2.4 Hz, 2H) 3.84 (s, 3H) 4.39 (d, J=6.0 Hz, 2H) 6.81 (t, J=6.1 Hz, 1H) 6.99-7.06 (m, 3H) 7.10 (m, 1H) 7.25 (t, J=7.9 Hz, 1H) 7.37 (ddd, J=8.2, 2.1, 1.0 Hz, 1H) 7.42 (s, 1H) 7.53-7.68 (m, 5H) 8.43 (s, 1H) 8.76 (s, 1H).

(ESI) m/z 560 [(M+H)$^+$]. HRMS (ESI) calculated for C$_{29}$H$_{25}$F$_3$N$_7$O$_2$ [(M+H)$^+$] 560.2017. found 560.2015.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[3-(4-ethyl-piperazin-1-ylmethyl)-4-trifluoromethyl-phenyl]-urea (cmpd 22)

$^1$H NMR (401 MHz, DMSO-d$_6$) δ ppm 0.98 (t, J=7.14 Hz, 3H) 2.27-2.36 (q, J=7.6, 2H) 2.36-2.46 (m, 8H) 2.89 (t, J=6.90 Hz, 2H) 3.45 (td, J=6.90, 2.56 Hz, 2H) 3.56 (s, 2H) 3.85 (s, 3H) 7.07 (s, 2H) 7.09-7.13 (m, 2H) 7.32 (t, J=7.93 Hz, 1H) 7.41-7.45 (m, 1H) 7.44 (s, 1H) 7.57-7.60 (m, 1H) 7.61 (t, J=1.83 Hz, 1H) 7.63-7.69 (m, 1H) 7.71-7.73 (m, 1H) 8.46 (s, 1H) 8.89 (s, 1H) 9.25 (s, 1H).

(ESI) m/z 672 [(M+H)$^+$]. HRMS (ESI) calculated for C$_{35}$H$_{37}$F$_3$N$_9$O$_2$ [(M+H)$^+$] 672.3017. found 672.3007.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(5-trifluoromethyl-[1,3,4]thiadiazol-2-yl)-urea trifluoroacetate (cmpd 23)

(ESI) m/z 554 [(M+H)$^+$]. HRMS (ESI) calculated for C$_{24}$H$_{18}$F$_3$N$_9$O$_2$S [(M+H)$^+$] 554.1329. found 554.1345.

1-(3-{2-Amino-4-[1-(2-amino-ethyl)-4-oxo-4,5,6,7-tetrahydro-1H-pyrrolo[3,2-c]pyridin-2-yl]-pyrimidin-5-ylethynyl}-phenyl)-3-[4-(4-ethyl-piperazin-1-ylmethyl)-3-trifluoromethyl-phenyl]-urea trihydrochloride (cmpd 24)

$^1$H NMR (401 MHz, DMSO-d$_6$) δ ppm 0.98 (t, J=7.45 Hz, 3H) 2.27-2.34 (q, J=7.45 Hz, 2H) 2.35-2.44 (m, 8H) 2.93 (t, J=6.84 Hz, 3H) 3.43-3.48 (m, 2H) 3.52 (s, 2H) 4.42-4.47 (m, 2H) 7.09 (s, 2H) 7.12 (dt, J=7.66, 1.24 Hz, 1H) 7.15 (br. s., 1H) 7.31 (t, J=7.87 Hz, 1H) 7.40-7.44 (m, 1H) 7.55-7.59 (m, 1H) 7.61 (br. s., 1H) 7.63 (s, 1H) 7.65 (t, J=1.71 Hz, 1H) 7.97 (d, J=2.07 Hz, 1H) 8.47 (s, 1H) 9.09 (s, 1H) 9.27 (s, 1H).

1-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-(4-trifluoromethyl-phenyl)-thiourea (cmpd 25)

$^1$H NMR (401 MHz, DMSO-$d_6$) δ ppm 2.88 (t, J=6.77 Hz, 2H) 3.41-3.49 (m, 2H) 3.85 (s, 3H) 7.08 (s, 2H) 7.11 (br. s., 1H) 7.26 (d, J=7.69 Hz, 1H) 7.38 (t, J=7.87 Hz, 1H) 7.44 (s, 1H) 7.47-7.51 (m, 1H) 7.56 (s, 1H) 7.66-7.76 (m, 4H) 8.45 (s, 1H) 10.09 (s, 1H) 10.18 (s, 1H).
(ESI) m/z 562 [(M+H)$^+$]. HRMS (ESI) calculated for $C_{28}H_{23}F_3N_7OS$ [(M+H)$^+$] 562.1631. found 562.1636.

1-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-(4-trifluoromethyl-cyclohexyl)-urea (cis isomer) (cmpd 26)

$^1$H NMR (401 MHz, DMSO-$d_6$) δ ppm 1.40-1.52 (m, 2H) 1.53-1.63 (m, 2H) 1.66-1.79 (m, 4H) 2.26-2.34 (m, 1H) 2.89 (t, J=6.8 Hz, 2H) 3.44 (td, J=6.8, 2.6 Hz, 2H) 3.85 (s, 3H) 3.85-3.90 (m, 1H) 6.47 (d, J=7.4 Hz, 1H) 7.01 (dt, J=7.5, 1.3 Hz, 1H) 7.05 (s, 2H) 7.10 (s, 1H) 7.24 (t, J=7.7 Hz, 1H) 7.29-7.33 (m, 1H) 7.42 (s, 1H) 7.55 (t, J=1.8 Hz, 1H) 8.40 (s, 1H) 8.44 (s, 1H).
(ESI) m/z 552 [(M+H)$^+$]. HRMS (ESI) calculated for $C_{28}H_{29}F_3N_7O_2$ [(M+H)$^+$] 552.2330. found 552.2330.

1-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-(4-trifluoromethyl-cyclohexyl)-urea (trans isomer) (cmpd 27)

$^1$H NMR (401 MHz, DMSO-$d_6$) δ ppm 1.15-1.28 (m, 2H) 1.28-1.41 (m, 2H) 1.83-2.02 (m, 4H) 2.17-2.29 (m, 1H) 2.88 (t, J=6.8 Hz, 2H) 3.38-3.42 (m, 1H) 3.42-3.48 (m, 2H) 3.84 (s, 3H) 6.13 (d, J=7.7 Hz, 1H) 6.97-7.02 (m, 1H) 7.04 (s, 2H) 7.09 (br. s., 1H) 7.23 (t, J=7.9 Hz, 1H) 7.29-7.34 (m, 1H) 7.41 (s, 1H) 7.52 (t, J=1.8 Hz, 1H) 8.39 (s, 1H) 8.43 (s, 1H).
(ESI) m/z 552 [(M+H)$^+$]. HRMS (ESI) calculated for $C_{28}H_{29}F_3N_7O_2$ [(M+H)$^+$] 552.2330. found 552.2317.

1-{4-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-(4-trifluoromethyl-phenyl)-urea (cmpd 28)

$^1$H NMR (401 MHz, DMSO-$d_6$) δ ppm 2.89 (t, J=6.84 Hz, 2H) 3.45 (td, J=6.77, 2.32 Hz, 2H) 3.85 (s, 3H) 7.01 (s, 2H) 7.11 (s, 1H) 7.41 (d, J=8.67 Hz, 2H) 7.48-7.53 (m, 3H) 7.60-7.70 (m, 4H) 8.41 (s, 1H) 9.00 (s, 1H) 9.16 (s, 1H).
(ESI) m/z 546 [(M+H)$^+$]. HRMS (ESI) calculated for $C_{28}H_{23}F_3N_7O_2$ [(M+H)$^+$] 546.1860. found 546.1839.

1-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-[3-(4-ethyl-piperazin-1-ylmethyl)-5-trifluoromethyl-phenyl]-urea (cmpd 29)

$^1$H NMR (401 MHz, DMSO-$d_6$) δ ppm 0.98 (t, J=7.08 Hz, 3H) 2.24-2.47 (m, 10H) 2.90 (t, J=6.71 Hz, 2H) 3.41-3.48 (m, 2H) 3.59 (s, 2H) 3.85 (s, 3H) 7.06 (s, 2H) 7.10-7.15 (m, 1H) 7.22 (s, 1H) 7.32 (t, J=7.69 Hz, 1H) 7.38-7.43 (m, 1H) 7.44 (s, 1H) 7.52-7.55 (m, 1H) 7.62-7.65 (m, 2H) 7.87-7.92 (m, 1H) 8.47 (s, 1H) 8.84 (s, 1H) 9.12 (s, 1H).
(ESI) m/z 672 [(M+H)$^+$]. HRMS (ESI) calculated for $C_{35}H_{37}F_3N_9O_2$ [(M+H)$^+$] 672.3017. found 672.2999.

1-{4-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-[4-(4-ethyl-piperazin-1-ylmethyl)-3-trifluoromethyl-phenyl]-urea (cmpd 30)

$^1$H NMR (401 MHz, DMSO-$d_6$) δ ppm 1.02 (br. s., 3H) 2.32-2.67 (m, 10H) 2.89 (t, J=6.8 Hz, 2H) 3.45 (td, J=6.8, 2.4 Hz, 2H) 3.55 (s, 2H) 3.85 (s, 3H) 7.01 (s, 2H) 7.10 (s, 1H) 7.40 (d, J=8.7 Hz, 2H) 7.48-7.53 (m, 3H) 7.56-7.66 (m, 2H) 7.95 (d, J=1.8 Hz, 2H) 8.41 (s, 1H) 8.99 (s, 1H) 9.09 (s, 1H).
(ESI) m/z 672 [(M+H)$^+$]. HRMS (ESI) calculated for $C_{35}H_{37}F_3N_9O_2$ [(M+H)$^+$] 672.3017. found 672.2985.

1-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-[3-(4-ethyl-piperazine-1-carbonyl)-5-trifluoromethyl-phenyl]-urea (cmpd 31)

$^1$H NMR (401 MHz, DMSO-$d_6$) δ ppm 1.00 (t, J=7.14 Hz, 3H) 2.25-2.47 (m, 6H) 2.89 (t, J=6.90 Hz, 2H) 3.30 (m, 2H overlapped by water signal) 3.44 (td, J=6.80, 2.14 Hz, 2H) 3.63 (br. s., 2H) 3.85 (s, 3H) 7.00-7.16 (m, 4H) 7.28 (s, 1H) 7.32 (t, J=7.87 Hz, 1H) 7.42 (s, 1H) 7.44 (s, 1H) 7.63-7.68 (m, 2H) 8.00 (s, 1H) 8.46 (s, 1H) 9.09 (br. s., 1H) 9.35 (br. s., 1H).
(ESI) m/z 686 [(M+H)$^+$]. HRMS (ESI) calculated for $C_{35}H_{35}F_3N_9O_3$ [(M+H)$^+$] 686.2809. found 686.2796.

1-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-[4-(4-methyl-piperazin-1-yl)-phenyl]-urea (cmpd 32)

$^1$H NMR (401 MHz, DMSO-$d_6$) δ ppm 2.21 (s, 3H) 2.39-2.47 (m, 4H) 2.89 (t, J=6.90 Hz, 2H) 3.00-3.09 (m, 4H) 3.45 (td, J=6.84, 2.44 Hz, 2H) 3.85 (s, 3H) 6.81-6.92 (m, 2H) 7.04-7.13 (m, 4H) 7.22-7.33 (m, 3H) 7.37-7.41 (m, 1H) 7.43 (s, 1H) 7.60 (s, 1H) 8.26 (s, 1H) 8.45-8.47 (m, 1H) 8.68 (s, 1H).
(ESI) m/z 576 [(M+H)$^+$]. HRMS (ESI) calculated for $C_{32}H_{34}N_9O_2$ [(M+H)$^+$] 576.2830. found 576.2827.

1-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-[3-(4-methyl-piperazin-1-yl)-phenyl]-urea (cmpd 33)

$^1$H NMR (401 MHz, DMSO-$d_6$) δ ppm 2.22 (s, 3H) 2.41-2.48 (m, 4H) 2.89 (t, J=6.77 Hz, 2H) 3.06-3.14 (m, 4H) 3.44 (td, J=6.77, 2.44 Hz, 2H) 3.85 (s, 3H) 6.57 (dd, J=8.24, 1.77 Hz, 1H) 6.77 (d, J=7.69 Hz, 1H) 7.02-7.13 (m, 5H) 7.17 (s, 1H) 7.29 (t, J=7.93 Hz, 1H) 7.35-7.40 (m, 1H) 7.44 (s, 1H) 7.62 (s, 1H) 8.46 (s, 1H) 8.60 (s, 1H) 8.75 (s, 1H).
(ESI) m/z 576 [(M+H)$^+$]. HRMS (ESI) calculated for $C_{32}H_{34}N_9O_2$ [(M+H)$^+$] 576.2830. found 576.2831.

1-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-[4-(4-methyl-piperazin-1-yl)-3-trifluoromethyl-phenyl]-urea (cmpd 34)

$^1$H NMR (401 MHz, DMSO-$d_6$) δ ppm 2.22 (s, 3H) 2.43 (br. s., 4H) 2.78-2.84 (m, 4H) 2.89 (t, J=6.84 Hz, 2H) 3.44

(td, J=6.77, 2.20 Hz, 2H) 3.85 (s, 3H) 7.00-7.14 (m, 4H) 7.31 (t, J=7.93 Hz, 1H) 7.38-7.43 (m, 1H) 7.44 (s, 1H) 7.48-7.52 (m, 1H) 7.56-7.60 (m, 1H) 7.62 (s, 1H) 7.90 (d, J=2.44 Hz, 1H) 8.46 (s, 1H) 8.83 (s, 1H) 8.97 (s, 1H).

(ESI) m/z 644 [(M+H)+]. HRMS (ESI) calculated for $C_{35}H_{35}F_3N_9O_3$ [(M+H)+] 644.2704. found 644.2726.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(4-fluoro-phenyl)-urea (cmpd 35)

$^1$H NMR (401 MHz, DMSO-$d_6$) δ ppm 2.89 (t, J=6.90 Hz, 2H) 3.45 (td, J=6.77, 2.69 Hz, 2H) 3.85 (s, 3H) 7.02-7.15 (m, 6H) 7.30 (t, J=7.93 Hz, 1H) 7.38-7.42 (m, 1H) 7.43-7.50 (m, 3H) 7.60 (t, J=1.65 Hz, 1H) 8.45 (s, 1H) 8.73 (s, 1H).

(ESI) m/z 496 [(M+H)+]. HRMS (ESI) calculated for $C_{27}H_{23}FN_7O_2$ [(M+H)+] 496.1892. found 496.1907.

1-{5-[2-Amino-4-(1-methyl-4-oxo-4,5,6,7-tetrahydro-1H-pyrrolo[3,2-c]pyridin-2-yl)-pyrimidin-5-ylethynyl]-2-fluoro-phenyl}-3-[4-(4-ethyl-piperazin-1-ylmethyl)-3-trifluoromethyl-phenyl]-urea (cmpd 36)

$^1$H NMR (401 MHz, DMSO-$d_6$) δ ppm 0.99 (t, J=7.1 Hz, 3H) 2.18-2.45 (m, 10H) 2.89 (t, J=6.8 Hz, 2H) 3.44 (td, J=6.9, 2.4 Hz, 2H) 3.54 (s, 2H) 3.85 (s, 3H) 6.99-7.10 (m, 3H) 7.13 (ddd, J=8.5, 4.8, 2.1 Hz, 1H) 7.30 (dd, J=11.1, 8.5 Hz, 1H) 7.40 (s, 1H) 7.52 (m, J=6.7 Hz, 1H) 7.65 (d, J=8.5 Hz, 1H) 7.98 (d, J=2.2 Hz, 1H) 8.23 (dd, J=7.8, 2.0 Hz, 1H) 8.47 (s, 1H) 8.70 (d, J=2.1 Hz, 1H) 9.39 (s, 1H).

(ESI) m/z 690 [(M+H)+]. HRMS (ESI) calculated for $C_{35}H_{36}F_4N_9O_2$ [(M+H)+] 690.2923. found 690.2919.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(3-fluoro-phenyl)-urea (cmpd 37)

$^1$H NMR (401 MHz, DMSO-$d_6$) δ ppm 2.89 (t, J=6.96 Hz, 2H) 3.45 (td, J=6.84, 2.32 Hz, 2H) 3.85 (s, 3H) 6.79 (td, J=8.45, 2.50 Hz, 1H) 7.06 (s, 2H) 7.25-7.35 (m, 2H) 7.39-7.42 (m, 1H) 7.44 (s, 1H) 7.46-7.53 (m, 1H) 7.59-7.62 (m, 1H) 8.45 (s, 1H) 8.82 (s, 1H) 8.94 (s, 1H).

(ESI) m/z 496 [(M+H)+]. HRMS (ESI) calculated for $C_{27}H_{23}FN_7O_2$ [(M+H)+] 496.1892. found 496.1889.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[4-(4-dimethylamino-piperidin-1-ylmethyl)-3-trifluoromethyl-phenyl]-urea (cmpd 39)

$^1$H NMR (600 MHz, DMSO-$d_6$) δ ppm 1.68-1.92 (m, 2H) 2.10-2.21 (m, 2H) 2.77 (br. s., 6H) 2.89 (t, J=6.87 Hz, 2H) 3.44 (m, 2H overlapped by water signal) 3.85 (s, 3H) 7.05-7.19 (m, 4H) 7.33 (t, J=7.97 Hz, 1H) 7.40-7.47 (m, 2H) 7.65 (s, 1H) 7.67-7.81 (m, 2H) 8.05 (br. s., 1H) 8.46 (s, 1H) 9.12 (br. s., 1H) 9.42 (br. s., 1H).

(ESI) m/z 686 [(M+H)+]. HRMS (ESI) calculated for $C_{36}H_{37}F_3N_9O_2$ [(M+H)+] 686.3174. found 686.3199.

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-[4-(4-methyl-piperazin-1-ylmethyl)-3-trifluoromethyl-phenyl]-urea (cmpd 40)

$^1$H NMR (600 MHz, DMSO-$d_6$) δ ppm 2.18 (s, 3H) 2.25-2.47 (m, 8H) 2.89 (t, J=6.78 Hz, 2H) 3.44 (td, J=6.87, 2.56 Hz, 2H) 3.53 (s, 2H) 3.85 (s, 3H) 7.06 (s, 2H) 7.09-7.13 (m, 2H) 7.31 (t, J=7.88 Hz, 1H) 7.41 (dd, J=8.24, 1.28 Hz, 1H) 7.44 (s, 1H) 7.57 (dd, J=8.33, 1.92 Hz, 1H) 7.60-7.64 (m, 2H) 7.96 (d, J=2.01 Hz, 1H) 8.46 (s, 1H) 8.85 (s, 1H) 9.04 (s, 1H).

(ESI) m/z 658 [(M+H)+]. HRMS (ESI) calculated for $C34H_{35}F_3N_9O_2$ [(M+H)+] 658.2861. found 658.2868.

6-[2-Amino-4-(1-methyl-4-oxo-4,5,6,7-tetrahydro-1H-pyrrolo[3,2-c]pyridin-2-yl)-pyrimidin-5-ylethynyl]-2,3-dihydro-indole-1-carboxylic acid [4-(4-ethyl-piperazin-1-ylmethyl)-3-trifluoromethyl-phenyl]-amide (cmpd 44)

$^1$H NMR (600 MHz, DMSO-$d_6$) δ ppm 1.07 (br. s., 3H) 2.34-2.67 (m, 10H) 2.88 (t, J=6.87 Hz, 2H) 3.21 (t, J=8.52 Hz, 2H) 3.44 (td, J=6.87, 2.38 Hz, 2H) 3.58 (br. s., 2H) 3.84 (s, 3H) 4.16 (t, J=8.61 Hz, 2H) 7.03 (s, 2H) 7.05-7.07 (m, 1H) 7.08 (br. s., 1H) 7.23 (d, J=7.69 Hz, 1H) 7.41 (s, 1H) 7.63 (d, J=8.79 Hz, 1H) 7.85 (d, J=8.06 Hz, 1H) 7.94 (s, 1H) 8.00 (d, J=1.83 Hz, 1H) 8.45 (s, 1H) 8.86 (s, 1H).

(ESI) m/z 698 [(M+H)+]. HRMS (ESI) calculated for $C_{37}H_{39}F_3N_9O_2$ [(M+H)+] 698.3174. found 698.3170.

5-[2-Amino-4-(1-methyl-4-oxo-4,5,6,7-tetrahydro-1H-pyrrolo[3,2-c]pyridin-2-yl)-pyrimidin-5-ylethynyl]-2,3-dihydro-indole-1-carboxylic acid [4-(4-ethyl-piperazin-1-ylmethyl)-3-trifluoromethyl-phenyl]-amide (cmpd 45)

$^1$H NMR (600 MHz, DMSO-$d_6$) δ ppm 0.98 (t, J=7.23 Hz, 3H) 2.31 (q, J=7.14 Hz, 2H) 2.38 (br. s., 8H) 2.89 (t, J=6.87 Hz, 2H) 3.19 (t, J=8.52 Hz, 2H) 3.45 (td, J=6.82, 2.47 Hz, 2H) 3.54 (s, 2H) 3.85 (s, 3H) 4.17 (t, J=8.70 Hz, 2H) 7.00 (s, 2H) 7.12 (br. s., 1H) 7.27 (d, J=8.43 Hz, 1H) 7.33 (s, 1H) 7.50 (s, 1H) 7.64 (d, J=8.43 Hz, 1H) 7.83-7.85 (m, 1H) 7.87 (d, J=8.43 Hz, 1H) 7.98 (d, J=2.01 Hz, 1H) 8.40 (s, 1H) 8.86 (s, 1H).

(ESI) m/z 698 [(M+H)+]. HRMS (ESI) calculated for $C_{37}H_{39}F_3N_9O_2$ [(M+H)+] 698.3174. found 698.3185.

Example 4

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-phenyl-acetamide (cmpd 79)

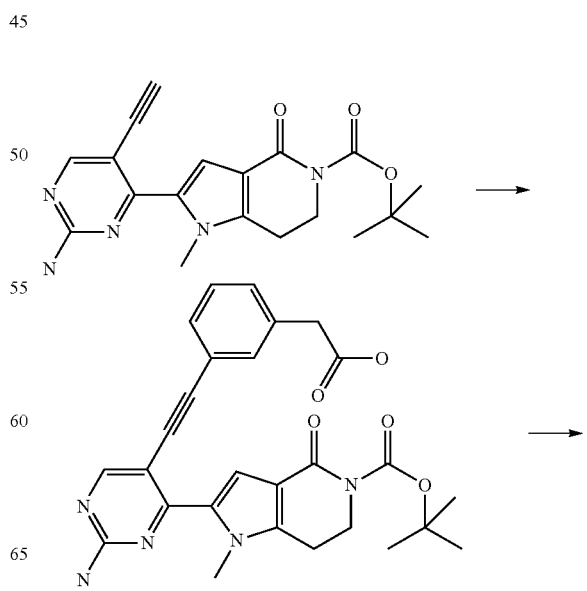

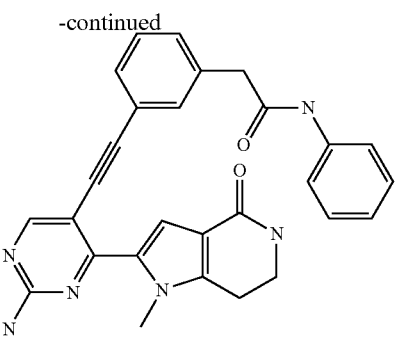

Step 1. 2-[2-Amino-5-(3-carboxymethyl-phenylethynyl)-pyrimidin-4-yl]-1-methyl-4-oxo-1,4,6,7-tetrahydro-pyrrolo[3,2-c]pyridine-5-carboxylic acid tert-butyl ester To a suspension of 2-(2-Amino-5-ethynyl-pyrimidin-4-yl)-1-methyl-4-oxo-1,4,6,7-tetrahydro-pyrrolo[3,2-c]pyridine-5-carboxylic acid tert-butyl ester (1.56 g, 4.25 mmol) in degassed MeCN (25 mL), CuI (10% mol, 81 mg, 0.425 mmol), 3-iodophenylacetic acid (1.17 g, 4.25 mmol), TEA (5.92 mL, 42.48 mmol) and PdCl$_2$(PPh$_3$)$_2$ (10% mol, 0.30 g, 0.425 mmol) were added. The mixture was degassed for three times back filling with argon each time and let under stirring at r.t. for 1 h. The reaction was quenched with 2 N HCl (21.2 mL) and the solvent was removed under reduced pressure. The residue was suspended in water and the resulting solid was filtered and rinsed with water affording the title product and brownish solid (1.62 g, 76%).

(ESI) m/z 502 [(M+H)$^+$]. HRMS (ESI) calculated for C$_{27}$H$_{28}$N$_5$O$_5$ [(M+H)$^+$] 502.2085. found 502.2074.

Step 2. 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-phenyl-acetamide (cmpd 79)

A mixture of 2-[2-amino-5-(3-carboxymethyl-phenylethynyl)-pyrimidin-4-yl]-1-methyl-4-oxo-1,4,6,7-tetrahydro-pyrrolo[3,2-c]pyridine-5-carboxylic acid tert-butyl ester (70 mg, 0.14 mmol), TBTU (47 mg, 0.15 mmol), aniline (0.015 mL, 0.17 mmol) and DIPEA (0.03 mL, 0.18 mmol) in DMA (4 mL) was let under stirring at r.t. overnight. The reaction was diluted with EtOAc and washed with saturated solution of NaHCO$_3$, water and brine. The organic layer was dried over anhydrous Na$_2$SO$_4$, filtered, concentrated and finally treated with 4 M HCl in dioxane for 2 h. After removal of the solvent, the compound was purified by preparative HPLC using a XTerra C18 column (19×100 mm; 5 μm). Mobile phase A was 0.05% NH$_3$/CH$_3$CN 95/5, and mobile layer B was MeCN. The gradient was from 10 to 90% B in 8 min then hold for 2 min before re-equilibration.

$^1$H NMR (401 MHz, DMSO-d$_6$) δ ppm 2.90 (t, J=6.90 Hz, 2H) 3.46 (td, J=6.87, 2.50 Hz, 2H) 3.65 (s, 2H) 3.85 (s, 3H) 7.01-7.05 (m, 1H) 7.07 (s, 2H) 7.21 (s, 1H) 7.26-7.32 (m, 2H) 7.32-7.39 (m, 3H) 7.51-7.54 (m, 2H) 7.56-7.61 (m, 2H) 8.44 (s, 1H) 10.17 (s, 1H).

(ESI) m/z 477 [(M+H)$^+$]. HRMS (ESI) calculated for C$_{28}$H$_{25}$N$_6$O$_2$ [(M+H)$^+$] 477.2034. found 477.2031.

According to this same methodology, but employing suitable substituted derivatives, the following compounds were prepared:

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-benzyl-acetamide (cmpd 80)

$^1$H NMR (401 MHz, DMSO-d$_6$) δ ppm 2.87 (t, J=6.84 Hz, 2H) 3.44 (td, J=6.80, 2.26 Hz, 2H) 3.49 (s, 2H) 3.85 (s, 3H) 4.27 (d, J=5.86 Hz, 2H) 7.06 (s, 2H) 7.16 (br. s., 1H) 7.18-7.24 (m, 4H) 7.24-7.35 (m, 6H) 7.47 (s, 1H) 7.51 (s, 1H) 8.43 (s, 1H) 8.55 (s, 1H).

(ESI) m/z 491 [(M+H)$^+$]. HRMS (ESI) calculated for C$_{28}$H$_{25}$N$_6$O$_2$ [(M+H)$^+$] 491.2190. found 491.2193.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-trifluoromethyl-phenyl)-acetamide (cmpd 81)

$^1$H NMR (401 MHz, DMSO-d$_6$) δ ppm 2.90 (t, J=6.90 Hz, 2H) 3.46 (td, J=6.90, 2.44 Hz, 2H) 3.70 (s, 2H) 3.85 (s, 3H) 7.07 (s, 2H) 7.21 (s, 1H) 7.30-7.40 (m, 3H) 7.50-7.54 (m, 2H) 7.66 (d, J=8.79 Hz, 2H) 7.81 (d, J=8.67 Hz, 2H) 8.43 (s, 1H) 10.54 (s, 1H).

(ESI) m/z 545 [(M+H)$^+$]. HRMS (ESI) calculated for C$_{29}$H$_{24}$F$_3$N$_6$O$_2$ [(M+H)$^+$] 545.1908. found 545.1906.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-(4-ethyl-piperazin-1-ylmethyl)-4-trifluoromethyl-phenyl]-acetamide (cmpd 82)

$^1$H NMR (600 MHz, DMSO-d$_6$) δ ppm 0.96 (t, J=7.23 Hz, 3H) 2.28 (q, J=7.20 Hz, 2H) 2.32-2.47 (m, 8H) 2.90 (t, J=6.87 Hz, 2H) 3.46 (td, J=6.78, 2.56 Hz, 2H) 3.54 (s, 2H) 3.69 (s, 2H) 3.85 (s, 3H) 7.07 (s, 2H) 7.19 (br. s., 1H) 7.31-7.41 (m, 3H) 7.51-7.55 (m, 2H) 7.60 (d, J=8.79 Hz, 1H) 7.79 (d, J=8.42 Hz, 1H) 7.89 (s, 1H) 8.43 (s, 1H) 10.52 (s, 1H).

(ESI) m/z 671 [(M+H)$^+$]. HRMS (ESI) calculated for C$_{36}$H$_{38}$F$_3$N$_8$O$_2$ [(M+H)$^+$] 671.3065. found 671.3067.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(1-methyl-piperidin-4-yloxy)-phenyl]-acetamide (cmpd 83)

$^1$H NMR (401 MHz, DMSO-d$_6$) δ ppm 1.49-1.64 (m, 2H) 1.83-1.92 (m, 2H) 2.08-2.14 (m, 2H) 2.15 (s, 3H) 2.54-2.63 (m, 2H) 2.90 (t, J=6.90 Hz, 2H) 3.46 (td, J=6.80, 2.38 Hz, 2H) 3.60 (s, 2H) 3.85 (s, 3H) 4.21-4.30 (m, 1H) 6.83-6.90 (m, 2H) 7.06 (s, 2H) 7.21 (s, 1H) 7.29-7.38 (m, 3H) 7.43-7.49 (m, 2H) 7.51 (s, 1H) 7.53 (s, 1H) 8.43 (s, 1H) 10.02 (s, 1H).

(ESI) m/z 590 [(M+H)$^+$]. HRMS (ESI) calculated for C$_{34}$H$_{36}$N$_7$O$_3$ [(M+H)$^+$] 590.2874. found 590.2886.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-fluoro-benzyl)-acetamide (cmpd 84)

$^1$H NMR (401 MHz, DMSO-d$_6$) δ ppm 2.84 (t, J=6.90 Hz, 2H) 3.81 (s, 3H) 4.21 (d, J=5.74 Hz, 2H) 6.98-7.17 (m, 4H) 7.17-7.27 (m, 3H) 7.29 (d, J=5.13 Hz, 2H) 7.41 (s, 1H) 8.40 (s, 1H) 8.51 (t, J=5.80 Hz, 1H).

(ESI) m/z 509 [(M+H)⁺]. HRMS (ESI) calculated for $C_{29}H_{26}FN_6O_2$ [(M+H)⁺] 509.2096. found 509.2091.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-isoquinolin-5-yl-acetamide (cmpd 85)

¹H NMR (401 MHz, DMSO-d₆) δ ppm 2.88 (t, J=6.84 Hz, 3H) 3.44 (td, J=6.87, 2.26 Hz, 3H) 3.84-3.88 (m, 5H) 7.07 (s, 2H) 7.15-7.19 (m, 1H) 7.30-7.45 (m, 4H) 7.55 (s, 1H) 7.61 (s, 1H) 7.66 (t, J=7.93 Hz, 1H) 7.86-7.97 (m, 2H) 8.00 (d, J=7.45 Hz, 1H) 8.43-8.45 (m, 1H) 8.50 (d, J=5.98 Hz, 1H) 9.31 (s, 1H) 10.27 (s, 1H).
(ESI) m/z 528 [(M+H)⁺]. HRMS (ESI) calculated for $C_{31}H_{26}N_7O_2$ [(M+H)⁺] 528.2143. found 528.2153.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-oxazol-5-yl-phenyl)-acetamide (cmpd 86)

¹H NMR (401 MHz, DMSO-d₆) δ ppm 2.90 (t, J=6.90 Hz, 2H) 3.43-3.49 (m, 2H) 3.68 (s, 2H) 3.84-3.87 (m, 3H) 7.07 (s, 2H) 7.22 (s, 1H) 7.34-7.38 (m, 3H) 7.40-7.43 (m, 2H) 7.52-7.58 (m, 3H) 7.61 (s, 1H) 8.03 (s, 1H) 8.43 (d, J=2.93 Hz, 2H) 10.32-10.36 (m, 1H) 10.34 (s, 1H).
(ESI) m/z 544 [(M+H)⁺]. HRMS (ESI) calculated for $C_{31}H_{26}N_7O_3$ [(M+H)⁺] 544.2091. found 544.2101.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(1H-indazol-5-yl)-acetamide (cmpd 87)

¹H NMR (401 MHz, DMSO-d₆) δ ppm 2.89 (d, J=7.08 Hz, 2H) 3.46 (d, J=6.47 Hz, 2H) 3.66 (s, 2H) 3.85 (s, 3H) 7.06 (br. s, 2H) 7.22 (br. s, 1H) 7.32-7.39 (m, 3H) 7.40-7.51 (m, 2H) 7.51-7.56 (m, 2H) 7.99 (s, 1H) 8.10 (s, 1H) 8.44 (s, 1H) 10.17 (s, 1H) 12.94 (br. s, 1H).
(ESI) m/z 517 [(M+H)⁺]. HRMS (ESI) calculated for $C_{29}H_{25}N_8O_2$ [(M+H)⁺] 517.2095. found 517.2096.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-pyridin-4-yl-phenyl)-acetamide (cmpd 88)

¹H NMR (401 MHz, DMSO-d₆) δ ppm 2.89 (t, J=6.90 Hz, 2H) 3.46 (td, J=6.96, 2.32 Hz, 2H) 3.69 (s, 2H) 3.86 (s, 3H) 7.07 (s, 2H) 7.25 (s, 1H) 7.36 (s, 3H) 8.03 (s, 1H) 8.43 (s, 1H) 8.59-8.66 (m, 2H) 10.36 (s, 1H).
(ESI) m/z 554 [(M+H)⁺]. HRMS (ESI) calculated for $C_{33}H_{28}N_7O_2$ [(M+H)⁺] 554.2299. found 554.2310.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-pyrazol-1-yl-phenyl)-acetamide (cmpd 89)

¹H NMR (401 MHz, DMSO-d₆) δ ppm 2.90 (t, J=6.90 Hz, 2H) 3.46 (td, J=6.90, 2.32 Hz, 2H) 3.67 (s, 2H) 3.86 (s, 3H) 6.49-6.52 (m, 1H) 7.07 (br. s, 2H) 7.22 (br. s, 1H) 7.34-7.39 (m, 3H) 7.51-7.66 (m, 2H) 7.69 (m, 1H) 7.70-7.78 (m, 4H) 8.40 (d, J=2.44 Hz, 1H) 8.44 (s, 1H) 10.31 (s, 1H).
(ESI) m/z 543 [(M+H)⁺]. HRMS (ESI) calculated for $C_{31}H_{27}N_8O_2$ [(M+H)⁺] 543.2252. found 543.2254.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-pyrazol-1-ylmethyl-phenyl)-acetamide (cmpd 90)

¹H NMR (401 MHz, DMSO-d₆) δ ppm 2.86 (t, J=6.90 Hz, 2H) 3.42 (td, J=6.84, 2.69 Hz, 2H) 3.59 (s, 2H) 3.82 (s, 3H) 5.24 (s, 2H) 6.21 (t, J=2.08 Hz, 1H) 6.84 (d, J=7.57 Hz, 1H) 7.03 (s, 2H) 7.16 (s, 1H) 7.19-7.24 (m, 1H) 7.26-7.34 (m, 3H) 7.73 (d, J=2.20 Hz, 1H) 8.40 (s, 1H) 10.14 (s, 1H).
(ESI) m/z 557 [(M+H)⁺]. HRMS (ESI) calculated for $C_{32}H_{29}N_8O_2$ [(M+H)⁺] 557.2408. found 557.2410.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-piperidin-1-yl-phenyl)-acetamide (cmpd 91)

¹H NMR (401 MHz, DMSO-d₆) δ ppm 1.45-1.67 (m, 6H) 2.90 (t, J=6.77 Hz, 2H) 3.03-3.12 (m, 4H) 3.46 (td, J=6.80, 2.38 Hz, 2H) 3.62 (s, 2H) 3.86 (s, 3H) 6.60 (dd, J=8.30, 2.07 Hz, 1H) 6.98 (d, J=8.79 Hz, 1H) 7.05-7.13 (m, 3H) 7.20-7.25 (m, 2H) 7.30-7.39 (m, 4H) 7.54 (s, 1H) 7.55 (s, 1H) 8.43 (s, 1H) 10.00 (s, 1H).
(ESI) m/z 560 [(M+H)⁺]. HRMS (ESI) calculated for $C_{33}H_{34}N_7O_2$ [(M+H)⁺] 560.2769. found 560.2764.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-trifluoromethyl-phenyl)-acetamide (cmpd 92)

¹H NMR (401 MHz, DMSO-d₆) δ ppm 2.90 (t, J=6.84 Hz, 2H) 3.46 (td, J=6.93, 2.26 Hz, 2H) 3.69 (s, 2H) 3.85 (s, 3H) 7.07 (s, 2H) 7.21 (s, 1H) 7.32-7.42 (m, 4H) 7.52-7.58 (m, 3H) 7.78 (d, J=8.18 Hz, 1H) 8.09 (s, 1H) 8.44 (s, 1H) 10.52 (s, 1H).
(ESI) m/z 545 [(M+H)⁺]. HRMS (ESI) calculated for $C_{29}H_{24}F_3N_6O_2$ [(M+H)⁺] 545.1908. found 545.1911.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(5,6,7,8-tetrahydro-naphthalen-1-yl)-acetamide (cmpd 93)

¹H NMR (401 MHz, DMSO-d₆) δ ppm 1.66 (t, J=3.23 Hz, 4H) 2.54 (br. s., 2H) 2.70 (br. s., 2H) 2.89 (t, J=6.84 Hz, 2H) 3.45 (td, J=6.87, 2.50 Hz, 2H) 3.67 (s, 2H) 3.85 (s, 3H) 6.89 (d, J=7.08 Hz, 1H) 7.03 (t, J=7.75 Hz, 1H) 7.07 (s, 1H) 7.14-7.19 (m, 2H) 7.36 (s, 3H) 7.54 (s, 1H) 7.56 (s, 1H) 8.44 (s, 1H) 9.35 (s, 1H).
(ESI) m/z 531 [(M+H)⁺]. HRMS (ESI) calculated for $C_{32}H_{31}N_6O_2$ [(M+H)⁺] 531.2503. found 531.2510.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(2-trifluoromethyl-phenyl)-acetamide (cmpd 94)

(ESI) m/z 545 [(M+H)⁺]. HRMS (ESI) calculated for $C_{29}H_{24}F_3N_6O_2$ [(M+H)⁺] 545.1908. found 545.192.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-naphthalen-1-yl-acetamide (cmpd 95)

$^1$H NMR (401 MHz, DMSO-d$_6$) δ ppm 2.87 (t, J=6.90 Hz, 2H) 3.44 (td, J=6.74, 2.50 Hz, 2H) 3.83 (s, 2H) 3.86 (s, 3H) 7.07 (s, 1H) 7.18 (t, J=2.62 Hz, 1H) 7.31-7.49 (m, 1H) 7.67 (d, J=7.20 Hz, 1H) 7.75 (d, J=8.18 Hz, 1H) 7.88-7.97 (m, 1H) 8.01-8.09 (m, 1H) 8.44 (s, 1H) 10.16 (s, 1H).

(ESI) m/z 527 [(M+H)$^+$]. HRMS (ESI) calculated for C$_{32}$H$_{27}$N$_6$O$_2$ [(M+H)$^+$] 527.2190. found 527.2190.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-benzyloxy-phenyl)-acetamide (cmpd 96)

$^1$H NMR (401 MHz, DMSO-d$_6$) δ ppm 2.90 (t, J=6.84 Hz, 2H) 3.46 (td, J=6.84, 2.44 Hz, 2H) 3.61 (s, 2H) 3.85 (s, 3H) 5.05 (s, 2H) 6.89-6.98 (m, 1H) 7.06 (s, 1H) 7.21 (t, J=2.32 Hz, 1H) 7.26-7.46 (m, 1H) 7.46-7.54 (m, 1H) 8.43 (s, 1H) 10.04 (s, 1H).

(ESI) m/z 583 [(M+H)$^+$]. HRMS (ESI) calculated for C$_{35}$H$_{31}$N$_6$O$_3$ [(M+H)$^+$] 583.2452. found 583.2467.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-methyl-cinnolin-5-yl)-acetamide (cmpd 97)

(ESI) m/z 543 [(M+H)$^+$]. HRMS (ESI) calculated for C$_{31}$H$_{27}$N$_8$O$_2$ [(M+H)$^+$] 543.2252. found 543.2253.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-benzyloxy-phenyl)-acetamide (cmpd 98)

$^1$H NMR (401 MHz, DMSO-d$_6$) δ ppm 2.89 (t, J=6.84 Hz, 2H) 3.46 (td, J=6.80, 2.38 Hz, 2H) 3.64 (s, 2H) 3.85 (s, 3H) 5.05 (s, 2H) 6.69 (dt, J=9.28, 1.10 Hz, 1H) 7.07 (s, 2H) 7.10-7.15 (m, 1H) 7.16-7.21 (m, 1H) 7.22 (t, J=2.14 Hz, 1H) 7.28-7.46 (m, 9H) 7.52 (s, 1H) 7.54 (s, 1H) 8.44 (s, 1H) 10.16 (s, 1H).

(ESI) m/z 583 [(M+H)$^+$]. HRMS (ESI) calculated for C$_{35}$H$_{31}$N$_6$O$_3$ [(M+H)$^+$] 583.2452. found 583.2452.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-benzo[1,3]dioxol-5-yl-acetamide (cmpd 99)

$^1$H NMR (401 MHz, DMSO-d$_6$) δ ppm 2.90 (t, J=6.96 Hz, 2H) 3.46 (td, J=6.90, 2.44 Hz, 2H) 3.60 (s, 2H) 3.85 (s, 3H) 5.96 (s, 2H) 6.83 (d, J=8.42 Hz, 1H) 6.96 (dd, J=8.42, 2.08 Hz, 1H) 7.07 (s, 2H) 7.21 (s, 1H) 7.29 (d, J=2.07 Hz, 1H) 7.30-7.39 (m, 3H) 7.50 (s, 1H) 7.53 (s, 1H) 8.44 (s, 1H) 10.08 (s, 1H).

(ESI) m/z 521 [(M+H)$^+$]. HRMS (ESI) calculated for C$_{29}$H$_{25}$N$_6$O$_4$ [(M+H)$^+$] 521.1932. found 521.1923.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-indan-5-yl-acetamide (cmpd 100)

$^1$H NMR (401 MHz, DMSO-d$_6$) δ ppm 1.93-2.03 (m, 2H) 2.74-2.84 (m, 4H) 2.90 (t, J=6.84 Hz, 2H) 3.46 (td, J=6.87, 2.50 Hz, 2H) 3.62 (s, 2H) 3.85 (s, 3H) 7.06 (s, 2H) 7.11 (d, J=8.06 Hz, 1H) 7.21 (s, 1H) 7.28 (dd, J=8.12, 1.77 Hz, 1H) 7.31-7.39 (m, 3H) 7.48-7.54 (m, 3H) 8.43 (s, 1H) 10.03 (s, 1H).

(ESI) m/z 517 [(M+H)$^+$]. HRMS (ESI) calculated for C$_{31}$H$_{29}$N$_6$O$_2$ [(M+H)$^+$] 517.2347. found 517.2346.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-phenoxy-phenyl)-acetamide (cmpd 101)

$^1$H NMR (401 MHz, DMSO-d$_6$) δ ppm 2.90 (t, J=6.90 Hz, 2H) 3.46 (d, J=2.44 Hz, 2H) 3.64 (s, 2H) 3.85 (s, 3H) 6.91-7.00 (m, 4H) 7.07 (s, 2H) 7.08-7.12 (m, 1H) 7.21 (s, 1H) 7.30-7.40 (m, 5H) 7.52 (br. s., 1H) 7.53 (s, 1H) 7.58-7.64 (m, 2H) 8.44 (s, 1H) 10.20 (s, 1H).

(ESI) m/z 569 [(M+H)$^+$]. HRMS (ESI) calculated for C$_{34}$H$_{29}$N$_6$O$_3$ [(M+H)$^+$] 569.2296. found 569.2306.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-benzothiazol-6-yl-acetamide (cmpd 102)

(ESI) m/z 534 [(M+H)$^+$]. HRMS (ESI) calculated for C$_{29}$H$_{24}$N$_7$O$_2$S [(M+H)$^+$] 534.1707. found 534.1707.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(2,3-dihydro-benzo[1,4]dioxin-6-yl)-acetamide (cmpd 103)

$^1$H NMR (401 MHz, DMSO-d$_6$) δ ppm 2.90 (t, J=6.84 Hz, 2H) 3.46 (td, J=6.84, 2.44 Hz, 2H) 3.59 (s, 2H) 3.85 (s, 3H) 4.15-4.22 (m, 4H) 6.76 (d, J=8.67 Hz, 1H) 6.97 (dd, J=8.79, 2.44 Hz, 1H) 7.06 (s, 2H) 7.21 (d, J=2.44 Hz, 1H) 7.27-7.38 (m, 3H) 7.49 (d, J=1.46 Hz, 1H) 7.52-7.54 (m, 1H) 8.43 (s, 1H) 10.00 (s, 1H).

(ESI) m/z 535 [(M+H)$^+$]. HRMS (ESI) calculated for C$_{30}$H$_{27}$N$_6$O$_4$ [(M+H)$^+$] 535.2089. found 535.2090.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(5-tert-butyl-isoxazol-3-yl)-acetamide (cmpd 104)

(ESI) m/z 524 [(M+H)$^+$]. HRMS (ESI) calculated for C$_{29}$H$_{30}$N$_7$O$_3$ [(M+H)$^+$] 524.2405. found 524.2411.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(5-tert-butyl-2-methyl-2H-pyrazol-3-yl)-acetamide (cmpd 105)

$^1$H NMR (600 MHz, DMSO-d$_6$) δ ppm 1.18 (s, 10H) 2.54 (s, 8H) 2.89 (t, J=6.87 Hz, 2H) 3.45 (td, J=6.87, 2.38 Hz, 2H) 3.56 (s, 3H) 3.68 (s, 2H) 3.85 (s, 3H) 6.05 (s, 1H) 7.07 (s, 2H) 7.18 (br. s., 1H) 7.30-7.39 (m, 3H) 7.50-7.54 (m, 2H) 8.44 (s, 1H) 10.07 (s, 1H).

(ESI) m/z 537 [(M+H)$^+$]. HRMS (ESI) calculated for C$_{30}$H$_{33}$N$_8$O$_2$ [(M+H)$^+$] 537.2721. found 537.2733.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-quinolin-3-yl-acetamide (cmpd 106)

$^1$H NMR (600 MHz, DMSO-d$_6$) δ ppm 2.90 (t, J=6.87 Hz, 2H) 3.46 (td, J=6.87, 2.38 Hz, 2H) 3.77 (s, 2H) 3.86 (s, 3H)

7.07 (s, 2H) 7.22 (br. s., 1H) 7.34-7.41 (m, 3H) 7.90 (d, J=7.69 Hz, 1H) 7.94 (d, J=8.43 Hz, 1H) 8.44 (s, 1H) 8.70 (d, J=2.38 Hz, 1H) 8.93 (d, J=2.56 Hz, 1H) 10.67 (s, 1H).

(ESI) m/z 528 [(M+H)$^+$]. HRMS (ESI) calculated for $C_{31}H_{26}N_7O_2$ [(M+H)$^+$] 528.2143. found 528.2151.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(2,5-dimethyl-2H-pyrazol-3-yl)-acetamide (cmpd 107)

(ESI) m/z 495 [(M+H)$^+$]. HRMS (ESI) calculated for $C_{27}H_{27}N_8O_2$ [(M+H)$^+$] 495.2252. found 495.2255.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-methyl-isothiazol-5-yl)-acetamide (cmpd 108)

$^1$H NMR (600 MHz, DMSO-d$_6$) δ ppm 2.30 (s, 3H) 2.90 (t, J=6.87 Hz, 2H) 3.46 (td, J=6.73, 2.29 Hz, 2H) 3.79 (s, 2H) 3.85 (s, 3H) 6.73 (s, 1H) 7.08 (s, 2H) 7.20 (br. s., 1H) 7.31 (m, J=4.40 Hz, 1H) 7.34-7.41 (m, 2H) 7.49 (s, 1H) 7.51-7.53 (m, 1H) 8.44 (s, 1H) 12.02 (s, 1H).

(ESI) m/z 498 [(M+H)$^+$]. HRMS (ESI) calculated for $C_{26}H_{24}N_7O_2S$ [(M+H)$^+$] 498.1707. found 498.1705.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N—(R)-1,2,3,4-tetrahydro-naphthalen-1-yl-acetamide (cmpd 109)

$^1$H NMR (600 MHz, DMSO-d$_6$) δ ppm 1.60-1.79 (m, 2H) 1.80-1.90 (m, 2H) 2.65-2.79 (m, 2H) 2.87 (td, J=6.87, 3.48 Hz, 2H) 3.40-3.52 (m, 4H) 3.85 (s, 3H) 4.89-4.97 (m, 1H) 7.02-7.14 (m, 8H) 7.26-7.37 (m, 3H) 7.48 (s, 1H) 7.49 (s, 1H) 8.43 (s, 1H) 8.45 (d, J=8.42 Hz, 1H).

(ESI) m/z 531 [(M+H)$^+$]. HRMS (ESI) calculated for $C_{32}H_{31}N_6O_2$ [(M+H)$^+$] 531.2503. found 531.2511.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N—(S)-1,2,3,4-tetrahydro-naphthalen-1-yl-acetamide (cmpd 110)

$^1$H NMR (600 MHz, DMSO-d$_6$) δ ppm 1.62-1.94 (m, 5H) 2.64-2.80 (m, 2H) 2.87 (td, J=6.87, 3.48 Hz, 2H) 3.40-3.45 (m, 2H) 3.45-3.51 (m, 2H) 3.85 (s, 3H) 4.88-4.96 (m, 1H) 7.02-7.16 (m, 8H) 7.27-7.37 (m, 3H) 7.48 (s, 1H) 7.49 (s, 1H) 8.43 (s, 1H) 8.45 (d, J=8.61 Hz, 1H).

(ESI) m/z 531 [(M+H)$^+$]. HRMS (ESI) calculated for $C_{32}H_{31}N_6O_2$ [(M+H)$^+$] 531.2503. found 531.2515.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-trifluoromethyl-benzyl)-acetamide (cmpd 111)

$^1$H NMR (600 MHz, DMSO-d$_6$) δ ppm 2.87 (t, J=6.78 Hz, 2H) 3.44 (td, J=6.87, 2.38 Hz, 2H) 3.51 (s, 2H) 3.85 (s, 3H) 4.36 (d, J=5.86 Hz, 2H) 7.07 (s, 2H) 7.17 (br. s., 1H) 7.26-7.35 (m, 3H) 7.47 (s, 1H) 8.42 (s, 1H) 8.67 (t, J=6.04 Hz, 1H).

(ESI) m/z 559 [(M+H)$^+$]. HRMS (ESI) calculated for $C_{30}H_{26}F_3N_6O_2$ [(M+H)$^+$] 559.2064. found 559.2065.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-trifluoromethyl-benzyl)-acetamide (cmpd 112)

$^1$H NMR (600 MHz, DMSO-d$_6$) δ ppm 2.87 (t, J=6.96 Hz, 2H) 3.44 (td, J=6.87, 2.56 Hz, 2H) 3.51 (s, 2H) 3.85 (s, 3H) 4.36 (d, J=5.86 Hz, 2H) 7.07 (s, 2H) 7.17 (br. s., 1H) 7.26-7.35 (m, 3H) 7.43 (d, J=7.88 Hz, 2H) 7.47 (s, 1H) 7.51 (s, 1H) 8.43 (s, 1H) 8.66 (t, J=5.95 Hz, 1H).

(ESI) m/z 559 [(M+H)$^+$]. HRMS (ESI) calculated for $C_{30}H_{26}F_3N_6O_2$ [(M+H)$^+$] 559.2064. found 559.2064.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N—((S)-1-phenyl-ethyl)-acetamide (cmpd 113)

$^1$H NMR (600 MHz, DMSO-d$_6$) δ ppm 1.35 (d, J=6.96 Hz, 3H) 2.88 (td, J=6.82, 2.47 Hz, 2H) 3.41-3.50 (m, 5H) 3.85 (s, 3H) 4.88 (m, 1H) 7.07 (s, 2H) 7.15-7.29 (m, 6H) 7.31 (d, J=5.13 Hz, 2H) 7.46 (s, 1H) 7.53 (s, 1H) 8.43 (s, 1H) 8.53 (d, J=8.06 Hz, 1H).

(ESI) m/z 505 [(M+H)$^+$]. HRMS (ESI) calculated for $C_{30}H_{29}N_6O_2$ [(M+H)$^+$] 505.2347. found 505.2355.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-fluoro-benzyl)-acetamide (cmpd 114)

$^1$H NMR (600 MHz, DMSO-d$_6$) δ ppm 2.87 (t, J=6.87 Hz, 2H) 3.44 (t, J=5.68 Hz, 2H) 3.50 (s, 2H) 3.85 (s, 3H) 4.29 (d, J=5.86 Hz, 2H) 6.95-7.09 (m, 5H) 7.17 (br. s., 1H) 7.25-7.38 (m, 4H) 7.48 (s, 1H) 7.51 (s, 1H) 8.43 (s, 1H) 8.60 (t, J=5.59 Hz, 1H).

(ESI) m/z 509 [(M+H)$^+$]. HRMS (ESI) calculated for $C_{29}H_{26}FN_6O_2$ [(M+H)$^+$] 509.2096. found 509.2106.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(2-fluoro-benzyl)-acetamide (cmpd 115)

$^1$H NMR (600 MHz, DMSO-d$_6$) δ ppm 2.84 (t, J=6.87 Hz, 2H) 3.41 (td, J=6.82, 2.47 Hz, 2H) 3.47 (s, 2H) 3.82 (s, 3H) 4.28 (d, J=5.49 Hz, 2H) 7.04 (s, 2H) 7.13 (s, 1H) 7.44 (s, 1H) 7.48 (s, 1H) 8.41 (s, 1H) 8.53 (t, J=5.68 Hz, 1H).

(ESI) m/z 509 [(M+H)$^+$]. HRMS (ESI) calculated for $C_{29}H_{26}FN_6O_2$ [(M+H)$^+$] 509.2096. found 509.2100.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N—((R)-1-phenyl-ethyl)-acetamide (cmpd 116)

$^1$H NMR (600 MHz, DMSO-d$_6$) δ ppm 1.35 (d, J=6.96 Hz, 3H) 2.88 (td, J=6.82, 2.66 Hz, 2H) 3.42-3.49 (m, 4H) 3.85 (s, 3H) 4.84-4.92 (m, 1H) 7.07 (s, 2H) 7.16-7.33 (m, 8H) 7.46 (s, 1H) 7.53 (s, 1H) 8.43 (s, 1H) 8.53 (d, J=8.1 Hz, 1H).

(ESI) m/z 505 [(M+H)$^+$]. HRMS (ESI) calculated for $C_{30}H_{29}N_6O_2$ [(M+H)$^+$] 505.2347. found 50.2350.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(2-trifluoromethyl-benzyl)-acetamide (cmpd 117)

$^1$H NMR (600 MHz, DMSO-d$_6$) δ ppm 2.84 (t, J=6.87 Hz, 2H) 3.43 (td, J=6.82, 2.66 Hz, 2H) 3.55 (s, 2H) 3.85 (s, 3H) 4.45 (br. s., 2H) 7.07 (s, 2H) 7.17 (s, 1H) 7.27-7.37 (m, 3H) 7.41-7.47 (m, 2H) 7.51 (s, 1H) 7.69 (d, J=7.69 Hz, 1H) 8.43 (s, 1H) 8.63 (t, J=5.86 Hz, 1H).
(ESI) m/z 559 [(M+H)$^+$]. HRMS (ESI) calculated for C$_{30}$H$_{26}$F$_3$N$_6$O$_2$ [(M+H)$^+$] 559.2064. found 559.2068.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N—((S)-1-phenyl-2-pyrrolidin-1-yl-ethyl)-acetamide (cmpd 118)

$^1$H NMR (600 MHz, DMSO-d$_6$) δ ppm 1.56-1.67 (m, 5H) 2.33-2.45 (m, 5H) 2.77 (dd, J=12.18, 9.80 Hz, 1H) 2.89 (t, J=6.78 Hz, 2H) 3.40-3.55 (m, 5H) 3.85 (s, 3H) 4.90 (td, J=8.75, 5.40 Hz, 1H) 7.07 (s, 2H) 7.16-7.24 (m, 2H) 7.25-7.34 (m, 8H) 7.49 (d, J=2.56 Hz, 1H) 7.55 (s, 1H) 8.41 (s, 1H) 8.53 (d, J=8.24 Hz, 1H).
(ESI) m/z 574 [(M+H)$^+$]. HRMS (ESI) calculated for C$_{34}$H$_{36}$N$_7$O$_2$ [(M+H)$^+$] 574.2925. found 574.2935.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N—((S)-2-morpholin-4-yl-1-phenyl-ethyl)-acetamide (cmpd 119)

$^1$H NMR (600 MHz, DMSO-d$_6$) δ ppm 2.22-2.44 (m, 5H) 2.58-2.64 (m, 1H) 2.89 (t, J=6.87 Hz, 2H) 3.36-3.52 (m, 8H) 3.55 (d, J=13.55 Hz, 1H) 3.86 (s, 3H) 4.99 (d, J=3.66 Hz, 1H) 7.07 (s, 2H) 7.18-7.24 (m, 2H) 7.27-7.34 (m, 7H) 7.54 (s, 1H) 7.56 (s, 1H) 8.42 (s, 1H) 8.51 (d, J=8.24 Hz, 1H).
(ESI) m/z 590 [(M+H)$^+$]. HRMS (ESI) calculated for C$_{34}$H$_{36}$N$_7$O$_3$ [(M+H)$^+$] 590.2874. found 590.2881.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-chloro-4-fluoro-phenyl)-acetamide (cmpd 130)

$^1$H NMR (600 MHz, DMSO-d$_6$) δ ppm 2.90 (t, J=6.87 Hz, 2H) 3.46 (td, J=6.87, 2.56 Hz, 2H) 3.65 (s, 2H) 3.86 (s, 3H) 7.07 (s, 2H) 7.22 (br. s., 1H) 7.30-7.38 (m, 5H) 7.46-7.50 (m, 1H) 7.51 (s, 1H) 7.52 (s, 1H) 7.91 (dd, J=6.78, 2.56 Hz, 1H) 8.44 (s, 1H) 10.40 (s, 1H).
(ESI) m/z 529 [(M+H)$^+$]. HRMS (ESI) calculated for C$_{28}$H$_{23}$ClFN$_6$O$_2$ [(M+H)$^+$] 529.1550. found 529.1541.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-methyl-3-trifluoromethyl-phenyl)-acetamide (cmpd 131)

$^1$H NMR (600 MHz, DMSO-d$_6$) δ ppm 2.35-2.38 (m, 3H) 2.90 (t, J=6.87 Hz, 2H) 3.46 (td, J=6.91, 2.47 Hz, 2H) 3.65-3.70 (m, 2H) 3.86 (s, 3H) 7.07 (s, 2H) 7.21 (br. s., 1H) 7.30-7.40 (m, 4H) 7.51 (s, 1H) 7.53 (s, 1H) 7.70 (dd, J=8.24, 1.83 Hz, 1H) 8.01 (d, J=2.01 Hz, 1H) 8.43 (s, 1H) 10.41 (s, 1H).
(ESI) m/z 559 [(M+H)$^+$]. HRMS (ESI) calculated for C$_{30}$H$_{26}$F$_3$N$_6$O$_2$ [(M+H)$^+$] 559.2064. found 559.2076.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-chloro-phenyl)-acetamide (cmpd 132)

(ESI) m/z 511 [(M+H)$^+$]. HRMS (ESI) calculated for C$_{28}$H$_{24}$ClN$_6$O$_2$ [(M+H)$^+$] 511.1644. found 511.1644.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-isopropyl-phenyl)-acetamide (cmpd 133)

$^1$H NMR (600 MHz, DMSO-d$_6$) δ ppm 1.16 (d, J=6.78 Hz, 6H) 2.82 (dt, J=13.74, 6.87 Hz, 1H) 2.90 (t, J=6.87 Hz, 2H) 3.46 (td, J=6.91, 2.47 Hz, 2H) 3.59-3.64 (m, 2H) 3.85 (s, 3H) 7.07 (s, 2H) 7.11-7.17 (m, 2H) 7.21 (br. s., 1H) 7.30-7.37 (m, 3H) 7.46-7.50 (m, 2H) 7.51 (s, 1H) 7.53 (s, 1H) 8.43 (s, 1H) 10.09 (s, 1H).
(ESI) m/z 519 [(M+H)$^+$]. HRMS (ESI) calculated for C$_{31}$H$_{31}$N$_6$O$_2$ [(M+H)$^+$] 519.2503. found 519.2513.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-chloro-3-methyl-phenyl)-acetamide (cmpd 134)

$^1$H NMR (600 MHz, DMSO-d$_6$) δ ppm 2.28 (s, 4H) 2.90 (t, J=6.78 Hz, 2H) 3.46 (td, J=6.87, 2.56 Hz, 2H) 3.64 (s, 2H) 3.86 (s, 3H) 7.07 (s, 2H) 7.22 (br. s., 1H) 7.28-7.38 (m, 5H) 7.44 (dd, J=8.61, 2.38 Hz, 1H) 7.51 (s, 1H) 7.53 (s, 1H) 7.58 (d, J=2.20 Hz, 1H) 8.43 (s, 1H) 10.23 (s, 1H).
(ESI) m/z 525 [(M+H)$^+$]. HRMS (ESI) calculated for C$_{29}$H$_{26}$ClN$_6$O$_2$ [(M+H)$^+$] 525.1801. found 525.1809.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-tert-butyl-phenyl)-acetamide (cmpd 135)

$^1$H NMR (600 MHz, DMSO-d$_6$) δ ppm 1.24 (s, 9H) 2.90 (t, J=6.78 Hz, 2H) 3.46 (td, J=6.87, 2.38 Hz, 2H) 3.63 (s, 2H) 3.86 (s, 3H) 7.07 (s, 2H) 7.21 (br. s., 1H) 7.30 (d, J=8.79 Hz, 3H) 7.31-7.37 (m, 4H) 7.47-7.52 (m, 4H) 7.53 (s, 1H) 8.43 (s, 1H) 10.10 (s, 1H).
(ESI) m/z 533 [(M+H)$^+$]. HRMS (ESI) calculated for C$_{32}$H$_{32}$N$_6$O$_2$ [(M+H)$^+$] 533.2660. found 533.2659.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-phenyl-thiazol-2-yl)-acetamide (cmpd 136)

$^1$H NMR (600 MHz, DMSO-d$_6$) δ ppm 2.86 (t, J=6.87 Hz, 2H) 3.43 (td, J=6.82, 2.29 Hz, 2H) 3.79 (s, 2H) 3.83 (s, 3H) 7.04 (s, 2H) 7.12 (br. s., 1H) 7.24-7.36 (m, 5H) 7.40 (t, J=7.69 Hz, 2H) 7.45-7.51 (m, 3H) 7.58 (s, 1H) 7.87 (d, J=7.33 Hz, 2H) 8.42 (s, 1H) 12.46 (br. s., 1H).
(ESI) m/z 560 [(M+H)$^+$]. HRMS (ESI) calculated for C$_{31}$H$_{26}$N$_7$O$_2$S [(M+H)$^+$] 560.1863. found 560.1868.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-chloro-4-methyl-phenyl)-acetamide (cmpd 137)

$^1$H NMR (600 MHz, DMSO-d$_6$) δ ppm 2.26 (s, 3H) 2.90 (t, J=6.87 Hz, 2H) 3.46 (td, J=6.82, 2.47 Hz, 2H) 3.64 (s, 2H)

3.86 (s, 3H) 7.07 (s, 2H) 7.22 (br. s., 1H) 7.26 (d, J=8.61 Hz, 1H) 7.31-7.39 (m, 5H) 7.50-7.54 (m, 2H) 7.78 (d, J=2.01 Hz, 1H) 8.44 (s, 1H) 10.26 (s, 1H).

(ESI) m/z 525 [(M+H)$^+$]. HRMS (ESI) calculated for $C_{29}H_{26}ClN_6O_2$ [(M+H)$^+$] 525.1801. found 525.1796.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-chloro-3-(4-ethyl-piperazin-1-ylmethyl)-phenyl]-acetamide (cmpd 138)

$^1$H NMR (600 MHz, DMSO-d$_6$) δ ppm 0.96 (t, J=7.14 Hz, 3H) 2.28 (q, J=7.14 Hz, 2H) 2.32-2.47 (m, 6H) 2.46 (br. s., 0H) 2.90 (t, J=6.87 Hz, 2H) 3.46 (td, J=6.87, 2.38 Hz, 2H) 3.48 (s, 2H) 3.65 (s, 2H) 3.86 (s, 3H) 7.07 (s, 2H) 7.21 (s, 1H) 7.30-7.40 (m, 4H) 7.51 (s, 1H) 7.53 (s, 1H) 7.60 (dd, J=8.61, 2.56 Hz, 1H) 7.68 (d, J=2.56 Hz, 1H) 8.43 (s, 1H) 10.30 (s, 1H).

(ESI) m/z 637 [(M+H)$^+$]. HRMS (ESI) calculated for $C_{35}H_{38}ClN_8O_2$ [(M+H)$^+$] 637.2801. found 637.2800.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(6-chloro-pyridin-3-yl)-acetamide (cmpd 139)

$^1$H NMR (600 MHz, DMSO-d$_6$) δ ppm 2.87 (t, J=6.87 Hz, 2H) 3.42-3.46 (m, 2H) 3.67 (s, 2H) 3.83 (s, 3H) 7.05 (s, 2H) 7.18 (br. s., 1H) 7.26-7.37 (m, 3H) 7.43 (d, J=8.61 Hz, 1H) 7.48 (s, 1H) 7.50 (s, 1H) 8.06 (dd, J=8.79, 2.75 Hz, 1H) 8.41 (s, 1H) 8.58 (d, J=2.38 Hz, 1H) 10.52 (br. s., 1H).

(ESI) m/z 512 [(M+H)$^+$]. HRMS (ESI) calculated for $C_{27}H_{23}ClN_7O_2$ [(M+H)$^+$] 512.1597. found 512.1594.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-pyridin-3-yl-acetamide (cmpd 140)

$^1$H NMR (600 MHz, DMSO-d$_6$) δ ppm 2.90 (t, J=6.87 Hz, 2H) 3.46 (td, J=6.87, 2.56 Hz, 2H) 3.69 (s, 2H) 3.86 (s, 3H) 7.07 (s, 2H) 7.22 (br. s., 1H) 7.29-7.41 (m, 4H) 7.51-7.54 (m, 2H) 8.02-8.06 (m, 1H) 8.25 (dd, J=4.67, 1.37 Hz, 1H) 8.44 (s, 1H) 8.74 (d, J=2.20 Hz, 1H) 10.40 (s, 1H).

(ESI) m/z 478 [(M+H)$^+$]. HRMS (ESI) calculated for $C_{27}H_{24}N_7O_2$ [(M+H)$^+$] 478.1986. found 478.1985.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-chloro-3-trifluoromethyl-phenyl)-acetamide (cmpd 141)

$^1$H NMR (600 MHz, DMSO-d$_6$) δ ppm 2.90 (t, J=6.87 Hz, 2H) 3.46 (td, J=6.82, 2.47 Hz, 2H) 3.69 (s, 2H) 3.86 (s, 3H) 7.07 (s, 2H) 7.21 (br. s., 1H) 7.29-7.40 (m, 4H) 7.50-7.53 (m, 2H) 7.65 (d, J=8.79 Hz, 1H) 7.84 (dd, J=8.61, 2.38 Hz, 1H) 8.19 (d, J=2.56 Hz, 1H) 8.43 (s, 1H) 10.64 (br. s., 1H).

(ESI) m/z 579 [(M+H)$^+$]. HRMS (ESI) calculated for $C_{29}H_{23}ClF_3N_7O_2$ [(M+H)$^+$] 579.1518. found 579.1526.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3,4-dimethoxy-phenyl)-acetamide (cmpd 142)

$^1$H NMR (600 MHz, DMSO-d$_6$) δ ppm 2.90 (t, J=6.78 Hz, 2H) 3.46 (td, J=6.91, 2.47 Hz, 2H) 3.61 (s, 2H) 3.70 (d, 6H) 3.86 (s, 3H) 6.87 (d, J=8.79 Hz, 1H) 7.07 (s, 2H) 7.09 (dd, J=8.61, 2.38 Hz, 1H) 7.23 (br. s., 1H) 7.30 (d, J=2.38 Hz, 1H) 7.32-7.39 (m, 3H) 7.52 (br. s., 1H) 7.54 (s, 1H) 8.44 (s, 1H) 10.04 (s, 1H).

(ESI) m/z 537 [(M+H)$^+$]. HRMS (ESI) calculated for $C_{30}H_{29}N_6O_4$ [(M+H)$^+$] 537.2245. found 537.2258.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-hydroxy-4-methoxy-phenyl)-acetamide (cmpd 143)

(ESI) m/z 523 [(M+H)$^+$]. HRMS (ESI) calculated for $C_{29}H_{27}N_6O_4$ [(M+H)$^+$] 523.2089. found 523.2084.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3,4-dichloro-phenyl)-acetamide (cmpd 144)

(ESI) m/z 545 [(M+H)$^+$]. HRMS (ESI) calculated for $C_{28}H_{23}Cl_2N_6O_2$ [(M+H)$^+$] 545.1254. found 545.1262.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-chloro-4-hydroxy-phenyl)-acetamide (cmpd 145)

(ESI) m/z 527 [(M+H)$^+$]. HRMS (ESI) calculated for $C_{28}H_{24}ClN_6O_3$ [(M+H)$^+$] 527.1593. found 527.1595.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(6-methoxy-pyridin-3-yl)-acetamide (cmpd 146)

(ESI) m/z 508 [(M+H)$^+$]. HRMS (ESI) calculated for $C_{28}H_{26}N_7O_3$ [(M+H)$^+$] 508.2092. found 508.2095.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(5-cyclopropyl-[1,3,4]thiadiazol-2-yl)-acetamide (cmpd 147)

$^1$H NMR (600 MHz, DMSO-d$_6$) δ ppm 0.82-0.94 (m, 2H) 1.01-1.08 (m, 2H) 2.22-2.32 (m, 1H) 2.89 (t, J=6.87 Hz, 2H) 3.45 (td, J=6.91, 2.47 Hz, 2H) 3.68 (s, 2H) 3.85 (s, 3H) 7.06 (s, 2H) 7.12 (br. s., 1H) 7.26-7.35 (m, 3H) 7.44 (s, 1H) 7.49 (s, 1H) 8.44 (s, 1H).

(ESI) m/z 525 [(M+H)$^+$]. HRMS (ESI) calculated for $C_{27}H_{25}N_8O_2S$ [(M+H)$^+$] 525.1816. found 525.1831.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-pyridin-4-yl-acetamide (cmpd 151)

(ESI) m/z 478 [(M+H)$^+$]. HRMS (ESI) calculated for $C_{27}H_{24}N_7O_2$ [(M+H)$^+$] 478.1986. found 478.1987.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-chloro-phenyl)-acetamide (cmpd 152)

$^1$H NMR (600 MHz, DMSO-d$_6$) δ ppm 2.90 (t, J=6.87 Hz, 2H) 3.46 (td, J=6.87, 2.56 Hz, 2H) 3.66 (s, 2H) 3.86 (s, 3H)

7.07 (s, 2H) 7.09-7.11 (m, 1H) 7.22 (br. s., 1H) 7.28-7.39 (m, 4H) 7.44-7.47 (m, 1H) 7.51 (s, 1H) 7.53 (s, 1H) 7.80 (t, J=1.92 Hz, 1H) 8.44 (s, 1H) 10.37 (s, 1H).

(ESI) m/z 511 [(M+H)+]. HRMS (ESI) calculated for $C_{28}H_{24}ClN_6O_2$ [(M+H)+] 511.1644. found 511.1642.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-chloro-4-(4-ethyl-piperazin-1-ylmethyl)-phenyl]-acetamide (cmpd 169)

$^1$H NMR (600 MHz, DMSO-$d_6$) δ ppm 0.96 (t, J=7.23 Hz, 3H) 2.23-2.46 (m, 10H) 2.90 (t, J=6.78 Hz, 2H) 3.44-3.50 (m, 4H) 3.65 (s, 2H) 3.86 (s, 3H) 7.07 (s, 2H) 7.22 (br. s., 1H) 7.30-7.38 (m, 4H) 7.43 (dd, J=8.52, 1.92 Hz, 1H) 7.51 (s, 1H) 7.53 (s, 1H) 7.79 (d, J=2.01 Hz, 1H) 8.44 (s, 1H) 10.32 (s, 1H).

(ESI) m/z 637 [(M+H)+]. HRMS (ESI) calculated for $C_{35}H_{38}ClN_8O_2$ [(M+H)+] 637.2801. found 637.2799.

Preparation 39

2-[2-Amino-5-(3-{[4-(4-propyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester

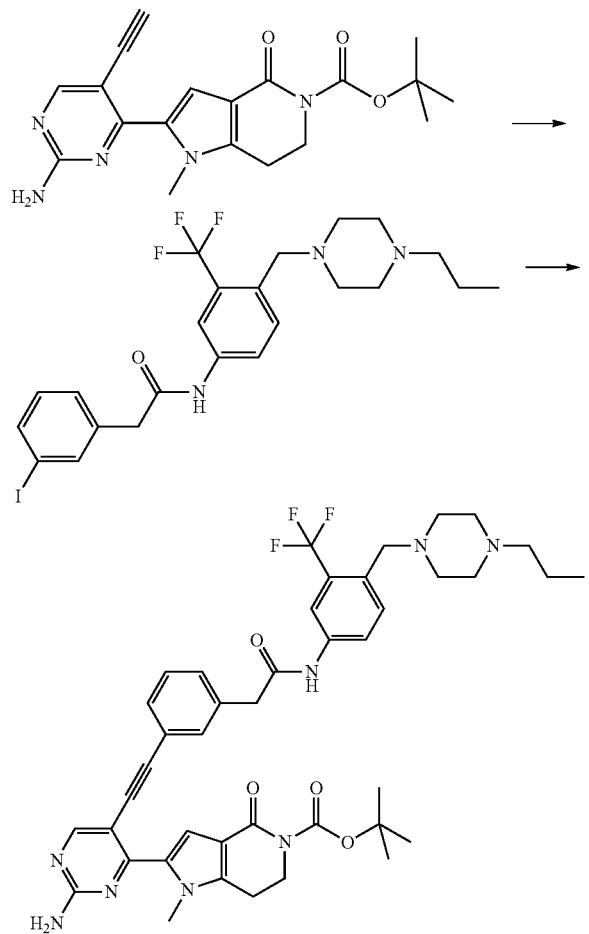

A solution of 2-(2-amino-5-ethynyl-pyrimidin-4-yl)-1-methyl-4-oxo-1,4,6,7-tetrahydro-pyrrolo[3,2-c]pyridine-5-carboxylic acid tert-butyl ester (0.10 g, 0.27 mmol), 2-(3-iodo-phenyl)-N-[4-(4-propyl-piperazin-1-ylmethyl)-3-trifluoromethyl-phenyl]-acetamide (0.14 g, 0.26 mmol), CuI (10% mol, 5 mg, 0.026 mmol), PdCl$_2$(PPh$_3$)$_2$ (10% mol, 18 mg, 0.026 mmol) and TEA (0.35 mL, 2.60 mmol) in DMF (3 mL) was degassed with argon and stirred at r.t. for 4 h. The reaction was poured in water (15 mL) and extracted with EtOAc (2×15 mL). The organic phase was washed with brine, dried with anhydrous Na$_2$SO$_4$ and evaporated under vacuum to give a crude that was purified by flash column chromatography (DCM/MeOH/NH$_3$ 90/10/0.4). The title product (0.10 g, 49%) was obtained as yellowish solid.

$^1$H NMR (600 MHz, DMSO-$d_6$) δ ppm 0.83 (t, J=7.33 Hz, 3H) 1.37-1.43 (m, 2H) 1.45 (s, 9H) 2.20 (t, J=7.05 Hz, 2H) 2.27-2.42 (m, 8H) 3.00 (t, J=6.32 Hz, 2H) 3.52 (s, 2H) 3.68 (s, 2H) 3.85 (s, 3H) 4.01 (t, J=6.32 Hz, 2H) 7.13 (s, 2H) 7.24-7.40 (m, 3H) 7.47 (s, 1H) 7.57 (s, 1H) 7.64 (d, J=8.61 Hz, 1H) 7.74-7.80 (m, 1H) 8.03 (d, J=1.83 Hz, 1H) 8.47 (s, 1H) 10.42 (s, 1H).

According to this same methodology, but employing suitable substituted derivatives, the following intermediates were prepared:

2-[2-Amino-5-(3-{[4-(4-ethyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 0.97 (t, J=7.14 Hz, 4H) 1.44 (s, 11H) 3.00 (t, J=6.32 Hz, 2H) 3.52 (s, 2H) 3.68 (s, 2H) 3.85 (s, 3H) 4.01 (t, J=6.23 Hz, 2H) 7.13 (s, 2H) 7.31-7.40 (m, 4H) 7.47 (s, 1H) 7.57 (s, 1H) 7.64 (d, J=8.61 Hz, 1H) 7.77 (d, J=8.06 Hz, 1H) 8.03 (d, J=1.65 Hz, 1H) 8.47 (s, 1H) 10.42 (s, 1H).

2-[2-(Acetyl-methyl-amino)-5-(3-{[4-(4-ethyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 0.97 (t, J=7.14 Hz, 3H) 1.45 (s, 9H) 2.29 (q, J=7.27 Hz, 3H) 2.31-2.39 (m, 5H) 2.42 (s, 3H) 3.03 (t, J=6.23 Hz, 2H) 3.39-3.43 (m, 3H) 3.52 (s, 2H) 3.71 (s, 2H) 3.86 (s, 3H) 3.99-4.06 (m, 2H) 7.34-7.48 (m, 3H) 7.56 (s, 1H) 7.65 (d, J=8.43 Hz, 1H) 7.75 (s, 1H) 7.77 (d, J=6.78 Hz, 1H) 8.04 (d, J=1.65 Hz, 1H) 8.92 (s, 1H) 10.44 (s, 1H).

2-[2-Amino-5-(3-{[4-(4-ethyl-piperazin-1-ylmethyl)-3-fluoro-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 0.95 (t, J=7.14 Hz, 3H) 1.45 (s, 9H) 2.19-2.43 (m, 11H) 3.00 (t, J=6.32 Hz, 2H) 3.66 (s, 2H) 3.84 (s, 3H) 4.01 (t, J=6.23 Hz, 2H) 7.13 (s, 2H) 7.23-7.30 (m, 2H) 7.31-7.39 (m, 3H) 7.46 (s, 1H) 7.54 (dd, J=12.36, 1.56 Hz, 1H) 7.55-7.57 (m, 1H) 7.70-7.77 (m, 2H) 8.47 (s, 1H) 10.32 (s, 1H).

2-[2-Amino-5-(3-{[4-(2-dimethylamino-ethylcarbamoyl)-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 1.45 (s, 9H) 2.19 (br. s., 6H) 2.41 (br. s., 2H) 3.00 (t, J=6.32 Hz, 2H) 3.69 (s, 2H) 3.85 (s, 3H) 4.01 (t, J=6.32 Hz, 2H) 7.13 (s, 2H) 7.30-7.41 (m, 3H) 7.47 (s, 1H) 7.57 (s, 1H) 7.65 (d, J=8.79 Hz, 2H) 7.78 (d, J=8.61 Hz, 2H) 8.24 (t, J=5.40 Hz, 1H) 8.47 (s, 1H) 10.35 (s, 1H).

2-[2-Amino-5-(4-{[4-(4-ethyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 0.97 (t, J=7.23 Hz, 3H) 1.45 (s, 10H) 2.18-2.47 (m, 10H) 2.98 (t, J=6.23 Hz, 2H) 3.52 (s, 2H) 3.69 (s, 2H) 3.84 (s, 3H) 3.99 (t, J=6.23 Hz, 2H) 7.11 (s, 2H) 7.36 (d, J=8.24 Hz, 2H) 7.41-7.45 (m, 2H) 7.55 (s, 1H) 7.65 (d, J=8.61 Hz, 1H) 7.77 (d, J=8.61 Hz, 1H) 8.04 (d, J=1.83 Hz, 1H) 8.46 (s, 1H) 10.47 (s, 1H).

2-[2-Amino-5-(3-{[2-(4-ethyl-piperazin-1-ylmethyl)-5-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 771 [(M+H)$^+$]. HRMS (ESI) calculated for $C_{41}H_{46}F_3N_8O_4^+$ [(M+H)$^+$] 771.8424. found 771.8422.

2-[2-Amino-5-(3-{[4-chloro-3-(4-ethyl-piperazine-1-carbonyl)-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 752 [(M+H)$^+$]. HRMS (ESI) calculated for $C_{40}H_{44}ClN_8O_5^+$ [(M+H)$^+$] 752.2730. found 752.2731.

2-[2-Amino-5-(3-{[3-(4-ethyl-piperazine-1-carbonyl)-4-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 785 [(M+H)$^+$]. HRMS (ESI) calculated for $C_{41}H_{44}F_3N_8O_5^+$ [(M+H)$^+$] 785.8259. found 785.8261.

2-[2-Amino-5-(3-{[4-(4-methyl-[1,4]diazepan-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 1.45 (s, 9H) 1.71 (quin, J=5.82 Hz, 2H) 2.27 (br. s., 3H) 2.53-2.67 (m, 8H) 3.00 (t, J=6.32 Hz, 2H) 3.67 (d, J=7.88 Hz, 4H) 3.85 (s, 3H) 4.01 (t, J=6.32 Hz, 2H) 7.13 (s, 2H) 7.26-7.41 (m, 3H) 7.47 (s, 1H) 7.57 (s, 1H) 7.70 (d, J=8.61 Hz, 1H) 7.77 (dd, J=8.61, 1.65 Hz, 1H) 8.02 (d, J=1.83 Hz, 1H) 8.47 (s, 1H) 10.41 (s, 1H).

2-[2-Amino-5-(3-{[4-((S)-3-dimethylamino-pyrrolidin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 1.43-1.46 (m, 9H) 1.61 (dd, J=12.64, 8.24 Hz, 1H) 1.84 (dd, J=13.28, 5.04 Hz, 1H) 2.05-2.11 (m, 6H) 2.29-2.34 (m, 1H) 2.43-2.48 (m, 1H) 2.53-2.58 (m, 1H) 2.59-2.64 (m, 1H) 2.73 (d, J=0.55 Hz, 1H) 3.00 (t, J=6.32 Hz, 2H) 3.54-3.70 (m, 4H) 3.85 (s, 3H) 4.01 (t, J=6.32 Hz, 2H) 7.13 (s, 2H) 7.31-7.40 (m, 3H) 7.47 (s, 1H) 7.57 (s, 1H) 7.63 (d, J=8.61 Hz, 1H) 7.77 (dd, J=8.52, 1.74 Hz, 1H) 8.02 (d, J=2.01 Hz, 1H) 8.47 (s, 1H) 10.41 (s, 1H).

2-[2-Amino-5-(3-{[4-(4-ethyl-piperazine-1-carbonyl)-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 0.99 (t, J=7.14 Hz, 3H) 1.46 (s, 9H) 2.25-2.44 (m, 6H) 3.00 (t, J=6.32 Hz, 2H) 3.33-3.64 (m, 4H) 3.68 (s, 2H) 3.85 (s, 3H) 4.01 (t, J=6.32 Hz, 2H) 7.13 (s, 2H) 7.31-7.34 (m, 2H) 7.35-7.40 (m, 2H) 7.47 (s, 1H) 7.56 (s, 1H) 7.64 (d, J=8.61 Hz, 2H) 8.47 (s, 1H) 10.31 (s, 1H).

2-[2-Amino-5-(3-{[3-cyclopropyl-4-(4-methyl-piperazin-1-ylmethyl)-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 0.46-0.58 (m, 2H) 0.84-0.94 (m, 2H) 1.45 (s, 9H) 2.10-2.18 (m, 4H) 2.21-2.48 (m, 7H) 3.00 (t, J=6.32 Hz, 2H) 3.51 (s, 2H) 3.62 (s, 2H) 3.85 (s, 2H) 4.01 (t, J=6.32 Hz, 2H) 7.08-7.18 (m, 4H) 7.29-7.39 (m, 4H) 7.46 (s, 1H) 7.57 (s, 1H) 8.47 (s, 1H) 10.01 (s, 1H).

2-[2-Amino-5-(3-{[4-((R)-3-dimethylamino-pyrrolidin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 1.43-1.47 (m, 10H) 1.56-1.68 (m, 1H) 1.77-1.88 (m, 1H) 2.07 (s, 6H) 2.32 (d, J=7.51 Hz, 1H) 2.46 (d, J=5.68 Hz, 1H) 2.52-2.59 (m, 1H) 2.60-2.64 (m, 1H) 2.73 (s, 1H) 3.00 (t, J=6.23 Hz, 2H) 3.56-3.67 (m, 2H) 3.68 (s, 2H) 3.85 (s, 3H) 4.01 (t, J=6.32 Hz, 2H) 7.13 (s, 2H) 7.32-7.41 (m, 3H) 7.47 (s, 1H) 7.57 (s, 1H) 7.63 (d, J=8.43 Hz, 1H) 7.77 (dd, J=8.52, 1.56 Hz, 1H) 8.02 (d, J=2.01 Hz, 1H) 8.47 (s, 1H) 10.41 (s, 1H).

2-[2-Amino-5-(3-{[4-(4-isopropyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 0.95 (d, J=5.49 Hz, 6H) 2.27-2.47 (m, 8H) 2.56-2.64 (m, 1H) 3.00 (t, J=6.32 Hz, 2H) 3.51 (br. s., 2H) 3.68 (s, 2H) 3.85 (s, 2H) 4.01 (t, J=6.32 Hz, 2H) 7.11-7.15 (m, 2H) 7.32-7.40 (m, 3H) 7.47 (s, 1H) 7.57 (s, 1H) 7.61-7.69 (m, 1H) 7.77 (d, J=8.24 Hz, 1H) 8.03 (d, J=1.83 Hz, 1H) 8.47 (s, 1H) 10.42 (s, 1H).

2-(2-Amino-5-{3-[(4-piperidin-1-ylmethyl-3-trifluoromethyl-phenylcarbamoyl)-methyl]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.44 (s, 10H) 1.46-1.54 (m, 4H) 2.31 (br. s., 4H) 3.00 (t, J=6.41 Hz, 2H) 3.48 (s, 2H) 3.68 (s, 2H) 3.85 (s, 3H) 4.01 (t, J=6.32 Hz, 2H) 7.13 (s, 2H) 7.29-7.39 (m, 3H) 7.47 (s, 1H) 7.57 (s, 1H) 7.66 (d, J=8.61 Hz, 1H) 7.76 (dd, J=8.70, 1.56 Hz, 1H) 8.03 (d, J=1.83 Hz, 1H) 8.47 (s, 1H) 10.41 (s, 1H).

2-(2-Amino-5-{3-[(4-morpholin-4-ylmethyl-3-trifluoromethyl-phenylcarbamoyl)-methyl]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.45 (s, 10H) 2.35 (br. s., 4H) 3.00 (t, J=6.32 Hz, 2H) 3.53 (s, 2H) 3.57 (t, J=4.40 Hz, 4H) 3.68 (s, 2H) 3.85 (s, 3H) 4.01 (t, J=6.32 Hz, 2H) 7.13 (s, 2H) 7.32-7.39 (m, 3H) 7.47 (s, 1H) 7.57 (s, 1H) 7.67 (d, J=8.43 Hz, 1H) 7.78 (dd, J=8.61, 1.83 Hz, 1H) 8.04 (d, J=2.02 Hz, 1H) 8.47 (s, 1H) 10.43 (s, 1H).

2-[2-Amino-5-(3-{[4-(4-methyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 757 [(M+H)$^+$]. HRMS (ESI) calculated for C$_{40}$H$_{44}$F$_3$N$_8$O$_4$$^+$ [(M+H)$^+$] 757.8158. found 757.8154.

2-[2-Amino-5-(3-{[4-(3-pyrrolidin-1-yl-azetidin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.45 (s, 9H) 1.60-1.71 (m, 4H) 2.34 (br. s., 4H) 2.91 (t, J=6.59 Hz, 2H) 3.00 (t, J=6.32 Hz, 2H) 3.03 (m, J=6.23 Hz, 1H) 3.33-3.37 (m, 2H) 3.65 (s, 2H) 3.68 (s, 2H) 3.85 (s, 3H) 4.01 (t, J=6.32 Hz, 2H) 7.13 (s, 2H) 7.30-7.40 (m, 3H) 7.47 (s, 1H) 7.54-7.62 (m, 2H) 7.76 (dd, J=8.70, 1.56 Hz, 1H) 8.01 (d, J=2.01 Hz, 1H) 8.47 (s, 1H) 10.40 (s, 1H).

2-[2-Amino-5-(3-{[4-(4-ethyl-piperazine-1-carbonyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.98 (t, J=7.14 Hz, 3H) 1.45 (s, 10H) 2.13-2.45 (m, 2H) 2.32 (q, J=7.20 Hz, 3H) 3.00 (t, J=6.41 Hz, 2H) 3.02-3.13 (m, 2H) 3.52-3.65 (m, 2H) 3.71 (s, 2H) 3.85 (s, 3H) 4.01 (t, J=6.32 Hz, 2H) 7.13 (s, 2H) 7.26 (br. s., 1H) 7.32-7.41 (m, 5H) 7.48 (s, 1H) 7.57 (s, 1H) 7.84 (dd, J=8.33, 1.56 Hz, 1H) 8.11 (d, J=1.83 Hz, 1H) 8.47 (s, 1H) 10.58 (s, 1H).

2-(2-Amino-5-{3-[(4-{[methyl-(1-methyl-piperidin-4-yl)-amino]-methyl}-3-trifluoromethyl-phenylcarbamoyl)-methyl]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.41-1.45 (m, 8H) 1.51 (d, J=9.34 Hz, 2H) 1.67 (d, J=11.54 Hz, 2H) 1.75-1.96 (m, 2H) 2.09 (s, 3H) 2.15 (br. s., 3H) 2.34 (br. s., 1H) 2.81 (br. s., 2H) 3.00 (t, J=6.32 Hz, 2H) 3.62 (s, 2H) 3.68 (s, 2H) 3.85 (s, 3H) 4.01 (t, J=6.41 Hz, 2H) 7.13 (s, 2H) 7.31-7.39 (m, 3H) 7.47 (s, 1H) 7.57 (s, 1H) 7.68 (d, J=8.42 Hz, 1H) 7.76 (dd, J=8.43, 1.65 Hz, 1H) 8.02 (d, J=2.01 Hz, 1H) 8.47 (s, 1H) 10.41 (s, 1H).

2-[2-Amino-5-(3-{[4-(4-dimethylamino-piperidin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.38 (d, J=8.97 Hz, 2H) 1.44 (s, 9H) 1.70 (d, J=11.72 Hz, 2H) 1.95 (t, J=10.81 Hz, 2H) 1.99-2.24 (m, 7H) 2.78 (d, J=11.17 Hz, 2H) 3.00 (t, J=6.23 Hz, 2H) 3.50 (s, 2H) 3.68 (s, 2H) 3.85 (s, 3H) 4.01 (t, J=6.32 Hz, 2H) 7.13 (s, 2H) 7.30-7.40 (m, 3H) 7.47 (s, 1H) 7.57 (s, 1H) 7.66 (d, J=8.61 Hz, 1H) 7.75-7.79 (m, 1H) 8.03 (d, J=2.01 Hz, 1H) 8.47 (s, 1H) 10.42 (s, 1H).

2-[2-Amino-5-(3-{[3-bromo-4-(4-ethyl-piperazin-1-ylmethyl)-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 782 [(M+H)$^+$]. HRMS (ESI) calculated for C$_{40}$H$_{46}$BrN$_8$O$_4$$^+$ [(M+H)$^+$] 782.7405. found 782.7408.

2-{5-[3-({4-[4-(2-Acetoxy-ethyl)-piperazin-1-ylmethyl]-3-trifluoromethyl-phenylcarbamoyl}-methyl)-phenylethynyl]-2-amino-pyrimidin-4-yl}-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.44 (s, 9H) 1.99 (s, 3H) 2.28-2.48 (m, 8H) 3.00 (t, J=6.23 Hz, 2H) 3.52 (s, 2H) 3.68 (s, 2H) 3.85 (s, 3H) 4.01 (t, J=6.32 Hz, 2H) 4.08 (t, J=5.86 Hz, 2H) 7.13 (s, 2H) 7.29-7.40 (m, 3H) 7.47 (s, 1H) 7.57 (s, 1H) 7.64 (d, J=8.61 Hz, 1H) 7.77 (dd, J=8.70, 1.74 Hz, 1H) 7.95 (s, 1H) 8.03 (d, J=1.83 Hz, 1H) 8.47 (s, 1H) 10.42 (s, 1H).

2-[2-Amino-5-(3-{[4-(4-cyclopropylmethyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.05 (br. s., 2H) 0.44 (d, J=4.21 Hz, 2H) 0.80 (br. s., 1H) 1.44 (s, 9H) 2.16 (br. s., 2H) 2.19-2.47 (m, 9H) 3.00 (t, J=6.23 Hz, 2H) 3.53 (br. s., 2H) 3.68 (s, 2H) 3.85 (s, 3H) 3.98-4.03 (m, 2H) 7.12-7.14 (m, 2H) 7.30-7.39 (m, 4H) 7.47 (s, 1H) 7.57 (s, 1H) 7.62-7.67 (m, 1H) 7.77 (d, J=7.88 Hz, 1H) 8.03 (d, J=1.47 Hz, 1H) 8.47 (s, 1H) 10.42 (s, 1H).

2-[2-Amino-5-(3-{[4-(1-methyl-piperidin-4-yloxy)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.42 (s, 9H) 1.63 (d, J=8.24 Hz, 2H) 1.80-1.91 (m, 2H) 2.14 (br. s., 3H) 2.20 (br. s., 2H) 2.97 (t, J=6.23 Hz, 2H) 3.61 (s, 2H) 3.82 (s, 3H) 3.98 (t, J=6.32 Hz, 2H) 4.50 (br. s., 1H) 7.10 (s, 2H) 7.22 (d, J=9.16 Hz, 1H) 7.28-7.38 (m, 3H) 7.44 (s, 1H) 7.54 (s, 1H) 7.69 (dd, J=8.97, 2.38 Hz, 1H) 7.89 (d, J=2.56 Hz, 1H) 8.44 (s, 1H) 10.21 (s, 1H).

2-[2-Amino-5-(3-{[4-(4-ethyl-piperazin-1-yl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.01 (t, J=7.23 Hz, 3H) 1.45 (s, 9H) 2.26-2.49 (m, 9H) 2.81 (t, J=4.40 Hz, 4H) 3.00 (t, J=6.23 Hz, 2H) 3.67 (s, 2H) 3.85 (s, 3H) 4.01 (t, J=6.32 Hz, 2H) 7.13 (s, 2H) 7.31-7.39 (m, 3H) 7.46 (s, 1H) 7.50-7.53 (m, 1H) 7.57 (s, 1H) 7.77 (dd, J=8.70, 2.11 Hz, 1H) 7.98 (d, J=2.38 Hz, 1H) 8.47 (s, 1H) 10.34-10.38 (m, 1H).

2-[2-(Acetyl-methyl-amino)-5-(3-{[4-(4-methyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 813 [(M+H)$^+$]. HRMS (ESI) calculated for C$_{43}$H$_{48}$F$_3$N$_8$O$_5$$^+$ [(M+H)$^+$] 813.8791. found 813.8788.

2-[2-(Acetyl-methyl-amino)-5-(3-{[4-(4-cyclopropyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 839 [(M+H)$^+$]. HRMS (ESI) calculated for C$_{45}$H$_{50}$F$_3$N$_8$O$_5$$^+$ [(M+H)$^+$] 839.9164. found 839.9167.

2-[2-(Acetyl-methyl-amino)-5-(3-{[4-(4-isopropyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 841 [(M+H)$^+$]. HRMS (ESI) calculated for C$_{45}$H$_{52}$F$_3$N$_8$O$_5$$^+$ [(M+H)$^+$] 841.9322. found 841.9319.

2-[2-Amino-5-(3-{[4-(1-methyl-piperidin-4-ylamino)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.45 (s, 9H) 1.47-1.52 (m, 2H) 1.86 (d, J=11.54 Hz, 3H) 2.06 (d, J=10.26 Hz, 3H) 2.16 (s, 4H) 2.65 (br. s., 2H) 3.00 (t, J=6.41 Hz, 2H) 3.60 (s, 2H) 3.85 (s, 3H) 4.01 (t, J=6.32 Hz, 2H) 4.36 (d, J=7.69 Hz, 1H) 7.25-7.39 (m, 4H) 7.46 (s, 1H) 7.51-7.58 (m, 2H) 7.78 (d, J=2.01 Hz, 1H) 8.47 (s, 1H) 10.03 (s, 1H).

2-{2-Amino-5-[3-({4-[methyl-(1-methyl-piperidin-4-yl)-amino]-3-trifluoromethyl-phenylcarbamoyl}-methyl)-phenylethynyl]-pyrimidin-4-yl}-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.29-1.39 (m, 2H) 1.45 (s, 9H) 1.62 (d, J=12.45 Hz, 2H) 1.78 (br. s., 2H) 2.10 (s, 3H) 2.62-2.79 (m, 3H) 3.00 (t, J=6.23 Hz, 2H) 3.67 (s, 2H) 3.85 (s, 3H) 4.01 (t, J=6.32 Hz, 2H) 7.13 (s, 2H) 7.31-7.40 (m, 3H) 7.47 (s, 1H) 7.49-7.52 (m, 1H) 7.57 (s, 1H) 7.78 (dd, J=8.88, 2.11 Hz, 1H) 7.96 (d, J=2.38 Hz, 1H) 8.47 (s, 1H) 10.36 (s, 1H).

2-[2-(Acetyl-methyl-amino)-5-(3-{[4-(4-propyl-piperazin-1-ylmethyl)-3-trifluoromethyl-phenylcarbamoyl]-methyl}-phenylethynyl)-pyrimidin-4-yl]-1-methyl-oxo-1,4,6,7-tetrahydro-pyrrolo[3,2-c]pyridine-5-carboxylic acid tert-butyl ester (ESI) m/z 841 [(M+H)$^+$]. HRMS (ESI) calculated for C$_{45}$H$_{52}$F$_3$N$_8$O$_5$$^+$ [(M+H)$^+$] 841.9322. found 841.9315.

2-[2-Amino-5-(3-{[3-trifluoromethyl-4-((2S,5R)-2,4,5-trimethyl-piperazin-1-ylmethyl)-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.83 (d, J=6.23 Hz, 3H) 0.99 (d, J=6.04 Hz, 3H) 1.43 (br. s., 9H) 1.75 (t, J=10.71 Hz, 1H) 1.89 (d, J=10.44 Hz, 3H) 2.11 (br. s., 4H) 2.31-2.44 (m, 3H) 2.66 (d, J=10.44 Hz, 1H) 3.00 (t, J=6.32 Hz, 2H) 3.09 (d, J=14.65 Hz, 1H) 3.68 (s, 2H) 3.85 (s, 3H) 3.99-4.02 (m, 2H) 4.05 (s, 1H) 7.13 (s, 2H) 7.31-7.40 (m, 4H) 7.47 (s, 1H) 7.57 (s, 1H) 7.69-7.72 (m, 1H) 7.75-7.77 (m, 1H) 8.03 (d, J=1.83 Hz, 1H) 8.47 (s, 1H) 10.41 (s, 1H).

2-[2-Amino-5-(3-{[3-trifluoromethyl-4-(3,4,5-trimethyl-piperazin-1-ylmethyl)-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 785 [(M+H)$^+$]. HRMS (ESI) calculated for C$_{42}$H$_{48}$F$_3$N$_8$O$_4$$^+$ [(M+H)$^+$] 785.8690. found 785.8688.

2-[2-Amino-5-(3-{[4-(4-tert-butoxycarbonyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.38 (s, 9H) 1.43-1.46 (m, 9H) 2.31 (t, J=4.85 Hz, 5H) 3.00 (t, J=6.23 Hz, 2H) 3.55 (s, 2H) 3.68 (s, 2H) 3.85 (s, 3H) 4.01 (t, J=6.23 Hz, 2H) 7.13 (s, 2H) 7.32-7.40 (m, 4H) 7.47 (s, 1H) 7.53-7.55 (m, 1H) 7.57 (s, 1H) 7.60-7.65 (m, 1H) 7.66 (d, J=8.43 Hz, 1H) 7.78 (dd, J=8.42, 1.83 Hz, 1H) 8.04 (d, J=2.01 Hz, 1H) 8.47 (s, 1H) 10.43 (s, 1H).

2-[2-Amino-5-(3-{[4-(3-oxo-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester ¹H NMR (600 MHz, DMSO-d₆) δ ppm 1.44 (s, 9H) 2.51-2.55 (m, 3H) 2.93 (s, 2H) 3.00 (t, J=6.41 Hz, 2H) 3.13 (br. s., 2H) 3.61 (s, 2H) 3.68 (s, 2H) 3.85 (s, 3H) 4.01 (t, J=6.23 Hz, 2H) 7.13 (s, 2H) 7.31-7.39 (m, 3H) 7.47 (s, 1H) 7.57 (s, 1H) 7.66 (d, J=8.61 Hz, 1H) 7.74 (s, 1H) 7.79 (dd, J=8.43, 1.83 Hz, 1H) 8.05 (d, J=2.01 Hz, 1H) 8.47 (s, 1H) 10.45 (s, 1H).

2-{2-Amino-5-[3-({4-[3-(tert-butyl-dimethyl-silanyloxy)-piperidin-1-ylmethyl]-3-trifluoromethyl-phenylcarbamoyl}-methyl)-phenylethynyl]-pyrimidin-4-yl}-1-methyl-4-oxo-1,4,6,7-tetrahydro-pyrrolo[3,2-c]pyridine-5-carboxylic acid tert-butyl ester (ESI) m/z 873 [(M+H)⁺]. HRMS (ESI) calculated for C₄₆H₅₇F₃N₇O₅Si⁺ [(M+H)⁺] 873.0614. found 873.0611.

2-[2-Amino-5-(3-cyclopropylcarbamoylmethyl-phenylethynyl)-pyrimidin-4-yl]-1-methyl-4-oxo-1,4,6,7-tetrahydro-pyrrolo[3,2-c]pyridine-5-carboxylic acid tert-butyl ester ¹H NMR (600 MHz, DMSO-d₆) δ ppm 0.36-0.41 (m, 2H) 0.57-0.61 (m, 2H) 1.47 (s, 9H) 2.60-2.63 (m, 1H) 3.00 (t, J=6.32 Hz, 2H) 3.34-3.36 (m, 2H) 3.85 (s, 3H) 4.01 (t, J=6.32 Hz, 2H) 7.13 (s, 2H) 7.24 (d, J=6.96 Hz, 1H) 7.29-7.35 (m, 2H) 7.37 (s, 1H) 7.55 (s, 1H) 8.09 (d, J=3.85 Hz, 1H) 8.47 (s, 1H).

2-[2-Amino-5-(3-{[4-(4-methyl-2-oxo-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester ¹H NMR (600 MHz, DMSO-d₆) δ ppm 1.44 (s, 10H) 2.23 (s, 4H) 2.55-2.64 (m, 3H) 3.00 (t, J=6.32 Hz, 2H) 3.06 (s, 2H) 3.18 (t, J=5.31 Hz, 2H) 3.69 (s, 2H) 3.85 (s, 3H) 4.01 (t, J=6.32 Hz, 2H) 4.62 (s, 2H) 7.13 (s, 2H) 7.24 (d, J=8.79 Hz, 1H) 7.31-7.40 (m, 4H) 7.47 (s, 1H) 7.57 (s, 1H) 7.75-7.79 (m, 1H) 7.95 (s, 1H) 8.11 (d, J=1.83 Hz, 1H) 8.47 (s, 1H) 10.48 (s, 1H).

2-{2-Amino-5-[3-({4-[4-(tert-butyl-dimethyl-silanyloxy)-piperidin-1-ylmethyl]-3-trifluoromethyl-phenylcarbamoyl}-methyl)-phenylethynyl]-pyrimidin-4-yl}-1-methyl-4-oxo-1,4,6,7-tetrahydro-pyrrolo[3,2-c]pyridine-5-carboxylic acid tert-butyl ester ¹H NMR (600 MHz, DMSO-d₆) δ ppm 0.03 (s, 6H) 1.39-1.48 (m, 11H) 1.68 (br. s., 2H) 2.14 (t, J=8.70 Hz, 2H) 3.68 (s, 2H) 3.72 (br. s., 1H) 3.85 (s, 3H) 4.01 (t, J=6.23 Hz, 2H) 7.13 (s, 2H) 7.31-7.39 (m, 3H) 7.47 (s, 1H) 7.52-7.58 (m, 2H) 7.66 (d, J=8.61 Hz, 1H) 7.76 (d, J=8.97 Hz, 1H) 8.02 (s, 1H) 8.47 (s, 1H) 10.41 (s, 1H).

tert-Butyl 2-(2-amino-5-{[3-(2-{[4-{[(2-{[tert-butyl(dimethyl)silyl]oxy}ethyl)(methyl)amino]methyl}-3-(trifluoromethyl)phenyl]amino}-2-oxoethyl)phenyl]ethynyl}pyrimidin-4-yl)-1-methyl-4-oxo-1,4,6,7-tetrahydro-5H-pyrrolo[3,2-c]pyridine-5-carboxylate ¹H NMR (600 MHz, DMSO-d₆) δ ppm −0.01-0.01 (m, 7H) 0.83 (s, 10H) 1.44 (s, 9H) 2.19 (s, 4H) 3.00 (t, J=6.32 Hz, 2H) 3.61 (s, 2H) 3.65-3.72 (m, 5H) 3.85 (s, 3H) 4.01 (t, J=6.32 Hz, 2H) 7.11-7.14 (m, 2H) 7.27-7.40 (m, 4H) 7.47 (s, 1H) 7.57 (s, 2H) 7.59-7.64 (m, 1H) 7.69-7.74 (m, 1H) 7.74-7.78 (m, 1H) 8.02 (d, J=2.01 Hz, 1H) 8.47 (s, 1H) 10.40 (s, 1H).

2-[2-(Acetyl-methyl-amino)-5-(2-fluoro-5-{[4-(4-methyl-piperazin-1-ylmethyl)-3-trifluoromethyl-phenyl carbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 831 [(M+H)⁺]. HRMS (ESI) calculated for C₄₃H₄₇F₄N₈O₅⁺ [(M+H)⁺] 831.8696. found 831.8690.

2-[2-Amino-5-(3-{[4-(4-ethyl-piperazin-1-ylmethyl)-3-trifluoromethyl-phenylcarbamoyl]-methyl}-phenylethynyl)-pyrimidin-4-yl]-4-oxo-1-[2-(tetrahydro-pyran-2-yloxy)-ethyl]-1,4,6,7-tetrahydro-pyrrolo[3,2-c]pyridine-5-carboxylic acid tert-butyl ester (ESI) m/z 885 [(M+H)⁺]. HRMS (ESI) calculated for C₄₇H₅₆F₃N₈O₆⁺ [(M+H)⁺] 885.9848. found 885.9845.

2-(2-Amino-5-{3-[(4-{[(2,2-dimethyl-[1,3]dioxolan-4-ylmethyl)-methyl-amino]-methyl}-3-trifluoromethyl-phenylcarbamoyl)-methyl]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 802 [(M+H)⁺]. HRMS (ESI) calculated for C₄₂H₄₇F₃N₇O₆⁺ [(M+H)⁺] 802.8531. found 802.8532.

2-[2-(Acetyl-ethyl-amino)-5-(3-{[4-(4-methyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 827 [(M+H)⁺]. HRMS (ESI) calculated for C₄₄H₅₀F₃N₈O₅⁺ [(M+H)⁺] 827.9057. found 827.9060.

2-[2-(Acetyl-methyl-amino)-5-(3-{[4-(4-cyclopropylmethyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester ¹H NMR (600 MHz, DMSO-d₆) δ ppm 0.06 (br. s., 2H) 0.44 (d, J=6.59 Hz, 2H) 0.80 (br. s., 1H) 2.06-2.24 (m, 2H) 2.26-2.48 (m, 9H) 2.93 (t, J=6.87 Hz, 2H) 3.41 (s, 3H) 3.48 (td, J=6.73, 2.29 Hz, 2H) 3.53 (s, 2H) 3.71 (s, 2H) 3.87 (s, 3H) 7.29 (br. s., 1H) 7.40-7.48 (m, 3H) 7.60 (s, 1H) 7.65 (d, J=8.42 Hz, 1H) 7.72 (s, 1H) 7.78 (d, J=8.06 Hz, 1H) 8.05 (d, J=1.65 Hz, 1H) 8.87 (s, 1H) 10.48 (s, 1H).

2-[2-(Acetyl-methyl-amino)-5-(3-{[4-((S)-3-dimethylamino-pyrrolidin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 827 [(M+H)⁺]. HRMS (ESI) calculated for C₄₄H₅₀F₃N₈O₅⁺ [(M+H)⁺] 827.9057. found 827.9054.

2-(2-Amino-5-{5-[4-(4-ethyl-piperazin-1-ylmethyl)-3-trifluoromethyl-phenylcarbamoyl]-2-methyl-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.98 (t, J=7.14 Hz, 3H) 1.41 (s, 9H) 2.30 (q, J=7.14 Hz, 2H) 2.48 (br. s., 3H) 2.99 (t, J=6.31 Hz, 2H) 3.56 (s, 3H) 3.84 (s, 3H) 3.96-4.00 (m, 2H) 7.23 (s, 2H) 7.48 (d, J=8.24 Hz, 1H) 7.55 (s, 1H) 7.70 (d, J=8.51 Hz, 1H) 7.86 (dd, J=7.96, 1.65 Hz, 1H) 8.00-8.06 (m, 2H) 8.21 (d, J=1.92 Hz, 1H) 8.50-8.61 (m, 2H) 10.52 (s, 1H).

2-[2-Acetylamino-5-(3-{[4-(4-methyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.45 (s, 9H) 2.19 (s, 5H) 2.22-2.47 (m, 7H) 3.03 (t, J=6.32 Hz, 2H) 3.53 (s, 2H) 3.71 (s, 2H) 3.97 (s, 3H) 4.02 (t, J=6.32 Hz, 2H) 7.37-7.46 (m, 3H) 7.55 (s, 1H) 7.64 (d, J=8.61 Hz, 1H) 7.74-7.79 (m, 2H) 8.03 (d, J=1.83 Hz, 1H) 8.82 (s, 1H) 10.44 (s, 1H) 10.80 (s, 1H).

2-[2-Amino-5-(3-{[4-chloro-3-(4-ethyl-piperazin-1-ylmethyl)-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 738 [(M+H)$^+$]. HRMS (ESI) calculated for C$_{40}$H$_{46}$ClN$_8$O$_4$$^+$ [(M+H)$^+$] 738.2895. found 738.2898.

2-(2-Amino-5-{3-[(5-bromo-pyridin-3-ylcarbamoyl)-methyl]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.45 (s, 9H) 3.00 (t, J=6.32 Hz, 2H) 3.72 (s, 2H) 3.85 (s, 3H) 4.02 (quin, J=6.87 Hz, 4H) 7.13 (s, 2H) 7.32-7.40 (m, 3H) 7.47 (s, 1H) 7.56 (s, 1H) 8.36-8.39 (m, 2H) 8.47 (s, 1H) 8.66 (d, J=2.01 Hz, 1H) 10.56 (s, 1H)

2-(2-Amino-5-{1-[4-(4-ethyl-piperazin-1-ylmethyl)-3-trifluoromethyl-phenylcarbamoyl]-2,3-dihydro-1H-indol-6-ylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.98 (t, J=7.14 Hz, 3H) 1.45 (s, 10H) 2.29-2.32 (m, 2H) 2.33-2.48 (m, 7H) 2.99 (t, J=6.32 Hz, 2H) 3.21 (t, J=8.61 Hz, 1H) 3.54 (s, 2H) 3.84 (s, 2H) 3.97-4.01 (m, 2H) 4.17 (t, J=8.79 Hz, 2H) 7.04 (dd, J=7.60, 1.37 Hz, 1H) 7.09 (s, 1H) 7.24 (d, J=7.69 Hz, 1H) 7.47 (s, 1H) 7.64 (d, J=8.61 Hz, 1H) 7.83 (dd, J=8.42, 1.83 Hz, 1H) 7.94 (d, J=0.92 Hz, 1H) 7.98 (d, J=2.02 Hz, 1H) 8.47-8.51 (m, 1H) 8.84 (s, 1H).

2-(2-Amino-5-{1-[4-(4-ethyl-piperazin-1-ylmethyl)-3-trifluoromethyl-phenylcarbamoyl]-2,3-dihydro-1H-indol-5-ylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (500 MHz, DMSO-d$_6$) δ ppm 1.02-1.17 (m, 3H) 1.44-1.50 (m, 10H) 2.99 (t, J=6.33 Hz, 2H) 3.20 (t, J=8.39 Hz, 2H) 3.58 (br. s., 2H) 3.84 (s, 3H) 4.00 (t, J=6.33 Hz, 2H) 4.17 (t, J=8.77 Hz, 2H) 7.09 (s, 2H) 7.23-7.29 (m, 1H) 7.32 (s, 1H) 7.56 (s, 1H) 7.64 (d, J=8.69 Hz, 1H) 7.83-7.90 (m, 2H) 7.99 (d, J=2.14 Hz, 1H) 8.43 (s, 1H) 8.92 (s, 1H).

2-(2-(Acetyl-methyl-amino)-5-{1-[4-(4-ethyl-piperazin-1-ylmethyl)-3-trifluoromethyl-phenylcarbamoyl]-2,3-dihydro-1H-indol-6-ylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.98 (t, J=7.14 Hz, 3H) 1.45 (s, 9H) 2.31 (q, J=7.14 Hz, 2H) 2.38 (br. s., 8H) 2.41 (s, 3H) 3.03 (t, J=6.23 Hz, 2H) 3.24 (t, J=8.61 Hz, 2H) 3.40 (s, 3H) 3.54 (s, 2H) 3.85 (s, 3H) 4.02 (t, J=6.32 Hz, 2H) 4.18 (t, J=8.70 Hz, 2H) 7.11-7.14 (m, 1H) 7.29 (d, J=7.69 Hz, 1H) 7.64 (d, J=8.61 Hz, 1H) 7.66 (s, 1H) 7.81-7.88 (m, 1H) 7.98 (d, J=2.01 Hz, 1H) 8.03 (s, 1H) 8.85 (s, 1H) 8.93 (s, 1H).

2-(2-(Acetyl-methyl-amino)-5-{1-[4-(4-ethyl-piperazin-1-ylmethyl)-3-trifluoromethyl-phenylcarbamoyl]-2,3-dihydro-1H-indol-5-ylethynyl}-pyrimidin-4-yl)-1-methyl-4-oxo-1,4,6,7-tetrahydro-pyrrolo[3,2-c]pyridine-5-carboxylic acid tert-butyl ester 1H NMR (600 MHz, DMSO-d$_6$) δ ppm 0.98 (t, J=7 Hz, 3H) 1.48 (s, 9H) 2.31 (q, J=7.02 Hz, 2H) 2.38 (br. s., 8H) 2.41 (s, 4H) 3.03 (t, J=6.23 Hz, 2H) 3.22 (t, J=8.52 Hz, 2H) 3.40 (s, 3H) 3.54 (s, 2H) 3.86 (s, 3H) 4.03 (t, J=6.41 Hz, 2H) 4.19 (t, J=8.61 Hz, 2H) 7.36 (d, J=8.06 Hz, 1H) 7.41 (s, 1H) 7.64 (d, J=8.79 Hz, 1H) 7.76 (s, 1H) 7.85 (d, J=8.42 Hz, 1H) 7.93 (d, J=8.42 Hz, 1H) 7.99 (d, J=1.83 Hz, 1H) 8.87 (s, 1H) 8.90 (s, 1H).

2-[2-Acetylamino-5-(3-{[4-(4-methyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.45 (s, 9H) 2.19 (s, 5H) 2.22-2.47 (m, 7H) 3.03 (t, J=6.32 Hz, 2H) 3.53 (s, 2H) 3.71 (s, 2H) 3.97 (s, 3H) 4.02 (t, J=6.32 Hz, 2H) 7.37-7.46 (m, 3H) 7.55 (s, 1H) 7.64 (d, J=8.61 Hz, 1H) 7.74-7.79 (m, 2H) 8.03 (d, J=1.83 Hz, 1H) 8.82 (s, 1H) 10.44 (s, 1H) 10.80 (s, 1H).

2-[2-(Acetyl-isopropyl-amino)-5-(3-{[4-(4-methyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.25 (d, J=6.96 Hz, 6H) 1.45 (s, 9H) 1.99 (s, 3H) 2.14 (s, 3H) 2.16-2.46 (m, 8H) 3.03 (t, J=6.23 Hz, 2H) 3.52 (s, 2H) 3.72 (s, 2H) 3.84 (s, 3H) 4.03 (t, J=6.32 Hz, 2H) 4.73-4.80 (m, 1H) 7.40-7.51 (m, 3H) 7.58 (s, 1H) 7.64 (d, J=8.43 Hz, 1H) 7.75-7.79 (m, 2H) 8.04 (d, J=1.83 Hz, 1H) 9.01 (s, 1H) 10.45 (s, 1H).

2-[2-(Acetyl-methyl-amino)-5-(5-{[4-(4-ethyl-piperazin-1-ylmethyl)-3-trifluoromethyl-phenylcarbamoyl]-methyl}-2-fluoro-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.99 (br. s., 3H) 1.44 (s, 10H) 2.26-2.47 (m, 3H) 2.42 (s, 4H) 3.03 (t, J=6.32

Hz, 2H) 3.53 (br. s., 2H) 3.71 (s, 2H) 3.85 (s, 3H) 4.01 (t, J=6.23 Hz, 2H) 7.33 (t, J=8.88 Hz, 1H) 7.43-7.48 (m, 1H) 7.60 (dd, J=6.69, 1.92 Hz, 1H) 7.65 (d, J=8.42 Hz, 1H) 7.71 (s, 1H) 7.77 (d, J=8.79 Hz, 1H) 8.03 (d, J=1.65 Hz, 1H) 8.92 (s, 1H) 10.45 (s, 1H).

2-[2-(Acetyl-ethyl-amino)-5-(2-fluoro-5-{[4-(4-methyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 1.16 (t, J=7.05 Hz, 3H) 1.44 (s, 9H) 2.14 (s, 3H) 2.36-2.38 (m, 4H) 3.03 (t, J=6.32 Hz, 2H) 3.52 (s, 2H) 3.71 (s, 2H) 3.84 (s, 3H) 3.98-4.07 (m, 4H) 7.33 (t, J=8.97 Hz, 1H) 7.43-7.48 (m, 1H) 7.59 (dd, J=6.78, 2.20 Hz, 1H) 7.64 (d, J=8.61 Hz, 1H) 7.70 (s, 1H) 7.76 (dd, J=8.52, 1.92 Hz, 1H) 8.03 (d, J=1.83 Hz, 1H) 8.92 (s, 1H) 10.43 (s, 1H).

2-(2-(Acetyl-methyl-amino)-5-{2-methyl-5-[4-(4-methyl-piperazin-1-ylmethyl)-3-trifluoromethyl-phenylcarbamoyl]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-$d_6$) δ ppm 1.40-1.44 (m, 9H) 2.16 (s, 3H) 2.26-2.42 (m, 7H) 2.43 (s, 3H) 2.54 (s, 3H) 3.03 (t, J=6.29 Hz, 2H) 3.42 (s, 3H) 3.56 (s, 2H) 3.86 (s, 3H) 4.01 (t, J=6.29 Hz, 2H) 7.53 (d, J=8.18 Hz, 1H) 7.70 (d, J=8.67 Hz, 1H) 7.75 (s, 1H) 7.94 (dd, J=7.99, 1.89 Hz, 1H) 8.04 (dd, J=8.42, 2.08 Hz, 1H) 8.12 (d, J=1.95 Hz, 1H) 8.20 (d, J=2.20 Hz, 1H) 8.98 (s, 1H) 10.52 (s, 1H).

Preparation 40

2-[2-Amino-5-(5-{[4-(4-ethyl-piperazin-1-ylmethyl)-3-trifluoromethyl-phenylcarbamoyl]-methyl}-pyridin-3-ylethynyl)-pyrimidin-4-yl]-1-methyl-4-oxo-1,4,6,7-tetrahydro-pyrrolo[3,2-c]pyridine-5-carboxylic acid tert-butyl ester

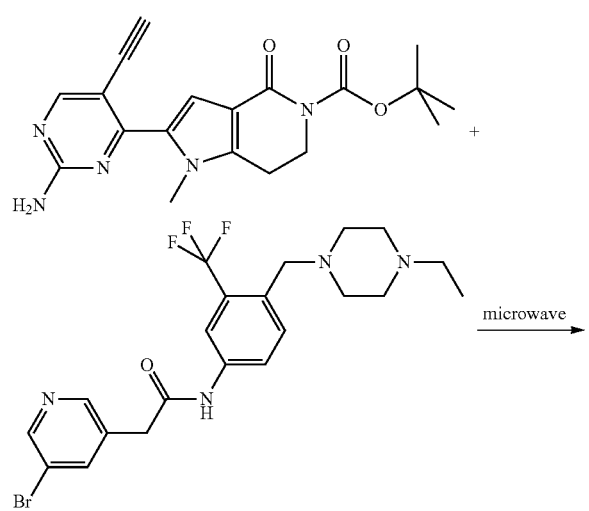

microwave

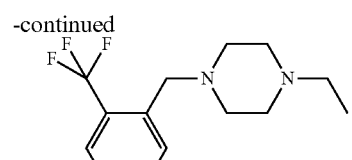

A solution of 2-(2-amino-5-ethynyl-pyrimidin-4-yl)-1-methyl-4-oxo-1,4,6,7-tetrahydro-pyrrolo[3,2-c]pyridine-5-carboxylic acid tert-butyl ester (0.05 g, 0.14 mmol), 2-(5-bromo-pyridin-3-yl)-N-[4-(4-ethyl-piperazin-1-ylmethyl)-3-trifluoromethyl-phenyl]-acetamide (0.05 g, 0.10 mmol), CuI (10% mol, 3 mg, 0.014 mmol), PdCl$_2$(PPh$_3$)$_2$ (10% mol, 10 mg, 0.014 mmol) and TEA (0.19 mL, 1.40 mmol) in DMF (2 mL) was degassed with argon and heated at 60° C., in microwave apparatus, for 1 h. The reaction was cooled at r.t., poured in water (15 mL) and extracted with EtOAc (2×15 mL). The organic phase was washed with brine, dried with anhydrous Na$_2$SO$_4$ and evaporated under vacuum to give a crude that was purified by flash column chromatography (DCM/MeOH/NH$_3$ 90/10/0.5). The title product (0.02 g, 26%) was obtained as yellowish solid.

$^1$H NMR (600 MHz, DMSO-$d_6$) δ ppm 0.97 (t, J=7.23 Hz, 3H) 1.41-1.47 (m, 9H) 2.11-2.46 (m, 10H) 2.99 (t, J=6.32 Hz, 2H) 3.52 (s, 2H) 3.76 (s, 2H) 3.84 (s, 3H) 4.00 (t, J=6.32 Hz, 2H) 7.20 (s, 2H) 7.54 (s, 1H) 7.65 (d, J=8.61 Hz, 1H) 7.76 (dd, J=8.52, 1.74 Hz, 1H) 7.83 (t, J=2.01 Hz, 1H) 8.03 (d, J=1.83 Hz, 1H) 8.49 (d, J=2.01 Hz, 1H) 8.50 (s, 1H) 8.54 (d, J=1.83 Hz, 1H) 10.50 (s, 1H).

According to this same methodology, but employing suitable substituted derivatives, the following intermediates were prepared:

2-[2-Amino-5-(5-{[4-(4-ethyl-piperazin-1-ylmethyl)-3-trifluoromethyl-phenylcarbamoyl]-methyl}-thiophen-3-ylethynyl)-pyrimidin-4-yl]-1-methyl-4-oxo-1,4,6,7-tetrahydro-pyrrolo[3,2-c]pyridine-5-carboxylic acid tert-butyl ester ESI) m/z 777 [(M+H)$^+$]. HRMS (ESI) calculated for C$_{39}$H$_{44}$F$_3$N$_8$O$_4$S$^+$ [(M+H)$^+$] 777.8701. found 777.8705.

2-[2-Amino-5-(4-{[4-(4-ethyl-piperazin-1-ylmethyl)-3-trifluoromethyl-phenylcarbamoyl]-methyl}-pyridin-2-ylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 772 [(M+H)$^+$]. HRMS (ESI) calculated for C$_{40}$H$_{45}$F$_3$N$_9$O$_4^+$ [(M+H)$^+$] 772.8305. found 772.8302.

2-[2-Amino-5-(5-{[4-(4-ethyl-piperazin-1-ylmethyl)-3-trifluoromethyl-phenylcarbamoyl]-methyl}-thiophen-2-ylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 777 [(M+H)$^+$]. HRMS (ESI) calculated for $C_{39}H_{44}F_3N_8O_4S^+$ [(M+H)$^+$] 777.8701. found 777.8698.

2-[2-Amino-5-(5-{[4-(4-ethyl-piperazin-1-ylmethyl)-3-trifluoromethyl-phenylcarbamoyl]-methyl}-2-fluoro-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.97 (t, J=7.14 Hz, 3H) 1.44 (s, 9H) 2.20-2.47 (m, 9H) 2.99 (t, J=6.32 Hz, 2H) 3.52 (s, 2H) 3.67 (s, 2H) 3.84 (s, 3H) 4.00 (t, J=6.32 Hz, 2H) 7.19 (s, 2H) 7.27 (t, J=8.97 Hz, 1H) 7.35-7.39 (m, 1H) 7.51 (dd, J=6.78, 2.01 Hz, 1H) 7.54 (s, 1H) 7.65 (d, J=8.43 Hz, 1H) 7.76 (dd, J=8.70, 1.74 Hz, 1H) 8.03 (d, J=2.01 Hz, 1H) 8.48 (s, 1H) 10.41 (s, 1H).

2-[2-Amino-5-(3-{[4-(4-ethyl-piperazin-1-ylmethyl)-3-trifluoromethyl-phenylcarbamoyl]-methyl}-2-fluoro-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.98 (t, J=7.14 Hz, 3H) 1.45 (s, 9H) 2.20-2.47 (m, 9H) 2.98 (t, J=6.32 Hz, 2H) 3.52 (s, 2H) 3.67 (s, 2H) 3.84 (s, 3H) 4.00 (t, J=6.32 Hz, 2H) 7.19 (s, 2H) 7.30 (t, J=8.97 Hz, 1H) 7.35-7.39 (m, 1H) 7.48 (dd, J=6.78, 2.01 Hz, 1H) 7.50 (s, 1H) 7.65 (d, J=8.43 Hz, 1H) 7.76 (dd, J=8.70, 1.74 Hz, 1H) 8.04 (d, J=2.01 Hz, 1H) 8.47 (s, 1H) 10.52 (s, 1H).

2-[2-(Acetyl-methyl-amino)-5-(2-fluoro-5-{[4-(4-isopropyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 859 [(M+H)$^+$]. HRMS (ESI) calculated for $C_{45}H_{51}F_4N_8O_5^+$ [(M+H)$^+$] 859.9227. found 859.9228.

2-[2-(Acetyl-methyl-amino)-5-(5-{[4-(4-ethyl-piperazin-1-ylmethyl)-3-trifluoromethyl-phenylcarbamoyl]-methyl}-thiophen-2-ylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 833 [(M+H)$^+$]. HRMS (ESI) calculated for $C_{42}H_{48}F_3N_8O_5S^+$ [(M+H)$^+$] 833.9334. found 833.9330.

2-[2-(Acetyl-methyl-amino)-5-(2-fluoro-5-{[4-(4-propyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 859 [(M+H)$^+$]. HRMS (ESI) calculated for $C_{45}H_{51}F_4N_8O_5^+$ [(M+H)$^+$] 859.9227. found 859.9233.

2-(2-Amino-5-{5-[4-(4-ethyl-piperazin-1-ylmethyl)-3-trifluoromethyl-phenylcarbamoyl]-thiophen-2-ylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.99 (t, J=7.14 Hz, 3H) 1.47 (s, 9H) 2.22-2.48 (m, 9H) 2.99 (t, J=6.32 Hz, 2H) 3.56 (s, 2H) 3.84 (s, 3H) 4.00 (t, J=6.32 Hz, 2H) 7.25 (s, 2H) 7.37 (d, J=3.85 Hz, 1H) 7.43 (s, 1H) 7.71 (d, J=8.61 Hz, 1H) 7.96-7.98 (m, 1H) 7.99 (d, J=4.03 Hz, 1H) 8.12 (d, J=2.20 Hz, 1H) 8.50 (s, 1H) 10.57 (s, 1H).

2-(2-Amino-5-{5-[4-(4-ethyl-piperazin-1-ylmethyl)-3-trifluoromethyl-phenylcarbamoyl]-thiazol-2-ylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 764 [(M+H)$^+$]. HRMS (ESI) calculated for $C_{37}H_{41}F_3N_9O_4S^+$ [(M+H)$^+$] 764.8316. found 764.8318.

2-(2-Amino-5-{5-[4-(4-ethyl-piperazin-1-ylmethyl)-3-trifluoromethyl-phenylcarbamoyl]-pyridin-3-ylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 758 [(M+H)$^+$]. HRMS (ESI) calculated for $C_{39}H_{43}F_3N_9O_4^+$ [(M+H)$^+$] 758.8039. found 758.8045.

2-(2-Amino-5-{3-[4-(4-ethyl-piperazin-1-ylmethyl)-3-trifluoromethyl-phenylcarbamoyl]-5-fluoro-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.98 (t, J=7.14 Hz, 3H) 2.31 (q, J=7.08 Hz, 3H) 2.33-2.47 (m, 5H) 3.00 (t, J=6.32 Hz, 2H) 3.57 (s, 2H) 3.85 (s, 3H) 4.00 (t, J=6.32 Hz, 2H) 7.24 (s, 2H) 7.51-7.53 (m, 1H) 7.54 (s, 1H) 7.72 (d, J=8.42 Hz, 1H) 7.78 (dd, J=8.97, 1.83 Hz, 1H) 7.89 (s, 1H) 8.02 (dd, J=8.61, 1.83 Hz, 1H) 8.19 (d, J=2.01 Hz, 1H) 8.52 (s, 1H) 10.61 (s, 1H).

2-(2-Amino-5-{3-[4-(4-ethyl-piperazin-1-ylmethyl)-3-trifluoromethyl-phenylcarbamoyl]-2-fluoro-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 775 [(M+H)$^+$]. HRMS (ESI) calculated for $C_{40}H_{43}F_4N_8O_4^+$ [(M+H)$^+$] 775.8063. found 775.8064.

2-(2-Amino-5-{3-[4-(4-ethyl-piperazin-1-ylmethyl)-3-trifluoromethyl-phenylsulfamoyl]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 793 [(M+H)$^+$]. HRMS (ESI) calculated for $C_{39}H_{44}F_3N_8O_5S^+$ [(M+H)$^+$] 793.8695. found 793.8698.

2-[2-Amino-5-(3-cyclopropylsulfamoyl-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.34-0.41 (m, 2H) 0.47-0.53 (m, 2H) 1.47 (s, 9H) 2.15 (td, J=6.69, 3.30 Hz, 1H) 3.00 (t, J=6.32 Hz, 2H) 3.85 (s, 3H) 4.00 (t, J=6.32 Hz, 2H) 7.21 (s, 2H) 7.51 (s, 1H) 7.64-7.68 (m, 1H) 7.69-7.72 (m, 1H) 7.79 (dt, J=7.69, 1.47 Hz, 1H) 7.82-7.84 (m, 1H) 7.90 (d, J=2.93 Hz, 1H) 8.53 (s, 1H).

Preparation 41

2-(2-Amino-5-{3-[(4-chloro-3-trifluoromethyl-phenylcarbamoyl)-methyl]-phenylethynyl}-pyrimidin-4-yl)-4-oxo-1-[2-(tetrahydro-pyran-2-yloxy)-ethyl]-1,4,6,7-tetrahydro-pyrrolo[3,2-c]pyridine-5-carboxylic acid tert-butyl ester

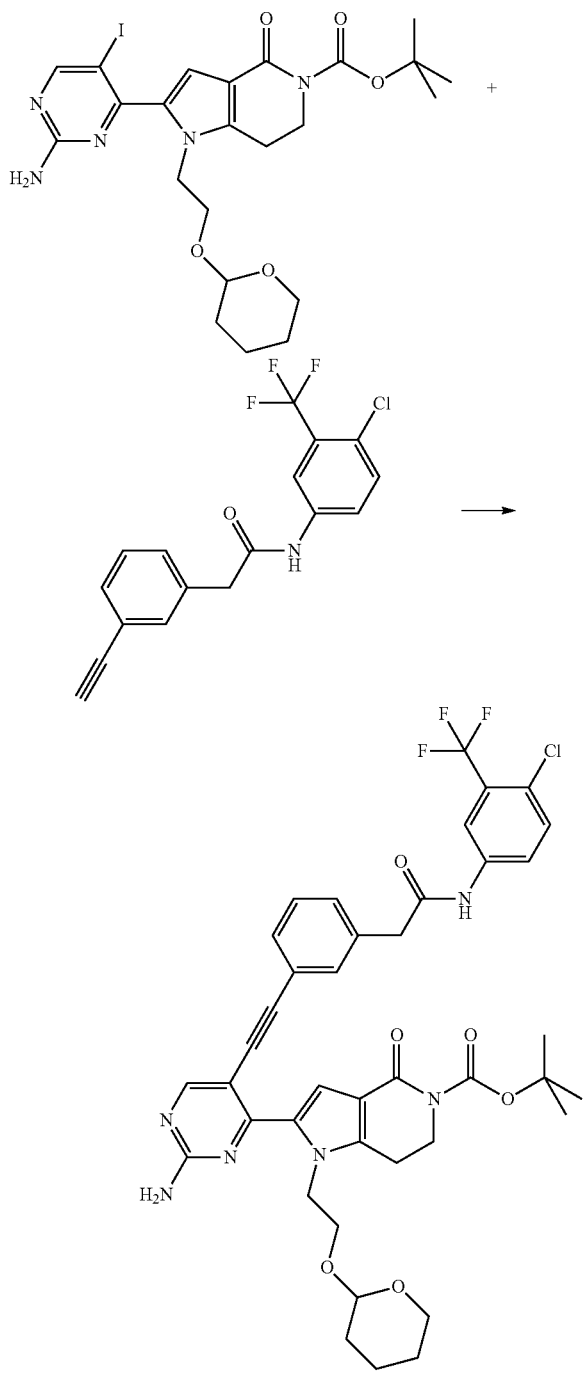

A solution of 2-(2-amino-5-iodo-pyrimidin-4-yl)-4-oxo-1-[2-(tetrahydro-pyran-2-yloxy)-ethyl]-1,4,6,7-tetrahydro-pyrrolo[3,2-c]pyridine-5-carboxylic acid tert-butyl ester (0.22 g, 0.38 mmol), N-(4-chloro-3-trifluoromethyl-phenyl)-2-(3-ethynyl-phenyl)-acetamide (0.15 g, 0.46 mmol), CuI (10% mol, 7 mg, 0.038 mmol), $PdCl_2(PPh_3)_2$ (10% mol, 27 mg, 0.038 mmol) and TEA (0.53 mL, 3.80 mmol) in MeCN (7 mL) was degassed with argon and stirred at r.t. for 2 h. The reaction was poured in water (15 mL) and extracted with EtOAc (2×15 mL). The organic phase was washed with brine, dried with anhydrous $Na_2SO_4$ and evaporated under vacuum to give a crude that was purified by flash column chromatography (DCM/MeOH 98/2) to afford the title product (0.15 g, 50% yield) was obtained as white solid.

(ESI) m/z 794 [(M+H)$^+$]. HRMS (ESI) calculated for $C_{40}H_{41}ClF_3N_6O_6^+$ [(M+H)$^+$] 794.2304. found 794.2301.

According to this same methodology, but employing suitable substituted derivatives, the following compounds or intermediates were prepared:

2-(3-{2-Amino-4-[1-(1-methyl-piperidin-4-yl)-4-oxo-4,5,6,7-tetrahydro-1H-pyrrolo[3,2-c]pyridin-2-yl]-pyrimidin-5-ylethynyl}-phenyl)-N-(4-chloro-3-trifluoromethyl-phenyl)-acetamide (cmpd 195)

$^1$H NMR (600 MHz, DMSO-d$_6$) δ ppm 1.94 (d, J=9.71 Hz, 4H) 2.08-2.16 (m, 2H) 2.18 (s, 3H) 2.84 (d, J=10.07 Hz, 2H) 3.04 (t, J=6.69 Hz, 2H) 3.41-3.44 (m, 2H) 3.68 (s, 2H) 4.64 (t, J=12.27 Hz, 1H) 7.03 (br. s., 2H) 7.25 (s, 1H) 7.27 (br. s., 1H) 7.30-7.38 (m, 4H) 7.48 (s, 1H) 7.65 (d, J=8.79 Hz, 1H) 7.84 (dd, J=8.79, 2.20 Hz, 1H) 8.19 (d, J=2.20 Hz, 1H) 8.46 (s, 1H) 10.62 (s, 1H).

2-(2-Amino-5-{3-[4-(4-ethyl-piperazin-1-ylmethyl)-3-trifluoromethyl-phenylcarbamoyl]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 757 [(M+H)$^+$]. HRMS (ESI) calculated for $C_{40}H_{44}F_3N_8O_4^+$ [(M+H)$^+$] 757.8158. found 757.8160.

N-[4-(4-Ethyl-piperazin-1-ylmethyl)-3-trifluoromethyl-phenyl]-3-[2-methylamino-4-(1-methyl-4-oxo-4,5,6,7-tetrahydro-1H-pyrrolo[3,2-c]pyridin-2-yl)-pyrimidin-5-ylethynyl]-benzamide (cmpd 49)

$^1$H NMR (600 MHz, DMSO-d$_6$) δ ppm 0.98 (t, J=7.14 Hz, 3H) 2.31 (q, J=7.20 Hz, 2H) 2.33-2.49 (m, 7H) 2.89 (d, J=4.76 Hz, 3H) 2.90-2.92 (m, 1H) 3.43-3.48 (m, 2H) 3.57 (s, 2H) 3.81-3.95 (m, 3H) 7.14 (br. s., 1H) 7.51-7.62 (m, 3H) 7.70 (dd, J=15.57, 8.06 Hz, 2H) 7.95 (d, J=7.88 Hz, 1H) 8.05 (d, J=8.43 Hz, 1H) 8.06 (s, 1H) 8.22 (d, J=2.01 Hz, 1H) 8.46-8.57 (m, 1H) 10.56 (br. s., 1H).

(ESI) m/z 671 [(M+H)$^+$]. HRMS (ESI) calculated for $C_{36}H_{38}F_3N_8O_2^+$ [(M+H)$^+$] 671.3065. found 671.3063.

2-[2-Amino-5-(3-cyclopropylcarbamoyl-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 0.56-0.61 (m, 2H) 0.66-0.71 (m, 2H) 1.47 (s, 9H) 2.82-2.88 (m, 1H) 2.99 (t, J=6.32 Hz, 2H) 3.84 (s, 3H) 4.00 (t, J=6.32 Hz, 2H) 7.16 (s, 2H) 7.45-7.50 (m, 1H) 7.52 (s, 1H) 7.58 (dt, J=7.74, 1.26 Hz, 1H) 7.80 (dt, J=7.83, 1.40 Hz, 1H) 7.86 (s, 1H) 8.46-8.51 (m, 2H).

2-[2-Amino-5-(3-phenylcarbamoylmethoxy-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.44 (s, 9H) 2.99 (t, J=6.16 Hz, 2H) 3.85 (s, 3H) 4.00 (t, J=6.23 Hz, 2H) 4.74 (s, 2H) 7.00-7.12 (m, 4H) 7.13 (s, 2H) 7.28-7.38 (m, 3H) 7.57 (s, 1H) 7.63 (d, J=8.18 Hz, 2H) 8.46 (s, 1H) 10.01 (s, 1H).

2-(2-Amino-5-{3-[(1-phenylcarbamoyl-cyclopropanecarbonyl)-amino]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.35-1.58 (m, 13H) 2.99 (t, J=6.35 Hz, 2H) 3.84 (s, 3H) 3.96-4.04 (m, 2H) 7.03-7.09 (m, 1H) 7.12 (s, 2H) 7.17 (d, J=7.57 Hz, 1H) 7.31 (dt, J=15.72, 7.83 Hz, 4H) 7.48 (s, 1H) 7.56 (d, J=8.91 Hz, 1H) 7.61 (d, J=8.18 Hz, 2H) 7.80 (s, 1H) 7.95 (s, 1H) 8.47 (s, 1H) 10.00 (s, 1H) 10.09 (s, 1H).

2-[2-Amino-5-(3-{[1-(4-trifluoromethyl-phenylcarbamoyl)-cyclopropanecarbonyl]-amino}-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 714 [(M+H)$^+$]. HRMS (ESI) calculated for C$_{37}$H$_{35}$F$_3$N$_7$O$_5^+$ [(M+H)$^+$] 714.7050. found 714.7055.

2-[2-Amino-5-(3-phenethyloxy-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.46 (s, 9H) 3.01 (dt, J=16.02, 6.45 Hz, 4H) 3.85 (s, 3H) 4.00 (t, J=5.98 Hz, 2H) 4.23 (t, J=6.71 Hz, 2H) 6.95 (d, J=8.30 Hz, 1H) 6.98-7.04 (m, 2H) 7.12 (s, 2H) 7.18-7.24 (m, 1H) 7.26-7.36 (m, 5H) 7.57 (s, 1H) 8.46 (s, 1H).

2-{2-Amino-5-[3-(3-phenyl-propionylamino)-phenylethynyl]-pyrimidin-4-yl}-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.46 (s, 8H) 2.60-2.66 (m, 2H) 2.88-2.93 (m, 2H) 2.99 (t, J=6.29 Hz, 2H) 3.84 (s, 3H) 4.01 (t, J=6.35 Hz, 2H) 7.11-7.15 (m, 3H) 7.16-7.21 (m, 1H) 7.22-7.37 (m, 5H) 7.47 (s, 1H) 7.49-7.52 (m, 1H) 7.76 (s, 1H) 8.48 (s, 1H) 9.98 (s, 1H).

2-(2-Amino-5-{3-[((1S,2S)-2-phenyl-cyclopropanecarbonyl)-amino]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.31-1.56 (m, 12H) 2.02-2.11 (m, 1H) 2.35-2.40 (m, 1H) 2.99 (t, J=6.23 Hz, 2H) 3.84 (s, 3H) 4.00 (t, J=6.23 Hz, 2H) 7.09-7.16 (m, 3H) 7.16-7.23 (m, 3H) 7.26-7.36 (m, 3H) 7.47 (s, 1H) 7.51-7.55 (m, 1H) 7.77 (s, 1H) 10.32 (s, 1H).

2-{2-Amino-5-[3-(3-phenyl-propoxy)-phenylethynyl]-pyrimidin-4-yl}-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.45 (s, 9H) 1.99-2.05 (m, 2H) 2.72-2.76 (m, 2H) 2.99 (t, J=6.23 Hz, 2H) 3.85 (s, 3H) 3.97-4.03 (m, 4H) 6.96 (dd, J=8.33, 2.47 Hz, 1H) 6.99 (s, 1H) 7.03 (d, J=7.69 Hz, 1H) 7.13 (s, 2H) 7.16-7.19 (m, 1H) 7.21-7.24 (m, 2H) 7.25-7.32 (m, 3H) 7.59 (s, 1H) 8.46 (s, 1H).

2-{2-Amino-5-[3-(benzoylamino-methyl)-phenylethynyl]-pyrimidin-4-yl}-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.44-1.49 (m, 9H) 2.99 (t, J=6.32 Hz, 2H) 3.84 (s, 3H) 4.00 (t, J=6.32 Hz, 2H) 7.12 (s, 2H) 7.30-7.39 (m, 3H) 7.44-7.50 (m, 3H) 7.51-7.55 (m, 1H) 7.56 (s, 1H) 7.87-7.91 (m, 2H) 8.46 (s, 1H) 9.03 (t, J=5.95 Hz, 1H).

2-{2-Amino-5-[3-(2-phenylcarbamoyl-ethyl)-phenylethynyl]-pyrimidin-4-yl}-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.44 (s, 9H) 2.65 (t, J=7.69 Hz, 2H) 2.92 (t, J=7.60 Hz, 2H) 3.00 (t, J=6.32 Hz, 2H) 3.85 (s, 3H) 4.01 (t, J=6.32 Hz, 2H) 6.98-7.03 (m, 1H) 7.12 (s, 2H) 7.23-7.30 (m, 4H) 7.31-7.34 (m, 1H) 7.40 (s, 1H) 7.55 (d, J=7.69 Hz, 2H) 7.60 (s, 1H) 8.45 (s, 1H) 9.85 (s, 1H).

2-[2-Amino-5-(3-benzyloxymethyl-phenylethynyl)-pyrimidin-4-yl]-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.46 (s, 9H) 2.99 (t, J=6.32 Hz, 2H) 3.85 (s, 3H) 4.00 (t, J=6.32 Hz, 1H) 4.54 (s, 2H) 4.55 (s, 2H) 7.13 (s, 2H) 7.29 (m, J=4.03 Hz, 1H) 7.36 (d, J=4.40 Hz, 3H) 7.38-7.42 (m, 2H) 7.47 (s, 1H) 7.57 (s, 1H) 8.47 (s, 1H).

2-(2-Amino-5-{3-[(benzyl-tert-butoxycarbonyl-amino)-methyl]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.36 (br. s., 9H) 1.43 (s, 9H) 2.99 (t, J=6.32 Hz, 2H) 3.85 (s, 3H) 4.00 (t, J=6.32 Hz, 2H) 4.18-4.51 (m, 4H) 7.13 (s, 2H) 7.19-7.28 (m, 4H) 7.29-7.41 (m, 5H) 7.56 (s, 1H) 8.46 (s, 1H).

2-(2-Amino-5-{3-[2-(3-trifluoromethyl-phenyl)-acetylamino]-phenylethynyl}-pyrimidin-4-yl)-1-methyl-4-oxo-1,4,6,7-tetrahydro-pyrrolo[3,2-c]pyridine-5-carboxylic acid tert-butyl ester $^1$H NMR (600 MHz, DMSO-d$_6$) δ ppm 1.43-1.47 (m, 9H) 2.99 (t, J=6.41 Hz, 2H) 3.79 (s, 2H) 3.83 (s, 3H) 3.99 (t, J=6.32 Hz, 2H) 7.13 (s, 2H) 7.15 (d, J=7.88 Hz, 1H) 7.34 (t, J=7.97 Hz, 1H) 7.47 (s, 1H) 7.52-7.65 (m, 5H) 7.69 (s, 1H) 7.76 (s, 1H) 8.47 (s, 1H) 10.31 (s, 1H).

2-(2-Amino-5-{3-[3-(4-trifluoromethyl-phenyl)-propionylamino]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 659 [(M+H)+]. HRMS (ESI) calculated for $C_{35}H_{34}F_3N_6O_4^+$ [(M+H)+] 659.6695. found 659.6697.

2-(2-Amino-5-{3-[3-(3-trifluoromethyl-phenyl)-propionylamino]-phenylethynyl}-pyrimidin-4-yl)-1-methyl-4-oxo-1,4,6,7-tetrahydro-pyrrolo[3,2-c]pyridine-5-carboxylic acid tert-butyl ester (ESI) m/z 659 [(M+H)+]. HRMS (ESI) calculated for $C_{35}H_{34}F_3N_6O_4^+$ [(M+H)+] 659.6695. found 659.6690.

2-{2-Amino-5-[3-(3-trifluoromethyl-benzylcarbamoyl)-phenylethynyl]-pyrimidin-4-yl}-1-methyl-4-oxo-1,4,6,7-tetrahydro-pyrrolo[3,2-c]pyridine-5-carboxylic acid tert-butyl ester (ESI) m/z 645 [(M+H)+]. HRMS (ESI) calculated for $C_{34}H_{32}F_3N_6O_4^+$ [(M+H)+] 645.6430. found 645.6432.

Preparation 42

2-{2-Amino-5-[3-(4-trifluoromethyl-benzoylamino)-phenylethynyl]-pyrimidin-4-yl}-1-methyl-4-oxo-1,4,6,7-tetrahydro-pyrrolo[3,2-c]pyridine-5-carboxylic acid tert-butyl ester

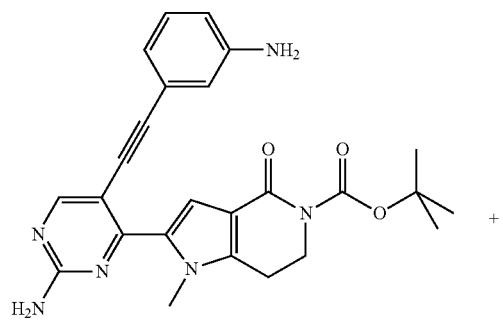

+

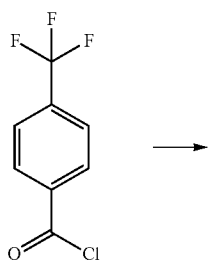

→

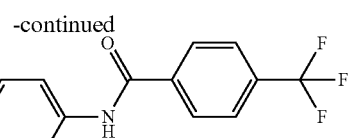

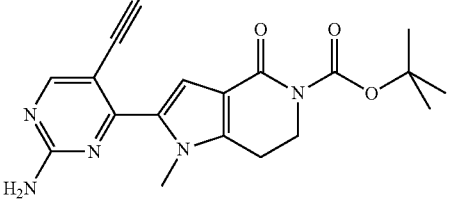

To a solution of 2-[2-amino-5-(3-amino-phenylethynyl)-pyrimidin-4-yl]-1-methyl-4-oxo-1,4,6,7-tetrahydro-pyrrolo[3,2-c]pyridine-5-carboxylic acid tert-butyl ester (0.12 g, 0.26 mmol) and pyridine (2 mL) in anhydrous THF (2 mL), cooled at 0-5° C., 4-trifluoromethyl-benzoyl chloride (0.05 mL, 0.31 mmol) dissolved in anhydrous THF (1 mL) was added drop wise. The reaction was stirred at r.t. for 2 h, then poured in water (20 mL) and extracted with EtOAc (2×15 mL). The organic phase was washed with brine, dried with anhydrous $Na_2SO_4$ and evaporated under vacuum to obtain a crude that was grounded with isopropyl ether. The title product (0.12 g, 78%) was obtained as grey solid.

$^1$H NMR (600 MHz, DMSO-$d_6$) ppm 1.35-1.43 (m, 9H) 2.97 (t, J=6.23 Hz, 2H) 3.82 (s, 3H) 3.93-4.01 (m, 2H) 7.11 (s, 2H) 7.21 (dt, J=7.78, 1.11 Hz, 1H) 7.38 (t, J=7.99 Hz, 1H) 7.66-7.77 (m, 1H) 7.87-7.95 (m, 3H) 8.13 (d, J=8.18 Hz, 1H) 8.47 (s, 1H) 10.49 (s, 1H).

According to this same methodology, but employing suitable substituted derivatives, the following intermediate was prepared:

2-[2-Amino-5-(3-phenylacetylamino-phenylethynyl)-pyrimidin-4-yl]-1-methyl-4-oxo-1,4,6,7-tetrahydro-pyrrolo[3,2-c]pyridine-5-carboxylic acid tert-butyl ester (ESI) m/z 577 [(M+H)+]. HRMS (ESI) calculated for $C_{33}H_{33}N_6O_4^+$ [(M+H)+] 577.6450. found 577.6449.

Preparation 43

2-(2-Amino-5-{3-[2-(4-trifluoromethyl-phenyl)-acetylamino]-phenylethynyl}-pyrimidin-4-yl)-1-methyl-4-oxo-1,4,6,7-tetrahydro-pyrrolo[3,2-c]pyridine-5-carboxylic acid tert-butyl ester A mixture of (4-trifluoromethyl-phenyl)-acetic acid (0.06 g, 0.29 mmol), 2-[2-amino-5-(3-amino-phenylethynyl)-pyrimidin-4-yl]-1-methyl-4-oxo-1,4,6,7-tetrahydro-pyrrolo[3,2-c]pyridine-5-carboxylic acid tert-butyl ester (0.09 g, 0.19 mmol), TBTU (0.10 g, 0.30 mmol) and DIPEA (0.10 mL, 0.57 mmol) in anhydrous DMF (3 mL) was stirred at r.t. for 2 h. The reaction was poured in a saturated solution of $NaHCO_3$ and extracted with EtOAc (2×15 mL), the organic phase was washed with brine, dried with anhydrous $Na_2SO_4$ and evaporated under vacuum. The crude was purified by flash column chromatography (EtOAc-Hex 65:35) to obtain the title compound (0.06 g, 49%) as white solid.

$^1$H NMR (600 MHz, DMSO-$d_6$) δ ppm 1.46 (s, 9H) 2.99 (t, J=6.35 Hz, 2H) 3.78 (s, 2H) 3.83 (s, 3H) 4.00 (t, J=6.23 Hz, 2H) 7.13 (s, 2H) 7.15 (d, J=7.81 Hz, 1H) 7.34 (t, J=7.99 Hz, 1H) 7.47 (s, 1H) 7.50-7.58 (m, 3H) 7.69 (d, J=8.30 Hz, 2H) 7.76 (s, 1H) 8.47 (s, 1H) 10.31 (s, 1H).

Example 6

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-propyl-piperazin-1-ylmethyl)-3-trifluoromethyl-phenyl]-acetamide (cmpd 164)

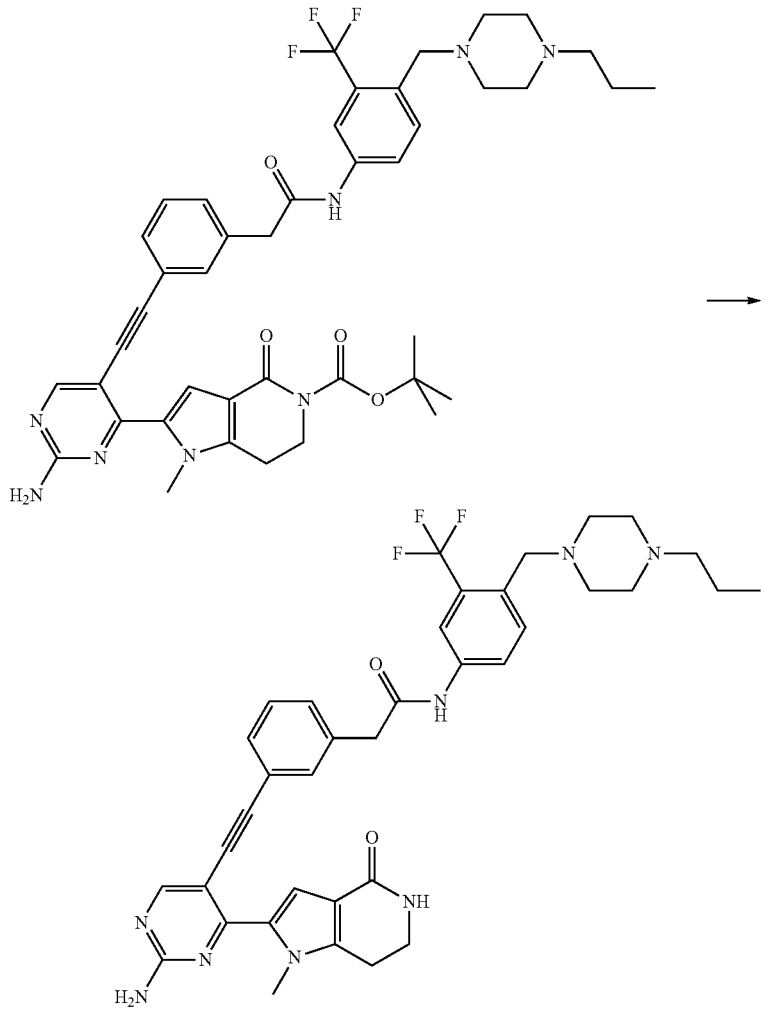

To a solution of 2-[2-amino-5-(3-{[4-(4-propyl-piperazin-1-ylmethyl)-3-trifluoromethyl-phenylcarbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (0.09 g, 0.12 mmol) in DCM (5 mL), 4 M HCl in dioxane (0.15 mL, 0.60 mmol) was added. The reaction was stirred at r.t. for 1 h, then evaporated under vacuum to obtain a crude that was purified by flash column chromatography (DCM-MeOH—NH₃ 90:10:0.8). The title compound (0.06 g, 74%) was obtained as white solid.

$^1$H NMR (600 MHz, DMSO-d$_6$) δ ppm 0.83 (t, J=7.33 Hz, 3H) 1.36-1.45 (m, 2H) 2.20 (br. s., 2H) 2.26-2.47 (m, 7H) 2.90 (t, J=6.87 Hz, 2H) 3.46 (td, J=6.87, 2.56 Hz, 2H) 3.52 (s, 2H) 3.67 (s, 2H) 3.86 (s, 4H) 7.07 (s, 2H) 7.21 (br. s., 1H) 7.31-7.38 (m, 4H) 7.52 (s, 1H) 7.53 (s, 1H) 7.64 (d, J=8.42 Hz, 1H) 7.77 (dd, J=8.33, 1.74 Hz, 1H) 8.04 (d, J=2.01 Hz, 1H) 8.43 (s, 1H) 10.46 (s, 1H). (ESI) m/z 685 [(M+H)$^+$].

HRMS (ESI) calculated for C$_{37}$H$_{40}$F$_3$N$_8$O$_2$$^+$ [(M+H)$^+$] 685.3221. found 685.3226.

According to this same methodology, but employing suitable substituted derivatives, the following compounds were prepared:

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-ethyl-piperazin-1-ylmethyl)-3-trifluoromethyl-phenyl]-acetamide (cmpd 77)

$^1$H NMR (600 MHz, DMSO-d$_6$) ppm 0.97 (t, J=7.14 Hz, 3H) 2.29 (q, J=7.14 Hz, 3H) 2.33-2.43 (m, 6H) 2.90 (t, J=6.87 Hz, 2H) 3.46 (td, J=6.82, 2.47 Hz, 2H) 3.52 (s, 2H) 3.67 (s, 2H) 3.85 (s, 3H) 7.07 (s, 2H) 7.21 (br. s., 1H) 7.29-7.39 (m, 3H) 7.50-7.56 (m, 2H) 7.65 (d, J=8.61 Hz, 1H) 7.75-7.79 (m, 1H) 8.04 (d, J=2.01 Hz, 1H) 8.43 (s, 1H) 10.48 (s, 1H).

(ESI) m/z 671 [(M+H)⁺]. HRMS (ESI) calculated for C₃₆H₃₈F₃N₈O₂⁺ [(M+H)⁺] 671.3064. found 671.3064.

2-{5-[2-Amino-4-(1-methyl-4-oxo-4,5,6,7-tetrahydro-1H-pyrrolo[3,2-c]pyridin-2-yl)-pyrimidin-5-ylethynyl]-pyridin-3-yl}-N-[4-(4-ethyl-piperazin-1-ylmethyl)-3-trifluoromethyl-phenyl]-acetamide (cmpd 122)

¹H NMR (600 MHz, DMSO-d₆) δ ppm 0.92-1.07 (m, 3H) 2.86-2.93 (m, 2H) 3.42-3.47 (m, 2H) 3.52-3.56 (m, 2H) 3.73-3.78 (m, 2H) 3.83-3.88 (m, 3H) 7.12-7.15 (m, 2H) 7.16-7.19 (m, 1H) 7.47-7.49 (m, 1H) 7.64-7.67 (m, 1H) 7.75-7.79 (m, 1H) 7.86-7.87 (m, 1H) 8.02-8.04 (m, 1H) 8.46-8.47 (m, 1H) 8.48-8.49 (m, 1H) 8.53-8.54 (m, 1H) 10.49-10.55 (m, 1H).
(ESI) m/z 672 [(M+H)⁺]. HRMS (ESI) calculated for C₃₅H₃₇F₃N₉O₂⁺ [(M+H)⁺] 672.3017. found 672.3015.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-ethyl-piperazin-1-ylmethyl)-3-fluoro-phenyl]-acetamide (cmpd 120)

¹H NMR (600 MHz, DMSO-d₆) δ ppm 0.95 (t, J=7.23 Hz, 3H) 2.27 (q, J=7.20 Hz, 2H) 2.30-2.41 (m, 6H) 2.90 (t, J=6.87 Hz, 2H) 3.42 (s, 2H) 3.46 (td, J=6.82, 2.47 Hz, 2H) 3.65 (s, 2H) 3.86 (s, 3H) 7.07 (s, 1H) 7.22 (br. s., 1H) 7.24-7.30 (m, 1H) 7.31-7.39 (m, 1H) 7.51 (s, 1H) 7.53 (s, 1H) 7.53-7.56 (m, 1H) 8.43 (s, 1H) 10.36 (s, 1H).
(ESI) m/z 621 [(M+H)⁺]. HRMS (ESI) calculated for C₃₅H₃₈FN₈O₂⁺ [(M+H)⁺] 621.3097. found 621.3105.

4-(2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-acetylamino)-N-(2-dimethylamino-ethyl)-benzamide dihydrochloride (cmpd 121)

¹H NMR (600 MHz, DMSO-d₆) δ ppm 2.82 (d, J=4.95 Hz, 6H) 2.91 (t, J=6.87 Hz, 2H) 3.24 (q, J=5.98 Hz, 2H) 3.45-3.48 (m, 4H) 3.59 (q, J=5.74 Hz, 2H) 3.70 (s, 2H) 3.86 (s, 3H) 7.15-7.34 (m, 2H) 7.37 (s, 3H) 7.53 (s, 1H) 7.59 (s, 1H) 7.70 (d, J=8.97 Hz, 2H) 7.85 (d, J=8.61 Hz, 2H) 8.46 (s, 1H) 8.65 (t, J=5.40 Hz, 1H) 9.75 (br. s., 1H) 10.50 (s, 1H).
(ESI) m/z 591 [(M+H)⁺]. HRMS (ESI) calculated for C₃₃H₃₇Cl₂N₈O₃⁺ [(M+H)⁺] 591.2827. found 591.2826.

2-{4-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-ethyl-piperazin-1-ylmethyl)-3-trifluoromethyl-phenyl]-acetamide (cmpd 123)

¹H NMR (600 MHz, DMSO-d₆) δ ppm 0.97 (t, J=7.23 Hz, 3H) 2.27-2.31 (m, 3H) 2.32-2.46 (m, 6H) 2.88 (t, J=6.87 Hz, 2H) 3.44 (td, J=6.87, 2.56 Hz, 2H) 3.52 (s, 2H) 3.69 (s, 2H) 3.85 (s, 3H) 7.05 (s, 2H) 7.09 (br. s., 1H) 7.35 (d, J=8.43 Hz, 2H) 7.43 (d, J=8.24 Hz, 2H) 7.48-7.50 (m, 1H) 7.65 (d, J=8.61 Hz, 1H) 7.77 (dd, J=8.42, 1.83 Hz, 1H) 8.03 (d, J=2.01 Hz, 1H) 8.42 (s, 1H) 10.46 (s, 1H).
(ESI) m/z 671 [(M+H)⁺]. HRMS (ESI) calculated for C₃₆H₃₈F₃N₈O₂⁺ [(M+H)⁺] 671.3065. found 671.3074.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[2-(4-ethyl-piperazin-1-ylmethyl)-5-trifluoromethyl-phenyl]-acetamide (cmpd 124)

¹H NMR (600 MHz, DMSO-d₆) δ ppm 0.85 (t, J=7.14 Hz, 3H) 2.18-2.22 (m, 3H) 2.23-2.36 (m, 4H) 2.86 (t, J=6.78 Hz, 2H) 3.39-3.44 (m, 2H) 3.55 (s, 2H) 3.74 (s, 2H) 3.82 (s, 3H) 7.05 (s, 2H) 7.10 (br. s., 1H) 7.27-7.39 (m, 4H) 7.40-7.42 (m, 1H) 7.52 (s, 2H) 8.36-8.40 (m, 2H) 10.76 (s, 1H).
(ESI) m/z 671 [(M+H)⁺]. HRMS (ESI) calculated for C₃₆H₃₈F₃N₈O₂⁺ [(M+H)⁺] 671.3065. found 671.3079.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-chloro-3-(4-ethyl-piperazine-1-carbonyl)-phenyl]-acetamide dihydrochloride (cmpd 125)

¹H NMR (600 MHz, DMSO-d₆) δ ppm 1.22 (br. s., 3H) 2.91 (t, J=6.78 Hz, 2H) 3.45-3.48 (m, 4H) 3.68 (br. s., 2H) 3.86 (s, 3H) 4.51-4.65 (m, 1H) 7.24 (br. s., 1H) 7.33-7.39 (m, 3H) 7.43-7.53 (m, 3H) 7.59 (br. s., 1H) 8.45 (s, 1H).
(ESI) m/z 651 [(M+H)⁺] HRMS (ESI) calculated for C₃₅H₃₈Cl₃N₈O₃⁺ [(M+H)⁺] 651.2594. found 651.2591.

2-{4-[2-Amino-4-(1-methyl-4-oxo-4,5,6,7-tetrahydro-1H-pyrrolo[3,2-c]pyridin-2-yl)-pyrimidin-5-ylethynyl]-thiophen-2-yl}-N-[4-(4-ethyl-piperazin-1-ylmethyl)-3-trifluoromethyl-phenyl]-acetamide (cmpd 126)

¹H NMR (600 MHz, DMSO-d₆) δ ppm 0.98 (t, J=6.87 Hz, 3H) 2.00-2.48 (m, 10H) 2.88 (t, J=6.87 Hz, 2H) 3.44 (td, J=6.87, 2.38 Hz, 2H) 3.54 (s, 2H) 3.84 (s, 3H) 3.91 (s, 2H) 7.03 (s, 2H) 7.08 (s, 1H) 7.11 (br. s., 1H) 7.45 (s, 1H) 7.61 (d, J=1.28 Hz, 1H) 7.67 (d, J=8.61 Hz, 1H) 7.78 (d, J=8.24 Hz, 1H) 8.03 (d, J=1.83 Hz, 1H) 8.39 (s, 1H) 10.52 (s, 1H).
(ESI) m/z 677 [(M+H)⁺]. HRMS (ESI) calculated for C₃₄H₃₆F₃N₈O₂S⁺ [(M+H)⁺] 677.2629. found 677.2647.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-(4-ethyl-piperazine-1-carbonyl)-4-trifluoromethyl-phenyl]-acetamide (cmpd 127)

¹H NMR (600 MHz, DMSO-d₆) δ ppm 0.84-1.07 (m, 3H) 2.15-2.44 (m, 6H) 2.90 (t, J=6.87 Hz, 2H) 2.99-3.17 (m, 2H) 3.46 (td, J=6.87, 2.38 Hz, 2H) 3.50-3.67 (m, 2H) 3.69-3.74 (m, 2H) 3.86 (s, 3H) 7.07 (s, 2H) 7.22 (br. s., 1H) 7.28-7.41 (m, 3H) 7.51-7.57 (m, 2H) 7.67 (br. s., 1H) 7.73-7.80 (m, 2H) 8.43 (s, 1H) 10.65 (s, 1H).
(ESI) m/z 685 [(M+H)⁺]. HRMS (ESI) calculated for C₃₆H₃₆F₃N₈O₃⁺ [(M+H)⁺] 685.2857. found 685.2858.

2-{2-[2-Amino-4-(1-methyl-4-oxo-4,5,6,7-tetrahydro-1H-pyrrolo[3,2-c]pyridin-2-yl)-pyrimidin-5-ylethynyl]-pyridin-4-yl}-N-[4-(4-ethyl-piperazin-1-ylmethyl)-3-trifluoromethyl-phenyl]-acetamide (cmpd 128)

¹H NMR (600 MHz, DMSO-d₆) δ ppm 0.97 (t, J=7.20 Hz, 3H) 2.24-2.33 (m, 2H) 2.36 (br. s., 8H) 2.90 (t, J=6.90 Hz, 2H) 3.46 (td, J=6.87, 2.50 Hz, 2H) 3.52 (s, 2H) 3.73 (s, 2H) 3.86 (s, 3H) 7.18 (s, 2H) 7.23 (t, J=2.08 Hz, 1H) 7.32 (dd, J=5.07, 1.53 Hz, 1H) 7.47 (s, 1H) 7.59 (s, 1H) 7.66 (d, J=8.54 Hz, 1H) 7.77 (dd, J=8.54, 1.83 Hz, 1H) 8.03 (d, J=1.95 Hz, 1H) 8.49 (s, 1H) 8.50 (d, J=5.13 Hz, 1H) 10.53 (s, 1H).

(ESI) m/z 672 [(M+H)⁺]. HRMS (ESI) calculated for $C_{35}H_{37}F_3N_9O_2^+$ [(M+H)⁺] 672.3017. found 672.3025.

2-{5-[2-Amino-4-(1-methyl-4-oxo-4,5,6,7-tetrahydro-1H-pyrrolo[3,2-c]pyridin-2-yl)-pyrimidin-5-ylethynyl]-thiophen-2-yl}-N-[4-(4-ethyl-piperazin-1-ylmethyl)-3-trifluoromethyl-phenyl]-acetamide (cmpd 129)

¹H NMR (600 MHz, DMSO-d₆) δ ppm 0.98 (t, J=6.87 Hz, 3H) 2.08-2.48 (m, 7H) 2.88 (t, J=6.87 Hz, 1H) 3.43 (td, J=6.82, 2.47 Hz, 1H) 3.54 (s, 1H) 3.84 (s, 2H) 3.92 (s, 1H) 6.97 (d, J=3.48 Hz, 1H) 7.08 (s, 2H) 7.17 (d, J=3.66 Hz, 1H) 7.35 (s, 1H) 7.67 (d, J=8.61 Hz, 1H) 7.77 (d, J=8.24 Hz, 1H) 8.02 (d, J=2.01 Hz, 1H) 8.41 (s, 1H) 10.52 (s, 1H).

(ESI) m/z 677 [(M+H)⁺]. HRMS (ESI) calculated for $C_{34}H_{36}F_3N_8O_2S^+$ [(M+H)⁺] 677.2629. found 677.2631.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-bromo-3-(4-ethyl-piperazine-1-carbonyl)-phenyl]-acetamide dihydrochloride (cmpd 148)

¹H NMR (600 MHz, DMSO-d₆) δ ppm 1.21 (br. s., 3H) 2.92 (t, J=6.78 Hz, 2H) 3.45-3.48 (m, 4H) 3.69 (br. s., 2H) 3.87 (s, 3H) 4.50-4.64 (m, 1H) 7.25 (br. s., 1H) 7.34-7.40 (m, 3H) 7.45-7.54 (m, 3H) 7.60 (br. s., 1H) 8.47 (s, 1H) 10.59 (br. s, 1H).

(ESI) m/z 769 [(M+H)⁺]. HRMS (ESI) calculated for $C_{35}H_{38}BrCl_2N_8O_3^+$ [(M+H)⁺] 769.5301. found 769.5304.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-[1,4]diazepan-1-ylmethyl)-3-trifluoromethyl-phenyl]-acetamide (cmpd 149)

¹H NMR (600 MHz, DMSO-d₆) δ ppm 1.71 (t, J=5.68 Hz, 2H) 2.27 (br. s., 3H) 2.54-2.66 (m, 7H) 2.90 (t, J=6.87 Hz, 2H) 3.46 (td, J=6.87, 2.38 Hz, 2H) 3.67 (s, 4H) 3.86 (s, 3H) 7.07 (s, 2H) 7.22 (br. s., 1H) 7.29-7.40 (m, 3H) 7.50-7.56 (m, 2H) 7.70 (d, J=8.43 Hz, 1H) 7.78 (dd, J=8.52, 1.56 Hz, 1H) 8.03 (d, J=2.02 Hz, 1H) 8.43 (s, 1H) 10.46 (s, 1H).

(ESI) m/z 671 [(M+H)⁺]. HRMS (ESI) calculated for $C_{36}H_{38}F_3N_8O_2^+$ [(M+H)⁺] 671.3065. found 671.3074.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-((S)-3-dimethylamino-pyrrolidin-1-ylmethyl)-3-trifluoromethyl-phenyl]-acetamide (cmpd 150)

¹H NMR (600 MHz, DMSO-d₆) δ ppm 1.63 (dd, J=12.27, 6.96 Hz, 1H) 1.86 (dd, J=13.28, 5.22 Hz, 1H) 2.05-2.17 (m, 5H) 2.34 (br. s., 1H) 2.44-2.48 (m, 1H) 2.53-2.57 (m, 1H) 2.60-2.64 (m, 1H) 2.77 (br. s., 1H) 2.90 (t, J=6.87 Hz, 2H) 3.46 (td, J=6.87, 2.38 Hz, 2H) 3.57-3.66 (m, 2H) 3.67 (s, 2H) 3.86 (s, 3H) 7.07 (s, 2H) 7.21 (br. s., 1H) 7.31-7.39 (m, 3H) 7.52 (s, 1H) 7.53 (s, 1H) 7.63 (d, J=8.61 Hz, 1H) 7.78 (dd, J=8.43, 1.83 Hz, 1H) 8.03 (d, J=2.01 Hz, 1H) 8.43 (s, 1H) 10.46 (s, 1H).

(ESI) m/z 671 [(M+H)⁺]. HRMS (ESI) calculated for $C_{36}H_{38}F_3N_8O_2^+$ [(M+H)⁺] 671.3065. found 671.3063.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-ethyl-piperazine-1-carbonyl)-phenyl]-acetamide dihydrochloride (cmpd 153)

¹H NMR (600 MHz, DMSO-d₆) δ ppm 1.24 (t, J=7.33 Hz, 3H) 2.92 (t, J=6.78 Hz, 2H) 2.97-3.05 (m, 2H) 3.08-3.15 (m, 2H) 3.87 (s, 3H) 7.27 (br. s., 1H) 7.35-7.39 (m, 3H) 7.42 (d, J=8.61 Hz, 2H) 7.54 (s, 1H) 7.64 (s, 1H) 7.70 (d, J=8.61 Hz, 2H) 8.48 (s, 1H) 10.50 (s, 1H) 10.68 (br. s., 1H).

(ESI) m/z 617 [(M+H)⁺]. HRMS (ESI) calculated for $C_{35}H_{39}Cl_2N_8O_3^+$ [(M+H)⁺] 617.2983. found 769.2990.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-cyclopropyl-4-(4-methyl-piperazin-1-ylmethyl)-phenyl]-acetamide (cmpd 154)

¹H NMR (600 MHz, DMSO-d₆) δ ppm 0.49-0.55 (m, 2H) 0.84-0.95 (m, 2H) 2.06-2.24 (m, 5H) 2.23-2.48 (m, 7H) 2.90 (t, J=6.87 Hz, 2H) 3.47 (td, J=6.82, 2.47 Hz, 2H) 3.51 (s, 2H) 3.61 (s, 2H) 3.86 (s, 3H) 7.07 (s, 2H) 7.12 (d, J=8.24 Hz, 1H) 7.15 (d, J=2.01 Hz, 1H) 7.24 (br. s., 1H) 7.25-7.36 (m, 3H) 7.38 (dd, J=8.24, 1.83 Hz, 1H) 7.53 (s, 1H) 7.55 (s, 1H) 8.43 (s, 1H) 10.06 (s, 1H).

(ESI) m/z 629 [(M+H)⁺]. HRMS (ESI) calculated for $C_{37}H_{41}N_8O_2^+$ [(M+H)⁺] 629.3347. found 629.3356.

2-{3-[2-Amino-4-(1-methyl-4-oxo-4,5,6,7-tetrahydro-1H-pyrrolo[3,2-c]pyridin-2-yl)-pyrimidin-5-ylethynyl]-4-fluoro-phenyl}-N-[4-(4-ethyl-piperazin-1-ylmethyl)-3-trifluoromethyl-phenyl]-acetamide (cmpd 155)

¹H NMR (600 MHz, DMSO-d₆) δ ppm 0.99 (br. s., 3H) 2.12-2.49 (m, 11H) 2.89 (t, J=6.87 Hz, 2H) 3.45 (td, J=6.87, 2.56 Hz, 2H) 3.53 (br. s., 2H) 3.67 (s, 2H) 3.85 (s, 3H) 7.13 (s, 2H) 7.19 (br. s., 1H) 7.26 (t, J=8.97 Hz, 1H) 7.35-7.39 (m, 1H) 7.48 (s, 1H) 7.56 (dd, J=6.78, 2.01 Hz, 1H) 7.65 (d, J=8.61 Hz, 1H) 7.77 (d, J=8.24 Hz, 1H) 8.03 (d, J=1.83 Hz, 1H) 8.44 (s, 1H).

(ESI) m/z 689 [(M+H)⁺]. HRMS (ESI) calculated for $C_{36}H_{37}F_4N_8O_2^+$ [(M+H)⁺] 689.2970. found 689.2987.

2-{3-[2-Amino-4-(1-methyl-4-oxo-4,5,6,7-tetrahydro-1H-pyrrolo[3,2-c]pyridin-2-yl)-pyrimidin-5-ylethynyl]-2-fluoro-phenyl}-N-[4-(4-ethyl-piperazin-1-ylmethyl)-3-trifluoromethyl-phenyl]-acetamide (cmpd 156)

¹H NMR (600 MHz, DMSO-d₆) δ ppm 0.99 (br. s., 3H) 2.15-2.50 (m, 45H) 2.88 (t, J=6.87 Hz, 2H) 3.43 (td, J=6.82, 2.47 Hz, 2H) 3.54 (br. s., 2H) 3.79 (s, 2H) 3.84 (s, 3H) 7.08 (br. s., 1H) 7.12 (s, 2H) 7.20 (t, J=7.69 Hz, 1H) 7.41 (t, J=7.42 Hz, 1H) 7.43 (s, 1H) 7.44-7.46 (m, 1H) 7.66 (d, J=8.43 Hz, 1H) 7.78 (d, J=8.24 Hz, 1H) 8.05 (d, J=1.83 Hz, 1H) 8.43 (s, 1H) 10.53 (s, 1H).

(ESI) m/z 689 [(M+H)⁺]. HRMS (ESI) calculated for $C_{36}H_{37}F_4N_8O_2^+$ [(M+H)⁺] 689.2970. found 689.2986.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-((R)-3-dimethylamino-pyrrolidin-1-ylmethyl)-3-trifluoromethyl-phenyl]-acetamide (cmpd 157)

$^1$H NMR (600 MHz, DMSO-d$_6$) δ ppm 1.63 (dd, J=12.73, 6.69 Hz, 1H) 1.80-1.91 (m, 1H) 2.00-2.18 (m, 6H) 2.33 (d, J=6.04 Hz, 1H) 2.53-2.57 (m, 1H) 2.59-2.64 (m, 1H) 2.77 (br. s., 1H) 2.90 (t, J=6.87 Hz, 2H) 3.46 (td, J=6.87, 2.56 Hz, 2H) 3.57-3.67 (m, 2H) 3.67 (s, 2H) 3.86 (s, 3H) 7.07 (s, 2H) 7.21 (s, 1H) 7.31-7.39 (m, 3H) 7.52 (s, 1H) 7.53 (s, 1H) 7.63 (d, J=8.61 Hz, 1H) 7.78 (dd, J=8.52, 1.74 Hz, 1H) 8.03 (d, J=2.01 Hz, 1H) 8.43 (s, 1H) 10.46 (s, 1H).

(ESI) m/z 671 [(M+H)$^+$]. HRMS (ESI) calculated for C$_{36}$H$_{38}$F$_3$N$_8$O$_2$$^+$ [(M+H)$^+$] 671.3065. found 671.3067.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-isopropyl-piperazin-1-ylmethyl)-3-trifluoromethyl-phenyl]-acetamide (cmpd 158)

$^1$H NMR (600 MHz, DMSO-d$_6$) δ ppm 0.95 (d, J=5.68 Hz, 6H) 2.23-2.47 (m, 8H) 2.61 (d, J=1.83 Hz, 1H) 2.90 (t, J=6.87 Hz, 2H) 3.46 (td, J=6.82, 2.47 Hz, 2H) 3.51 (s, 2H) 3.67 (s, 2H) 3.86 (s, 3H) 7.07 (s, 2H) 7.21 (s, 1H) 7.31-7.39 (m, 3H) 7.52 (s, 1H) 7.53 (s, 1H) 7.65 (d, J=8.43 Hz, 1H) 7.76-7.79 (m, 1H) 8.04 (d, J=2.01 Hz, 1H) 8.43 (s, 1H) 10.47 (s, 1H).

(ESI) m/z 685 [(M+H)$^+$]. HRMS (ESI) calculated for C$_{37}$H$_{40}$F$_3$N$_8$O$_2$$^+$ [(M+H)$^+$] 685.3221. found 685.3224.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-(4-piperidin-1-ylmethyl-3-trifluoromethyl-phenyl)-acetamide (cmpd 159)

$^1$H NMR (600 MHz, DMSO-d$_6$) δ ppm 1.36 (br. s., 2H) 1.43-1.51 (m, 4H) 2.28 (br. s., 4H) 2.82-2.91 (m, 2H) 3.40-3.49 (m, 4H) 3.65 (s, 2H) 3.83 (s, 3H) 7.05 (s, 2H) 7.19 (br. s., 1H) 7.30-7.36 (m, 3H) 7.49 (s, 1H) 7.51 (s, 1H) 7.64 (d, J=8.61 Hz, 1H) 7.74 (d, J=8.79 Hz, 1H) 8.01 (s, 1H) 8.41 (s, 1H) 10.43 (s, 1H).

(ESI) m/z 642 [(M+H)$^+$]. HRMS (ESI) calculated for C$_{35}$H$_{35}$F$_3$N$_7$O$_2$$^+$ [(M+H)$^+$] 642.2799. found 642.2798.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-(4-morpholin-4-ylmethyl-3-trifluoromethyl-phenyl)-acetamide (cmpd 160)

$^1$H NMR (600 MHz, DMSO-d$_6$) δ ppm 2.33-2.38 (m, 4H) 2.90 (t, J=6.87 Hz, 2H) 3.46 (td, J=6.82, 2.47 Hz, 2H) 3.53 (s, 2H) 3.57 (t, J=4.40 Hz, 4H) 3.67 (s, 2H) 3.86 (s, 3H) 7.07 (s, 1H) 7.21 (br. s., 1H) 7.31-7.39 (m, 3H) 7.52 (s, 1H) 7.53 (s, 1H) 7.67 (d, J=8.61 Hz, 1H) 7.78 (dd, J=8.52, 1.56 Hz, 1H) 8.05 (d, J=2.01 Hz, 1H) 8.43 (s, 1H) 10.47 (s, 1H).

(ESI) m/z 644 [(M+H)$^+$]. HRMS (ESI) calculated for C$_{34}$H$_{33}$F$_3$N$_7$O$_3$$^+$ [(M+H)$^+$] 644.2592. found 644.2605.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (cmpd 161)

$^1$H NMR (600 MHz, DMSO-d$_6$) δ ppm 2.12 (s, 2H) 2.15-2.44 (m, 8H) 2.87 (t, J=6.87 Hz, 2H) 3.43 (td, J=6.87, 2.56 Hz, 2H) 3.49 (s, 2H) 3.64 (s, 2H) 3.83 (s, 3H) 7.05 (s, 2H) 7.19 (br. s., 1H) 7.28-7.37 (m, 3H) 7.49 (s, 1H) 7.50 (s, 1H) 7.61 (d, J=8.61 Hz, 1H) 7.75 (dd, J=8.52, 1.92 Hz, 1H) 8.01 (d, J=2.01 Hz, 1H) 8.41 (s, 1H) 10.44 (s, 1H).

(ESI) m/z 657 [(M+H)$^+$]. HRMS (ESI) calculated for C$_{35}$H$_{36}$F$_3$N$_8$O$_2$$^+$ [(M+H)$^+$] 657.2908. found 657.2905.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-(5-bromo-pyridin-3-yl)-acetamide (cmpd 162)

$^1$H NMR (600 MHz, DMSO-d$_6$) δ ppm 2.90 (t, J=6.87 Hz, 2H) 3.46 (td, J=6.87, 2.38 Hz, 2H) 3.71 (s, 2H) 3.86 (s, 3H) 7.07 (s, 2H) 7.22 (br. s., 1H) 7.30-7.38 (m, 3H) 7.52 (s, 1H) 7.53 (s, 1H) 8.34-8.40 (m, 2H) 8.44 (s, 1H) 8.67 (d, J=1.83 Hz, 1H) 10.60 (s, 1H)

(ESI) m/z 556 [(M+H)$^+$]. HRMS (ESI) calculated for C$_{27}$H$_{23}$BrN$_7$O$_2$$^+$ [(M+H)$^+$] 556.1091. found 556.1105.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(3-pyrrolidin-1-yl-azetidin-1-ylmethyl)-3-trifluoromethyl-phenyl]-acetamide (cmpd 163)

$^1$H NMR (600 MHz, DMSO-d$_6$) δ ppm 1.67 (br. s., 4H) 2.21-2.43 (m, 4H) 2.90 (t, J=6.87 Hz, 2H) 2.93 (br. s., 1H) 3.02-3.11 (m, 1H) 3.36 (t, J=6.32 Hz, 2H) 3.46 (td, J=6.87, 2.56 Hz, 2H) 3.65 (br. s., 1H) 3.67 (s, 2H) 3.86 (s, 3H) 7.07 (s, 1H) 7.21 (br. s., 1H) 7.29-7.39 (m, 1H) 7.52 (s, 1H) 7.53 (s, 1H) 7.58 (d, J=8.42 Hz, 1H) 7.77 (d, J=8.06 Hz, 1H) 8.02 (d, J=1.83 Hz, 1H) 8.43 (s, 1H) 10.45 (s, 1H).

(ESI) m/z 683 [(M+H)$^+$]. HRMS (ESI) calculated for C$_{37}$H$_{38}$F$_3$N$_8$O$_2$$^+$ [(M+H)$^+$] 683.3065. found 683.3077.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-ethyl-piperazine-1-carbonyl)-3-trifluoromethyl-phenyl]-acetamide (cmpd 165)

$^1$H NMR (600 MHz, DMSO-d$_6$) δ ppm 0.98 (t, J=7.14 Hz, 3H) 2.13-2.46 (m, 2H) 2.32 (q, J=7.08 Hz, 3H) 2.90 (t, J=6.87 Hz, 2H) 2.98-3.16 (m, 2H) 3.46 (td, J=6.82, 2.47 Hz, 2H) 3.60 (d, J=15.57 Hz, 2H) 3.70 (s, 2H) 3.86 (s, 3H) 7.07 (s, 2H) 7.22 (s, 1H) 7.32-7.40 (m, 4H) 7.51-7.54 (m, 2H) 7.85 (dd, J=8.43, 1.65 Hz, 1H) 8.12 (d, J=1.83 Hz, 1H) 8.44 (s, 1H) 10.62 (s, 1H).

(ESI) m/z 685 [(M+H)$^+$]. HRMS (ESI) calculated for C$_{36}$H$_{36}$F$_3$N$_8$O$_2$$^+$ [(M+H)$^+$] 685.2857. found 685.2866.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-(4-{[methyl-(1-methyl-piperidin-4-yl)-amino]-methyl}-3-trifluoromethyl-phenyl)-acetamide (cmpd 166)

(ESI) m/z 685 [(M+H)$^+$]. HRMS (ESI) calculated for C$_{37}$H$_{40}$F$_3$N$_8$O$_2$$^+$ [(M+H)$^+$] 685.3221. found 685.3221.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-dimethylamino-piperidin-1-ylmethyl)-3-trifluoromethyl-phenyl]-acetamide (cmpd 167)

$^1$H NMR (600 MHz, DMSO-d$_6$) δ ppm 1.31-1.44 (m, 2H) 1.70 (d, J=11.54 Hz, 2H) 1.95 (t, J=10.90 Hz, 2H) 2.05-2.14

(m, 1H) 2.18 (br. s., 5H) 2.78 (d, J=11.72 Hz, 2H) 2.86-2.92 (m, 2H) 3.46 (td, J=6.91, 2.47 Hz, 2H) 3.50 (s, 2H) 3.67 (s, 2H) 3.86 (s, 3H) 7.07 (s, 2H) 7.21 (s, 1H) 7.31-7.41 (m, 3H) 7.52 (s, 1H) 7.53 (s, 1H) 7.66 (d, J=8.61 Hz, 1H) 7.77 (dd, J=8.52, 1.74 Hz, 1H) 8.04 (d, J=2.01 Hz, 1H) 8.43 (s, 1H) 10.47 (s, 1H).

(ESI) m/z 685 [(M+H)$^+$]. HRMS (ESI) calculated for $C_{37}H_{40}F_3N_8O_2^+$ [(M+H)$^+$] 685.3221. found 685.3224.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[3-bromo-4-(4-ethyl-piperazin-1-ylmethyl)-phenyl]-acetamide (cmpd 168)

$^1$H NMR (600 MHz, DMSO-d$_6$) δ ppm 0.97 (t, J=7.14 Hz, 3H) 2.20-2.48 (m, 9H) 2.90 (t, J=6.87 Hz, 2H) 3.43-3.49 (m, 5H) 3.65 (s, 2H) 3.86 (s, 3H) 7.07 (s, 2H) 7.22 (br. s., 1H) 7.37 (br. s., 5H) 7.47-7.50 (m, 1H) 7.51 (s, 1H) 7.53 (s, 1H) 7.96 (d, J=2.01 Hz, 1H) 8.43 (s, 1H) 10.31 (s, 1H).

(ESI) m/z 681 [(M+H)$^+$]. HRMS (ESI) calculated for $C_{35}H_{38}BrN_8O_2^+$ [(M+H)$^+$] 681.2296. found 681.2308.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-{4-[4-(2-hydroxy-ethyl)-piperazin-1-ylmethyl]-3-trifluoromethyl-phenyl}-acetamide dihydrochloride (cmpd 170)

$^1$H NMR (600 MHz, DMSO-d$_6$) δ ppm 2.89-2.94 (m, 2H) 3.71 (s, 2H) 3.75 (t, J=4.67 Hz, 3H) 3.87 (s, 3H) 7.21-7.30 (m, 1H) 7.32-7.41 (m, 3H) 7.54 (s, 1H) 7.64 (d, J=3.85 Hz, 1H) 7.81 (br. s., 1H) 7.88 (d, J=6.96 Hz, 1H) 8.11 (br. s., 1H) 8.46-8.49 (m, 1H) 10.20 (br. s., 1H) 10.71 (br. s., 1H).

(ESI) m/z 687 [(M+H)$^+$]. HRMS (ESI) calculated for $C_{36}H_{40}Cl_2F_3N_8O_3^+$ [(M+H)$^+$] 687.3014. found 687.3027.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-cyclopropylmethyl-piperazin-1-ylmethyl)-3-trifluoromethyl-phenyl]-acetamide (cmpd 171)

$^1$H NMR (600 MHz, DMSO-d$_6$) δ ppm 0.07 (br. s., 2H) 0.45 (br. s., 2H) 0.81 (br. s., 1H) 1.98-2.49 (m, 9H) 2.90 (t, J=6.87 Hz, 2H) 3.43-3.48 (m, 2H) 3.53 (br. s., 2H) 3.67 (s, 2H) 3.86 (s, 3H) 7.07 (s, 2H) 7.21 (s, 1H) 7.32-7.39 (m, 3H) 7.52 (s, 1H) 7.53 (s, 1H) 7.65 (d, J=8.42 Hz, 1H) 7.78 (d, J=8.24 Hz, 1H) 8.04 (d, J=2.01 Hz, 1H) 8.43 (s, 1H) 10.47 (s, 1H).

(ESI) m/z 697 [(M+H)$^+$]. HRMS (ESI) calculated for $C_{38}H_{40}F_3N_8O_2^+$ [(M+H)$^+$] 697.3221. found 697.3225.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(1-methyl-piperidin-4-yloxy)-3-trifluoromethyl-phenyl]-acetamide (cmpd 172)

$^1$H NMR (600 MHz, DMSO-d$_6$) δ ppm 1.66 (d, J=7.88 Hz, 2H) 1.84-1.94 (m, 2H) 2.17 (br. s., 3H) 2.23 (br. s., 2H) 2.90 (t, J=6.87 Hz, 2H) 3.46 (td, J=6.82, 2.47 Hz, 2H) 3.63 (s, 2H) 3.86 (s, 3H) 4.53 (br. s., 1H) 7.07 (s, 2H) 7.22 (br. s., 1H) 7.25 (d, J=8.97 Hz, 1H) 7.31-7.39 (m, 3H) 7.51 (s, 1H) 7.53 (s, 1H) 7.73 (dd, J=8.97, 2.38 Hz, 1H) 7.92 (d, J=2.56 Hz, 1H) 8.43 (s, 1H) 10.28 (s, 1H).

(ESI) m/z 658 [(M+H)$^+$]. HRMS (ESI) calculated for $C_{35}H_{35}F_3N_7O_3^+$ [(M+H)$^+$] 658.2748. found 658.2747.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-ethyl-piperazin-1-yl)-3-trifluoromethyl-phenyl]-acetamide (cmpd 173)

$^1$H NMR (600 MHz, DMSO-d$_6$) δ ppm 0.97-1.06 (m, 3H) 2.30-2.48 (m, 5H) 2.81 (br. s., 4H) 2.90 (t, J=6.87 Hz, 2H) 3.46 (td, J=6.78, 2.38 Hz, 2H) 3.66 (s, 2H) 3.86 (s, 3H) 7.07 (s, 2H) 7.21 (br. s., 1H) 7.31-7.39 (m, 3H) 7.50-7.55 (m, 3H) 7.78 (d, J=8.24 Hz, 1H) 7.99 (d, J=2.20 Hz, 1H) 8.43 (s, 1H) 10.41 (s, 1H).

(ESI) m/z 657 [(M+H)$^+$]. HRMS (ESI) calculated for $C_{35}H_{36}F_3N_8O_2^+$ [(M+H)$^+$] 657.2908. found 657.2908.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(1-methyl-piperidin-4-ylamino)-3-trifluoromethyl-phenyl]-acetamide (cmpd 177)

$^1$H NMR (600 MHz, DMSO-d$_6$) δ ppm 1.48 (q, J=9.83 Hz, 2H) 1.86 (d, J=10.99 Hz, 2H) 2.06 (d, J=7.51 Hz, 2H) 2.16 (s, 3H) 2.66 (br. s., 2H) 2.90 (t, J=6.87 Hz, 2H) 3.46 (td, J=6.69, 2.20 Hz, 2H) 3.60 (s, 2H) 3.85 (s, 3H) 4.36 (d, J=7.69 Hz, 1H) 6.88 (d, J=9.16 Hz, 1H) 7.07 (s, 2H) 7.21 (br. s., 1H) 7.29-7.39 (m, 3H) 7.50 (s, 1H) 7.53 (s, 1H) 7.55 (d, J=8.97 Hz, 1H) 7.79 (d, J=2.20 Hz, 1H) 8.43 (s, 1H) 10.08 (s, 1H).

(ESI) m/z 657 [(M+H)$^+$]. HRMS (ESI) calculated for $C_{35}H_{36}F_3N_8O_2^+$ [(M+H)$^+$] 657.2908. found 657.2915.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-{4-[methyl-(1-methyl-piperidin-4-yl)-amino]-3-trifluoromethyl-phenyl}-acetamide (cmpd 178)

$^1$H NMR (600 MHz, DMSO-d$_6$) δ ppm 1.30-1.42 (m, 2H) 1.63 (d, J=11.17 Hz, 2H) 1.85 (br. s., 2H) 2.14 (br. s., 3H) 2.62-2.79 (m, 3H) 2.90 (t, J=6.87 Hz, 2H) 3.44-3.49 (m, 2H) 3.66 (s, 2H) 3.86 (s, 3H) 7.07 (s, 2H) 7.22 (br. s., 1H) 7.30-7.38 (m, 3H) 7.50 (d, J=6.04 Hz, 3H) 7.77-7.81 (m, 1H) 7.98 (d, J=2.01 Hz, 1H) 8.43 (s, 1H) 10.42 (s, 1H).

(ESI) m/z 671 [(M+H)$^+$]. HRMS (ESI) calculated for $C_{36}H_{38}F_3N_8O_2^+$ [(M+H)$^+$] 671.3065. found 671.3066.

2-(3-{2-Amino-4-[1-(2-hydroxy-ethyl)-4-oxo-4,5,6,7-tetrahydro-1H-pyrrolo[3,2-c]pyridin-2-yl]-pyrimidin-5-ylethynyl}-phenyl)-N-(4-chloro-3-trifluoromethyl-phenyl)-acetamide (cmpd 180)

$^1$H NMR (600 MHz, DMSO-d$_6$) δ ppm 2.95 (t, J=6.87 Hz, 2H) 3.44 (td, J=6.82, 2.47 Hz, 3H) 3.64 (q, J=5.68 Hz, 2H) 3.70 (s, 2H) 4.50 (t, J=5.59 Hz, 2H) 4.83 (t, J=5.49 Hz, 1H) 7.02 (br. s., 2H) 7.23 (s, 1H) 7.30-7.41 (m, 4H) 7.55 (s, 1H) 7.65 (d, J=8.79 Hz, 1H) 7.67 (s, 1H) 7.84 (dd, J=8.79, 2.56 Hz, 1H) 8.18 (d, J=2.38 Hz, 1H) 8.43 (s, 1H) 10.63 (s, 1H).

(ESI) m/z 609 [(M+H)$^+$]. HRMS (ESI) calculated for $C_{30}H_{25}ClF_3N_6O_3^+$ [(M+H)$^+$] 609.1624. found 609.1634.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[3-trifluoromethyl-4-((2S,5R)-2,4,5-trimethyl-piperazin-1-ylmethyl)-phenyl]-acetamide (cmpd 181)

$^1$H NMR (600 MHz, DMSO-d$_6$) δ ppm 0.83 (d, J=6.23 Hz, 3H) 0.99 (d, J=6.04 Hz, 3H) 1.76 (t, J=10.71 Hz, 1H)

1.90 (d, J=11.36 Hz, 2H) 2.11 (br. s., 3H) 2.34-2.43 (m, 2H) 2.66 (d, J=10.62 Hz, 1H) 2.90 (t, J=6.87 Hz, 2H) 3.09 (d, J=15.20 Hz, 1H) 3.46 (td, J=6.82, 2.47 Hz, 2H) 3.67 (s, 2H) 3.86 (s, 3H) 4.04 (d, J=14.84 Hz, 1H) 7.07 (s, 2H) 7.21 (br. s., 1H) 7.30-7.40 (m, 3H) 7.52 (s, 1H) 7.53 (s, 1H) 7.69-7.72 (m, 1H) 7.75-7.78 (m, 1H) 8.04 (d, J=2.01 Hz, 1H) 8.43 (s, 1H) 10.46 (s, 1H).

(ESI) m/z 685 [(M+H)$^+$]. HRMS (ESI) calculated for $C_{37}H_{40}F_3N_8O_2^+$ [(M+H)$^+$] 685.3221. found 685.3231.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[3-trifluoromethyl-4-(3,4,5-trimethyl-piperazin-1-ylmethyl)-phenyl]-acetamide (cmpd 182)

$^1$H NMR (600 MHz, DMSO-d$_6$) δ ppm 0.95 (br. s., 5H) 1.81 (br. s., 2H) 2.16 (d, J=15.02 Hz, 4H) 2.55-2.70 (m, 2H) 2.90 (t, J=6.87 Hz, 2H) 3.42-3.50 (m, 4H) 3.67 (s, 2H) 3.86 (s, 3H) 7.07 (s, 2H) 7.22 (s, 1H) 7.30-7.39 (m, 3H) 7.52 (s, 1H) 7.53 (s, 1H) 7.64 (d, J=8.43 Hz, 1H) 7.78 (d, J=8.24 Hz, 1H) 8.03 (d, J=2.01 Hz, 1H) 8.43 (s, 1H) 10.48 (s, 1H).

(ESI) m/z 685 [(M+H)$^+$]. HRMS (ESI) calculated for $C_{37}H_{40}F_3N_8O_2^+$ [(M+H)$^+$] 685.3221. found 685.3224.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-(4-piperazin-1-ylmethyl-3-trifluoromethyl-phenyl)-acetamide (cmpd 183)

$^1$H NMR (600 MHz, DMSO-d$_6$) δ ppm 2.28 (br. s., 4H) 2.69 (br. s., 4H) 2.90 (t, J=6.87 Hz, 2H) 3.46 (td, J=6.91, 2.47 Hz, 2H) 3.49 (s, 2H) 3.67 (s, 2H) 3.85 (s, 3H) 7.07 (s, 2H) 7.21 (br. s., 1H) 7.30-7.39 (m, 3H) 7.52 (s, 1H) 7.53 (s, 1H) 7.66 (d, J=8.61 Hz, 1H) 7.77 (dd, J=8.61, 1.65 Hz, 1H) 8.04 (d, J=1.83 Hz, 1H) 8.43 (s, 1H) 10.46 (s, 1H).

(ESI) m/z 643 [(M+H)$^+$]. HRMS (ESI) calculated for $C_{34}H_{34}F_3N_8O_2^+$ [(M+H)$^+$] 643.2752. found 643.2770.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(3-oxo-piperazin-1-ylmethyl)-3-trifluoromethyl-phenyl]-acetamide (cmpd 184)

$^1$H NMR (600 MHz, DMSO-d$_6$) δ ppm 2.52-2.54 (m, 2H) 2.90 (t, J=6.87 Hz, 2H) 2.94 (s, 2H) 3.10-3.15 (m, 2H) 3.46 (td, J=6.82, 2.47 Hz, 2H) 3.61 (s, 2H) 3.68 (s, 2H) 3.85 (s, 3H) 7.07 (s, 2H) 7.21 (s, 1H) 7.26-7.40 (m, 3H) 7.52 (s, 1H) 7.53 (s, 1H) 7.66 (d, J=8.61 Hz, 1H) 7.74 (s, 1H) 7.80 (dd, J=8.52, 1.74 Hz, 1H) 8.06 (d, J=2.01 Hz, 1H) 8.43 (s, 1H) 10.49 (s, 1H).

(ESI) m/z 657 [(M+H)$^+$]. HRMS (ESI) calculated for $C_{34}H_{32}F_3N_8O_3^+$ [(M+H)$^+$] 657.2544. found 657.2536.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(3-hydroxy-piperidin-1-ylmethyl)-3-trifluoromethyl-phenyl]-acetamide (cmpd 185)

$^1$H NMR (600 MHz, DMSO-d$_6$) δ ppm 1.02-1.12 (m, 1H) 1.41 (d, J=12.45 Hz, 1H) 1.56-1.64 (m, 1H) 1.73 (t, J=9.71 Hz, 1H) 1.79 (d, J=8.79 Hz, 1H) 1.89 (t, J=10.26 Hz, 1H) 2.55-2.62 (m, 1H) 2.72 (d, J=8.97 Hz, 1H) 2.88-2.91 (m, 2H) 3.40-3.49 (m, 4H) 3.53-3.57 (m, 1H) 3.67 (s, 2H) 3.85 (s, 3H) 4.55 (d, J=4.95 Hz, 1H) 7.07 (s, 2H) 7.21 (s, 1H) 7.32-7.37 (m, 3H) 7.52 (s, 1H) 7.53 (s, 1H) 7.66 (d, J=8.43 Hz, 1H) 7.77 (d, J=8.61 Hz, 1H) 8.03 (d, J=1.83 Hz, 1H) 8.43 (s, 1H) 10.46 (s, 1H).

(ESI) m/z 658 [(M+H)$^+$]. HRMS (ESI) calculated for $C_{35}H_{35}F_3N_7O_3^+$ [(M+H)$^+$] 658.2748. found 658.2747.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-cyclopropyl-acetamide (cmpd 186)

$^1$H NMR (600 MHz, DMSO-d$_6$) δ ppm 0.36-0.42 (m, 2H) 0.56-0.61 (m, 2H) 2.59-2.64 (m, 1H) 2.89 (t, J=6.87 Hz, 2H) 3.35 (s, 2H) 3.46 (td, J=6.87, 2.38 Hz, 2H) 3.85 (s, 3H) 7.07 (s, 2H) 7.18 (br. s., 1H) 7.22-7.26 (m, 1H) 7.29-7.34 (m, 2H) 7.41 (s, 1H) 7.51 (s, 1H) 8.13 (d, J=4.21 Hz, 1H) 8.43 (s, 1H).

(ESI) m/z 441 [(M+H)$^+$]. HRMS (ESI) calculated for $C_{25}H_{25}N_6O_2^+$ [(M+H)$^+$] 441.2034. found 441.2025.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-methyl-2-oxo-piperazin-1-ylmethyl)-3-trifluoromethyl-phenyl]-acetamide (cmpd 187)

$^1$H NMR (600 MHz, DMSO-d$_6$) δ ppm 2.23 (s, 3H) 2.57-2.63 (m, 2H) 2.90 (t, J=6.87 Hz, 2H) 3.06 (s, 2H) 3.18 (t, J=5.40 Hz, 2H) 3.46 (td, J=6.87, 2.56 Hz, 2H) 3.68 (s, 2H) 3.85 (s, 3H) 4.62 (s, 2H) 7.07 (s, 2H) 7.21 (s, 1H) 7.24 (d, J=8.61 Hz, 1H) 7.32-7.39 (m, 3H) 7.51 (s, 1H) 7.53 (s, 1H) 7.75-7.80 (m, 1H) 8.11 (d, J=1.83 Hz, 1H) 8.43 (s, 1H) 10.52 (s, 1H).

(ESI) m/z 671 [(M+H)$^+$]. HRMS (ESI) calculated for $C_{35}H_{34}F_3N_8O_3^+$ [(M+H)$^+$] 671.2701. found 671.2691.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-[4-(4-hydroxy-piperidin-1-ylmethyl)-3-trifluoromethyl-phenyl]-acetamide (cmpd 188)

$^1$H NMR (600 MHz, DMSO-d$_6$) δ ppm 1.33-1.42 (m, 2H) 1.69 (d, J=9.52 Hz, 2H) 2.00-2.08 (m, 2H) 2.60-2.66 (m, 2H) 2.90 (t, J=6.87 Hz, 2H) 3.46 (td, J=6.78, 2.56 Hz, 3H) 3.49 (s, 2H) 3.67 (s, 2H) 3.86 (s, 3H) 4.53 (d, J=4.21 Hz, 1H) 7.07 (s, 2H) 7.21 (br. s., 1H) 7.30-7.39 (m, 3H) 7.52 (s, 1H) 7.53 (s, 1H) 7.65 (d, J=8.43 Hz, 1H) 7.77 (d, J=8.43 Hz, 1H) 8.03 (d, J=2.01 Hz, 1H) 8.42-8.45 (m, 1H) 10.46 (s, 1H).

(ESI) m/z 658 [(M+H)$^+$]. HRMS (ESI) calculated for $C_{35}H_{35}F_3N_7O_3^+$ [(M+H)$^+$] 658.2748. found 658.2752.

2-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-N-(4-{[(2-hydroxy-ethyl)-methyl-amino]-methyl}-3-trifluoromethyl-phenyl)-acetamide (cmpd 189)

$^1$H NMR (600 MHz, DMSO-d$_6$) δ ppm 2.15 (s, 3H) 2.44 (t, J=6.23 Hz, 2H) 2.90 (t, J=6.87 Hz, 2H) 3.46 (td, J=6.82, 2.29 Hz, 2H) 3.50 (q, J=5.98 Hz, 2H) 3.57 (s, 2H) 3.67 (s, 2H) 3.86 (s, 3H) 4.37 (t, J=5.40 Hz, 1H) 7.07 (s, 2H) 7.21 (br. s., 1H) 7.32-7.39 (m, 4H) 7.52 (s, 1H) 7.53 (s, 1H) 7.70-7.75 (m, 1H) 7.76-7.79 (m, 1H) 8.03 (s, 1H) 8.42-8.45 (m, 1H) 10.46 (s, 1H).

(ESI) m/z 632 [(M+H)⁺]. HRMS (ESI) calculated for $C_{33}H_{33}F_3N_7O_3^+$ [(M+H)⁺] 632.2592. found 632.2602.

2-(3-{2-Amino-4-[1-(2-hydroxy-ethyl)-4-oxo-4,5,6,7-tetrahydro-1H-pyrrolo[3,2-c]pyridin-2-yl]-pyrimidin-5-ylethynyl}-phenyl)-N-[4-(4-ethyl-piperazin-1-ylmethyl)-3-trifluoromethyl-phenyl]-acetamide (cmpd 191)

¹H NMR (600 MHz, DMSO-d₆) δ ppm 0.99 (br. s., 3H) 2.38 (br. s., 10H) 2.95 (t, J=6.87 Hz, 2H) 3.44 (td, J=6.78, 2.38 Hz, 2H) 3.53 (s, 2H) 3.64 (q, J=5.56 Hz, 2H) 3.68 (s, 2H) 4.50 (t, J=5.59 Hz, 1H) 4.83 (t, J=5.49 Hz, 1H) 7.02 (br. s., 2H) 7.23 (br. s., 1H) 7.29-7.42 (m, 4H) 7.55 (s, 1H) 7.65 (d, J=8.61 Hz, 1H) 7.68 (s, 1H) 7.78 (d, J=8.61 Hz, 1H) 8.04 (d, J=1.83 Hz, 1H) 8.43 (s, 1H) 10.48 (s, 1H).

(ESI) m/z 701 [(M+H)⁺]. HRMS (ESI) calculated for $C_{37}H_{40}F_3N_8O_3^+$ [(M+H)⁺] 701.3170. found 701.3159.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-{[(2,3-dihydroxy-propyl)-methyl-amino]-methyl}-3-trifluoromethyl-phenyl)-acetamide (cmpd 192)

¹H NMR (600 MHz, DMSO-d₆) δ ppm 2.14 (s, 3H) 2.30 (dd, J=12.55, 6.87 Hz, 1H) 2.44 (dd, J=12.45, 5.13 Hz, 1H) 2.90 (t, J=6.78 Hz, 2H) 3.23-3.29 (m, 1H) 3.33-3.37 (m, 2H) 3.46 (td, J=6.73, 2.29 Hz, 2H) 3.53-3.64 (m, 3H) 3.67 (s, 2H) 3.86 (s, 3H) 4.38 (d, J=4.58 Hz, 1H) 4.42 (t, J=5.40 Hz, 1H) 7.07 (s, 2H) 7.21 (br. s., 1H) 7.31-7.40 (m, 3H) 7.52 (s, 1H) 7.53 (s, 1H) 7.71-7.75 (m, 1H) 7.76-7.80 (m, 1H) 8.03 (s, 1H) 8.44 (s, 1H) 10.46 (s, 1H).

(ESI) m/z 662 [(M+H)⁺]. HRMS (ESI) calculated for $C_{34}H_{35}F_3N_7O_4^+$ [(M+H)⁺] 662.2697. found 662.2684.

2-{3-[2-Acetylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (cmpd 200)

¹H NMR (600 MHz, DMSO-d₆) δ ppm 2.15-2.20 (m, 6H) 2.23-2.48 (m, 8H) 2.92 (t, J=6.78 Hz, 2H) 3.47 (td, J=6.87, 2.38 Hz, 2H) 3.52 (s, 2H) 3.70 (s, 2H) 3.98 (s, 3H) 7.27 (br. s., 1H) 7.37-7.46 (m, 3H) 7.60 (s, 1H) 7.64 (d, J=8.61 Hz, 1H) 7.73 (s, 1H) 7.78 (d, J=8.43 Hz, 1H) 8.04 (d, J=1.65 Hz, 1H) 8.78 (s, 1H) 10.48 (s, 1H) 10.75 (s, 1H).

(ESI) m/z 699 [(M+H)⁺]. HRMS (ESI) calculated for $C_{37}H_{38}F_3N_8O_3^+$ [(M+H)⁺] 699.3014. found 699.3002.

3-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-benzenesulfonamide (cmpd 75)

¹H NMR (600 MHz, DMSO-d₆) δ ppm 0.96 (t, J=7.05 Hz, 3H) 2.12-2.48 (m, 10H) 2.91 (t, J=6.87 Hz, 2H) 3.44-3.51 (m, 5H) 3.85 (s, 3H) 7.17 (s, 2H) 7.34 (s, 1H) 7.36-7.41 (m, 2H) 7.45 (s, 1H) 7.54-7.62 (m, 2H) 7.65 (d, J=7.88 Hz, 1H) 7.69-7.72 (m, 1H) 7.82 (s, 1H) 8.46 (s, 1H).

(ESI) m/z 693 [(M+H)⁺]. HRMS (ESI) calculated for $C_{34}H_{36}F_3N_8O_3S^+$ [(M+H)⁺] 693.2578. found 693.2571.

3-[2-Amino-4-(1-methyl-4-oxo-4,5,6,7-tetrahydro-1H-pyrrolo[3,2-c]pyridin-2-yl)-pyrimidin-5-ylethynyl]-N-cyclopropyl-benzenesulfonamide hydrochloride (cmpd 76)

¹H NMR (600 MHz, DMSO-d₆) δ ppm 0.31-0.42 (m, 2H) 0.47-0.53 (m, 2H) 2.14 (td, J=6.59, 3.11 Hz, 1H) 2.91 (t, J=6.78 Hz, 2H) 3.86 (s, 3H) 7.09-7.46 (m, 2H) 7.53 (s, 1H) 7.63-7.68 (m, 1H) 7.72 (d, J=7.69 Hz, 1H) 7.79 (d, J=7.69 Hz, 1H) 7.86 (s, 1H) 7.96 (d, J=2.56 Hz, 1H) 8.52 (s, 1H).

(ESI) m/z 463 [(M+H)⁺]. HRMS (ESI) calculated for $C_{23}H_{24}ClN_6O_3S^+$ [(M+H)⁺] 463.1547. found 463.1538.

N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-4-trifluoromethyl-benzamide (cmpd 57)

¹H NMR (600 MHz, DMSO-d₆) δ ppm 2.90 (t, J=6.84 Hz, 2H) 3.46 (td, J=6.87, 2.50 Hz, 2H) 3.86 (s, 3H) 7.08 (s, 2H) 7.14 (s, 1H) 7.24 (dt, J=7.81, 1.22 Hz, 1H) 7.41 (t, J=7.93 Hz, 1H) 7.47 (s, 1H) 7.83 (ddd, J=8.27, 2.11, 0.98 Hz, 1H) 7.91-7.96 (m, 3H) 8.19 (d, J=8.18 Hz, 2H) 8.46 (s, 1H) 10.48 (s, 1H). (ESI) m/z 531 [(M+H)⁺]. HRMS (ESI) calculated for $C_{28}H_{22}F_3N_6O_2^+$ [(M+H)⁺] 531.1751. found 531.1742.

N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-2-(4-trifluoromethyl-phenyl)-acetamide (cmpd 58)

¹H NMR (600 MHz, DMSO-d₆) δ ppm 2.89 (t, J=6.84 Hz, 2H) 3.44 (td, J=6.84, 2.32 Hz, 2H) 3.79 (s, 2H) 3.84 (s, 3H) 7.07 (s, 2H) 7.16 (d, J=7.81 Hz, 2H) 7.33 (t, J=7.99 Hz, 1H) 7.42 (s, 1H) 7.54-7.59 (m, 3H) 7.67-7.72 (m, 2H) 7.74 (s, 1H) 8.43 (s, 1H) 10.31 (s, 1H).

(ESI) m/z 545 [(M+H)⁺]. HRMS (ESI) calculated for $C_{29}H_{24}F_3N_6O_2^+$ [(M+H)⁺] 545.1907. found 545.1932.

2-{3-[2-Amino-4-(1-methyl-4-oxo-4,5,6,7-tetrahydro-1H-pyrrolo[3,2-c]pyridin-2-yl)-pyrimidin-5-ylethynyl]-phenoxy}-N-phenyl-acetamide hydrochloride (cmpd 59)

¹H NMR (600 MHz, DMSO-d₆) δ ppm 2.91 (t, J=6.77 Hz, 2H) 3.86 (s, 3H) 4.75-4.78 (m, 2H) 7.01-7.14 (m, 5H) 7.29-7.38 (m, 4H) 7.63 (t, J=4.09 Hz, 4H) 8.47 (s, 1H) 10.13 (s, 1H).

(ESI) m/z 493 [(M+H)⁺]. HRMS (ESI) calculated for $C_{28}H_{26}ClN_6O_3^+$ [(M+H)⁺] 493.1983. found 493.1985.

Cyclopropane-1,1-dicarboxylic acid {3-[2-amino-4-(1-methyl-4-oxo-4,5,6,7-tetrahydro-1H-pyrrolo[3,2-c]pyridin-2-yl)-pyrimidin-5-ylethynyl]-phenyl}-amide phenylamide (cmpd 60)

¹H NMR (600 MHz, DMSO-d₆) δ ppm 1.47 (d, J=3.54 Hz, 4H) 2.89 (t, J=6.96 Hz, 2H) 3.44 (td, J=6.74, 2.01 Hz, 2H) 3.85 (s, 3H) 7.00-7.08 (m, 3H) 7.10 (br. s., 1H) 7.17 (d, J=7.81 Hz, 1H) 7.26-7.35 (m, 3H) 7.43 (s, 1H) 7.57 (d, J=8.54 Hz, 1H) 7.61 (d, J=8.18 Hz, 2H) 7.80 (s, 1H) 8.43 (s, 1H) 10.02 (s, 1H) 10.08 (s, 1H).

(ESI) m/z 546 [(M+H)⁺]. HRMS (ESI) calculated for $C_{31}H_{28}N_7O_3^+$ [(M+H)⁺] 546.2248. found 546.2250.

2-[2-Amino-5-(3-phenethyloxy-phenylethynyl)-pyrimidin-4-yl]-1-methyl-1,5,6,7-tetrahydro-pyrrolo[3,2-c]pyridin-4-one (cmpd 61)

$^1$H NMR (600 MHz, DMSO-d$_6$) δ ppm 2.88 (t, J=6.96 Hz, 2H) 3.03 (t, J=6.59 Hz, 2H) 3.41-3.47 (m, 2H) 3.85 (s, 3H) 4.20-4.26 (m, 2H) 6.93 (dd, J=8.36, 2.38 Hz, 1H) 7.01 (d, J=5.98 Hz, 2H) 7.06 (s, 2H) 7.10 (br. s., 1H) 7.18-7.24 (m, 1H) 7.26-7.37 (m, 6H) 8.43 (s, 1H).

(ESI) m/z 464 [(M+H)$^+$]. HRMS (ESI) calculated for C$_{28}$H$_{26}$N$_5$O$_2^+$ [(M+H)$^+$] 464.2081. found 464.2076.

N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-2-phenyl-acetamide (cmpd 62)

$^1$H NMR (600 MHz, DMSO-d$_6$) δ ppm 2.89 (t, J=6.90 Hz, 2H) 3.42-3.47 (m, 3H) 3.64-3.66 (m, 2H) 3.83-3.86 (m, 3H) 7.06 (s, 2H) 7.11-7.17 (m, 2H) 7.21-7.28 (m, 1H) 7.29-7.37 (m, 5H) 7.42 (s, 1H) 7.58 (dd, J=8.30, 1.10 Hz, 1H) 7.75 (t, J=1.65 Hz, 1H) 8.43 (s, 1H) 10.23 (s, 1H).

(ESI) m/z 477 [(M+H)$^+$]. HRMS (ESI) calculated for C$_{28}$H$_{25}$N$_6$O$_2^+$ [(M+H)$^+$] 477.2034. found 477.2035.

N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-phenyl-propionamide (cmpd 63)

$^1$H NMR (600 MHz, DMSO-d$_6$) δ ppm 2.64 (t, J=7.69 Hz, 2H) 2.83-2.95 (m, 5H) 3.44 (td, J=6.82, 2.47 Hz, 2H) 3.84 (s, 3H) 7.07 (s, 2H) 7.10-7.15 (m, 2H) 7.16-7.20 (m, 1H) 7.22-7.33 (m, 5H) 7.41 (s, 1H) 7.54 (d, J=8.24 Hz, 1H) 7.74 (s, 1H) 8.45 (s, 1H) 9.98 (s, 1H).

(ESI) m/z 491 [(M+H)$^+$]. HRMS (ESI) calculated for C$_{29}$H$_{27}$N$_6$O$_2^+$ [(M+H)$^+$] 491.2190. found 491.2190.

(1R,2R)-2-Phenyl-cyclopropanecarboxylic acid {3-[2-amino-4-(1-methyl-4-oxo-4,5,6,7-tetrahydro-1H-pyrrolo[3,2-c]pyridin-2-yl)-pyrimidin-5-ylethynyl]-phenyl}-amide (cmpd 64)

$^1$H NMR (600 MHz, DMSO-d$_6$) δ ppm 1.35-1.53 (m, 2H) 2.04-2.09 (m, 1H) 2.36-2.42 (m, 1H) 2.89 (t, J=6.96 Hz, 2H) 3.44 (td, J=6.78, 2.56 Hz, 2H) 3.84 (s, 3H) 7.07 (s, 2H) 7.11 (br. s., 1H) 7.14 (d, J=7.88 Hz, 1H) 7.17-7.22 (m, 3H) 7.27-7.35 (m, 3H) 7.41 (s, 1H) 7.53-7.58 (m, 1H) 7.75 (s, 1H) 8.44 (s, 1H) 10.32 (s, 1H).

(ESI) m/z 503 [(M+H)$^+$]. HRMS (ESI) calculated for C$_{30}$H$_{27}$N$_6$O$_2^+$ [(M+H)$^+$] 503.2190. found 503.2188.

2-{2-Amino-5-[3-(3-phenyl-propoxy)-phenylethynyl]-pyrimidin-4-yl}-1-methyl-1,5,6,7-tetrahydro-pyrrolo[3,2-c]pyridin-4-one (cmpd 65)

$^1$H NMR (600 MHz, DMSO-d$_6$) δ ppm 1.98-2.05 (m, 2H) 2.72-2.76 (m, 2H) 2.89 (t, J=6.87 Hz, 2H) 3.44 (td, J=6.78, 2.38 Hz, 2H) 3.85 (s, 3H) 4.01 (t, J=6.41 Hz, 2H) 6.94 (dd, J=8.24, 2.38 Hz, 1H) 7.00 (s, 1H) 7.03 (d, J=7.51 Hz, 1H) 7.07 (s, 2H) 7.12 (br. s., 1H) 7.16-7.20 (m, 1H) 7.23-7.25 (m, 2H) 7.27-7.30 (m, 3H) 7.51 (s, 1H) 8.43 (s, 1H).

(ESI) m/z 478 [(M+H)$^+$]. HRMS (ESI) calculated for C$_{29}$H$_{28}$N$_5$O$_2^+$ [(M+H)$^+$] 478.2238. found 478.2243.

N-{3-[2-Amino-4-(1-methyl-4-oxo-4,5,6,7-tetrahydro-1H-pyrrolo[3,2-c]pyridin-2-yl)-pyrimidin-5-ylethynyl]-benzyl}-benzamide hydrochloride (cmpd 66)

$^1$H NMR (600 MHz, DMSO-d$_6$) δ ppm 2.90 (t, J=6.69 Hz, 2H) 3.86 (s, 3H) 4.49 (d, J=5.86 Hz, 2H) 7.25 (br. s., 1H) 7.31-7.41 (m, 3H) 7.43-7.56 (m, 5H) 7.62 (s, 1H) 7.90 (d, J=7.69 Hz, 2H) 8.47 (d, J=1.65 Hz, 1H) 9.07 (t, J=5.68 Hz, 1H).

(ESI) m/z 477 [(M+H)$^+$]. HRMS (ESI) calculated for C$_{28}$H$_{26}$ClN$_6$O$_2^+$ [(M+H)$^+$] 477.1983. found 477.1985.

3-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-phenyl-propionamide (cmpd 67)

$^1$H NMR (600 MHz, DMSO-d$_6$) δ ppm 2.67 (t, J=7.69 Hz, 2H) 2.89-2.96 (m, 4H) 3.46 (td, J=6.87, 2.56 Hz, 2H) 3.84-3.88 (m, 3H) 6.97-7.04 (m, 2H) 7.06 (s, 2H) 7.21 (br. s., 1H) 7.24-7.34 (m, 5H) 7.42 (s, 1H) 7.54 (s, 1H) 7.56 (d, J=7.69 Hz, 2H) 8.42 (s, 1H) 9.95 (s, 1H).

(ESI) m/z 491 [(M+H)$^+$]. HRMS (ESI) calculated for C$_{29}$H$_{27}$N$_6$O$_2^+$ [(M+H)$^+$] 491.2190. found 491.2193.

Cyclopropane-1,1-dicarboxylic acid {3-[2-amino-4-(1-methyl-4-oxo-4,5,6,7-tetrahydro-1H-pyrrolo[3,2-c]pyridin-2-yl)-pyrimidin-5-ylethynyl]-phenyl}-amide (4-trifluoromethyl-phenyl)-amide hydrochloride (cmpd 68)

$^1$H NMR (600 MHz, DMSO-d$_6$) δ ppm 1.44-1.51 (m, 4H) 2.91 (t, J=6.96 Hz, 2H) 3.86 (s, 3H) 7.19 (d, J=7.69 Hz, 2H) 7.34 (t, J=7.97 Hz, 1H) 7.54 (s, 1H) 7.56-7.59 (m, 1H) 7.66 (d, J=8.61 Hz, 2H) 7.83 (s, 1H) 7.86 (d, J=8.42 Hz, 2H) 8.48 (s, 1H) 10.01 (s, 1H) 10.48 (s, 1H).

(ESI) m/z 614 [(M+H)$^+$]. HRMS (ESI) calculated for C$_{32}$H$_{28}$ClF$_3$N$_7$O$_3^+$ [(M+H)$^+$] 614.2122. found 614.2136.

2-[2-Amino-5-(3-benzyloxymethyl-phenylethynyl)-pyrimidin-4-yl]-1-methyl-1,5,6,7-tetrahydro-pyrrolo[3,2-c]pyridin-4-one (cmpd 69)

$^1$H NMR (600 MHz, DMSO-d$_6$) δ ppm 2.89 (t, J=6.87 Hz, 2H) 3.44 (td, J=6.87, 2.38 Hz, 2H) 3.85 (s, 3H) 4.54 (s, 2H) 4.55 (s, 2H) 7.07 (s, 2H) 7.13 (br. s., 1H) 7.29 (td, J=5.40, 3.11 Hz, 1H) 7.33-7.38 (m, 5H) 7.38-7.41 (m, 2H) 7.47 (s, 1H) 7.50 (s, 1H) 8.44 (s, 1H).

(ESI) m/z 464 [(M+H)$^+$]. HRMS (ESI) calculated for C$_{28}$H$_{26}$N$_5$O$_2^+$ [(M+H)$^+$] 464.2081. found 464.2076.

2-{2-Amino-5-[3-(benzylamino-methyl)-phenylethynyl]-pyrimidin-4-yl}-1-methyl-1,5,6,7-tetrahydro-pyrrolo[3,2-c]pyridin-4-one dihydrochloride (cmpd 70)

$^1$H NMR (600 MHz, DMSO-d$_6$) δ ppm 2.91 (t, J=6.87 Hz, 2H) 3.86 (s, 3H) 4.20 (q, J=5.98 Hz, 4H) 7.25 (br. s., 1H) 7.41-7.46 (m, 2H) 7.49 (quin, J=7.92 Hz, 2H) 7.53-7.56 (m, 2H) 7.58 (s, 1H) 7.73 (s, 1H) 8.46 (s, 1H) 9.46 (br. s., 1H).

(ESI) m/z 463 [(M+H)$^+$]. HRMS (ESI) calculated for C$_{28}$H$_{29}$Cl$_2$N$_6$O$^+$ [(M+H)$^+$] 463.2241. found 463.2241.

N-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-2-(3-trifluoromethyl-phenyl)-acetamide hydrochloride (cmpd 71)

$^1$H NMR (600 MHz, DMSO-d$_6$) δ ppm 3.80 (s, 2H) 3.85 (s, 3H) 7.17 (d, J=7.69 Hz, 2H) 7.34 (t, J=7.88 Hz, 1H) 7.50 (s, 1H) 7.52-7.66 (m, 7H) 7.70 (s, 1H) 7.77 (s, 1H) 7.77-7.77 (m, 1H) 8.46 (s, 1H) 10.35 (s, 1H).

(ESI) m/z 545 [(M+H)$^+$]. HRMS (ESI) calculated for C$_{29}$H$_{25}$ClF$_3$N$_6$O$_2{}^+$ [(M+H)$^+$] 545.1908. found 545.1922.

N-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-(4-trifluoromethyl-phenyl)-propionamide hydrochloride (cmpd 72)

$^1$H NMR (600 MHz, DMSO-d$_6$) δ ppm 2.69 (t, J=7.60 Hz, 2H) 2.90 (t, J=6.96 Hz, 2H) 3.01 (t, J=7.42 Hz, 2H) 3.85 (s, 3H) 7.16 (d, J=7.69 Hz, 2H) 7.32 (t, J=7.88 Hz, 1H) 7.48-7.50 (m, 2H) 7.51-7.55 (m, 2H) 7.65 (d, J=8.24 Hz, 2H) 7.77 (s, 1H) 8.48 (s, 1H) 10.06 (s, 1H).

(ESI) m/z 559 [(M+H)$^+$]. HRMS (ESI) calculated for C$_{30}$H$_{27}$ClF$_3$N$_6$O$_2{}^+$ [(M+H)$^+$] 559.2064. found 559.2080.

N-{3-[2-Amino-4-(1-methyl-4-oxo-4,5,6,7-tetra-hydro-1H-pyrrolo[3,2-c]pyridin-2-yl)-pyrimidin-5-ylethynyl]-phenyl}-3-(3-trifluoromethyl-phenyl)-propionamide hydrochloride (cmpd 73)

$^1$H NMR (600 MHz, DMSO-d$_6$) δ ppm 2.69 (t, J=7.60 Hz, 2H) 2.90 (t, J=6.87 Hz, 2H) 3.01 (t, J=7.69 Hz, 2H) 3.85 (s, 3H) 7.16 (d, J=7.88 Hz, 1H) 7.18 (br. s., 1H) 7.32 (t, J=7.97 Hz, 1H) 7.50-7.59 (m, 5H) 7.62 (s, 1H) 7.75 (s, 1H) 8.48 (s, 1H) 10.04 (s, 1H).

(ESI) m/z 559 [(M+H)$^+$]. HRMS (ESI) calculated for C$_{30}$H$_{27}$ClF$_3$N$_6$O$_2{}^+$ [(M+H)$^+$] 559.2064. found 559.2079.

3-[2-Amino-4-(1-methyl-4-oxo-4,5,6,7-tetrahydro-1H-pyrrolo[3,2-c]pyridin-2-yl)-pyrimidin-5-ylethynyl]-N-(3-trifluoromethyl-benzyl)-benzamide hydrochloride (cmpd 74)

$^1$H NMR (600 MHz, DMSO-d$_6$) δ ppm 2.87-2.94 (m, 2H) 3.86 (s, 3H) 4.58 (d, J=5.86 Hz, 2H) 7.27 (br. s., 2H) 7.51-7.67 (m, 7H) 7.69 (s, 1H) 7.88 (d, J=7.88 Hz, 1H) 7.97 (s, 1H) 8.48 (s, 1H) 9.22 (t, J=5.95 Hz, 1H).

(ESI) m/z 545 [(M+H)$^+$]. HRMS (ESI) calculated for C$_{29}$H$_{25}$ClF$_3$N$_6$O$_2{}^+$ [(M+H)$^+$] 545.1908. found 545.1925.

3-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-benzamide (cmpd 48)

$^1$H NMR (600 MHz, DMSO-d$_6$) δ ppm 1.00 (t, J=6.96 Hz, 3H) 2.22-2.54 (m, 10H) 2.89 (t, J=6.87 Hz, 2H) 3.45 (td, J=6.82, 2.47 Hz, 2H) 3.58 (s, 2H) 3.86 (s, 3H) 7.06-7.16 (m, 3H) 7.51 (s, 1H) 7.59 (t, J=7.78 Hz, 1H) 7.69 (d, J=7.51 Hz, 1H) 7.72 (d, J=8.42 Hz, 1H) 7.95 (d, J=7.88 Hz, 1H) 8.03-8.07 (m, 2H) 8.22 (d, J=2.01 Hz, 1H) 8.48 (s, 1H) 10.55 (s, 1H).

(ESI) m/z 657 [(M+H)$^+$]. HRMS (ESI) calculated for C$_{35}$H$_{36}$F$_3$N$_8$O$_2{}^+$ [(M+H)$^+$] 657.2908. found 657.2914.

3-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-4-methyl-benzamide (cmpd 50)

$^1$H NMR (600 MHz, DMSO-d$_6$) δ ppm 0.99 (t, J=7.14 Hz, 3H) 2.19-2.48 (m, 8H) 2.89 (t, J=6.90 Hz, 2H) 3.44 (td, J=6.87, 2.50 Hz, 2H) 3.57 (s, 2H) 3.86 (s, 3H) 7.05-7.14 (m, 3H) 7.47 (d, J=8.18 Hz, 1H) 7.51 (s, 1H) 7.71 (d, J=8.54 Hz, 1H) 7.86 (dd, J=7.93, 1.95 Hz, 1H) 8.01-8.07 (m, 2H) 8.21 (d, J=2.20 Hz, 1H) 8.50 (s, 1H) 10.45-10.48 (m, 1H).

(ESI) m/z 671 [(M+H)$^+$]. HRMS (ESI) calculated for C$_{36}$H$_{38}$F$_3$N$_8$O$_2{}^+$ [(M+H)$^+$] 671.3065. found 671.3069.

5-[2-Amino-4-(1-methyl-4-oxo-4,5,6,7-tetrahydro-1H-pyrrolo[3,2-c]pyridin-2-yl)-pyrimidin-5-ylethynyl]-thiophene-2-carboxylic acid [4-(4-ethyl-piperazin-1-ylmethyl)-3-trifluoromethyl-phenyl]-amide (cmpd 51)

$^1$H NMR (600 MHz, DMSO-d$_6$) δ ppm 0.98 (t, J=7.23 Hz, 3H) 2.31 (q, J=7.14 Hz, 2H) 2.28-2.33 (m, 2H) 2.39 (dd, J=3.66, 1.83 Hz, 6H) 2.33-2.48 (m, 6H) 2.89 (t, J=6.87 Hz, 2H) 2.87-2.91 (m, 2H) 3.45 (td, J=6.87, 2.56 Hz, 2H) 3.56 (s, 2H) 3.85 (s, 3H) 7.11-7.14 (m, 1H) 7.19 (s, 2H) 7.36 (s, 1H) 7.38 (d, J=4.03 Hz, 1H) 7.71 (d, J=8.61 Hz, 1H) 7.97 (dd, J=8.61, 2.01 Hz, 1H) 7.99 (d, J=4.03 Hz, 1H) 8.12 (d, J=2.01 Hz, 1H) 8.47 (s, 1H) 10.56 (s, 1H).

(ESI) m/z 663 [(M+H)$^+$]. HRMS (ESI) calculated for C$_{33}$H$_{34}$F$_3$N$_8$O$_2$S$^+$ [(M+H)$^+$] 663.2472. found 663.2473.

2-[2-Amino-4-(1-methyl-4-oxo-4,5,6,7-tetrahydro-1H-pyrrolo[3,2-c]pyridin-2-yl)-pyrimidin-5-ylethynyl]-thiazole-5-carboxylic acid [4-(4-ethyl-piperazin-1-ylmethyl)-3-trifluoromethyl-phenyl]-amide (cmpd 52)

$^1$H NMR (600 MHz, DMSO-d$_6$) δ ppm 1.00 (br. s., 3H) 2.24-2.47 (m, 10H) 2.90 (t, J=6.78 Hz, 2H) 3.45 (td, J=6.87, 2.38 Hz, 2H) 3.58 (br. s., 2H) 3.85 (s, 3H) 7.14 (br. s., 1H) 7.29 (s, 1H) 7.38 (s, 2H) 7.74 (d, J=8.61 Hz, 1H) 7.97 (dd, J=8.52, 1.01 Hz, 1H) 8.11 (d, J=2.20 Hz, 1H) 8.57 (s, 1H) 8.66 (s, 1H) 10.75 (s, 1H).

(ESI) m/z 664 [(M+H)$^+$]. HRMS (ESI) calculated for C$_{32}$H$_{33}$F$_3$N$_9$O$_2$S$^+$ [(M+H)$^+$] 664.2425. found 664.2425.

5-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-nicotinamide (cmpd 53)

$^1$H NMR (600 MHz, DMSO-d$_6$) δ ppm 1.00 (br. s., 3H) 2.00-2.48 (m, 9H) 2.90 (t, J=6.87 Hz, 2H) 3.45 (td, J=6.87, 2.38 Hz, 2H) 3.58 (br. s., 2H) 3.86 (s, 3H) 7.12-7.24 (m, 3H) 7.49-7.52 (m, 1H) 7.74 (d, J=8.61 Hz, 1H) 8.03 (d, J=8.43 Hz, 1H) 8.21 (d, J=2.01 Hz, 1H) 8.37 (t, J=2.11 Hz, 1H) 8.51 (s, 1H) 8.82 (d, J=2.01 Hz, 1H) 9.05 (d, J=2.20 Hz, 1H) 10.71 (s, 1H).

(ESI) m/z 658 [(M+H)$^+$]. HRMS (ESI) calculated for C$_{34}$H$_{35}$F$_3$N$_9$O$_2{}^+$ [(M+H)$^+$] 658.2861. found 658.2861.

3-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-5-fluoro-benzamide (cmpd 54)

$^1$H NMR (600 MHz, DMSO-d$_6$) δ ppm 1.02 (br. s., 2H) 2.21-2.48 (m, 7H) 2.87-2.92 (m, 2H) 3.43-3.47 (m, 3H) 3.59

(br. s., 2H) 3.86 (s, 3H) 7.15 (br. s., 1H) 7.18 (s, 2H) 7.49 (s, 1H) 7.53 (dd, J=8.97, 1.10 Hz, 1H) 7.73 (d, J=8.43 Hz, 1H) 7.76-7.79 (m, 1H) 7.90 (s, 1H) 8.05 (d, J=8.97 Hz, 1H) 8.20 (d, J=2.01 Hz, 1H) 8.49 (s, 1H) 10.61 (s, 1H).

(ESI) m/z 675 [(M+H)$^+$]. HRMS (ESI) calculated for $C_{35}H_{35}F_4N_8O_2^+$ [(M+H)$^+$] 675.2814. found 675.2832.

3-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-2-fluoro-benzamide (cmpd 55)

$^1$H NMR (600 MHz, DMSO-d$_6$) δ ppm 0.98 (t, J=7.14 Hz, 3H) 2.31 (q, J=7.20 Hz, 3H) 2.33-2.48 (m, 5H) 2.89 (t, J=6.96 Hz, 2H) 3.44 (td, J=6.87, 2.38 Hz, 2H) 3.57 (s, 2H) 3.85 (s, 3H) 7.11 (br. s., 1H) 7.17 (s, 2H) 7.37 (t, J=7.78 Hz, 1H) 7.46 (s, 1H) 7.63-7.76 (m, 3H) 7.93 (d, J=8.42 Hz, 1H) 8.17 (d, J=1.65 Hz, 1H) 8.46 (s, 1H) 10.75 (s, 1H).

(ESI) m/z 675 [(M+H)$^+$]. HRMS (ESI) calculated for $C_{35}H_{35}F_4N_8O_2^+$ [(M+H)$^+$] 675.2814. found 675.2804.

3-[2-Amino-4-(1-methyl-4-oxo-4,5,6,7-tetrahydro-1H-pyrrolo[3,2-c]pyridin-2-yl)-pyrimidin-5-ylethynyl]-N-cyclopropyl-benzamide (cmpd 56)

$^1$H NMR (600 MHz, DMSO-d$_6$) δ ppm 0.58-0.63 (m, 2H) 0.67-0.72 (m, 2H) 2.83-2.87 (m, 1H) 2.89 (t, J=6.87 Hz, 2H) 3.45 (td, J=6.87, 2.38 Hz, 2H) 3.86 (s, 3H) 7.08-7.12 (m, 2H) 7.14-7.17 (m, 1H) 7.47-7.50 (m, 1H) 7.50 (s, 1H) 7.59 (d, J=7.88 Hz, 1H) 7.80 (d, J=7.88 Hz, 1H) 7.87 (s, 1H) 8.45 (s, 1H) 8.46 (d, J=4.40 Hz, 1H).

(ESI) m/z 427 [(M+H)$^+$]. HRMS (ESI) calculated for $C_{24}H_{23}N_6O_2^+$ [(M+H)$^+$] 427.1877. found 427.1880.

Example 7

N-[4-(4-Isopropyl-piperazin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (cmpd 176)

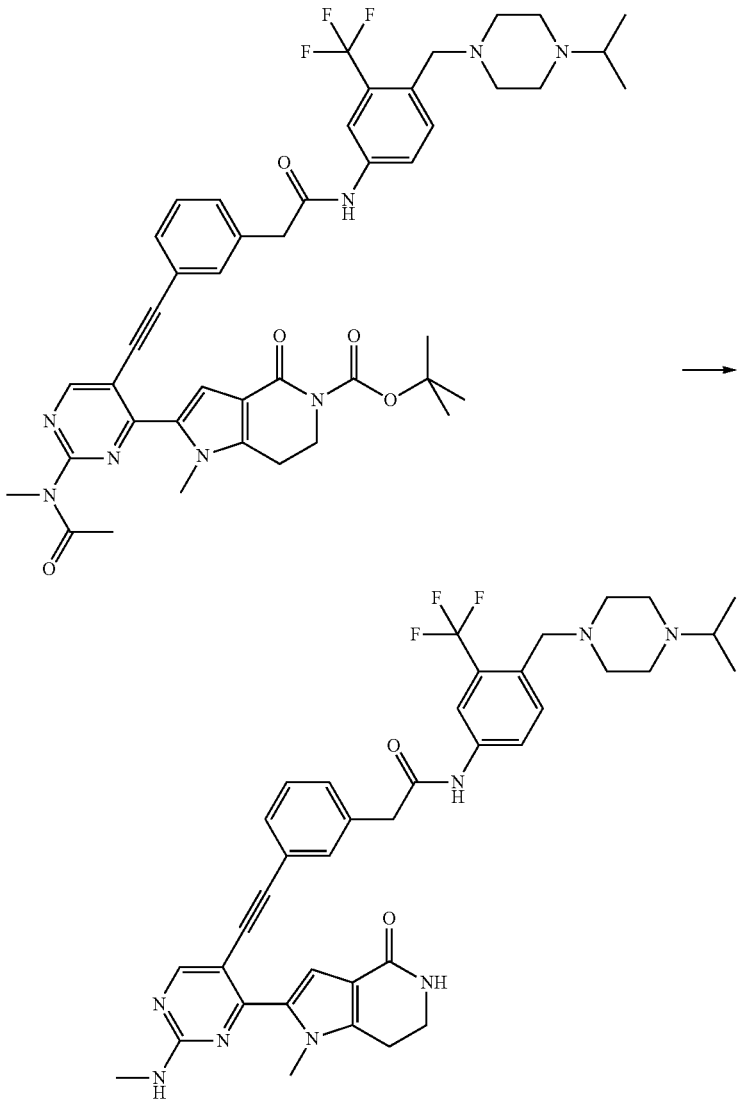

To a solution of 2-[2-(acetyl-methyl-amino)-5-(3-{[4-(4-isopropyl-piperazin-1-yl methyl)-3-trifluoromethyl-phenyl-carbamoyl]-methyl}-phenylethynyl)-pyrimidin-4-yl]-1-methyl-4-oxo-1,4,6,7-tetrahydro-pyrrolo[3,2-c]pyridine-5-carboxylic acid tert-butyl ester (0.49 g, 0.58 mmol) in DCM (15 mL), 4 M HCl in dioxane (0.73 mL, 2.90 mmol) was added. The resulting suspension was stirred at r.t. for 1 h, then the solvent was evaporated under vacuum. The solid was dissolved in MeOH (15 mL), $K_2CO_3$ (0.32 g, 2.32 mmol) was added and the mixture was stirred at reflux for 3 h. After removal of the solvent under vacuum the crude was purified by flash column chromatography (DCM/MeOH/NH$_3$ 90/10/0.5) to give the title compound (0.32 g, 78%) as white solid.

$^1$H NMR (600 MHz, DMSO-d$_6$) δ ppm 0.84-1.09 (m, 6H) 2.24-2.48 (m, 6H) 2.88 (d, J=4.76 Hz, 3H) 2.90 (t, J=6.87 Hz, 2H) 3.46 (td, J=6.73, 2.11 Hz, 2H) 3.52 (br. s., 2H) 3.67 (s, 2H) 3.82-3.94 (m, 3H) 7.24 (br. s., 1H) 7.31-7.39 (m, 3H) 7.50-7.62 (m, 3H) 7.65 (d, J=8.43 Hz, 1H) 7.78 (d, J=8.24 Hz, 1H) 8.04 (d, J=2.01 Hz, 1H) 8.39-8.55 (m, 1H) 10.48 (s, 1H).

(ESI) m/z 699 [(M+H)$^+$]. HRMS (ESI) calculated for $C_{38}H_{42}F_3N_8O_2^+$ [(M+H)$^+$] 699.3378. found 699.3375.

According to this same methodology, but employing suitable substituted derivatives, the following compounds were prepared:

6-[2-Methylamino-4-(1-methyl-4-oxo-4,5,6,7-tetrahydro-1H-pyrrolo[3,2-c]pyridin-2-yl)-pyrimidin-5-ylethynyl]-2,3-dihydro-indole-1-carboxylic acid [4-(4-ethyl-piperazin-1-ylmethyl)-3-trifluoromethyl-phenyl]-amide (cmpd 46)

$^1$H NMR (600 MHz, DMSO-d$_6$) δ ppm 1.01 (t, J=6.69 Hz, 3H) 2.23-2.46 (m, 10H) 2.82-2.95 (m, 5H) 3.18-3.25 (m, 2H) 3.44 (td, J=6.78, 2.38 Hz, 2H) 3.55 (s, 2H) 3.89 (br. s., 3H) 4.16 (t, J=8.70 Hz, 2H) 7.06 (dd, J=7.60, 1.19 Hz, 1H) 7.09 (br. s., 1H) 7.23 (d, J=7.51 Hz, 1H) 7.49 (s, 2H) 7.59-7.68 (m, 1H) 7.84 (dd, J=8.42, 1.83 Hz, 1H) 7.95 (d, J=0.55 Hz, 1H) 7.99 (d, J=2.01 Hz, 1H) 8.36-8.58 (m, 1H) 8.84 (s, 1H).

(ESI) m/z 712 [(M+H)$^+$]. HRMS (ESI) calculated for $C_{38}H_{41}F_3N_9O_2^+$ [(M+H)$^+$] 712.3330. found 712.3332.

5-[2-Methylamino-4-(1-methyl-4-oxo-4,5,6,7-tetrahydro-1H-pyrrolo[3,2-c]pyridin-2-yl)-pyrimidin-5-ylethynyl]-2,3-dihydro-indole-1-carboxylic acid [4-(4-ethyl-piperazin-1-ylmethyl)-3-trifluoromethyl-phenyl]-amide (cmpd 47)

$^1$H NMR (401 MHz, DMSO-d$_6$) δ ppm 0.98 (t, J=7.14 Hz, 3H) 2.30 (q, J=7.12 Hz, 2H) 2.38 (br. s., 8H) 2.85-2.93 (m, 5H) 3.14-3.24 (m, 2H) 3.45 (td, J=6.71, 1.95 Hz, 2H) 3.54 (s, 2H) 3.88 (br. s., 3H) 4.17 (t, J=8.61 Hz, 2H) 7.12 (br. s., 1H) 7.28 (d, J=8.91 Hz, 1H) 7.33 (s, 1H) 7.43-7.49 (m, 1H) 7.56 (br. s., 1H) 7.63 (d, J=8.79 Hz, 1H) 7.81-7.90 (m, 2H) 7.98 (d, J=1.95 Hz, 1H) 8.42 (br. s., 1H) 8.86 (s, 1H).

(ESI) m/z 712 [(M+H)$^+$]. HRMS (ESI) calculated for $C_{38}H_{41}F_3N_9O_2$ [(M+H)$^+$] 712.3330. found 712.3331.

N-[4-(4-Ethyl-piperazin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (cmpd 78)

$^1$H NMR (600 MHz, DMSO-d$_6$) δ ppm 0.97 (t, J=7.20 Hz, 3H) 1.09 (t, J=7.02 Hz, 2H) 2.29 (q, J=7.12 Hz, 4H) 2.36 (br. s., 8H) 2.81-2.96 (m, 8H) 3.47 (td, J=6.84, 2.44 Hz, 3H) 3.52 (s, 3H) 3.67 (s, 3H) 3.89 (d, J=6.35 Hz, 3H) 7.22 (s, 1H) 7.30-7.40 (m, 3H) 7.53 (s, 1H) 7.59 (br. s., 1H) 7.65 (d, J=8.54 Hz, 1H) 7.78 (dd, J=8.48, 2.01 Hz, 1H) 8.04 (d, J=2.20 Hz, 1H) 8.32-8.63 (m, 1H) 10.46 (s, 1H).

(ESI) m/z 685 [(M+H)$^+$]. HRMS (ESI) calculated for $C_{37}H_{40}F_3N_8O_2^+$ [(M+H)$^+$] 685.3221. found 685.3223.

2-{3-[2-Methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (cmpd 174)

$^1$H NMR (600 MHz, DMSO-d$_6$) δ ppm 2.14 (s, 2H) 2.22-2.43 (m, 8H) 2.79-2.97 (m, 5H) 3.43-3.49 (m, 2H) 3.52 (s, 2H) 3.67 (s, 2H) 3.79-3.99 (m, 3H) 7.22 (br. s., 1H) 7.30-7.39 (m, 3H) 7.53 (s, 2H) 7.59 (br. s., 1H) 7.64 (d, J=8.54 Hz, 1H) 7.77 (dd, J=8.61, 1.77 Hz, 1H) 8.04 (d, J=1.95 Hz, 1H) 8.44 (br. s., 1H) 10.47 (s, 1H).

(ESI) m/z 671 [(M+H)$^+$]. HRMS (ESI) calculated for $C_{36}H_{38}F_3N_8O_2^+$ [(M+H)$^+$] 671.3065. found 671.3066.

N-[4-(4-Cyclopropyl-piperazin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (cmpd 175)

$^1$H NMR (600 MHz, DMSO-d$_6$) δ ppm 0.26 (d, J=2.01 Hz, 2H) 0.36-0.40 (m, 2H) 1.55-1.61 (m, 1H) 2.31 (br. s., 3H) 2.88 (d, J=4.76 Hz, 3H) 2.89-2.92 (m, 2H) 3.47 (td, J=6.78, 2.38 Hz, 2H) 3.50 (s, 2H) 3.66-3.69 (m, 2H) 3.81-3.94 (m, 3H) 7.23 (br. s., 1H) 7.31-7.39 (m, 3H) 7.51-7.62 (m, 3H) 7.65 (d, J=8.61 Hz, 1H) 7.76-7.80 (m, 1H) 8.04 (d, J=1.83 Hz, 1H) 8.44 (br. s., 1H) 10.47 (s, 1H).

(ESI) m/z 697 [(M+H)$^+$]. HRMS (ESI) calculated for $C_{38}H_{40}F_3N_8O_2^+$ [(M+H)$^+$] 697.3221. found 697.3244.

2-{3-[2-Methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-propyl-piperazin-1-ylmethyl)-3-trifluoromethyl-phenyl]-acetamide (cmpd 179)

$^1$H NMR (600 MHz, DMSO-d$_6$) δ ppm 0.83 (t, J=7.33 Hz, 3H) 1.42 (m, J=5.13 Hz, 2H) 2.12-2.46 (m, 9H) 2.83-2.93 (m, 5H) 3.46 (td, J=6.55, 1.92 Hz, 1H) 3.52 (br. s., 2H) 3.67 (s, 2H) 3.76-3.99 (m, 3H) 7.22 (br. s., 1H) 7.31-7.38 (m, 3H) 7.50-7.61 (m, 3H) 7.64 (d, J=8.61 Hz, 1H) 7.78 (d, J=8.06 Hz, 1H) 8.04 (s, 1H) 8.36-8.61 (m, 1H) 10.47 (s, 1H).

(ESI) m/z 699 [(M+H)$^+$]. HRMS (ESI) calculated for $C_{38}H_{42}F_3N_8O_2^+$ [(M+H)$^+$] 699.3378. found 699.3383.

2-{4-Fluoro-3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (cmpd 190)

$^1$H NMR (600 MHz, DMSO-d$_6$) δ ppm 2.15 (s, 3H) 2.21-2.46 (m, 8H) 2.88-2.89 (m, 3H) 2.90-2.92 (m, 2H) 3.42-3.48 (m, 2H) 3.52 (s, 2H) 3.67 (s, 2H) 3.79-3.93 (m, 3H) 7.20 (br. s., 1H) 7.26 (d, J=8.97 Hz, 1H) 7.37 (ddd, J=8.15, 5.40, 2.20 Hz, 1H) 7.53-7.62 (m, 3H) 7.64 (d, J=8.43 Hz, 1H) 7.75-7.78 (m, 1H) 8.03 (d, J=1.83 Hz, 1H) 8.40-8.55 (m, 1H) 10.45 (s, 1H).

(ESI) m/z 689 [(M+H)+]. HRMS (ESI) calculated for $C_{36}H_{37}F_4N_8O_2^+$ [(M+H)+] 689.2970. found 689.2973.

2-{3-[2-Ethylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (cmpd 193)

$^1$H NMR (600 MHz, DMSO-$d_6$) δ ppm 1.16 (t, J=7.14 Hz, 3H) 2.15 (s, 3H) 2.21-2.44 (m, 7H) 2.90 (t, J=6.78 Hz, 2H) 3.34-3.39 (m, 3H) 3.46 (td, J=6.82, 2.29 Hz, 2H) 3.52 (s, 2H) 3.67 (s, 2H) 3.87 (br. s., 3H) 7.22 (br. s., 1H) 7.28-7.40 (m, 3H) 7.52 (s, 2H) 7.59 (br. s., 2H) 7.64 (d, J=8.43 Hz, 1H) 7.77 (dd, J=8.61, 1.47 Hz, 1H) 8.04 (d, J=1.83 Hz, 1H) 8.44 (br. s., 1H) 10.46 (s, 1H).

(ESI) m/z 685 [(M+H)+]. HRMS (ESI) calculated for $C_{37}H_{40}F_3N_8O_2^+$ [(M+H)+] 685.3221. found 685.3221.

2-{4-Fluoro-3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-isopropyl-piperazin-1-ylmethyl)-3-trifluoromethyl-phenyl]-acetamide (cmpd 194)

$^1$H NMR (600 MHz, DMSO-$d_6$) δ ppm 0.95 (d, J=5.86 Hz, 6H) 2.20-2.48 (m, 7H) 2.61 (br. s., 1H) 2.83-2.94 (m, 5H) 3.42-3.48 (m, 2H) 3.51 (s, 2H) 3.67 (s, 2H) 3.77-3.94 (m, 3H) 7.20 (br. s., 1H) 7.26 (t, J=8.97 Hz, 1H) 7.37 (td, J=5.49, 2.38 Hz, 1H) 7.51-7.63 (m, 3H) 7.65 (d, J=8.42 Hz, 1H) 7.76 (d, J=8.61 Hz, 1H) 8.03 (d, J=1.83 Hz, 1H) 8.44 (br. s., 1H) 10.45 (s, 1H).

(ESI) m/z 717 [(M+H)+]. HRMS (ESI) calculated for $C_{38}H_{41}F_4N_8O_2^+$ [(M+H)+] 717.3283. found 717.3288.

N-[4-(4-Ethyl-piperazin-1-ylmethyl)-3-trifluoromethyl-phenyl]-2-{5-[2-methylamino-4-(1-methyl-4-oxo-4,5,6,7-tetrahydro-1H-pyrrolo[3,2-c]pyridin-2-yl)-pyrimidin-5-ylethynyl]-thiophen-2-yl}-acetamide (cmpd 196)

$^1$H NMR (600 MHz, DMSO-$d_6$) δ ppm 2.16 (s, 3H) 2.38 (br. s., 7H) 2.84-2.92 (m, 6H) 3.41-3.47 (m, 2H) 3.53 (s, 2H) 3.81-3.90 (m, 3H) 3.92 (s, 2H) 6.97 (d, J=3.48 Hz, 1H) 7.09 (br. s., 1H) 7.17 (d, J=3.66 Hz, 1H) 7.34-7.45 (m, 1H) 7.55 (br. s., 1H) 7.66 (d, J=8.42 Hz, 1H) 7.77 (d, J=8.43 Hz, 1H) 8.02 (d, J=1.83 Hz, 1H) 8.41 (br. s., 1H) 10.52 (s, 1H).

(ESI) m/z 677 [(M+H)+]. HRMS (ESI) calculated for $C_{34}H_{35}F_3N_8O_2S^+$ [(M+H)+] 677.2629. found 677.2623.

N-[4-(4-Cyclopropylmethyl-piperazin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (cmpd 197)

$^1$H NMR (600 MHz, DMSO-$d_6$) δ ppm 0.07 (br. s., 2H) 0.45 (d, J=6.78 Hz, 2H) 0.69-0.88 (m, 1H) 2.82-2.94 (m, 5H) 3.43-3.49 (m, 2H) 3.53 (br. s., 2H) 3.67 (s, 2H) 3.90 (br. s., 3H) 7.22 (br. s., 1H) 7.29-7.39 (m, 3H) 7.50-7.61 (m, 3H) 7.65 (d, J=8.61 Hz, 1H) 7.77 (d, J=7.69 Hz, 1H) 8.04 (s, 1H) 8.44 (br. s., 1H) 10.47 (s, 1H).

(ESI) m/z 711 [(M+H)+]. HRMS (ESI) calculated for $C_{39}H_{41}F_3N_8O_2^+$ [(M+H)+] 711.3378. found 711.3376.

N-[4-((S)-3-Dimethylamino-pyrrolidin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (cmpd 198)

$^1$H NMR (600 MHz, DMSO-$d_6$) δ ppm 1.52-1.66 (m, 1H) 1.84 (dd, J=13.28, 5.77 Hz, 1H) 2.07 (s, 6H) 2.27-2.35 (m, 1H) 2.43-2.48 (m, 1H) 2.52-2.57 (m, 2H) 2.61 (t, J=8.06 Hz, 1H) 2.73 (m, J=6.96 Hz, 1H) 2.83-2.93 (m, 5H) 3.46 (t, J=5.86 Hz, 3H) 3.56-3.63 (m, 1H) 3.65 (s, 1H) 3.67 (s, 2H) 3.77-3.98 (m, 3H) 7.22 (br. s., 1H) 7.28-7.41 (m, 3H) 7.53 (s, 2H) 7.59 (br. s., 1H) 7.63 (d, J=8.24 Hz, 1H) 7.77 (d, J=8.24 Hz, 1H) 8.03 (s, 1H) 8.44 (br. s., 1H) 10.46 (s, 1H).

(ESI) m/z 685 [(M+H)+]. HRMS (ESI) calculated for $C_{37}H_{40}F_3N_8O_2^+$ [(M+H)+] 685.3221. found 685.3228.

2-{4-Fluoro-3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-propyl-piperazin-1-ylmethyl)-3-trifluoromethyl-phenyl]-acetamide (cmpd 199)

$^1$H NMR (600 MHz, DMSO-$d_6$) δ ppm 0.78-0.88 (m, 3H) 1.40 (sxt, J=7.29 Hz, 2H) 2.16-2.22 (m, 2H) 2.26-2.46 (m, 7H) 2.80-2.96 (m, 5H) 3.45 (t, J=5.59 Hz, 2H) 3.52 (s, 2H) 3.67 (s, 2H) 3.77-3.95 (m, 3H) 7.20 (br. s., 1H) 7.23-7.29 (m, 1H) 7.36 (dt, J=5.54, 2.82 Hz, 1H) 7.55 (br. s., 1H) 7.57 (dd, J=6.78, 1.83 Hz, 1H) 7.59 (br. s., 1H) 7.64 (d, J=8.42 Hz, 1H) 7.76 (dd, J=8.52, 1.19 Hz, 1H) 8.03 (s, 1H) 8.37-8.61 (m, 1H) 10.46 (s, 1H).

(ESI) m/z 717 [(M+H)+]. HRMS (ESI) calculated for $C_{38}H_{41}F_4N_8O_2^+$ [(M+H)+] 717.3283. found 717.3284.

2-{3-[2-Isopropylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (cmpd 202)

$^1$H NMR (600 MHz, DMSO-$d_6$) δ ppm 1.19 (d, J=6.41 Hz, 5H) 2.15 (s, 3H) 2.20-2.47 (m, 7H) 2.90 (t, J=6.87 Hz, 2H) 3.46 (td, J=6.87, 2.20 Hz, 2H) 3.52 (s, 2H) 3.67 (s, 2H) 3.87 (s, 3H) 4.11 (dd, J=14.29, 6.78 Hz, 1H) 7.22 (br. s., 1H) 7.31-7.40 (m, 3H) 7.38-7.61 (m, 3H) 7.64 (d, J=8.42 Hz, 1H) 7.77 (dd, J=8.33, 1.56 Hz, 1H) 8.04 (d, J=1.83 Hz, 1H) 8.45 (br. s., 1H) 10.47 (s, 1H).

(ESI) m/z 699 [(M+H)+]. HRMS (ESI) calculated for $C_{38}H_{42}F_3N_8O_2^+$ [(M+H)+] 699.3378. found 699.3372.

N-[4-(4-Ethyl-piperazin-1-ylmethyl)-3-trifluoromethyl-phenyl]-2-{4-fluoro-3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (cmpd 205)

$^1$H NMR (600 MHz, DMSO-$d_6$) δ ppm 1.01 (br. s., 3H) 2.86-2.92 (m, 5H) 3.43-3.48 (m, 2H) 3.54 (br. s., 2H) 3.67 (s, 2H) 3.80-3.94 (m, 3H) 7.20 (br. s., 1H) 7.26 (t, J=8.97 Hz, 1H) 7.33-7.39 (m, 1H) 7.48-7.62 (m, 3H) 7.65 (d, J=8.42 Hz, 1H) 7.78 (d, J=7.51 Hz, 1H) 8.03 (d, J=2.01 Hz, 1H) 8.38-8.57 (m, 1H) 10.47 (s, 1H).

(ESI) m/z 703 [(M+H)+]. HRMS (ESI) calculated for $C_{37}H_{39}F_4N_8O_2^+$ [(M+H)+] 703.3127. found 703.3138.

2-{3-[2-Ethylamino-4-(1-methyl-4-oxo-4,5,6,7-tetrahydro-1H-pyrrolo[3,2-c]pyridin-2-yl)-pyrimidin-5-ylethynyl]-4-fluoro-phenyl}-N-[4-(4-methyl-piperazin-1-ylmethyl)-3-trifluoromethyl-phenyl]-acetamide (cmpd 206)

$^1$H NMR (600 MHz, DMSO-$d_6$) δ ppm 1.16 (t, J=7.05 Hz, 3H) 1.44 (s, 9H) 2.14 (s, 3H) 2.36-2.38 (m, 4H) 3.03 (t, J=6.32 Hz, 2H) 3.52 (s, 2H) 3.71 (s, 2H) 3.84 (s, 3H) 3.98-4.07 (m, 4H) 7.33 (t, J=8.97 Hz, 1H) 7.43-7.48 (m, 1H) 7.59 (dd, J=6.78, 2.20 Hz, 1H) 7.64 (d, J=8.61 Hz, 1H) 7.70 (s, 1H) 7.76 (dd, J=8.52, 1.92 Hz, 1H) 8.03 (d, J=1.83 Hz, 1H) 8.92 (s, 1H) 10.43 (s, 1H).

(ESI) m/z 703 [(M+H)$^+$]. HRMS (ESI) calculated for $C_{37}H_{39}F_4N_8O_2^+$ [(M+H)$^+$] 703.3127. found 703.3147.

4-Methyl-3-[2-methylamino-4-(1-methyl-4-oxo-4,5,6,7-tetrahydro-1H-pyrrolo[3,2-c]pyridin-2-yl)-pyrimidin-5-ylethynyl]-N-[4-(4-methyl-piperazin-1-ylmethyl)-3-trifluoromethyl-phenyl]-benzamide (cmpd 207)

$^1$H NMR (600 MHz, DMSO-$d_6$) δ ppm 1.40-1.44 (m, 9H) 2.16 (s, 3H) 2.26-2.42 (m, 7H) 2.43 (s, 3H) 2.54 (s, 3H) 3.03 (t, J=6.29 Hz, 2H) 3.42 (s, 3H) 3.56 (s, 2H) 3.86 (s, 3H) 4.01 (t, J=6.29 Hz, 2H) 7.53 (d, J=8.18 Hz, 1H) 7.70 (d, J=8.67 Hz, 1H) 7.75 (s, 1H) 7.94 (dd, J=7.99, 1.89 Hz, 1H) 8.04 (dd, J=8.42, 2.08 Hz, 1H) 8.12 (d, J=1.95 Hz, 1H) 8.20 (d, J=2.20 Hz, 1H) 8.98 (s, 1H) 10.52 (s, 1H).

(ESI) m/z 671 [(M+H)$^+$]. HRMS (ESI) calculated for $C_{36}H_{38}F_3N_8O_2^+$ [(M+H)$^+$] 671.3065. found 671.3061.

Example 8

N-[4-(4-Ethyl-piperazin-1-ylmethyl)-3-trifluoromethyl-phenyl]-2-{3-[6-methylamino-4-(1-methyl-4-oxo-4,5,6,7-tetrahydro-1H-pyrrolo[3,2-c]pyridin-2-yl)-pyridin-3-ylethynyl]-phenyl}-acetamide (cmpd 209)

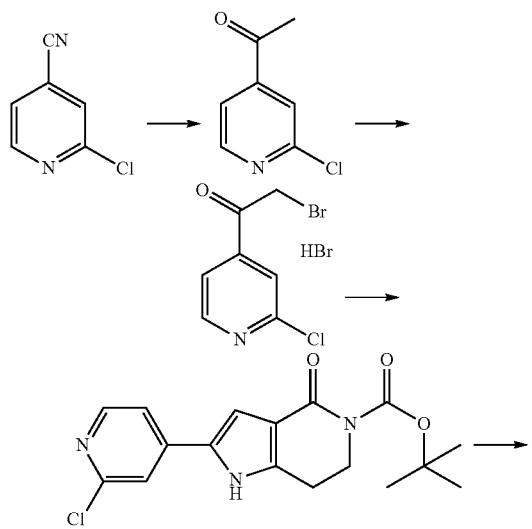

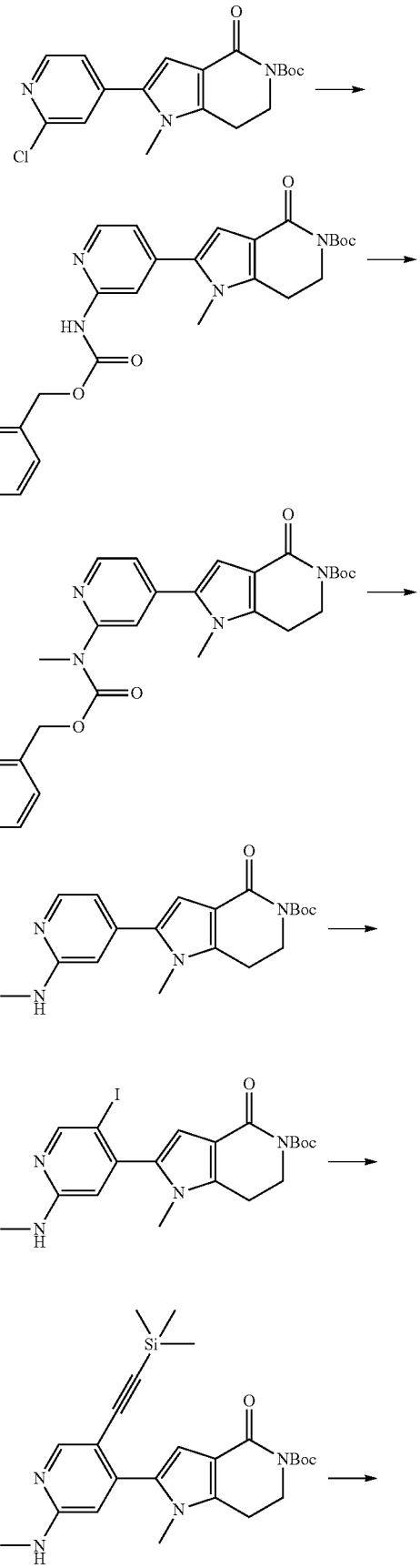

-continued

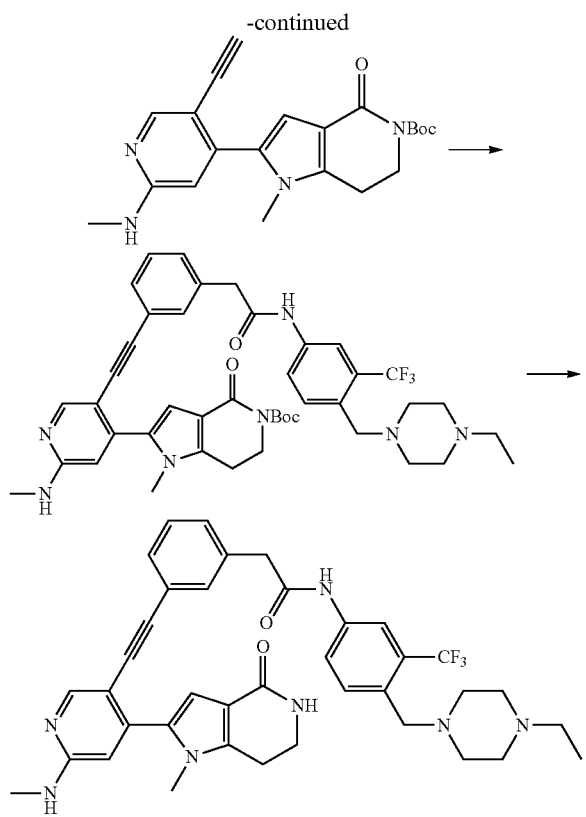

Step 1. 1-(2-Chloro-pyridin-4-yl)-ethanone

To a solution of 2-chloro-isonicotinonitrile (5 g, 36.08 mmol) in dry Et₂O (50 mL), 1 M methylmagnesium bromide in Bu₂O (72 mL, 72.16 mmol) was slowly added. The mixture was let under stirring overnight at room temperature, then the precipitate was filtered and washed con i-Pr₂O. The solid was suspended in a mixture of ice (50 g), water (37 mL) and HCl 6N (25 mL) and the product was extracted with EtOAc (4×12 mL). The organic layer was dried over Na₂SO₄ and evaporated to dryness. The crude yellow oil was treated with warm hexane (4×12 mL) and the extracts were let at 4° C. overnight. The product precipitated as white needles (2.66 g, 47%).

$^1$H NMR (600 MHz, DMSO-d$_6$) δ ppm 2.63 (s, 3H) 7.81 (dd, J=5.04, 1.37 Hz, 1H) 7.91 (dd, J=1.37, 0.64 Hz, 1H) 8.63 (dd, J=5.04, 0.64 Hz, 1H).

Step 2. 2-Bromo-1-(2-chloro-pyridin-4-yl)-ethanone hydrobromide

To a solution of 1-(2-chloro-pyridin-4-yl)-ethanone (2.66 g, 17.09 mmol) and 48% HBr (2.9 mL) in AcOH (12 mL), a solution of Br₂ (0.875 mL, 17.09 mmol) in AcOH (2.5 mL) was added dropwise and the mixture was let under stirring overnight. The precipitate was filtered, washed with absolute ethanol and dried at 40° C. under vacuum affording the title compound as white solid (4.8 g, 53%).

$^1$H NMR (401 MHz, DMSO-d$_6$) δ ppm 4.81 (s, 2H) 7.79 (dd, J=5.06, 1.40 Hz, 1H) 7.89 (dd, J=1.34, 0.85 Hz, 1H) 8.62-8.64 (m, 1H).

Step 3. 2-(2-Chloro-pyridin-4-yl)-4-oxo-1,4,6,7-tetrahydro-pyrrolo[3,2-c]pyridine-5-carboxylic acid tert-butyl ester A mixture of 2-bromo-1-(2-chloro-pyridin-4-yl)-ethanone hydrobromide (1.528 g, 4.84 mmol), 2,4-dioxo-piperidine-1-carboxylic acid tert-butyl ester (2.58 g, 12.1 mmol) and ammonium acetate (2.49 g, 32.29 mmol) in absolute ethanol (42 mL) was let under stirring overnight. The product precipitated as a white solid that was filtered off and dried under vacuum (1.56, 93%).

$^1$H NMR (600 MHz, DMSO-d$_6$) δ ppm 1.46 (s, 9H) 2.96 (t, J=6.32 Hz, 2H) 3.98 (t, J=6.32 Hz, 2H) 7.26 (s, 1H) 7.67 (dd, J=5.31, 1.47 Hz, 1H) 7.78 (d, J=0.92 Hz, 1H) 8.33 (d, J=5.31 Hz, 1H) 12.22 (br. s., 1H).

Step 4. 2-(2-Chloro-pyridin-4-yl)-1-methyl-4-oxo-1,4,6,7-tetrahydro-pyrrolo[3,2-c]pyridine-5-carboxylic acid tert-butyl ester The mixture of 2-(2-chloro-pyridin-4-yl)-4-oxo-1,4,6,7-tetrahydro-pyrrolo[3,2-c]pyridine-5-carboxylic acid tert-butyl ester (1.56 g, 4.49 mmol), Cs₂CO₃ (2.19 g, 6.72 mmol) and MeI (0.363 mL, 5.83 mmol) in dry DMF (40 mL) was heated at 80° C. for 1 h. The suspension was then poured in ice and water and let under stirring for 30 min. The product was isolated by filtration as a white solid (1.46 g, 90%).

$^1$H NMR (500 MHz, DMSO-d$_6$) δ ppm 1.47 (s, 9H) 2.97 (t, J=6.25 Hz, 2H) 3.65 (s, 3H) 3.98 (t, J=6.38 Hz, 2H) 6.88 (s, 1H) 7.55 (dd, J=5.22, 1.51 Hz, 1H) 7.63-7.65 (m, 1H) 8.42 (dd, J=5.22, 0.55 Hz, 1H).

Step 5. 2-(2-Benzyloxycarbonylamino-pyridin-4-yl)-1-methyl-4-oxo-1,4,6,7-tetrahydro-pyrrolo[3,2-c]pyridine-5-carboxylic acid tert-butyl ester 2-(2-Chloro-pyridin-4-yl)-1-methyl-4-oxo-1,4,6,7-tetrahydro-pyrrolo[3,2-c]pyridine-5-carboxylic acid tert-butyl ester (1.84 g, 5.07 mmol) and benzyl carbamate (3.83 g, 25.35 mmol) were charged in a Schlenk tube under argon and dissolved in dry dioxane (60 mL). Xantphos (440 mg, 0.76 mmol), Cs₂CO₃ (3.3 g, 10.14 mmol) and Pd(OAc)₂ (114 mg, 0.507 mmol) were added. The resulting mixture was degassed three times back filling with argon each time and then heated at 120° C. for 1.5 h. The solvent was removed under reduced pressure and the crude dissolved in DCM and washed with water and brine. The organic layer was dried over Na₂SO₄ and evaporated to dryness. The title compound was purified by column chromatography (Hexane/EtOAc 1/1) and isolated as white solid (1.41 g, 58%).

$^1$H NMR (401 MHz, DMSO-d$_6$) δ ppm 1.44 (s, 9H) 2.96 (t, J=6.35 Hz, 2H) 3.61 (s, 3H) 3.98 (t, J=6.35 Hz, 2H) 5.19 (s, 2H) 6.68 (s, 1H) 7.18 (dd, J=5.19, 1.65 Hz, 1H) 7.26-7.48 (m, 8H) 7.90-7.94 (m, 1H) 8.29 (dd, J=5.31, 0.67 Hz, 1H) 10.33 (s, 1H).

Step 6. 2-[2-(Benzyloxycarbonyl-methyl-amino)-pyridin-4-yl]-1-methyl-4-oxo-1,4,6,7-tetrahydro-pyrrolo[3,2-c]pyridine-5-carboxylic acid tert-butyl ester 2-(2-Benzyloxycarbonylamino-pyridin-4-yl)-1-methyl-4-oxo-1,4,6,7-tetrahydro-pyrrolo[3,2-c]pyridine-5-carboxylic acid tert-butyl ester (405 mg, 0.849 mmol) was dissolved in dry DMF, (17 mL) and treated with Cs₂CO₃ (684 mg, 2.1 mmol) and MeI (0.130 mL, 2.1 mmol). The mixture was let under stirring at room temperature for 2.5 h then it was diluted with EtOAc and washed with water and brine. The organic layer was dried over Na₂SO₄ and evaporated to dryness. The product was isolated as foaming solid (387 mg, 93%).

¹H NMR (401 MHz, DMSO-d₆) δ ppm 1.47 (s, 9H) 2.95 (t, J=6.41 Hz, 2H) 3.40 (s, 3H) 3.54 (s, 3H) 3.94-4.02 (m, 2H) 5.21 (s, 2H) 6.69 (s, 1H) 7.29 (dd, J=5.19, 1.53 Hz, 1H) 7.31-7.44 (m, 6H) 7.73 (d, J=0.73 Hz, 1H) 8.42 (dd, J=5.25, 0.73 Hz, 1H).

Step 7. 1-Methyl-2-(2-methylamino-pyridin-4-yl)-4-oxo-1,4,6,7-tetrahydro-pyrrolo[3,2-c]pyridine-5-carboxylic acid tert-butyl ester The suspension of 2-[2-(benzyloxycarbonyl-methyl-amino)-pyridin-4-yl]-1-methyl-4-oxo-1,4,6,7-tetrahydro-pyrrolo[3,2-c]pyridine-5-carboxylic acid tert-butyl ester (374 mg, 0.7632 mmol) with ammonium formate (333 mg, 4.892 mmol) and 5% Pd/C (50 mg) in ethanol was heated at reflux. The reaction was monitored by TLC (Hexane/EtOAc 1/1) and five subsequent additions of the reagents were required in order to reach total conversion of the starting material. The suspension was then filtered over a pad of celite that was repeatedly washed with ethanol. After solvent removal under reduced pressure, the crude was dissolved in DCM and washed with water and brine. The product was isolated as bright white solid (204 mg, 75%).

¹H NMR (401 MHz, DMSO-d₆) δ ppm 1.47 (s, 9H) 2.80 (d, J=4.76 Hz, 3H) 2.90-2.98 (m, 2H) 3.57 (s, 3H) 3.97 (t, J=6.35 Hz, 2H) 6.49 (s, 1H) 6.57 (s, 1H) 6.59 (dd, J=5.31, 1.40 Hz, 1H) 8.00 (d, J=5.25 Hz, 1H).

According to this same methodology, but employing suitable substituted derivatives, the following intermediates were prepared:

2-(2-Amino-pyridin-4-yl)-1-methyl-4-oxo-1,4,6,7-tetrahydro-pyrrolo[3,2-c]pyridine-5-carboxylic acid tert-butyl ester ¹H NMR (401 MHz, DMSO-d₆) δ ppm 1.46 (s, 9H) 2.94 (t, J=6.29 Hz, 2H) 3.57 (s, 3H) 3.92-4.01 (m, 2H) 5.98 (s, 2H) 6.51 (d, J=0.73 Hz, 1H) 6.54 (s, 1H) 6.58 (dd, J=5.37, 1.59 Hz, 1H) 7.30-7.43 (m, 2H) 7.93 (dd, J=5.25, 0.61 Hz, 1H).

Step 8. 2-(5-Iodo-2-methylamino-pyridin-4-yl)-1-methyl-4-oxo-1,4,6,7-tetrahydro-pyrrolo[3,2-c]pyridine-5-carboxylic acid tert-butyl ester To a solution of 1-methyl-2-(2-methylamino-pyridin-4-yl)-4-oxo-1,4,6,7-tetrahydro-pyrrolo[3,2-c]pyridine-5-carboxylic acid tert-butyl ester (156 mg, 0.437 mmol) in dry DMF (8 mL), silver acetate (84 mg, 0.505 mmol) and iodine (128 mg, 0.505 mmol) were added at 0° C. The mixture was allowed to reach room temperature and let under stirring for 2 h. The suspension was filtered over a pad of celite that was exhaustively washed with EtOAC. The filtrate was concentrated under reduced pressure and the residue was treated with water. The yellow precipitate was filtered and dried under vacuum (130 mg, 61%).

¹H NMR (401 MHz, DMSO-d₆) δ ppm 1.47 (s, 9H) 2.77 (d, J=3.42 Hz, 3H) 2.93 (t, J=6.7 Hz, 2H) 3.99 (t, J=6.29 Hz, 2H) 6.35 (s, 1H) 6.48 (s, 1H) 6.87 (br. s., 1H) 8.33 (d, J=0.61 Hz, 1H).

According to this same methodology, but employing suitable substituted derivatives, the following intermediates were prepared:

2-(2-Amino-5-iodo-pyridin-4-yl)-1-methyl-4-oxo-1,4,6,7-tetrahydro-pyrrolo[3,2-c]pyridine-5-carboxylic acid tert-butyl ester ¹H NMR (401 MHz, DMSO-d₆) δ ppm 1.46 (s, 9H) 2.93 (t, J=6.29 Hz, 2H) 3.98 (t, J=6.35 Hz, 2H) 6.37 (s, 1H) 6.50 (s, 1H) 8.26 (s, 1H).

Step 9. 1-Methyl-2-(2-methylamino-5-trimethylsilanylethynyl-pyridin-4-yl)-4-oxo-1,4,6,7-tetrahydro-pyrrolo[3,2-c]pyridine-5-carboxylic acid tert-butyl ester As described for the synthesis of 2-(2-amino-5-trimethylsilanylethynyl-pyrimidin-4-yl)-1-methyl-4-oxo-1,4,6,7-tetrahydro-pyrrolo[3,2-c]pyridine-5-carboxylic acid tert-butyl ester, heating the reaction mixture at 50° C. for 1 h.

¹H NMR (401 MHz, DMSO-d₆) δ ppm 0.10 (s, 9H) 1.46 (s, 9H) 2.82 (d, J=4.76 Hz, 3H) 2.92 (t, J=6.29 Hz, 2H) 3.46 (s, 3H) 3.97 (t, J=6.23 Hz, 2H) 6.40 (s, 1H) 6.54 (s, 1H) 7.08 (d, J=4.88 Hz, 1H) 8.17 (s, 1H).

According to this same methodology, but employing suitable substituted derivatives, the following intermediates were prepared:

2-(2-Amino-5-trimethylsilanylethynyl-pyridin-4-yl)-1-methyl-4-oxo-1,4,6,7-tetrahydro-pyrrolo[3,2-c]pyridine-5-carboxylic acid tert-butyl ester ¹H NMR (401 MHz, DMSO-d₆) δ ppm 0.10 (s, 9H) 1.46 (s, 9H) 2.92 (t, J=6.41 Hz, 2H) 3.46 (s, 3H) 3.97 (t, J=6.2 Hz, 2H) 6.40 (d, J=0.49 Hz, 1H) 6.53 (br. s., 2H) 6.55 (s, 1H) 8.09 (s, 1H).

Step 10. 2-(5-Ethynyl-2-methylamino-pyridin-4-yl)-1-methyl-4-oxo-1,4,6,7-tetrahydro-pyrrolo[3,2-c]pyridine-5-carboxylic acid tert-butyl ester As described for the synthesis of 2-(2-amino-5-ethynyl-pyrimidin-4-yl)-1-methyl-4-oxo-1,4,6,7-tetrahydro-pyrrolo[3,2-c]pyridine-5-carboxylic acid tert-butyl ester.

¹H NMR (401 MHz, DMSO-d₆) δ ppm 1.46 (s, 9H) 2.81 (d, J=5 Hz, 3H) 2.93 (t, J=6.35 Hz, 2H) 3.45 (s, 3H) 3.99 (t, J=6.22 Hz, 2H) 3.98 (s, 1H) 6.37 (s, 1H) 6.53 (s, 1H) 7.00-7.06 (m, 1H) 8.21 (s, 1H).

According to this same methodology, but employing suitable substituted derivatives, the following intermediates were prepared:

2-(2-Amino-5-ethynyl-pyridin-4-yl)-1-methyl-4-oxo-1,4,6,7-tetrahydro-pyrrolo[3,2-c]pyridine-5-carboxylic acid tert-butyl ester (ESI) m/z 367 [(M+H)⁺]. HRMS (ESI) calculated for $C_{20}H_{23}N_4O_3^+$ [(M+H)⁺] 367.1765. found 367.1783.

Step 11. 2-[5-(3-{[4-(4-Ethyl-piperazin-1-ylmethyl)-3-trifluoromethyl-phenylcarbamoyl]-methyl}-phenylethynyl)-2-methylamino-pyridin-4-yl]-1-methyl-4-oxo-1,4,6,7-tetrahydro-pyrrolo[3,2-c]pyridine-5-carboxylic acid tert-butyl ester A solution of 2-(5-ethynyl-2-methylamino-pyridin-4-yl)-1-methyl-4-oxo-1,4,6,7-tetrahydro-pyrrolo[3,2-c]pyridine-5-carboxylic acid tert-butyl ester (25 mg, 0.0644 mmol), 2-(3-iodo-phenyl)-N-[4-(4-ethyl-piperazin-1-ylmethyl)-3-trifluoromethyl-phenyl]-acetamide (68 mg, 0.1288 mmol), CuI (2.7 mg, 0.014 mmol), PdCl$_2$(PPh$_3$)$_2$ (10 mg, 0.014 mmol) and TEA (0.2 mL, 1.43 mmol) in DMF (6 mL) was degassed with argon and stirred at 50° C. for 3 h. The reaction was poured in water (15 mL) and extracted with EtOAc (2×15 mL). The organic phase was washed with brine, dried over anhydrous Na$_2$SO$_4$ and evaporated under vacuum to give the crude mixture that was purified by flash column chromatography (EtOAc/MeOH/NH$_3$ 95/15/0.5). The title product was obtained as yellowish solid (38 mg, 76%).

$^1$H NMR (401 MHz, DMSO-d$_6$) δ ppm 0.97 (t, J=7.14 Hz, 3H) 1.45 (s, 9H) 2.22-2.44 (m, 10H) 2.84 (d, J=4.88 Hz, 3H) 2.96 (t, J=6.35 Hz, 2H) 3.51 (s, 3H) 3.52 (s, 2H) 3.64 (s, 2H) 3.99 (t, J=6.23 Hz, 2H) 6.47 (s, 1H) 6.64 (s, 1H) 7.07-7.14 (m, 1H) 7.19 (dt, J=7.05, 1.66 Hz, 1H) 7.25-7.38 (m, 3H) 7.65 (d, J=8.54 Hz, 1H) 7.77 (dd, J=8.54, 1.95 Hz, 1H) 8.03 (d, J=2.20 Hz, 1H) 8.28 (s, 1H) 10.42 (br. s., 1H).

According to this same methodology, but employing suitable substituted derivatives, the following intermediates were prepared:

2-[2-Amino-5-(3-{[4-(4-ethyl-piperazin-1-ylmethyl)-3-trifluoromethyl-phenylcarbamoyl]-methyl}-phenylethynyl)-pyridin-4-yl]-1-methyl-4-oxo-1,4,6,7-tetrahydro-pyrrolo[3,2-c]pyridine-5-carboxylic acid tert-butyl ester (ESI) m/z 770 [(M+H)$^+$]. HRMS (ESI) calculated for C$_{42}$H$_{47}$F$_3$N$_7$O$_4^+$ [(M+H)$^+$] 770.3636. found 770.3615.

Step 12. N-[4-(4-Ethyl-piperazin-1-ylmethyl)-3-trifluoromethyl-phenyl]-2-{3-[6-methylamino-4-(1-methyl-4-oxo-4,5,6,7-tetrahydro-1H-pyrrolo[3,2-c]pyridin-2-yl)-pyridin-3-ylethynyl]-phenyl}-acetamide (cmpd 209)

2-[5-(3-{[4-(4-Ethyl-piperazin-1-yl methyl)-3-trifluoromethyl-phenylcarbamoyl]-methyl}-phenylethynyl)-2-methylamino-pyridin-4-yl]-1-methyl-4-oxo-1,4,6,7-tetrahydro-pyrrolo[3,2-c]pyridine-5-carboxylic acid tert-butyl ester (35 mg, 0.0457 mmol) was treated with TFA (0.5 mL) in DCM (3 mL) for 1 h. The solvents were removed under vacuum. The resulting crude was dissolved in water, treated with a saturated solution of NaHCO$_3$ and extracted with DCM (3×4 mL). The combined organic layers were dried over Na$_2$SO$_4$ and taken to dryness under reduced pressure. The title compound was purified by column chromatography (DCM/EtOH/NH$_3$ 95/5/0.5) and isolated as pale yellow solid (25 mg, 81%).

$^1$H NMR (401 MHz, DMSO-d$_6$) δ ppm 0.97 (t, J=7.14 Hz, 3H) 2.23-2.45 (m, 10H) 2.79-2.89 (m, 5H) 3.44 (td, J=6.96, 2.44 Hz, 2H) 3.49-3.55 (m, 5H) 3.64 (s, 2H) 6.45 (s, 1H) 6.56 (s, 1H) 7.01-7.09 (m, 2H) 7.19 (dt, J=7.11, 1.69 Hz, 1H) 7.26-7.36 (m, 3H) 7.65 (d, J=8.54 Hz, 1H) 7.77 (dd, J=8.67, 1.95 Hz, 1H) 8.04 (d, J=2.20 Hz, 1H) 8.27 (s, 1H) 10.45 (s, 1H).

(ESI) m/z 684 [(M+H)$^+$]. HRMS (ESI) calculated for C$_{38}$H$_{41}$F$_3$N$_7$O$_2^+$ [(M+H)$^+$] 684.3269. found 684.3280.

According to this same methodology, but employing suitable substituted derivatives, the following intermediates were prepared:

2-{3-[6-Amino-4-(1-methyl-4-oxo-4,5,6,7-tetrahydro-1H-pyrrolo[3,2-c]pyridin-2-yl)-pyridin-3-ylethynyl]-phenyl}-N-[4-(4-ethyl-piperazin-1-ylmethyl)-3-trifluoromethyl-phenyl]-acetamide (cmpd 208)

$^1$H NMR (401 MHz, DMSO-d$_6$) δ ppm 1.00 (t, J=6.65 Hz, 3H) 2.20-2.47 (m, 10H) 2.86 (t, J=6.96 Hz, 2H) 3.41-3.46 (m, 2H) 3.51 (s, 3H) 3.54 (s, 2H) 3.64 (s, 2H) 6.46 (d, J=0.61 Hz, 1H) 6.51 (s, 2H) 6.56 (s, 1H) 7.06 (t, J=2.20 Hz, 1H) 7.19 (dt, J=7.02, 1.68 Hz, 1H) 7.26-7.35 (m, 2H) 7.65 (d, J=8.54 Hz, 1H) 7.78 (dd, J=8.42, 1.71 Hz, 1H) 8.04 (d, J=2.20 Hz, 1H) 8.19 (d, J=0.61 Hz, 1H) 10.46 (s, 1H).

(ESI) m/z 670 [(M+H)$^+$]. HRMS (ESI) calculated for C$_{37}$H$_{39}$F$_3$N$_7$O$_2^+$ [(M+H)$^+$] 670.3112. found 670.3091.

Example 9

{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-carbamic acid phenyl ester (cmpd 203)

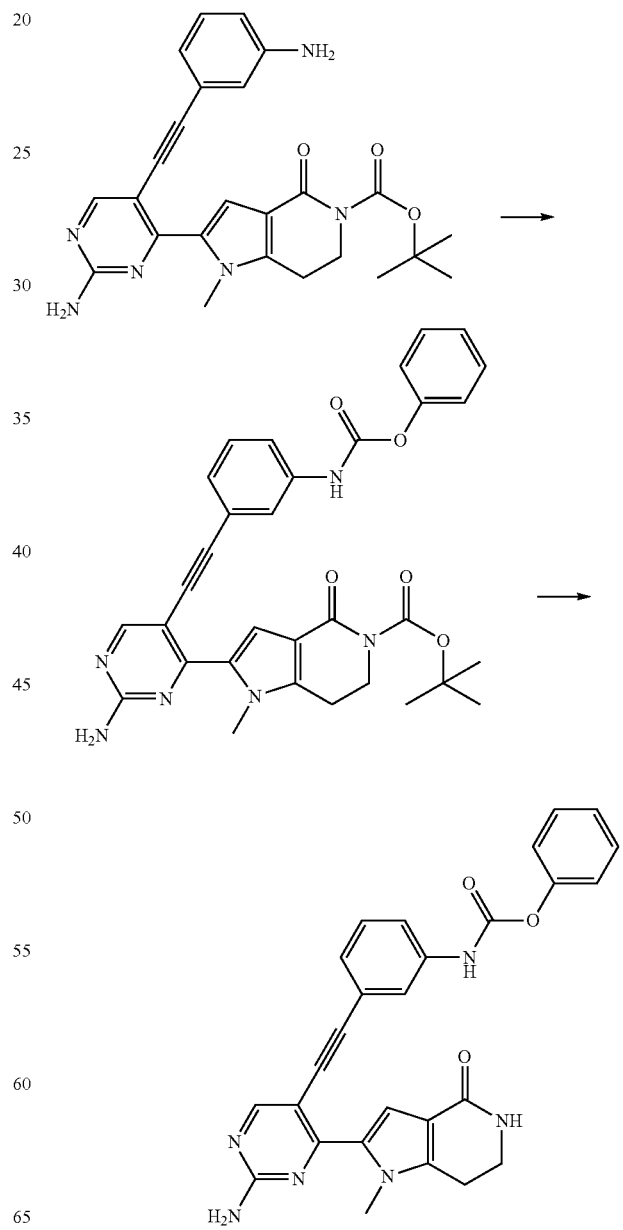

Step 1. 2-[2-Amino-5-(3-phenoxycarbonylamino-phenylethynyl)-pyrimidin-4-yl]-1-methyl-4-oxo-1,4,6,7-tetrahydro-pyrrolo[3,2-c]pyridine-5-carboxylic acid tert-butyl ester A suspension of 2-[2-amino-5-(3-amino-phenylethynyl)-pyrimidin-4-yl]-1-methyl-4-oxo-1,4,6,7-tetrahydro-pyrrolo[3,2-c]pyridine-5-carboxylic acid tert-butyl ester (100 mg, 0.218 mmol) in DCM (3 mL) and pyridine (1.5 mL) was treated with phenylchloroformate (0.027 mL, 0.218 mmol) for 4 h at room temperature. The mixture was then diluted with DCM and washed with water, 0.5N HCl, water and brine. The organic layer was dried over $Na_2SO_4$ and evaporated to dryness under reduced pressure affording the title compound as yellow solid that was used in the subsequent step without any further purification.

Step 2. {3-[2-Amino-4-(1-methy-4-ox-4,5,6,7-tetrahydro-1H-pyrrolo[3,2-c]pyrimidin-2-yl)-pyrimidin-5-ylethynyl]-phenyl}-carbamic acid phenyl ester (cmpd 203)

2-[2-amino-5-(3-amino-phenylethynyl)-pyrimidin-4-yl]-1-methyl-4-oxo-1,4,6,7-tetrahydro-pyrrolo[3,2-c]pyridine-5-carboxylic acid tert-butyl ester was dissolved in dioxane (3 mL) and treated with 4M HCL in dioxane (2 mL) for 1 h. The solvent was removed under vacuum and the crude was purified by column chromatography (EtOAc/MeOH/$NH_3$ 97/3/0.5) affording the title compound as white solid (48.6 mg, 46%).

$^1$H NMR (401 MHz, DMSO-$d_6$) δ ppm 2.87 (t, J=6.8 Hz, 2H), 3.43 (m, 2H), 3.82 (s, 3H), 7.04 (s, 2H), 7.09-7.27 (m, 6H), 7.35 (t, J=7.9 Hz, 1H), 7.40-7.45 (m, 2H), 7.50 (m, 1H), 7.59 (m, 1H), 8.43 (s, 1H), 10.30 (br. s., 1H).

The invention claimed is:
1. A compound of formula (I),

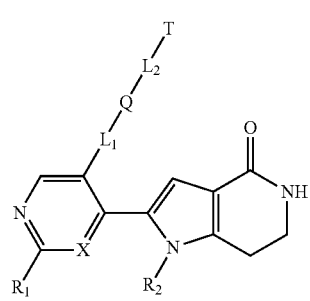

(I)

wherein
X is CH or N;
$R_1$ is H or $NHR_3$, wherein $R_3$ is H, an optionally substituted group selected from straight or branched $C_1$-$C_6$ alkyl, heterocyclyl and COR', wherein R' is an optionally substituted group selected from straight or branched $C_1$-$C_6$ alkyl, a $C_3$-$C_6$ carbocyclyl, aryl and heteroaryl;
$L_1$ is $CH_2$—$CH_2$, CH=CH or C≡C;
Q is an optionally substituted group selected from aryl and heteroaryl;
$L_2$ is C(RaRb)NRa, C(RaRb)C(RaRb)NRa, C(RaRb)NRaC(RaRb), NRaC(RaRb), NRaC(RaRb)C(RaRb), COO, C(RaRb)COO, C(RaRb)C(RaRb)COO, $SO_2$NRa, C(RaRb)$SO_2$NRa, CONRa, C(RaRb)CONRa, C(RaRb)C(RaRb)CONRa, CONRaC(RaRb), CONRaC(RaRb)C(RaRb), C(RaRb)NRaCO, C(RaRb)C(RaRb)NRaCO, NRaCOC(RaRb),NRaCOC(RaRb)C(RaRb), OC(RaRb)CONRa, C(RaRb)OC(RaRb), OC(RaRb)(C(RaRb))nC(RaRb),

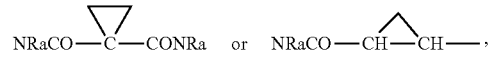

wherein Ra and Rb are independently H or an optionally substituted straight or branched $C_1$-$C_6$ alkyl and n is 0 or 1;
T is H or an optionally substituted group selected from straight or branched $C_1$-$C_6$ alkyl, $C_3$-$C_6$ carbocyclyl, heterocyclyl, aryl and heteroaryl;
$R_2$ is H or an optionally substituted group selected from straight or branched $C_1$-$C_6$ alkyl, $C_3$-$C_6$ carbocyclyl, heterocyclyl, aryl and heteroaryl;
or pharmaceutically acceptable salts thereof.

2. A compound of formula (I), according to claim 1, wherein
$R_1$ is H or $NHR_3$, wherein $R_3$ is H, an optionally substituted group selected from straight or branched $C_1$-$C_3$ alkyl, heterocyclyl and COR';
$L_1$ is C≡C;
Q is an optionally substituted group selected from aryl and heteroaryl, wherein the heteroaryl is monocyclic or bicyclic, and said bicyclic heteroaryl contains a nitrogen atom which the $L_2$ group is attached to.

3. A compound of formula (I), according to claim 1, wherein Q is an optionally substituted aryl or heteroaryl selected from:

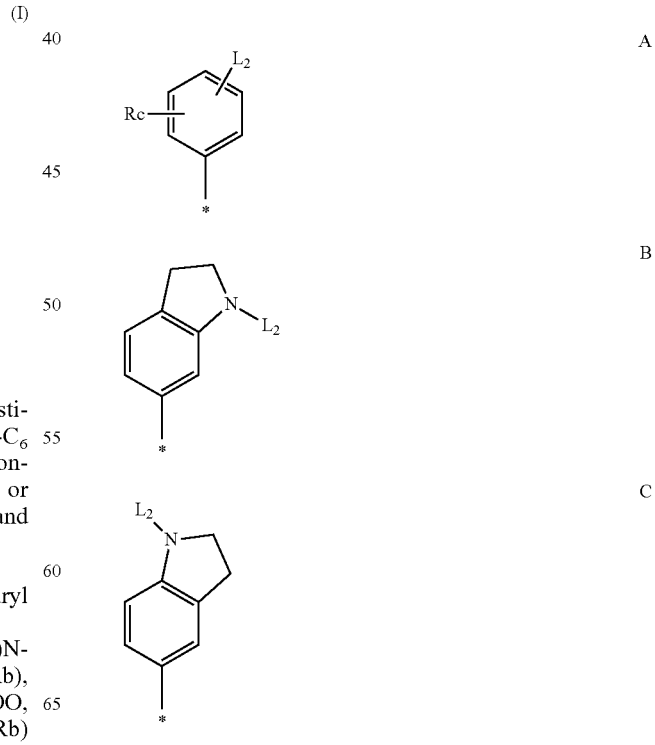

-continued

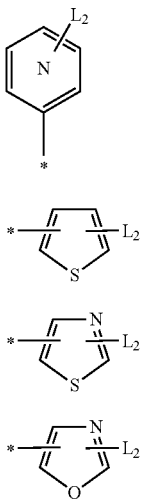

wherein Rc is selected from methyl and halogen;
L₂ is CONRa, C(RaRb)CONRa, C(RaRb)C(RaRb)CONRa, CONRaC(RaRb), OC(RaRb)CONRa, SO₂NRa or C(RaRb)SO₂NRa, wherein Ra and Rb are both hydrogen;
T is a substituted aryl of formula J:

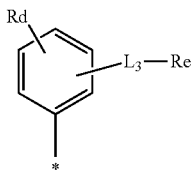

wherein
Rd is halogen, optionally substituted straight or branched $C_1$-$C_4$ alkyl, $C_3$-$C_6$ cycloalkyl or trifluoromethyl;
L₃ is direct linkage, O, NH, NCH₃, CH₂, CH₂NH, CH₂NCH₃ or C=O;
Re is
an optionally substituted heterocyclyl or
an optionally substituted straight or branched $C_1$-$C_6$ alkyl chain, wherein from 1 to 3 carbon atoms of said alkyl may be substituted independently by N or O, or
NRfRg, wherein Rf and Rg are each independently hydrogen or an optionally substituted straight or branched $C_1$-$C_6$ alkyl chain, wherein from 1 to 3 carbon atoms of said alkyl may be substituted independently by N or O, or Rf and Rg joined together with the nitrogen atom might represent a heterocyclic ring.

4. A compound of formula (I), according to claim 1, wherein L₂ is C(RaRb)NRaC(RaRb), C(RaRb)OC(RaRb), and OC(RaRb)(C(RaRb))nC(RaRb), wherein Ra and Rb are both hydrogen and n is 0 or 1.

5. A compound or a pharmaceutically acceptable salt thereof according to claim 1, which is selected from the group consisting of:
6-[2-Amino-4-(1-methyl-4-oxo-4,5,6,7-tetrahydro-1H-pyrrolo[3,2-c]pyridin-2-yl)-pyrimidin-5-ylethynyl]-2,3-dihydro-indole-1-carboxylic acid [4-(4-ethyl-piperazin-1-ylmethyl)-3-trifluoromethyl-phenyl]-amide (Cmpd 44),
5-[2-Amino-4-(1-methyl-4-oxo-4,5,6,7-tetrahydro-1H-pyrrolo[3,2-c]pyridin-2-yl)-pyrimidin-5-ylethynyl]-2,3-dihydro-indole-1-carboxylic acid [4-(4-ethyl-piperazin-1-ylmethyl)-3-trifluoromethyl-phenyl]-amide (Cmpd 45),
3-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-benzamide (Cmpd 48),
N-[4-(4-Ethyl-piperazin-1-ylmethyl)-3-trifluoromethyl-phenyl]-3-[2-methylamino-4-(1-methyl-4-oxo-4,5,6,7-tetrahydro-1H-pyrrolo[3,2-c]pyridin-2-yl)-pyrimidin-5-ylethynyl]-benzamide (Cmpd 49),
3-[2-Amino-4-(1-methyl-4-oxo-4,5,6,7-tetrahydro-1H-pyrrolo[3,2-c]pyridin-2-yl)-pyrimidin-5-ylethynyl]-N-[4-(4-ethyl-piperazin-1-ylmethyl)-3-trifluoromethyl-phenyl]-4-methyl-benzamide (Cmpd 50),
5-[2-Amino-4-(1-methyl-4-oxo-4,5,6,7-tetrahydro-1H-pyrrolo[3,2-c]pyridin-2-yl)-pyrimidin-5-ylethynyl]-thiophene-2-carboxylic acid [4-(4-ethyl-piperazin-1-ylmethyl)-3-trifluoromethyl-phenyl]-amide (Cmpd 51),
2-[2-Amino-4-(1-methyl-4-oxo-4,5,6,7-tetrahydro-1H-pyrrolo[3,2-c]pyridin-2-yl)-pyrimidin-5-ylethynyl]-thiazole-5-carboxylic acid [4-(4-ethyl-piperazin-1-ylmethyl)-3-trifluoromethyl-phenyl]-amide (Cmpd 52),
N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-4-trifluoromethyl-benzamide (Cmpd 57),
N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-2-(4-trifluoromethyl-phenyl)-acetamide (Cmpd 58),
2-{3-[2-Amino-4-(1-methyl-4-oxo-4,5,6,7-tetrahydro-1H-pyrrolo[3,2-c]pyridin-2-yl)-pyrimidin-5-ylethynyl]-phenoxy}-N-phenyl-acetamide hydrochloride (Cmpd 59),
N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(3-trifluoromethyl-phenyl)-propionamide hydrochloride (Cmpd 73),
3-[2-Amino-4-(1-methyl-4-oxo-4,5,6,7-tetrahydro-1H-pyrrolo[3,2-c]pyridin-2-yl)-pyrimidin-5-ylethynyl]-N-(3-trifluoromethyl-benzyl)-benzamide hydrochloride (Cmpd 74),
2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-ethyl-piperazin-1-ylmethyl)-3-trifluoromethyl-phenyl]-acetamide (Cmpd 77),
N-[4-(4-Ethyl-piperazin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (Cmpd 78),
2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-(4-ethyl-piperazin-1-ylmethyl)-4-trifluoromethyl-phenyl]-acetamide (Cmpd 82),
2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-indan-5-yl-acetamide (Cmpd 100),
2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-benzothiazol-6-yl-acetamide (Cmpd 102), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(5-tert-butyl-2-methyl-2H-pyrazol-3-yl)-acetamide (Cmpd 105), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-quinolin-3-yl-acetamide (Cmpd 106), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(3-trifluoromethyl-benzyl)-acetamide (Cmpd 111), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-ethyl-piperazin-1-ylmethyl)-3-fluoro-phenyl]-acetamide (Cmpd 120), 2-{5-[2-Amino-4-(1-methyl-4-oxo-4,5,6,7-tetrahydro-1H-pyrrolo[3,2-c]pyridin-2-yl)-pyrimidin-5-ylethynyl]-pyridin-3-yl}-N-[4-(4-ethyl-piperazin-1-ylmethyl)-3-trifluoromethyl-phenyl]-acetamide (Cmpd 122), 2-{4-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-ethyl-piperazin-1-ylmethyl)-3-trifluoromethyl-phenyl]-acetamide (Cmpd 123), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-(4-ethyl-piperazine-1-carbonyl)-4-trifluoromethyl-phenyl]-acetamide (Cmpd 127), 2-{5-[2-Amino-4-(1-methyl-4-oxo-4,5,6,7-tetrahydro-1H-pyrrolo[3,2-c]pyridin-2-yl)-pyrimidin-5-ylethynyl]-thiophen-2-yl}-N-[4-(4-ethyl-piperazin-1-ylmethyl)-3-trifluoromethyl-phenyl]-acetamide (Cmpd 129), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-isopropyl-phenyl)-acetamide (Cmpd 133), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-chloro-3-(4-ethyl-piperazin-1-ylmethyl)-phenyl]-acetamide (Cmpd 138), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-chloro-3-trifluoromethyl-phenyl)-acetamide (Cmpd 141), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-[1,4]diazepan-1-ylmethyl)-3-trifluoromethyl-phenyl]-acetamide (Cmpd 149), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[3-cyclopropyl-4-(4-methyl-piperazin-1-ylmethyl)-phenyl]-acetamide (Cmpd 154), 2-{3-[2-Amino-4-(1-methyl-4-oxo-4,5,6,7-tetrahydro-1H-pyrrolo[3,2-c]pyridin-2-yl)-pyrimidin-5-ylethynyl]-4-fluoro-phenyl}-N-[4-(4-ethyl-piperazin-1-ylmethyl)-3-trifluoromethyl-phenyl]-acetamide (Cmpd 155), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-propyl-piperazin-1-ylmethyl)-3-trifluoromethyl-phenyl]-acetamide (Cmpd 164), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-{[methyl-(1-methyl-piperidin-4-yl)-amino]-methyl}-3-trifluoromethyl-phenyl)-acetamide (Cmpd 166), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(1-methyl-piperidin-4-yloxy)-3-trifluoromethyl-phenyl]-acetamide (Cmpd 172), 2-{3-[2-Methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (Cmpd 174), N-[4-(4-Isopropyl-piperazin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (Cmpd 176), 2-{3-[2-Methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-propyl-piperazin-1-ylmethyl)-3-trifluoromethyl-phenyl]-acetamide (Cmpd 179), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-[4-(3-oxo-piperazin-1-ylmethyl)-3-trifluoromethyl-phenyl]-acetamide (Cmpd 184), 2-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-N-(4-{[(2-hydroxy-ethyl)-methyl-amino]-methyl}-3-trifluoromethyl-phenyl)-acetamide (Cmpd 189), 2-{4-Fluoro-3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (Cmpd 190), 2-(3-{2-Amino-4-[1-(2-hydroxy-ethyl)-4-oxo-4,5,6,7-tetrahydro-1H-pyrrolo[3,2-c]pyridin-2-yl]-pyrimidin-5-ylethynyl}-phenyl)-N-[4-(4-ethyl-piperazin-1-ylmethyl)-3-trifluoromethyl-phenyl]-acetamide (Cmpd 191), 2-{3-[2-Ethylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (cmpd 193), 2-(3-{2-Amino-4-(1-(1-methyl-piperidin-4-yl)-4-oxo-4,5,6,7-tetrahydro-1H-pyrrolo[3,2-c]pyridin-2-yl)-pyrimidin-5-ylethynyl}-phenyl)-N-(4-chloro-3-trifluoromethyl-phenyl)-acetamide (Cmpd 195), N-[4-((S)-3-Dimethylamino-pyrrolidin-1-ylmethyl)-3-trifluoromethyl-phenyl]-2-{3-[2-methylamino-4-(1-methyl-4-oxo-4,5,6,7-tetrahydro-1H-pyrrolo[3,2-c]pyridin-2-yl)-pyrimidin-5-ylethynyl]-phenyl}-acetamide (Cmpd 198), 2-{3-[2-Acetylamino-4-(1-methyl-4-oxo-4,5,6,7-tetrahydro-1H-pyrrolo[3,2-c]pyridin-2-yl)-pyrimidin-5-ylethynyl]-phenyl}-N-[4-(4-methyl-piperazin-1-ylmethyl)-3-trifluoromethyl-phenyl]-acetamide (Cmpd 200), 2-{3-[6-Amino-4-(1-methyl-4-oxo-4,5,6,7-tetrahydro-1H-pyrrolo[3,2-c]pyridin-2-yl)-pyridin-3-ylethynyl]-phenyl}-N-[4-(4-methyl-piperazin-1-ylmethyl)-3-trifluoromethyl-phenyl]-acetamide (Cmpd 201), 2-{3-[2-Isopropylamino-4-(1-methyl-4-oxo-4,5,6,7-tetra-hydro-1H-pyrrolo[3,2-c]pyridin-2-yl)-pyrimidin-5-yl-ethynyl]-phenyl}-N-[4-(4-methyl-piperazin-1-ylm-ethyl)-3-trifluoromethyl-phenyl]-acetamide (Cmpd 202) and {3-[2-Amino-4-(1-methyl-4-oxo-4,5,6,7-tetrahydro-1H-pyrrolo[3,2-c]pyridin-2-yl)-pyrimidin-5-ylethynyl]-phenyl}-carbamic acid phenyl ester (Cmpd 203).

6. A process for preparing a compound of formula (I) as defined in claim 1, or the pharmaceutically acceptable salts thereof, characterized in that the process comprises the following steps:

Method A:

step a: coupling of a pyrrolopyridinone derivative of formula (III)

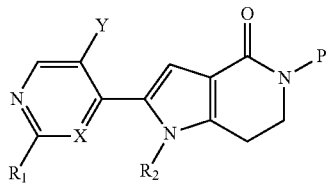

(III)

wherein X, $R_1$ and $R_2$ are as defined in claim 1, Y is halogen and P is a suitable protecting group, with an intermediate of formula (1a)-(1h)

≡-Q-$L_2$T     (1a-1h)

wherein Q, T and $L_2$ are as defined in claim 1, under Sonogashira reaction conditions;

step b: deprotection of the resultant intermediate of formula (II)

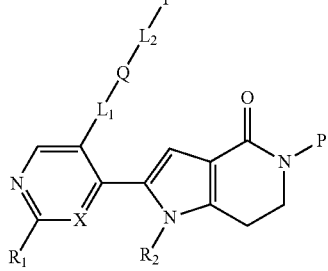

(II)

wherein X, $R_1$, $R_2$, $L_1$, $L_2$, Q and T are as defined in claim 1 and P is as defined above, under acid conditions to yield a compound of formula (I) as defined in claim 1;

alternatively, Method B:

step c: coupling of a pyrrolopyridinone derivative of formula (III), as defined above, with ethynyl-trimethyl-silane under Sonogashira reaction conditions, followed by removal of the trimethylsilyl group under basic conditions;

step d: reaction of the resultant intermediate of formula (IV)

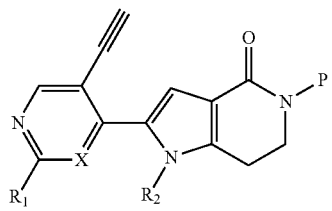

(IV)

wherein X, $R_1$ and $R_2$ are as defined in claim 1 and P is as defined above, with an intermediate of formula (3a)-(3h)

Y-Q-$L_2$-T     (3a)-(3h)

wherein Y is halogen and Q, $L_2$ and T are as defined in claim 1, under Sonogashira reaction conditions;

step b: deprotection of the resultant intermediate of formula (II) as defined above;

alternatively, Method C:

step c: coupling of a pyrrolopyridinone derivative of formula (III), as defined above, with ethynyl-trimethyl-silane under Sonogashira reaction conditions, followed by removal of the trimethylsilyl group under basic conditions;

step e: reaction of the resultant intermediate of formula (IV) as defined above, with an intermediate of formula Y-Q-$L_2$'-CO-Y' wherein $L_2$' is direct linkage, —C(RaRb)—, —C(RaRb)C(RaRb)— or —OC(RaRb)—, Y is halogen, Y' is OH and Q, Ra and Rb are as defined in claim 1, or with an intermediate of formula Y-Q-$L_2$'-NH—Ra wherein Y, Q, $L_2$' and Ra are as defined above under Sonogashira reaction conditions;

step f: coupling the resultant intermediate of formula (V)

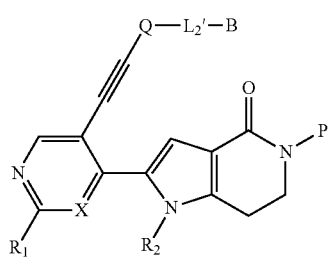

(V)

wherein B is COOH or NHRa and X, Q, Ra, $R_1$, $R_2$, $L_2$' and P are as defined above, with an intermediate in the presence of a coupling agent to give an intermediate of formula (II) as defined above;

step b: deprotection of the intermediate of formula (II) as defined above;

alternatively, Method D:

step g: reaction of an intermediate of formula (III) as defined above with an intermediate of formula ≡-Q-$L_2$'-CO-Y' wherein $L_2$', Y, Y' and Q are as defined above, or with an intermediate of formula ≡-Q-$L_2$'-NH-Ra wherein Y, Q, $L_2$' and Ra are as defined above under Sonogashira reaction conditions to yield an intermediate of formula (V), as defined above;

step f: coupling the resultant intermediate of formula (V) with a suitable intermediate in the presence of a coupling agent to give an intermediate of formula (II) as defined above;

step b: deprotection of the intermediate of formula (II) as defined above;

optionally converting a compound of formula (I) into a different compound of formula (I) by known chemical reactions; and/or, if desired, converting a compound of formula (I) into a pharmaceutically acceptable salt thereof or converting a salt into a free compound of formula (I).

7. A method for treating a disease caused by and/or associated with a dysregulated protein kinase activity which comprises administering to a mammal in need thereof an effective amount of a compound of formula (I) as defined in claim 1, wherein the disease is a carcinoma selected from the group consisting of breast, lung, ovary and thyroid.

8. The method according to claim 7 wherein the mammal in need thereof is a human.

9. The method according to claim 7 which provides tumor angiogenesis and metastasis inhibition.

10. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

\* \* \* \* \*